US012344597B2

(12) United States Patent
Bolli et al.

(10) Patent No.: US 12,344,597 B2
(45) Date of Patent: Jul. 1, 2025

(54) ALKOXY-SUBSTITUTED PYRIDINYL DERIVATIVES AS LPA1 RECEPTOR ANTAGONISTS AND THEIR USE IN THE TREATMENT OF FIBROSIS

(71) Applicant: IDORSIA PHARMACEUTICALS LTD, Allschwil (CH)

(72) Inventors: Martin Bolli, Allschwil (CH); Christine Brotschi, Allschwil (CH); Cyrille Lescop, Allschwil (CH); Jodi T. Williams, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 1024 days.

(21) Appl. No.: 16/972,878

(22) PCT Filed: Jun. 5, 2019

(86) PCT No.: PCT/EP2019/064690
§ 371 (c)(1),
(2) Date: Dec. 7, 2020

(87) PCT Pub. No.: WO2019/234115
PCT Pub. Date: Dec. 12, 2019

(65) Prior Publication Data
US 2021/0246116 A1 Aug. 12, 2021

(30) Foreign Application Priority Data

Jun. 7, 2018 (WO) .................. PCT/EP2018/065016

(51) Int. Cl.
*C07D 401/12* (2006.01)
*A61P 9/14* (2006.01)
*C07D 401/14* (2006.01)

(52) U.S. Cl.
CPC .............. *C07D 401/12* (2013.01); *A61P 9/14* (2018.01); *C07D 401/14* (2013.01)

(58) Field of Classification Search
None
See application file for complete search history.

(56) References Cited

U.S. PATENT DOCUMENTS

| 3,097,209 A | 7/1963 | Janssen |
| 6,734,184 B1 | 5/2004 | Barlaam et al. |
| 7,288,558 B2 | 10/2007 | Nakade et al. |
| 7,855,290 B2 | 12/2010 | Matsushima et al. |
| 8,466,115 B2 | 6/2013 | Curtis et al. |
| 2007/0078120 A1 | 4/2007 | Ban et al. |
| 2008/0207573 A1 | 8/2008 | Yager et al. |

FOREIGN PATENT DOCUMENTS

| EP | 1 364 659 | 11/2003 |
| EP | 2 481 725 | 8/2012 |
| JP | 2008110971 | 5/2008 |
| WO | WO 1996/011940 | 4/1996 |
| WO | WO 2000/012478 | 3/2000 |
| WO | WO 2001/032173 | 5/2001 |
| WO | WO 2001/077077 | 10/2001 |
| WO | WO 2002/062389 | 8/2002 |
| WO | WO 2003/088908 | 10/2003 |
| WO | WO 2004/085385 | 10/2004 |
| WO | WO 2004/110350 | 12/2004 |
| WO | WO 2005/023761 | 3/2005 |
| WO | WO 2005/037269 | 4/2005 |
| WO | WO 2005/049605 | 6/2005 |
| WO | WO 2006/073967 | 7/2006 |
| WO | WO 2006/091862 | 8/2006 |
| WO | WO 2007/058990 | 5/2007 |
| WO | WO 2007/146712 | 12/2007 |
| WO | WO 2008/115281 | 9/2008 |
| WO | WO 2009/051715 | 4/2009 |
| WO | WO 2009/131940 A1 | 10/2009 |
| WO | WO 2009/135590 | 11/2009 |
| WO | WO 2010/023181 | 3/2010 |
| WO | WO 2011/037192 | 3/2011 |
| WO | WO 2012/017359 | 2/2012 |
| WO | WO 2012/055995 | 5/2012 |
| WO | WO 2012/078805 | 6/2012 |
| WO | WO 2012/082817 | 6/2012 |
| WO | WO 2012/120399 | 9/2012 |
| WO | WO 2013/096771 | 6/2013 |
| WO | WO 2014/079805 | 5/2014 |
| WO | WO 2017/177004 | 10/2017 |

(Continued)

OTHER PUBLICATIONS

Datta. British Journal of Pharmacology, 2011, 163, 141-172 (Year: 2011).*
Cuzick. The Lancet, 2014, 15, e484-e492 (Year: 2014).*
Gonzalez-Gil. Medicinal Chemistry Communications, 2015, 6, 13-23 (Year: 2015).*
Teo. Biochemical Journal, 2014, 463, 157-165 (Year: 2014).*
Azoury. Surgical Clinics of North America, 2014, 94, 945-962 (Year: 2014).*
Ulrich. British Journal of Dermatology, 2009, 161, 78-84 (Year: 2009).*
Simpson. Journal of the American Academy of Dermatology, 2010, 587-593 (Year: 2010).*
Wilson. Mucosa/Immunology, 2009, 2(2), 103-121 (Year: 2009).*
Davenport. Organic Process Research & Development, 2024, 28, 577-587 (Year: 2024).*
U.S. Appl. No. 17/620,520, filed Dec. 17, 2021 (371(c) Date), Bolli et al.

(Continued)

*Primary Examiner* — Noble E Jarrell
(74) *Attorney, Agent, or Firm* — Hoxie & Associates LLC

(57) ABSTRACT

The present invention relates to pyridinyl derivatives of Formula (I) Formula (I) wherein $R^1$, $R^2$, $R^3$, $R^4$, $R^5$, $R^6$, $Ar^1$, L, W, Z, m and n are as described in the description, their preparation, to pharmaceutically acceptable salts thereof, and to their use as pharmaceuticals, to pharmaceutical compositions containing one or more compounds of Formula (I), and especially to their use as LPA1 receptor modulators.

21 Claims, No Drawings

(56) References Cited

FOREIGN PATENT DOCUMENTS

| WO | WO 2020/254408 A1 | 12/2020 |
|---|---|---|
| WO | WO 2021/110805 A1 | 6/2021 |

OTHER PUBLICATIONS

Sakamoto, K. et al., "Effect of ASP6432, a Novel Type 1 Lysophosphatidic Acid Receptor Antagonist, on Urethral Function and Prostate Cell Proliferation," The Journal of Pharmacology and Experimental Therapeutics, 2018, 366, 390-396.

U.S. Appl. No. 17/782,530, filed Jun. 3, 2022 (371(c) Date), Birker et al.

Ahmed et al., "Expression of autotaxin and acylglycerol kinase in proliferative vitreoretinal epiretinal membranes," Acta Ophthalmol, vol. 90, pp. e84-e89, (2012).

An et al., "Molecular Cloning of the Human Edg2 Protein and Its Identification as a Functional Cellular Receptor for Lysophosphatidic Acid," Biochem. Biophys. Res. Comm., vol. 231, pp. 619-622, (1997).

Baker et al., "Direct Quantitative Analysis of Lysophosphatidic Acid Molecular Species by Stable Isotope Dilution Electrospray Ionization Liquid Chromatography—Mass Spectrometry," Biochem., vol. 292, pp. 287-295, (2001).

Boucharaba et al., "Platelet-derived lysophosphatidic acid supports the progression of osteolytic bone metastases in breast cancer," J. Clin. Invest., vol. 114, No. 12, pp. 1714-1725, (2004); https://doi.org/10.1172/JCI22123.

Boucharaba et al., "The type 1 lysophosphatidic acid receptor is a target for therapy in bone metastases," Proc. Natl. Acad. Sci., vol. 103, No. 25, pp. 9643-9648, (2006).

Bremner et al., "The Synthesis of Thienopyridines from ortho-Halogenated Pyridine Derivatives," Synthesis, vol. 6, pp. 528-530, (1992).

Brindley, "Lipid Phosphate Phosphatases and Related Proteins: Signaling Functions in Development, Cell Division, and Cancer," J. Cell Biochem., vol. 92, pp. 900-912, (2004).

Castelino et al., "Amelioration of Dermal Fibrosis by Genetic Deletion or Pharmacologic Antagonism of Lysophosphatidic Acid Receptor 1 in a Mouse Model of Scleroderma," Arthritis Rheum., vol. 63, No. 5, pp. 1405-1415, (2011).

Choi et al., "LPA Receptors: Subtypes and Biological Actions," Pharmacol. Toxicol., vol. 50, pp. 157-186, (2010).

Choi et al., "Lysophospholipids and their receptors in the central nervous system," Biochim. Biophys. Acta, vol. 1831, pp. 20-32, (2013).

Chun, J., Hla, T., Spiegel, S., Moolenaar, W., Editors, Lysophospholipid Receptors: Signaling and Biochemistry, 2013, Wiley; ISBN: 978-0-470-56905-4.

Dollé et al., "Studies towards 4-C-Alkylation of Pyridin-2(1H)-one Derivatives," Tetrahedron, vol. 53, No. 37, pp. 12505-12524, (1997).

D'Souza et al., "Lysophosphatidic Acid Signaling in Obesity and Insulin Resistance," Nutrients, vol. 10, No. 399, pp. 1-20, (2018).

Fujiwara et al., "Identification of Residues Responsible for Ligand Recognition and Regioisomeric Selectivity of Lysophosphatidic Acid Receptors Expressed in Mammalian Cells," J. Biol. Chem., vol. 280, No. 41, pp. 35038-35050, (2005).

Georas et al., "Lysophosphatidic acid is detectable in human bronchoalveolar lavage fluids at baseline and increased after segmental allergen challenge," Clin. Exp. Allergy, vol. 37, No. 3, pp. 311-322, (2007).

Gill et al., "Pigments of Fungi. LIX*† Synthesis of (1S,3S)- and (1R,3R)-Austrocortilutein and (1S,3S)-Austrocortirubin from Citramalic Acid," Aust. J. Chem., vol. 53, pp. 245-256, (2000).

Goetzl et al., "Lysophospholipid Growth Factors and Their G Protein-Coupled Receptors in Immunity, Coronary Artery Disease, and Cancer," Scientific World J., vol. 2, pp. 324-338, (2002).

Guo et al., "Mitogenic Signaling in Androgen Sensitive and Insensitive Prostate Cancer Cell Lines," J. Urology, vol. 163, pp. 1027-1032, (2000).

"Handbook of Pharmaceutical Salts. Properties, Selection and Use," P. Heinrich Stahl, Camille G. Wermuth (Eds.), Wiley-VCH, 2008.

Hecht et al., "Ventricular Zone Gene-1 (vzg-1) Encodes a Lysophosphatidic Acid Receptor Expressed in Neurogenic Regions of the Developing Cerebral Cortex," J. Cell. Biol., vol. 135, pp. 1071-1083, (1996).

Inoue et al., "Initiation of neuropathic pain requires lysophosphatidic acid receptor signaling," Nat. Med., vol. 10, No. 7, pp. 712-718, (2004).

Kerins et al., "Generation of Substituted Styrenes via Suzuki Cross-Coupling of Aryl Halides with 2,4,6-Trivinylcyclotriboroxane," J. Org. Chem., vol. 67, pp. 4968-4971, (2002).

Kocienski, P. J., Protecting Groups, Thieme Stuttgart, 1994.

Komachi et al., "Orally active lysophosphatidic acid receptor antagonist attenuates pancreatic cancer invasion and metastisi in vivo," Cancer Sci., vol. 103, No. 6, pp. 1099-1104, (2012).

Kropp et al., "Characterization of Cultured Bladder Smooth Muscle Cells: Assessment of in Vitro Contractility," J. Urology, vol. 162, pp. 1779-1784, (1999).

Kuner, "Central mechanisms of pathological pain," Nat. Med., vol. 16, No. 11, pp. 1258-1266, (2010).

Li et al., "Blocking lysophosphatidic acid receptor 1 signaling inhibits diabetic nephropathy in db/db mice," Kidney International, vol. 91, No. 6, pp. 1362-1372, (2017).

Lin et al., "Lysophosphatidic acid receptor 1 is important for intestinal epithelial barrier function and susceptibility to colitis," Am. J. Pathol., vol. 188, No. 2, pp. 353-366, (2018).

Liu et al., "Highly controlling selectivity of copper(I)-catalyzed azide/alkyne cycloaddition (CuAAC) between sulfonyl azids and normal alkynes or propynoates," Tetrahedron, vol. 67, pp. 6294-6299, (2011).

Matsushita et al., "Palladium-Catalyzed Reactions of Allylic Electrophiles with Organometallic Reagents. A Regioselective 1,4-Elimination and a Regio- and Stereoselective Reduction of Allylic Derivatives," Org. Chem., vol. 47, pp. 4161-4165, (1982).

Möbus et al., "Hydrogenation of Aromatic Nitrogroups with Precious Metal Powder Catalysts: Influence of Modifier on Selectivity and Activity," Top. Catal., vol. 53, pp. 1126-1131, (2010).

Montalbetti et al., "Amide bond formation and peptide coupling," Tetrahedron, vol. 46, pp. 10827-10852, (2005).

Moolenaar et al., "The ins and outs of lysophosphatidic acid signaling," BioEssays, vol. 26, pp. 870-881, (2004).

Nagai et al., "Autotaxin and lysophosphatidic acid$_1$ receptor-mediated demyelination of dorsal root fibers by sciatic nerve injury and intrathecal lysophosphatidylcholine," Molecular Pain, vol. 6, No. 78, pp. 1-11, (2010).

Onorato et al., "Challenges in accurate quantitation of lysophosphatidic acids in human biofluids," J. Lipid Res., vol. 55, pp. 1984-1796, (2014).

"Pharmaceutical Salts and Co-crystals," John Wouters and Luc Quéré (Eds.), RSC Publishing, 2012.

Pradère et al., "LPA$_1$ Receptor Activation Promotes Renal Interstitial Fibrosis," J. Am. Soc. Nephro., vol. 18, pp. 3110-3118, (2007).

"Protective Groups in Organic Synthesis," T.W. Greene, P.G.M. Wuts, Wiley-Interscience, 1999.

Rancoule et al., "Lysophosphatidic acid-1-receptor targeting agents for fibrosis," Expert. Opin. Inv. Drug, vol. 20, No. 85, pp. 657-667, (2011).

Remington, The Science and Practice of Pharmacy, 21st Edition (2005), Part 5, "Pharmaceutical Manufacturing" [published by Lippincott Williams & Wilkins].

Rockey et al., "Fibrosis—A Common Pathway to Organ Injury and Failure," New Engl. J. Med., vol. 372, pp. 1138-1149, (2015).

Simon et al., "Lysophosphatidic Acid Inhibits Adipocyte Differentiation via Lysophosphatidic Acid 1 Receptor-dependent Down-regulation of Peroxisome Proliferator-activated Receptor $_γ2^*$," J. Biol. Chem., vol. 280, pp. 14656-14662, (2005).

Sperry et al., "A Safe and Practical Procedure for the Difluoromethylation of Methyl 4-Hydroxy-3-iodobenzoate," Org. Process Res. Dev., vol. 15, pp. 721-725, (2011).

(56) References Cited

OTHER PUBLICATIONS

Stepan et al., "Application of the Bicyclo[1.1.1]pentane Motif as a Nonclassical Phenyl Ring Bioisostere in the Design of a Potent and Orally Active $_\gamma$-Secretase Inhibitor," J. Med. Chem., vol. 55, No. 7, pp. 3414-3424, (2012).

Stoddard et al., "Promising Pharmacological Directions in the World of Lysophosphatidic Acid Signaling," Biomol. Ther., vol. 23, No. 1, pp. 1-11, (2015).

Tager et al., "The lysophosphatidic acid receptor $LPA_1$ links pulmonary fibrosis to lung injury by mediating fibroblast recruitment and vascular leak," Nature Med., vol. 14, pp. 45-54, (2008).

Thomoson et al., "Use of fluoroform as a source of difluorocarbene in the synthesis of N-$CF_2$H heterocycles and difluoromethoxypyridines," J. Fluorine. Chem., vol. 168, pp. 34-39, (2014).

Valeur et al., "Amide bond formation: beyond the myth of coupling reagents," Chem. Soc. Rev., vol. 389, pp. 606-631, (2009).

Van Leeuwen, "Lysophosphatidic acid: mitogen and motility factor," Biochem. Soc. Trans., vol. 31, pp. 1209-1212, (2003).

Watanabe et al., "Both Plasma Lysophosphatidic Acid and Serum Autotaxin Levels are Increased in Chronic Hepatitis C," J. Clin. Gastroenterol., vol. 41, No. 6, pp. 616-623, (2007).

Watanabe et al., "Plasma lysophosphatidic acid level and serum autotaxin activity are increased in liver injury in rats in relation to its severity," Life Sciences, vol. 81, pp. 1009-1015, (2007).

Yamada et al., "Lysophosphatidic acid stimulates the proliferation and motility of malignant pleural mesothelioma cells through lysophosphatidic acid receptors, $LPA_1$ and $LPA_2$," Cancer Sci., vol. 99, No. 8, pp. 1603-1610, (2008).

Yang et al., "The Role of Lysophosphatidic Acid Receptor ($LPA_1$) in the Oxygen-Induced Retinal Ganglion Cell Degeneration," IOVS, vol. 50, No. 3, pp. 1290-1298, (2009).

Zeng et al., "Gene expression Profiles of Lysophosphatidic Acid-Related Molecules in the Prostate: Relevance to Prostate Cancer and Benign Hyperplasia," The Prostate, vol. 69, pp. 283-292, (2009).

Zhao et al., "Lysophosphatidic acid (LPA) and its receptors: Role in airway inflammation and remodeling," Biochim. Biophys. Acta (BBA)-Mol. Cell Biol. Of Lipids, vol. 1831, pp. 86-92, (2013).

Allanore, Y. et al., "Lysophosphatidic Acid Receptor 1 Antagonist SAR100842 for Patients With Diffuse Cutaneous Systemic Sclerosis," Arthritis & Rheumatology, 2018, 70 (10), 1634-1643.

Bristol Myers Squibb, "Bristol Myers Squibb's Investigational LPA1 Antagonist Reduces Rate of Lung Function Decline in Progressive Pulmonary Fibrosis Cohort of Phase 2 Study," dated Sep. 9, 2023, 3 pages, retrieved on Apr. 19, 2024, from: https://news.bms.com/news/details/2023/Bristol-Myers-Squibbs-Investigational-LPA1-Antagonist-Reduces-Rate-of-Lung-Function-Decline-in-Progressive-Pulmonary-Fibrosis-Cohort-of-Phase-2-Study/default.aspx.

ClinicalTrials.gov, "Proof of Biological Activity of SAR100842 in Systemic Sclerosis," ClinicalTrials.gov ID: NCT01651143, Document states last update posted: Mar. 25, 2016, 9 pages, retrieved on Apr. 19, 2024, from: https://clinicaltrials.gov/study/NCT01651143?intr=SAR100842&rank=1.

ClinicalTrials.gov, "A Multicenter Trial to Evaluate the Efficacy, Safety, Tolerability and Pharmacokinetics of HZN-825 in Patients With Diffuse Cutaneous Systemic Sclerosis," ClinicalTrials.gov ID: NCT04781543, Document states last update posted: Apr. 3, 2024, 12 pages, retrieved on Apr. 19, 2024, from: https://clinicaltrials.gov/study/NCT04781543?intr=HZN-825&rank=2.

ClinicalTrials.gov, "An Open-label Extension Trial of HZNP-HZN-825-301 in Adult Participants With Diffuse Cutaneous Systemic Sclerosis (Diffuse Cutaneous SSc)," ClinicalTrials.gov ID: NCT05626751, Document states last update posted: Mar. 27, 2024, 9 pages, retrieved on Apr. 19, 2024, from: https://clinicaltrials.gov/study/NCT05626751?intr=HZN-825&rank=1.

Corte, T. et al., "Phase 2 trial design of BMS-986278, a lysophosphatidic acid receptor 1 ($LPA_1$) antagonist, in patients with idiopathic pulmonary fibrosis (IPF) or progressive fibrotic interstitial lung disease (PF-ILD)," BMJ Open Respiratory Research, 2021, 8:e001026, doi: 10.1136/bmjresp-2021-001026, 9 pages.

Ledein, L. et al., "Translational engagement of lysophosphatidic acid receptor 1 in skin fibrosis: from dermal fibroblasts of patients with scleroderma to tight skin 1 mouse," British Journal of Pharmacology, 2020, 177, 4296-4309.

U.S. Appl. No. 17/620,520, Preliminary Amendment filed Dec. 17, 2021, 25 pages.

U.S. Appl. No. 17/782,530, Preliminary Amendment filed Jun. 3, 2022, 11 pages.

\* cited by examiner

ALKOXY-SUBSTITUTED PYRIDINYL DERIVATIVES AS LPA1 RECEPTOR ANTAGONISTS AND THEIR USE IN THE TREATMENT OF FIBROSIS

CROSS-REFERENCE TO RELATED APPLICATIONS

This application is a U.S. National Stage application under 35 U.S.C. § 371 of International Application No. PCT/EP2019/064690, filed on Jun. 5, 2019, which claims priority to and the benefit of PCT Application No. PCT/EP2018/065016, filed on Jun. 7, 2018, the contents of each of which are hereby incorporated by reference in their entireties.

The present invention relates to $LPA_1$ receptor antagonists of Formula (I) and their use as active ingredients in the preparation of pharmaceutical compositions. The invention also concerns related aspects including processes for the preparation of the compounds, pharmaceutical compositions containing a compound of the Formula (I), and their use as medicaments inhibiting fibrotic processes or other disorders in which $LPA_1$ receptors play a role, either alone or in combination with other active compounds or therapies.

Lysophospholipids are membrane-derived bioactive lipid mediators, of which one of the most medically important is lysophosphatidic acid (LPA). LPA is not a single molecular entity but a collection of endogenous structural variants with fatty acids of varied lengths and degrees of saturation (Fujiwara et al., J. Biol. Chem. 2005, 280, 35038-35050). The structural backbone of the LPAs is derived from glycerol-based phospholipids such as phosphatidylcholine (PC) or phosphatidic acid (PA). The LPAs are bioactive lipids (signaling lipids) that regulate various cellular signaling pathways by binding to the same class of 7-transmembrane domain G protein-coupled (GPCR) receptors (Chun, J., Hla, T., Spiegel, S., Moolenaar, W., Editors, Lysophospholipid Receptors: Signaling and Biochemistry, 2013, Wiley; ISBN: 978-0-470-56905-4; Zhao, Y. et al, Biochim. Biophys. Acta (BBA)-Mol. Cell Biol. Of Lipids, 2013, 1831, 86-92). The currently known LPA receptors are designated as $LPA_1$, $LPA_2$, $LPA_3$, $LPA_4$, $LPA_5$ and $LPA_6$ (Choi, J. W., Annu. Rev. Pharmacol. Toxicol. 2010, 50, 157-186). The nucleotide sequence and the amino acid sequence for the human $LPA_1$ receptor is known in the art and are published (Hecht et al 1996 J. Cell. Biol. 135:1071-83, An et al 1997 Biochem. Biophys. Res. Comm. 231:619-622).

The LPAs have long been known as precursors of phospholipid biosynthesis in both eukaryotic and prokaryotic cells, but the LPAs have emerged only recently as signaling molecules that are rapidly produced and released by activated cells, notably platelets, to influence target cells by acting on specific cell-surface receptors (see, e.g., Moolenaar et al., BioEssays, 2004, 26, 870-881, and van Leewen et al, Biochem. Soc. Trans., 2003, 31, 1209-1212). Besides being synthesized and processed to more complex phospholipids in the endoplasmic reticulum, LPAs can be generated through the hydrolysis of pre-existing phospholipids following cell activation; for example, the sn-2 position is commonly missing a fatty acid residue due to deacylation, leaving only the sn-1 hydroxyl esterified to a fatty acid. Moreover, a key enzyme in the production of LPA, autotaxin (lysoPLD/NPP2), may be the product of an oncogene, as many tumor types up-regulate autotaxin (Brindley, D., J. Cell Biochem. 2004, 92, 900-12). The concentrations of LPAs in human plasma & serum as well as human bronchoalveolar lavage fluid (BALF) have been reported, including determinations made using sensitive and specific LC/MS & LC/MS/MS procedures (Baker et al., Anal. Biochem. 2001, 292, 287-295; Onorato et al., J. Lipid Res., 2014, 55, 1784-1796).

LPA influences a wide range of biological responses, ranging from induction of cell proliferation, stimulation of cell migration and neurite retraction, gap junction closure, and even slime mold chemotaxis (Goetzl, et al, Scientific World J., 2002, 2, 324-338; Chun, J., Hla, T., Spiegel, S., Moolenaar, W., Editors, Lysophospholipid Receptors: Signaling and Biochemistry, 2013, Wiley; ISBN: 978-0-470-56905-4). The body of knowledge about the biology of LPA continues to grow as more and more cellular systems are tested for LPA responsiveness. For instance, it is now known that, in addition to stimulating cell growth and proliferation, LPAs promote cellular tension and cell-surface fibronectin binding, which are important events in wound repair and regeneration (Moolenaar et al., BioEssays, 2004, 26, 870-881). Recently, anti-apoptotic activity has also been ascribed to LPA, and it has recently been reported that PPARγ is a receptor/target for LPA (Simon et al., J. Biol. Chem., 2005, 280, 14656-14662).

Fibrosis is the result of an uncontrolled tissue healing process leading to excessive accumulation and insufficient resorption of extracellular matrix (ECM) which ultimately results in end-organ failure (Rockey et al., New Engl. J. Med., 2015, 372, 1138-1149). Recently it was reported that the $LPA_1$ receptor was over-expressed in idiopathic pulmonary fibrosis (IPF) patients. $LPA_1$ receptor knockout mice were also protected from bleomycin-induced lung fibrosis (Tager et al., Nature Med., 2008, 14, 45-54). Thus, antagonizing the $LPA_1$ receptor may be useful for the treatment of fibrosis (Stoddard et al., Biomol. Ther., 2015, 23 (1), 1-11; Rancoule et al., Expert. Opin. Inv. Drug 2011, 20 (85), 657-667; Yang et al., IOVS 2009, 50 (3) 1290-1298; Pradère et al., J. Am. Soc. Nephro. 2007, 18, 3110-3118; Abu El-Asrar et al., Acta Ophthalmol. 2012, 90, e84-e89) such as pulmonary fibrosis, hepatic fibrosis, renal fibrosis, arterial fibrosis and systemic sclerosis, and thus the diseases that result from fibrosis (pulmonary fibrosis-Idiopathic Pulmonary Fibrosis [IPF], hepatic fibrosis-Non-alcoholic Steatohepatitis [NASH], renal fibrosis-diabetic nephropathy, systemic sclerosis-scleroderma (Castellino et al., Arthritis Rheum. 2011, 63 (5), 1405-1415).

Corticosteroids in combination with immunosuppressant drugs, cytostatic drugs and antioxidants are used in the treatment of IPF. Corticosteroids may cause side effects when used in long term treatment. Pirefinidone is approved for treatment of IPF but the therapeutic mechanism of action is not known and also, side effects are associated with the use of pirfenidone. Therefore, orally active compounds which specifically target the fibrotic processes with reduced side effects would significantly improve current treatments of uncontrolled fibrotic diseases.

The use of $LPA_1$ receptor antagonists is not limited to fibrosis, and can apply to other disorders where $LPA/LPA_1$ receptor axis plays a role in the pathology; such as pain including acute pain, chronic pain, and neuropathic pain (Inoue et al, Nat. Med. 2004, 10 (7) 712-718; Kuner, Nat. Med. 2010, 16 (11), 1258-1266) including fibromyalgia stemming from the formation of fibrous scar tissue in contractile (voluntary) muscles, wherein fibrosis binds the tissue and inhibits blood flow, resulting in pain, and cancer pain; malignant and benign proliferative diseases including cancer (Stoddard et al., Biomol. Ther., 2015, 23 (1), 1-11; Komachi et al., Cancer Sci. 2012, 103 (6), 1099-1104; Zeng et al., The Prostate 2009, 69, 283-292), and the control of proliferation of tumor cells, invasion and metastasis of carcinomas, pleural mesothelioma (Yamada, Cancer Sci., 2008, 99 (8), 1603-1610), peritoneal mesothelioma, or bone metastases (Boucharaba et al, J. Clin. Invest., 2004, 1 14(12), 1714-1725; Boucharaba et al, Proc. Natl. acad. Sci., 2006, 103(25) 9643-9648); inflammation (Li et al., Kidney International 2017, 91(6), 1362-1373; Lin et al., Am. J. Pathol. 2018, 188 (2), 353-366; Watanabe et al., J. Clin. Gastroenterol. 2007, 41 (6), 616-623; Watanabe et al., Life Sciences 2007, 81, 1009-1015); nervous system disorders (Stoddard et al., Biomol. Ther., 2015, 23 (1), 1-11; Choi et al., Biochim. Biophys. Acta 2013, 1831, 20-32; Nagai et al., Molecular Pain 2010, 6, 78); and respiratory diseases including allergic respiratory diseases, and hypoxia (Georas et al., Clin. Exp. Allergy 2007, 37 (3), 311-322). LPA has been shown to have contracting action on bladder smooth muscle cell isolated from bladder, and promotes growth of prostate-derived epithelial cell (J. Urology, 1999, 162, 1779-1784; J. Urology, 2000, 163, 1027-1032). LPA further has been shown to contract the urinary tract and prostate in vitro and increases intraurethral pressure in vivo (WO 02/062389). LPA has further been linked to obesity and insulin resistance (K. D'Souza et al., Nutrients 2018, 10, 399).

WO2013/096771 discloses a broad generic scope of TGR5 agonists, claimed to be active in the treatment of diabetes. US2007/0078120 (WO2005/037269) discloses a broad generic scope of piperidine derivatives claimed to be useful to lower the blood concentration of LDL cholesterol. WO2003/088908 discloses a broad generic scope of potassium channel inhibitors exemplifying some piperidine derivatives which, however, are different form the present compounds by at least the absence of present mandatory substituent $R^4$. WO2012/078805 and WO2009/135590 disclose structurally remote compounds that act as antagonists of the $LPA_1$ receptor and are claimed to show certain anti-fibrotic effects.

The present invention provides novel compounds of Formula (I) that are antagonists for the G protein-coupled receptor $LPA_1$ and may have a potent and long-lasting anti-fibrotic effect which may be mediated by inhibiting vascular leakage, inhibiting the conversion of fibroblasts to myofibroblasts, and/or inhibiting the subsequent release of pro-fibrotic cytokines by myofibroblasts. The present compounds may thus be useful to treat e.g. uncontrolled fibrotic diseases and other diseases and disorders related to $LPA_1$ signalling.

1) A first aspect of the invention relates to compounds of the Formula (I),

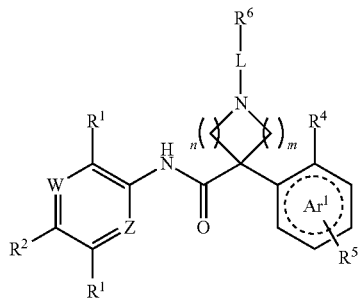

Formula (I)

wherein
  W represents N, and Z represents CH; or
  Z represents N, and W represents CH;

$R^1$ is hydrogen or fluoro;
$R^2$ is hydrogen, halogen (especially chloro), methyl, ethyl, methoxy or ethoxy;
$R^3$ is $C_{1-3}$-alkoxy (especially methoxy, isopropoxy) or $C_{1-3}$-fluoroalkoxy (especially difluoromethoxy);
$Ar^1$ represents phenyl, or 6-membered heteroaryl containing one or two nitrogen atoms (especially pyridinyl); (notably, $Ar^1$ represents phenyl), wherein said group $Ar^1$ is substituted with $R^4$ and $R^5$, wherein
  $R^4$ is n-propyl, isopropyl, $C_{3-6}$-cycloalkyl optionally containing a ring oxygen atom (especially cyclopropyl, cyclobutyl, cyclopentyl, cyclohexyl, tetrahydro-2H-pyran-4-yl), or cyclopent-1-en-1-yl; [wherein it is understood that said substituent $R^4$ is attached in ortho-position with regard to the point of the attachment of the rest of the molecule] and
  $R^5$ represents one substituent independently selected from hydrogen, fluoro, methyl or methoxy [in a sub-embodiment, in case $Ar^1$ represents phenyl, $R^5$ especially represents hydrogen; fluoro in position 5 or 6; methyl in position 4, 5 or 6; or methoxy in position 5 of said phenyl group; in particular, in such case, $R^5$ represents one substituent independently selected from hydrogen, fluoro, methyl and methoxy in position 5 of said phenyl group];
m and n independently represent the integer 1 or 2; and
the group -L—$R^6$ represents
  hydrogen;
  -$C_{1-4}$-alkyl;
  -$C_{0-6}$-alkylene-$C_{3-6}$-cycloalkyl; wherein the $C_{3-6}$-cycloalkyl independently is unsubstituted or mono-substituted with halogen (especially fluoro);
  —CO—H;
  -$L^1$—CO—$R^{C11}$ wherein $R^{C11}$ independently represents hydroxy; —O-benzyl; —O-$C_{1-6}$-alkyl; $C_1$-fluoroalkyl; or —$NR^{N11}R^{N12}$; wherein independently $R^{N11}$ is hydrogen or $C_{1-4}$-alkyl, and $R^{N12}$ is hydrogen, $C_{1-4}$-alkyl, —$SO_2$-$C_{1-6}$-alkyl, or —O—$R^{C11}$, wherein $R^{C11}$ independently represents hydrogen, $C_{1-6}$-alkyl, or benzyl; and
  -$L^1$- independently represents
    -$C_{1-6}$-alkylene-, —CO-$C_{1-6}$-alkylene-, —SO2-$C_{1-6}$-alkylene-, —CO—O-$C_{1-6}$-alkylene-, —CO—NH-$C_{1-6}$-alkylene-, or —$SO_2$—NH-$C_{1-6}$-alkylene-;
    -$C_{1-6}$-alkylene-, —CO-$C_{1-6}$-alkylene-, or —SO2-$C_{1-6}$-alkylene-; wherein in the above groups said $C_{1-6}$-alkylene independently is mono-substituted with hydroxy, $C_{1-3}$-alkoxy, —O—CO-$C_{1-4}$-alkyl, or —$NR^{N13}R^{N14}$; wherein independently $R^{N13}$ is hydrogen or $C_{1-4}$-alkyl, and $R^{N14}$ is hydrogen, $C_{1-4}$-alkyl or —CO—O-$C_{1-4}$-alkyl;
    -$C_{2-6}$-alkylene-, —CO-$C_{2-6}$-alkylene-, or —$SO_2$-$C_{2-6}$-alkylene-; wherein in the above groups said $C_{2-6}$-alkylene independently is di-substituted wherein the substituents are independently selected from hydroxy and —$NR^{N15}R^{N16}$; wherein independently $R^{N15}$ is hydrogen or $C_{1-4}$-alkyl, and $R^{N16}$ is hydrogen, $C_{1-4}$-alkyl or —CO-O-$C_{1-4}$-alkyl;
    -$C_{0-4}$-alkylene-$C_{3-8}$-cycloalkylene-$C_{0-4}$-alkylene-, —CO-$C_{0-4}$-alkylene-$C_{3-8}$-cycloalkylene-$C_{0-4}$-alkylene-, —$SO_2$-$C_{0-4}$-alkylene-$C_{3-8}$-cycloalkylene-$C_{0-4}$-alkylene-, —CO—NH-$C_{0-4}$alkylene-$C_{3-8}$-cycloalkylene-$C_{0-4}$-alkylene-, or —CO—O-$C_{0-4}$-alkylene-$C_{3-8}$-cycloalkylene-$C_{0-4}$-alkylene-;
    -$C_{0-4}$-alkylene-$Cy^1$-$C_{0-4}$-alkylene-, —CO-$C_{0-4}$-alkylene-$Cy^1$-$C_{0-4}$-alkylene-, —CO—O-$C_{0-4}$-alkylene-Cy$^1$-C$_{0-4}$-alkylene-, —CO—NH-C$_{0-4}$-alkylene-Cy$^1$-C$_{0-4}$-alkylene-, —SO$_2$-C$_{0-4}$-alkylene-Cy$^1$-C$_{0-4}$-alkylene-, or —SO$_2$—NH-C$_{0-4}$-alkylene-Cy$^1$-C$_{0-4}$-alkylene-; wherein Cy$^1$ independently represents a C$_{3-6}$-heterocycloalkylene containing one ring oxygen atom, or one ring nitrogen atom, wherein said ring nitrogen, in case it has a free valency, independently is unsubstituted, or mono-substituted with C$_{1-4}$-alkyl or —CO—O-C$_{1-4}$-alkyl;

-C$_{2-4}$-alkylene-O-C$_{2-4}$-alkylene-O-C$_{1-4}$-alkylene-, or —CO-C$_{1-4}$-alkylene-O-C$_{2-4}$-alkylene-O-C$_{1-4}$-alkylene-;

-C$_{2-4}$-alkylene-X$^{11}$-C$_{1-4}$-alkylene-, —CO—O-C$_{2-4}$-alkylene-X$^{11}$-C$_{1-4}$-alkylene-, —CO—NH-C$_{2-4}$-alkylene-X$^{11}$-C$_{1-4}$-alkylene-, or —SO$_2$—NH-C$_{2-4}$-alkylene-X$^{11}$-C$_{1-4}$-alkylene-; wherein X$^{11}$ independently represents oxygen, or a nitrogen atom which is independently unsubstituted, or mono-substituted with C$_{1-4}$-alkyl, C$_{3-6}$-cycloalkyl, or —CO—O-C$_{1-4}$-alkyl;

—CO-C$_{1-4}$-alkylene-X$^{12}$-C$_{1-4}$-alkylene-, —SO$_2$-C$_{1-4}$-alkylene-X$^{12}$-C$_{1-4}$-alkylene-, or —CO-C$_{1-4}$-alkylene-X$^{12}$-C$_{0-4}$-alkylene-C$_{3-6}$-cycloalkylene-C$_{0-4}$-alkylene-; wherein X$^{12}$ independently represents oxygen, or a nitrogen atom which is independently unsubstituted, or mono-substituted with C$_{1-4}$-alkyl, C$_{3-6}$-cycloalkyl, —CO—O-C$_{1-4}$-alkyl, or C$_{1-3}$-alkoxy-C$_{2-4}$-alkyl;

-C$_{2-4}$-alkylene-X$^{13}$-C$_{1-4}$-alkylene-; wherein X$^{13}$ represents —NH—CO—, and wherein said C$_{2-4}$-alkylene independently is unsubstituted, or mono-substituted with hydroxy;

-C$_{1-4}$-alkylene-X$^{14}$-C$_{1-4}$-alkylene-; wherein X$^{14}$ represents —CO—NH—;

—CO-C$_{2-6}$-alkenylene- or —SO$_2$-C$_{2-6}$-alkenylene-; or

—CO-C$_{2-6}$-fluoroalkylene-;

-L$^2$-hydroxy; wherein -L$^2$- represents

—CO-C$_{1-6}$-alkylene- or —SO$_2$-C$_{1-6}$-alkylene-; wherein in the above groups said C$_{1-6}$-alkylene independently is unsubstituted, or mono-substituted with hydroxy, C$_1$-fluoroalkyl, or —NR$^{N21}$R$^{N22}$ wherein independently R$^{N21}$ is hydrogen or C$_{1-4}$-alkyl, and R$^{N22}$ is hydrogen, C$_{1-4}$-alkyl or —CO—O-C$_{1-4}$-alkyl;

-C$_{2-6}$-alkylene-, —CO—O-C$_{2-6}$-alkylene-, —CO—NH-C$_{2-6}$-alkylene-, or —SO$_2$—NH-C$_{2-6}$-alkylene-, wherein in the above groups said C$_{2-6}$-alkylene independently is unsubstituted, or mono-substituted with hydroxy, C$_1$-fluoroalkyl, or —NR$^{N23}$R$^{N24}$ wherein independently R$^{N23}$ is hydrogen or C$_{1-4}$-alkyl, and R$^{N24}$ is hydrogen, C$_{1-4}$-alkyl or —CO—O-C$_{1-4}$-alkyl;

C$_{0-4}$-alkylene-C$_{3-6}$-cycloalkylene-C$_{0-4}$-alkylene-, —CO-C$_{0-4}$-alkylene-C$_{3-6}$-cycloalkylene-C$_{0-4}$-alkylene-, or —SO$_2$-C$_{0-4}$-alkylene-C$_{3-6}$-cycloalkylene-C$_{0-4}$-alkylene-;

-C$_{0-4}$-alkylene-Cy$^2$-C$_{0-4}$-alkylene-, —CO-C$_{0-4}$-alkylene-Cy$^2$-C$_{0-4}$-alkylene-, or —SO$_2$-C$_{0-4}$-alkylene-Cy$^2$-C$_{0-4}$-alkylene-; wherein Cy$^2$ independently represents a C$_{3-6}$-heterocycloalkylene group containing one ring oxygen atom, or one ring nitrogen atom; wherein said ring nitrogen, in case it has a free valency, is independently unsubstituted, or mono-substituted with C$_{1-4}$-alkyl or —CO—O-C$_{1-4}$-alkyl;

-C$_{2-4}$-alkylene-(O-C$_{2-4}$-alkylene)$_p$- or —CO-C$_{1-4}$-alkylene-(O-C$_{2-4}$-alkylene)$_p$-; wherein p independently represents the integer 1 or 2;

-C$_{2-4}$-alkylene-X$^{21}$-C$_{2-4}$-alkylene-; wherein X$^{21}$ represents a nitrogen atom which is unsubstituted, or mono-substituted with C$_{1-4}$-alkyl, C$_{3-6}$-cycloalkyl, or —CO—O-C$_{1-4}$-alkyl;

—CO-C$_{1-4}$-alkylene-X$^{22}$-C$_{2-4}$-alkylene-, —CO-C$_{1-4}$-alkylene-X$^{22}$-C$_{1-4}$-alkylene-C$_{3-6}$-cycloalkylene-, or —SO$_2$-C$_{1-4}$-alkylene-X$^{22}$-C$_{2-4}$-alkylene-; wherein X$^{22}$ represents a nitrogen atom which is independently unsubstituted, or mono-substituted with C$_{1-4}$-alkyl, C$_{3-6}$-cycloalkyl, or —CO—O-C$_{1-4}$-alkyl;

-C$_{2-4}$-alkylene-X$^{23}$-C$_{1-4}$-alkylene-; wherein X$^{23}$ represents —NH—CO—, and wherein said C$_{2-4}$-alkylene independently is unsubstituted, or mono-substituted with hydroxy;

-C$_{1-4}$-alkylene-X$^{24}$-C$_{2-4}$-alkylene-; wherein X$^{24}$ represents —CO—NH—, and wherein said C$_{2-4}$-alkylene independently is unsubstituted, or mono-substituted with hydroxy; or 3,4-dioxocyclobut-1-ene-1,2-diyl;

-L$^3$—O—R$^{O31}$ wherein R$^{O31}$ is -C$_{1-4}$-alkyl, —CO-C$_{1-4}$-alkyl or —CO-C$_{2-4}$-alkenyl; and -L$^3$- independently represents -C$_{2-6}$-alkylene-, —CO-C$_{1-6}$-alkylene- or —SO$_2$-C$_{1-6}$-alkylene-, —CO—O-C$_{2-6}$-alkylene-, —CO—NH-C$_{2-6}$-alkylene-, or —SO$_2$—NH-C$_{2-6}$-alkylene-;

-L$^4$—NR$^{N1}$R$^{N2}$ wherein independently R$^{N1}$ is hydrogen or C$_{1-4}$-alkyl; and R$^{N2}$ is hydrogen; C$_{1-4}$-alkyl; C$_{1-3}$-fluoroalkyl; C$_{3-6}$-cycloalkyl; C$_{1-3}$-alkoxy-C$_{2-4}$-alkylene; —CO-C$_{1-4}$-alkyl; —SO$_2$-C$_{1-4}$-alkyl; or —SO$_2$-C$_1$-fluoroalkyl; and -L4- independently represents -C$_{2-6}$-alkylene-, —CO-C$_{1-6}$-alkylene-, —SO$_2$-C$_{1-6}$-alkylene-, —CO—O-C$_{2-6}$-alkylene-, —CO—NH-C$_{2-6}$-alkylene-, or —SO$_2$—NH-C$_{2-6}$-alkylene-; or -C$_{0-4}$-alkylene-Cy$^4$-C$_{0-4}$-alkylene-, —CO-C$_{0-4}$-alkylene-Cy$^4$-C$_{0-4}$-alkylene-, or —SO$_2$-C$_{0-4}$-alkylene-Cy$^4$-C$_{0-4}$-alkylene-; wherein Cy$^4$ independently represents a C$_{3-6}$-heterocycloalkylene group containing one ring oxygen atom;

-L$^5$—NR$^{N3}$R$^{N4}$ wherein R$^{N3}$ is hydrogen, C$_{1-4}$-alkyl, or C$_{1-3}$-alkoxy-C$_{2-4}$-alkylene; and R$^{N4}$ is —CO—O-C$_{1-4}$-alkyl; —CO—NR$^{N51}$R$^{N52}$ wherein R$^{N51}$ and R$^{N52}$ are independently selected from hydrogen and C$_{1-4}$-alkyl; or —SO$_2$—NR$^{N53}$R$^{N54}$ wherein independently R$^{N53}$ is hydrogen or C$_{1-4}$-alkyl, and R$^{N54}$ is hydrogen, C$_{1-4}$-alkyl, or —CO-C$_{1-4}$-alkyl;

and-L$^5$- independently represents

-C$_{2-6}$-alkylene-, —CO-C$_{1-6}$-alkylene- or —SO$_2$-C$_{1-6}$-alkylene-, —CO—O-C$_{2-6}$-alkylene-, —CO—NH-C$_{2-6}$-alkylene-, or —SO$_2$—NH-C$_{2-6}$-alkylene-;

-L$^6$—N(R$^{N61}$)—O—R$^{O61}$ wherein R$^{N61}$ is hydrogen, —CO-C$_{1-4}$-alkyl, or —CO—O-C$_{1-4}$-alkyl; and R$^{O61}$ independently represents hydrogen, C$_{1-6}$-alkyl, or benzyl;

and -L$^6$- independently represents

-C$_{2-6}$-alkylene-, —CO-C$_{1-6}$-alkylene-, —SO$_2$-C$_{1-6}$-alkylene-, —CO—O-C$_{2-6}$-alkylene-, —CO—NH-C$_{2-6}$-alkylene-, or —SO$_2$—NH-C$_{2-6}$-alkylene-;

-L$^7$—NR$^{N5}$R$^{N6}$ wherein R$^{N5}$ is hydrogen or C$_{1-4}$-alkyl (especially hydrogen); R$^{N6}$ is hydrogen, C$_{1-4}$-alkyl, —CO-$C_{1-4}$-alkyl, $C_{1-3}$-fluoroalkyl, or $C_{3-6}$-cycloalkyl (especially hydrogen); and
-$L^7$- independently represents
  —CO—, or —$SO_2$—;
-$L^8$—$SO_2$—$R^{S81}$ wherein $R^{S81}$ independently represents -$C_{1-6}$-alkyl; $C_1$-fluoroalkyl; hydroxy; —$NR^{N81}R^{N82}$ wherein independently $R^{N81}$ is hydrogen or $C_{1-4}$-alkyl, and $R^{N82}$ is hydrogen, $C_{1-4}$-alkyl, —CO-$C_{1-6}$-alkyl; and
L8- independently represents
  -$C_{1-6}$-alkylene-, —CO-$C_{1-6}$-alkylene-, —$SO_2$-$C_{1-6}$-alkylene-, —CO—O-$C_{2-6}$-alkylene-, —CO—NH-$C_{1-6}$-alkylene-, or —$SO_2$—NH-$C_{1-6}$-alkylene-;
-$L^9$-$HET^1$, wherein $HET^1$ represents 5- or 6-membered heteroaryl (especially pyrrolyl, pyrazolyl, imidazolyl, triazolyl, tetrazolyl, furanyl, oxazolyl, isoxazolyl, thiazolyl, isothiazolyl, oxadiazolyl, thiadiazolyl, pyridinyl, pyrimidinyl, pyridazinyl, pyrazinyl), wherein said $HET^1$ independently is unsubstituted or mono-, or di-substituted wherein the substituents are independently selected from $C_{1-4}$-alkyl (especially methyl); halogen; cyano; hydroxy; hydroxymethyl; -$C_{0-2}$-alkylene-$Cy^{91}$-$COOR^{O91}$ wherein $R^{O91}$ is hydrogen or $C_{1-4}$-alkyl, and wherein $Cy^{91}$ represents a $C_{3-6}$-cycloalkylene group; or -$C_{0-4}$-alkylene-CO-$OR^{O92}$ wherein $R^{O92}$ is hydrogen or $C_{1-4}$-alkyl; and
-$L^9$- independently represents
  -$C_{0-6}$-alkylene-, —CO-$C_{0-6}$-alkylene-, —$SO_2$-$C_{0-6}$-alkylene-, —CO—O-$C_{1-6}$-alkylene-, —CO—NH-$C_{1-6}$-alkylene-, or —$SO_2$—NH-$C_{1-6}$-alkylene-;
-$L^{10}$-$C_{4-6}$-heterocyclyl, wherein the $C_{4-6}$-heterocyclyl independently contains one or two ring heteroatoms independently selected from nitrogen, sulfur and oxygen; wherein in the above groups said $C_{4-6}$-heterocyclyl independently is unsubstituted, or mono-, di-, or tri-substituted wherein the substituents are independently selected from:
  one or two oxo substituents each attached to a ring carbon atom in alpha position to a ring nitrogen atom (thus forming together with the nitrogen an amide group, or, in case a ring oxygen is additionally adjacent, a carbamate group, or, in case second ring nitrogen is additionally adjacent, a urea group); and/or
  two methyl substituents attached to a ring carbon atom in alpha position to a ring nitrogen atom or a ring oxygen atom (thus forming together with the nitrogen a —$C(CH_3)_2$—N— or with the oxygen a —$C(CH_3)_2$—O— group); and/or
  two oxo substituents at a ring sulfur ring atom (thus forming a —$SO_2$— group); and/or
  $C_{1-4}$-alkyl, $C_{1-3}$-alkoxy-$C_{2-4}$-alkyl, $C_{2-3}$-fluoroalkyl, or —CO-$C_{1-4}$-alkyl attached to a ring nitrogen atom having a free valency; and
-$L^{10}$- independently represents
  -$C_{0-6}$-alkylene-, —CO-$C_{0-6}$-alkylene-, —$SO_2$-$C_{0-6}$-alkylene-, —CO—O-$C_{1-6}$-alkylene-, —CO—NH-$C_{1-6}$-alkylene-, or —$SO_2$—NH-$C_{1-6}$-alkylene-;
-$L^{11}$-cyano; wherein -$L^{11}$- represents —CO-$C_{1-6}$-alkylene-, —SO2-$C_{1-6}$-alkylene, or -$C_{0-6}$-alkylene-;
-$L^{12}$—$NO_2$; wherein -$L^{12}$- represents -$C_{2-6}$-alkylene-; or
-$L^{13}$-$C_{1-4}$-alkyl; wherein -$L^{13}$- represents —CO—, —CO—O—, or —$SO_2$—.

In a sub-embodiment, the present invention especially relates to compounds of Formula (I) as defined in embodiment 1), wherein the linker L in the group -L—$R^6$ is as defined hereinbefore (or, mutatis mutandis, in any one of embodiments below) wherein the length of such linker L (i.e. each of the particular linker groups-$L^1$-, -$L^2$-, -$L^3$, -$L^4$-, -$L^5$-, -$L^6$-, -$L^7$-, -$L^8$-, -$L^9$-, -$L^{10}$-, -$L^{11}$-, -$L^{12}$-, and -$L^{13}$-) is such that the group $R^6$ is distanced from the nitrogen atom to which L is attached by at maximum 9 atoms (preferably it is distanced by at maximum 5 atoms).

It is understood that the linker groups in group -L—$R^6$ (such as -$L^1$-, -$L^2$-, -$L^3$-, -$L^4$-, -$L^5$-, -$L^6$-, -$L^7$-, -$L^8$-, -$L^9$-, -$L^{10}$-, -$L^{11}$, -L12, and -$L^{13}$-) are to be read from left to right: for example a linker group —CO-$C_{0-6}$-alkylene- is attached to the rest of the molecule on the-CO-group part of said linker.

The compounds of formulae (I), (II) and (III) may contain one or more stereogenic or asymmetric centers, such as one or more asymmetric carbon atoms, which are allowed to be present in (R)- as well as (S)-configuration. The compounds of formulae (I), (II) and (III) may further encompass compounds with one or more double bonds which are allowed to be present in Z- as well as E-configuration and/or compounds with substituents at a ring system which are allowed to be present, relative to each other, in cis- as well as trans-configuration. The compounds of formulae (I), (II) and (III) may thus be present as mixtures of stereoisomers or preferably as pure stereoisomers. Mixtures of stereoisomers may be separated in a manner known to a person skilled in the art.

In case a particular compound (or generic structure) is designated as (R)- or (S)-enantiomer, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center. In analogy, cis- or trans-designations are to be understood as referring to the respective stereoisomer of the respective relative configuration in enriched, especially essentially pure, form. Likewise, in case a particular compound (or generic structure) is designated as Z- or E-stereoisomer (or in case a specific double bond in a compound is designated as being in Z- or E-configuration), such designation is to be understood as referring to the respective compound (or generic structure) in enriched, especially essentially pure, stereoisomeric form (or to the compound that is in enriched, especially essentially pure, form with regard to the respective configuration of the double bond).

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

The present invention also includes isotopically labelled, especially $^2H$ (deuterium) labelled compounds of Formula (I) according to embodiments 1) to 36), which compounds are identical to the compounds of Formula (I) except that one or more atoms have each been replaced by an atom having the same atomic number but an atomic mass different from the atomic mass usually found in nature. Isotopically labelled, especially $^2$H (deuterium) labelled compounds of formulae (I), (II) and (III) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formulae (I), (II) and (III) are not isotopically labelled, or they are labelled only with one or more deuterium atoms. In a sub-embodiment, the compounds of formulae (I), (II) and (III) are not isotopically labelled at all. Isotopically labelled compounds of formulae (I), (II) and (III) may be prepared in analogy to the methods described hereinafter, but using the appropriate isotopic variation of suitable reagents or starting materials.

In this patent application, a bond drawn with a wavy line or with a dotted line shows the point of attachment of the radical drawn. For example, the radical

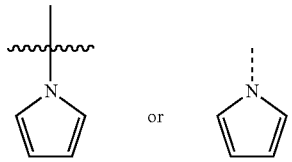

is a 1H-pyrrol-1-yl group.

Whenever a substituent $R^5$ is designated to be in a specific position of the phenyl moiety to which it is attached, it is understood that the point of attachment of the substituent $R^4$ is considered position 2 of said phenyl moiety.

In some instances, the compounds of formulae (I), (II) and (III) may contain tautomeric forms. Such tautomeric forms are encompassed in the scope of the present invention. In case tautomeric forms exist of a certain residue, and only one form of such residue is disclosed or defined, the other tautomeric form(s) are understood to be encompassed in such disclosed residue. For example, the group 3-hydroxy-1H-pyrazol-4-yl is to be understood as also encompassing its tautomeric form 3-oxo-2,3-dihydro-1H-pyrazol-4-yl. Likewise, the group 3-hydroxy-1H-pyrazol-5-yl is to be understood as also encompassing its tautomeric form 3-oxo-2,3-dihydro-1H-pyrazol-5-yl; the group 3-hydroxy-1H-1,2,4-triazole-5-yl is to be understood as also encompassing its tautomeric forms 3-hydroxy-4H-1,2,4-triazol-5-yl, 3-hydroxy-3H-1,2,4-triazol-5-yl, as well as 3-oxo-2,5-dihydro-1H-1,2,4-triazol-5-yl and 3-oxo-4,5-dihydro-1H-1,2,4-triazol-5-yl; the group 3-hydroxyisoxazole-5-yl is to be understood as also encompassing its tautomeric form 3-oxo-2,3-dihydroisoxazole-5-yl; the group 5-hydroxy-[1,2,4]oxadiazol-3-yl is to be understood as also encompassing its tautomeric form 5-oxo-4,5-dihydro-[1,2,4]oxadiazol-3-yl and the group 5-hydroxy-[1,3,4]oxadiazol-2-yl is to be understood as also encompassing its tautomeric form 5-oxo-4,5-dihydro-1,3,4-oxadiazol-2-yl; the group 4-oxo-4,5-dihydro-oxazole-2-yl is to be understood as also encompassing its tautomeric form 4-hydroxy-oxazole-2-yl; the group 2,4-dioxoimidazolidin-1-yl is to be understood as also encompassing its tautomeric form 2,4-dihydroxy-imidazol-1-yl; and the group 2,5-dioxoimidazolidin-1-yl is to be understood as also encompassing its tautomeric form 2,5-dihydroxy-imidazol-1-yl.

Where the plural form is used for compounds, salts, pharmaceutical compositions, diseases and the like, this is intended to mean also a single compound, salt, or the like.

Any reference to compounds of formulae (I), (II) and (III) according to embodiments 1) to 36) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Phramaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of formulae (I), (II) and (III), as defined in any one of embodiments 1) to 33), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

Whenever a substituent is denoted as optional, it is understood that such substituent may be absent (i.e. the respective residue is unsubstituted with regard to such optional substituent), in which case all positions having a free valency (to which such optional substituent could have been attached to; such as for example in an aromatic ring the ring carbon atoms and/or the ring nitrogen atoms having a free valency) are substituted with hydrogen where appropriate. Likewise, in case the term "optionally" is used in the context of (ring) heteroatom(s), the term means that either the respective optional heteroatom(s), or the like, are absent (i.e. a certain moiety does not contain heteroatom(s)/is a carbocycle/or the like), or the respective optional heteroatom(s), or the like, are present as explicitly defined.

The term "halogen" means fluorine, chlorine, or bromine, preferably fluorine or chlorine.

The term "alkyl", used alone or in combination, refers to a saturated straight or branched chain hydrocarbon group containing one to six carbon atoms. The term "$C_{x-y}$-alkyl" (x and y each being an integer), refers to an alkyl group as defined before, containing x to y carbon atoms. For example a $C_{1-6}$-alkyl group contains from one to six carbon atoms. Examples of alkyl groups are methyl, ethyl, propyl, isopropyl, butyl, isobutyl, tert.-butyl, 3-methyl-butyl, 2,2-dimethyl-propyl and 3,3-dimethyl-butyl. For avoidance of any doubt, in case a group is referred to as e.g. propyl or butyl, it is meant to be n-propyl, respectively n-butyl. Preferred are methyl and ethyl. Most preferred is methyl.

The term "-$C_{x-y}$-alkylene-", used alone or in combination, refers to bivalently bound alkyl group as defined before containing x to y carbon atoms. The term "-$C_{0-y}$-alkylene-" refers to a direct bond, or to a -($C_{1-y}$)alkylene- as defined before. Preferably, the points of attachment of a -$C_{1-y}$-alkylene group are in 1,1-diyl, in 1,2-diyl, or in 1,3-diyl arrangement. Preferably, the points of attachment of a -$C_2$-

$y$-alkylene group are in 1,2-diyl or in 1,3-diyl arrangement. In case a $C_{0-y}$-alkylene group is used in combination with another substituent, the term means that either said substituent is linked through a $C_{1-y}$-alkylene group to the rest of the molecule, or it is directly attached to the rest of the molecule (i.e. a $C_0$-alkylene group represents a direct bond linking said substituent to the rest of the molecule). The alkylene group —$C_2H_4$— refers to —$CH_2$—$CH_2$— if not explicitly indicated otherwise. Examples of -$C_{0-4}$-alkylene- groups are notably methylene, ethylene, and propane-1,3-diyl. Examples of -$C_{0-6}$-alkylene- groups are notably methylene, ethylene, propane-1,3-diyl, and 3-methylbutane-1,3-diyl (especially methylene, ethylene, and propane-1,3-diyl). Examples of -$C_{1-6}$-alkylene- groups are notably methylene, ethylene, ethane-1,1-diyl, propane-1,3-diyl, propane-1,2-diyl, propane-2,2-diyl, 2-methylpropane-1,2-diyl, 2-methylpropane-1,1-diyl, 2,2-dimethylpropane-1,3-diyl, butane-1,4-diyl, 3-methylbutane-1,3-diyl, and 4-methylpentane-1,4-diyl. Examples of -$C_{1-4}$-alkylene- groups are notably methylene, ethylene, propane-2,2-diyl, and 2-methylpropane-1,2-diyl (especially methylene). Examples of -$C_{2-6}$-alkylene- groups are notably ethylene, propane-1,3-diyl, propane-1,2-diyl, 2,2-dimethylpropane-1,3-diyl, 2-methylpropane-1,2-diyl, 3-methylbutane-1,3-diyl, and 4-methylpentane-1,4-diyl (most preferably ethylene, propane-1,3-diyl, propane-1,2-diyl, 2-methylpropane-1,2-diyl, 3-methylbutane-1,3-diyl, and 4-methylpentane-1,4-diyl). Examples of -$C_{2-4}$-alkylene- groups are notably ethylene, propane-1,2-diyl and propane-1,3-diyl.

An example of a group -$L^2$-hydroxy wherein -$L^2$- represents $C_{2-6}$-alkylene which is mono-substituted with hydroxy is 2,3-dihydroxypropyl.

The term "alkenyl", used alone or in combination, refers to a straight or branched hydrocarbon chain containing two to five carbon atoms and one carbon-carbon double bond. The term "$C_{x-y}$-alkenyl" (x and y each being an integer), refers to an alkenyl group as defined before containing x to y carbon atoms. For example a $C_{2-5}$-alkenyl group contains from two to five carbon atoms. An example of alkenyl group is notably prop-1-en-2-yl.

The term "-$C_{x-y}$-alkenylene-", used alone or in combination, refers to bivalently bound alkenyl group as defined before containing x to y carbon atoms. Examples of -$C_{2-6}$-alkenylene- groups are notably ethen-1,2-diyl, prop-1-en-2,3-diyl, and prop-1-en-1,3-diyl.

The term "fluoroalkyl", used alone or in combination, refers to an alkyl group as defined before containing one to three carbon atoms in which one or more (and possibly all) hydrogen atoms have been replaced with fluorine. The term "$C_{x-y}$-fluoroalkyl" (x and y each being an integer) refers to a fluoroalkyl group as defined before containing x to y carbon atoms. For example a $C_{1-3}$-fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $C_1$-fluoroalkyl groups such as trifluoromethyl.

The term "fluoroalkoxy", used alone or in combination, refers to an alkoxy group as defined before containing one to three carbon atoms in which one or more (and possibly all) hydrogen atoms have been replaced with fluorine. The term "$C_{x-y}$-fluoroalkoxy" (x and y each being an integer) refers to a fluoroalkoxy group as defined before containing x to y carbon atoms. For example a $C_{1-3}$-fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $C_1$-fluoroalkoxy groups such as trifluoromethoxy and difluoromethoxy, as well as 2,2,2-trifluoroethoxy.

The term "cycloalkyl", used alone or in combination, refers especially to a saturated monocyclic, or to a fused-, bridged-, or spiro-bicyclic hydrocarbon ring containing three to eight carbon atoms. The term "$C_{x-y}$-cycloalkyl" (x and y each being an integer), refers to a cycloalkyl group as defined before containing x to y carbon atoms. For example a $C_{3-6}$-cycloalkyl group contains from three to six carbon atoms. Examples of cycloalkyl groups are cyclopropyl, cyclobutyl, cyclopentyl, cyclohexyl, and cycloheptyl, as well as the bicyclic group bicyclo[1.1.1]pentane. Preferred are cyclopropyl, cyclobutyl, and cyclopentyl; especially cyclopropyl.

The term "$C_{x-y}$-cycloalkyl optionally containing a ring oxygen atom" refers to a cycloalkyl group as defined before containing x to y carbon atoms, wherein one ring carbon atom of said $C_{x-y}$-cycloalkyl may be replaced by an oxygen atom. Such groups are unsubstituted or substituted as explicitly defined. Examples are especially the $C_{3-6}$-cycloalkyl groups cyclopropyl, cyclobutyl, cyclopentyl, cyclohexyl; as well as oxetanyl, tetrahydrofuranyl, and tetrahydropyranyl. A particular "$C_{3-6}$-cycloalkyl, wherein said $C_{3-6}$-cycloalkyl contains one ring oxygen atom" is tetrahydro-2H-pyran-4-yl.

The term "-$C_{x-y}$-cycloalkylene-", used alone or in combination, refers to bivalently bound cycloalkyl group as defined before containing x to y carbon atoms. Preferably, the points of attachment of any bivalently bound cycloalkyl group are in 1,1-diyl, or in 1,2-diyl arrangement. An example of a -$C_{3-6}$-cycloalkylene- group is notably cyclopropane-1,1-diyl. Examples of -$C_{3-8}$-cycloalkylene- groups are notably cyclopropane-1,1-diyl, cyclopropane-1,2-diyl, cyclobutane-1,1-diyl, bicyclo[1.1.1]pentane-1,3-diyl, cyclohexane-1,3-diyl, and cyclohexane-1,4-diyl (especially cyclopropane-1,1-diyl, cyclopropane-1,2-diyl, and cyclobutane-1,1-diyl).

The term "alkoxy", used alone or in combination, refers to an alkyl-O— group wherein the alkyl group is as defined before. The term "$C_{x-y}$-alkoxy" (x and y each being an integer) refers to an alkoxy group as defined before containing x to y carbon atoms. For example a $C_{1-4}$-alkoxy group means a group of the formula $C_{1-4}$-alkyl-O— in which the term "$C_{1-4}$-alkyl" has the previously given significance. Examples of alkoxy groups are methoxy, ethoxy, n-propoxy, isopropoxy, n-butoxy, isobutoxy, sec.-butoxy and tert.-butoxy. Preferred are ethoxy and especially methoxy.

The term "heterocyclyl", used alone or in combination, and if not explicitly defined in a broader or more narrow way, refers to a saturated or unsaturated non-aromatic monocyclic hydrocarbon ring containing one or two ring heteroatoms independently selected from nitrogen, sulfur, and oxygen (especially one oxygen atom, one sulfur atom, one nitrogen atom, two nitrogen atoms, two oxygen atoms, one nitrogen atom and one oxygen atom). The term "$C_{x-y}$-heterocyclyl" refers to such a heterocycle containing x to y ring atoms. Examples of heterocyclyl groups as used in the group -$L^{10}$-$C_{4-6}$-heterocyclyl are notably oxetan-3-yl, thietane-3-yl, imidazolidin-1-yl, 4,5-dihydrooxazol-2-yl, 1,3-dioxolan-4-yl, piperidin-4-yl, piperazin-1-yl, piperazin-2-yl, morpholin-3-yl, morpholin-4-yl and morpholin-2-yl. Heterocyclyl group are unsubstituted or substituted as explicitly defined.

The term "-C$_{x-y}$-heterocycloalkylene-", used alone or in combination, refers to bivalently bound heterocyclyl group as defined before containing x to y ring atoms. Examples of C$_{3-6}$-heterocycloalkylene containing one ring oxygen atom, or containing one ring nitrogen atom as used in the groups Cy$^1$, Cy$^2$, and, mutatis mutandis, Cy$^4$ are notably the nitrogen containing groups azetidin-1,3-diyl, azetidin-3,3-diyl, pyrrolidine-2,4-diyl, piperidin-1,4-diyl and piperidin-4,4-diyl; and the oxygen containing groups oxetan-3,3-diyl, tetrahydrofuran-3,3-diyl, and tetrahydro-2H-pyran-4,4-diyl.

The term "heteroaryl", used alone or in combination, means a 5- to 10-membered monocyclic or bicyclic aromatic ring containing one to a maximum of four heteroatoms, each independently selected from oxygen, nitrogen and sulfur. Examples of such heteroaryl groups are furanyl, oxazolyl, isoxazolyl, oxadiazolyl, thiophenyl, thiazolyl, isothiazolyl, thiadiazolyl, pyrrolyl, imidazolyl, pyrazolyl, triazolyl, tetrazolyl, pyridinyl, pyrimidinyl, pyridazinyl, pyrazinyl, indolyl, isoindolyl, benzofuranyl, isobenzofuranyl, benzothiophenyl, indazolyl, benzimidazolyl, benzoxazolyl, benzothiazolyl, benzisoxazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl groups are unsubstituted or substituted as explicitly defined. For the substituent Ar$^1$ representing "6-membered heteroaryl containing one or two nitrogen atoms", the term means the respective above-mentioned 6-membered groups; especially pyridinyl or pyrazinyl; in particular pyridin-2-yl, pyridin-4-yl, or pyrazin-2-yl. For the substituent HET$^1$ representing "5- or 6-membered heteroaryl", the term means the above-mentioned 5- or 6-membered groups. Notably, the term refers to 5-membered heteroaryl containing one to four heteroatoms, such as especially furanyl, imidazolyl, pyrrolyl, pyrazolyl, oxazolyl, isoxazolyl, oxadiazolyl, triazolyl, or tetrazolyl; or to 6-membered heteroaryl containing one or two nitrogen atoms; such as especially pyrimidinyl, pyrazinyl, pyridazinyl, or pyridinyl. Particular examples of 5-membered heteroaryl as used for HET$^1$ are furan-2-yl, 1H-imidazol-2-yl, 1H-imidazol-4-yl, 1H-pyrrol-2-yl, 1H-pyrazol-3-yl, 1H-pyrazol-4-yl, 1H-pyrazol-5-yl, oxazol-2-yl, oxazol-4-yl, isoxazol-5-yl, 1,2,4-oxadiazol-3-yl, 2H-1,2,3-triazol-2-yl, 1H-1,2,3-triazol-4-yl, 4H-1,2,4-triazol-4-yl, 1H-1,2,4-triazol-5-yl, 1H-tetrazol-1-yl, and 1H-tetrazol-5-yl; and in addition to the above-listed 1H-1,2,3-triazol-1-yl, and 2H-tetrazol-2-yl. Particular examples of 6-membered heteroaryl as used for HET$^1$ are pyrimidin-2-yl, pyrimidin-4-yl, pyrimidin-5-yl, pyridin-2-yl, pyridin-4-yl, pyridin-3-yl, pyridazin-3-yl, and pyrazin-2-yl.

For avoidance of doubt, certain groups having tautomeric forms which may be considered predominantly aromatic (such as for example 3-hydroxy-isoxazolyl, 5-hydroxy-[1,2,4]oxadiazol-3-yl, 3-hydroxy-[1,2,4]oxadiazol-5-yl, 3-hydroxy-1H-pyrazol-4-yl, or 2-hydroxy-[1,3,4]oxadiazolyl groups) are defined herein as heteroaryl groups HET$^1$, even though their corresponding tautomeric forms (3-oxo-2,3-dihydro-2H-isoxazolyl, respectively, 5-oxo-4,5-dihydro-[1,2,4]oxadiazol-3-yl, 3-oxo-4,5-dihydro-[1,2,4]oxadiazol-5-yl, 3-oxo-2,3-dihydro-1H-pyrazol-4-yl, 2-oxo-2,3-dihydro-3H-[1,3,4]oxadiazolyl) could also be considered as a non-aromatic heterocyclyl group. Likewise, certain groups having tautomeric forms which may be considered predominantly non-aromatic (such as 2,4-dioxoimidazolidin-1-yl, 4-oxo-4,5-dihydro-oxazole-2-yl) as defined for the substituent -L$^{10}$-C$_{4-6}$-heterocyclyl, are defined herein as not being part of substituted heteroaryl groups as defined for HET$^1$, even though their corresponding tautomeric form (4-hydroxy-oxazole-2-yl, respectively, 2,4-dihydroxy-imidazol-1-yl), could also be considered as an heteroaryl group HET$^1$. It is understood that the corresponding tautomers are encompassed in the respective scope -L$^9$-HET$^1$, respectively, -L$^{10}$-C$_{4-6}$-heterocyclyl as defined.

The term "cyano" refers to a group —CN.

The term "oxo" refers to a group =O which is preferably attached to a chain or ring carbon or sulfur atom as for example in a carbonyl group —(CO)—, or a sulfonyl group —(SO$_2$)—.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C.

Further embodiments of the invention are presented hereinafter:

2) A second embodiment relates to compounds according to embodiment 1), wherein R$^1$ is hydrogen.

3) Another embodiment relates to compounds according to embodiment 1), wherein R$^1$ is fluoro.

4) Another embodiment relates to compounds according to any one of embodiments 1) to 3), wherein R$^2$ is hydrogen, chloro, methyl, ethyl, methoxy or ethoxy.

5) Another embodiment relates to compounds according to any one of embodiments 1) to 3), wherein W represents N, Z represents CH; and R$^2$ is hydrogen, methyl, methoxy or ethoxy (especially methyl); or Z represents N, W represents CH; and R$^2$ is chloro, bromo, methyl, or methoxy (especially chloro).

6) Another embodiment relates to compounds according to any one of embodiments 1) to 5), wherein R$^3$ is methoxy, isopropoxy, or difluoromethoxy (especially methoxy or difluoromethoxy).

7) Another embodiment relates to compounds according to any one of embodiments 1) to 5), wherein R$^3$ is C$_{1-3}$-alkoxy (notably methoxy, isopropoxy, especially methoxy).

8) Another embodiment relates to compounds according to any one of embodiments 1) to 5), wherein R$^3$ is C$_{1-3}$-fluoroalkoxy (especially difluoromethoxy).

9) Another embodiment relates to compounds according to embodiment 1), wherein the fragment:

represents:

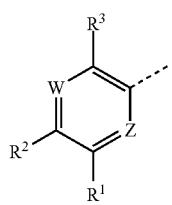

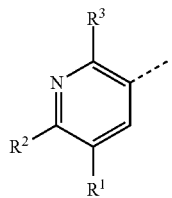

wherein $R^1$ is hydrogen or fluoro (especially hydrogen); $R^2$ is hydrogen, chloro, methyl, ethyl, methoxy or ethoxy (especially methyl); and $R^3$ is $C_{1-3}$-alkoxy (especially methoxy, isopropoxy) or $C_{1-3}$-fluoroalkoxy (especially difluoromethoxy); or

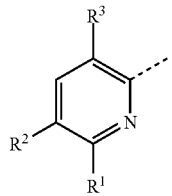

wherein $R^1$ is hydrogen; $R^2$ is halogen (especially chloro), methyl, or methoxy; and $R^3$ is $C_{1-3}$-alkoxy (especially methoxy) or $C_{1-3}$-fluoroalkoxy (especially difluoromethoxy).

10) Another embodiment relates to compounds according to embodiment 1), wherein the fragment:

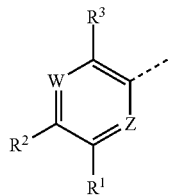

represents:

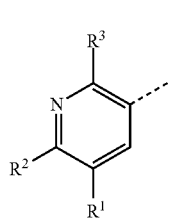

wherein $R^1$ is hydrogen; $R^2$ is hydrogen, methyl, methoxy (especially methyl); and $R^3$ is $C_{1-3}$-alkoxy (especially methoxy) or $C_{1-3}$-fluoroalkoxy (especially difluoromethoxy); or

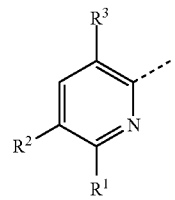

wherein $R^1$ is hydrogen; $R^2$ is halogen (especially chloro); and $R^3$ is methoxy, or difluoromethoxy.

11) Another embodiment relates to compounds according to embodiment 1), wherein the fragment:

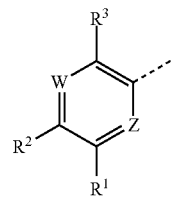

represents a ring independently selected from the following groups A) or B):

A)

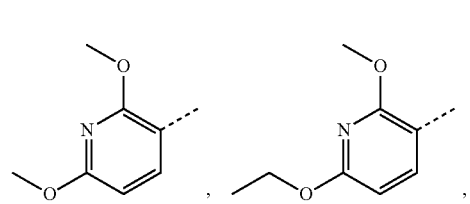

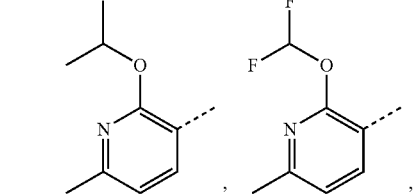

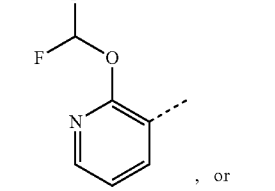

, or

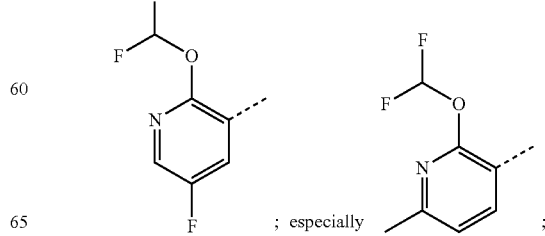

B)

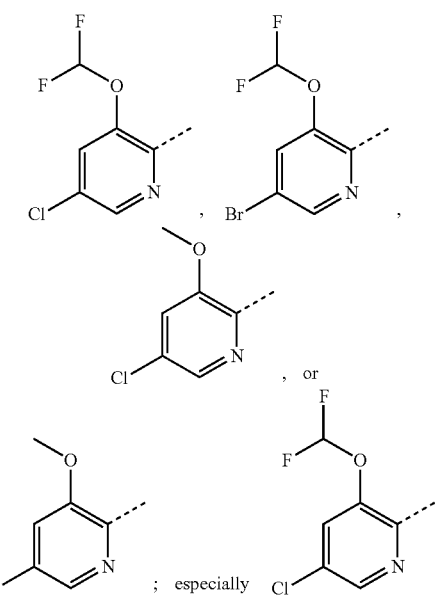
; especially

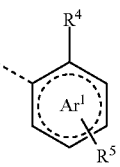
;

wherein each of the above groups A) and B) form a particular sub-embodiment.

12) Another embodiment relates to compounds according to any one of embodiments 1) to 11), wherein $Ar^1$ represents phenyl [wherein it is understood that said phenyl is substituted with $R^4$ and $R^5$ as explicitly defined].

13) Another embodiment relates to compounds according to any one of embodiments 1) to 11), wherein $Ar^1$ represents a 6-membered heteroaryl containing one or two nitrogen atoms (especially pyridinyl, pyrimidinyl, or pyrazinyl; in particular pyridin-2-yl, pyridin-4-yl, or pyrazin-2-yl) [wherein it is understood that said heteroaryl is substituted with $R^4$ and $R^5$ as explicitly defined].

14) Another embodiment relates to compounds according to any one of embodiments 1) to 13) [especially according to embodiment 12)], wherein $R^4$ is n-propyl, iso-propyl, or monocyclic $C_{3-6}$-cycloalkyl (especially cyclobutyl, or cyclopentyl).

15) Another embodiment relates to compounds according to any one of embodiments 1) to 13) [especially according to embodiments 12) or 13)], wherein $R^4$ is n-propyl, isopropyl.

16) Another embodiment relates to compounds according to any one of embodiments 1) to 13) [especially according to embodiment 12)], wherein $R^4$ is monocyclic $C_{3-6}$-cycloalkyl (especially cyclobutyl, cyclopentyl).

17) Another embodiment relates to compounds according to any one of embodiments 1) to 16), wherein $R^5$ represents hydrogen, fluoro, or methyl (notably hydrogen, or fluoro in position 5 or 6 of the phenyl moiety, or methyl in position 5 of the phenyl moiety; especially hydrogen, or fluoro in position 5 or 6 of the phenyl moiety).

18) Another embodiment relates to compounds according to any one of embodiments 1) to 16), wherein $R^5$ represents hydrogen.

19) Another embodiment relates to compounds according to any one of embodiments 1) to 11), wherein the fragment:

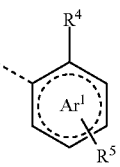

represents a ring independently selected from the following groups A) or B):

A)

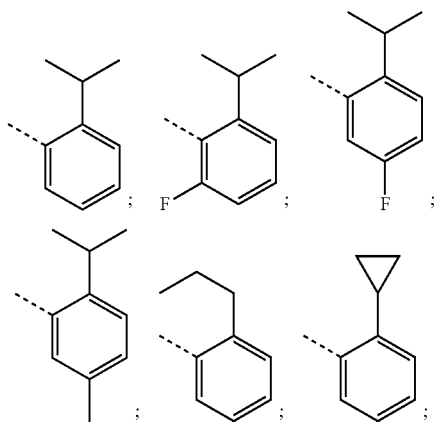

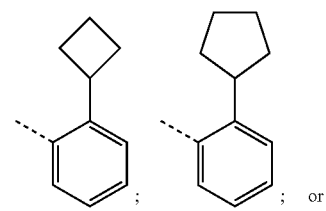

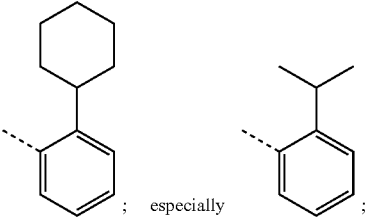
; especially

B)

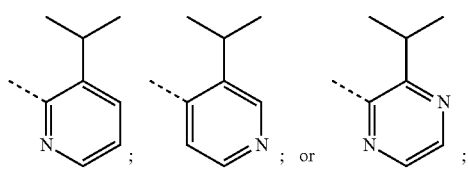

wherein each of the above groups A) and B) form a particular sub-embodiment.

20) Another embodiment relates to compounds according to any one of embodiments 1) to 19), wherein m and n both are 1, or m and n both are 2.

21) Another embodiment relates to compounds according to any one of embodiments 1) to 19), wherein m and n both are 1.

22) Another embodiment relates to compounds according to any one of embodiments 1) to 21), wherein the group-L-R6 represents hydrogen;

-$L^1$—CO—$R^{C11}$ wherein $R^{C11}$ independently represents hydroxy; —O-benzyl; —O-$C_{1-6}$-alkyl; $C_1$-fluoroalkyl; or —$NR^{N11}R^{N12}$; wherein independently $R^{N11}$ is hydrogen or $C_{1-4}$-alkyl, and $R^{N12}$ is hydrogen, $C_{1-4}$-alkyl, —$SO_2$-$C_{1-6}$-alkyl, or —O—$R^{O11}$, wherein $R^{O11}$ independently represents hydrogen, $C_{1-6}$-alkyl, or benzyl; and -$L^1$- independently represents -$C_{1-6}$-alkylene-, —CO-$C_{1-6}$-alkylene-, —SO2-$C_{1-6}$-alkylene-, —CO—O-$C_{1-6}$-alkylene-, —CO—NH-$C_{1-6}$-alkylene-, or —$SO_2$—NH-$C_{1-6}$-alkylene-;

-$C_{1-6}$-alkylene-, —CO-$C_{1-6}$-alkylene-, or —SO2-$C_{1-6}$-alkylene-; wherein in the above groups said $C_{1-6}$-alkylene independently is mono-substituted with hydroxy, $C_{1-3}$-alkoxy, —O—CO-$C_{1-4}$-alkyl, or —$NR^{N13}R^{N14}$; wherein independently $R^{N13}$ is hydrogen or $C_{1-4}$-alkyl, and $R^{N14}$ is hydrogen, $C_{1-4}$-alkyl or —CO—O-$C_{1-4}$-alkyl;

-$C_{2-6}$-alkylene-, —CO-$C_{2-6}$-alkylene-, or —$SO_2$-$C_{2-6}$-alkylene-; wherein in the above groups said $C_{2-6}$-alkylene independently is di-substituted wherein the substituents are independently selected from hydroxy and —$NR^{N15}R^{N16}$; wherein independently $R^{N15}$ is hydrogen or $C_{1-4}$-alkyl, and $R^{N16}$ is hydrogen, $C_{1-4}$-alkyl or —CO-O-$C_{1-4}$-alkyl;

-$C_{0-4}$-alkylene-$C_{3-8}$-cycloalkylene-$C_{0-4}$-alkylene-, —CO-$C_{0-4}$-alkylene-$C_{3-8}$-cycloalkylene-$C_{0-4}$-alkylene-, —$SO_2$-$C_{0-4}$-alkylene-$C_{3-8}$-cycloalkylene-$C_{0-4}$-alkylene-, —CO—NH-$C_{0-4}$alkylene-$C_{3-8}$-cycloalkylene-$C_{0-4}$-alkylene-, or —CO—O-$C_{0-4}$-alkylene-$C_{3-8}$-cycloalkylene-$C_{0-4}$-alkylene-;

-$C_{0-4}$-alkylene-$Cy^1$-$C_{0-4}$-alkylene-, —CO-$C_{0-4}$-alkylene-$Cy^1$-$C_{0-4}$-alkylene-, —CO—O-$C_{0-4}$-alkylene-$Cy^1$-$C_{0-4}$-alkylene-, —CO—NH-$C_{0-4}$-alkylene-$Cy^1$-$C_{0-4}$-alkylene-, —$SO_2$-$C_{0-4}$-alkylene-$Cy^1$-$C_{0-4}$-alkylene-, or —$SO_2$—NH-$C_{0-4}$-alkylene-$Cy^1$-$C_{0-4}$-alkylene-; wherein $Cy^1$ independently represents a $C_{3-6}$-heterocycloalkylene containing one ring oxygen atom, or one ring nitrogen atom, wherein said ring nitrogen, in case it has a free valency, independently is unsubstituted, or mono-substituted with $C_{1-4}$-alkyl or —CO—O-$C_{1-4}$-alkyl;

-$C_{2-4}$-alkylene-O-$C_{2-4}$-alkylene-O-$C_{1-4}$-alkylene-, or —CO-$C_{1-4}$-alkylene-O-$C_{2-4}$-alkylene-O-$C_{1-4}$-alkylene-;

-$C_{2-4}$-alkylene-$X^{11}$-$C_{1-4}$-alkylene-, —CO—O-$C_{2-4}$-alkylene-$X^{11}$-$C_{1-4}$-alkylene-, —CO—NH-$C_{2-4}$-alkylene-$X^{11}$-$C_{1-4}$-alkylene-, or —$SO_2$—NH-$C_{2-4}$-alkylene-$X^{11}$-$C_{1-4}$-alkylene-; wherein $X^{11}$ independently represents oxygen, or a nitrogen atom which is independently unsubstituted, or mono-substituted with $C_{1-4}$-alkyl, $C_{3-6}$-cycloalkyl, or —CO—O-$C_{1-4}$-alkyl;

—CO-$C_{1-4}$-alkylene-$X^{12}$-$C_{1-4}$-alkylene-, —$SO_2$-$C_{1-4}$-alkylene-$X^{12}$-$C_{1-4}$-alkylene-, or —CO-$C_{1-4}$-alkylene-$X^{12}$-$C_{0-4}$-alkylene-$C_{3-6}$-cycloalkylene-$C_{0-4}$-alkylene-; wherein $X^{12}$ independently represents oxygen, or a nitrogen atom which is independently unsubstituted, or mono-substituted with $C_{1-4}$-alkyl, $C_{3-6}$-cycloalkyl, or —CO—O-$C_{1-4}$-alkyl;

-$C_{2-4}$-alkylene-$X^{13}$-$C_{1-4}$-alkylene-; wherein $X^{13}$ represents —NH—CO—, and wherein said $C_{2-4}$-alkylene independently is unsubstituted, or mono-substituted with hydroxy;

-$C_{1-4}$-alkylene-$X^{14}$-$C_{1-4}$-alkylene-; wherein $X^{14}$ represents —CO—NH—;

—CO-$C_{2-6}$-alkenylene- or —$SO_2$-$C_{2-6}$-alkenylene-; or

—CO-$C_{2-6}$-fluoroalkylene-;

-$L^2$-hydroxy; wherein -$L^2$- represents

—CO-$C_{1-6}$-alkylene- or —$SO_2$-$C_{1-6}$-alkylene-; wherein in the above groups said $C_{1-6}$-alkylene independently is unsubstituted, or mono-substituted with hydroxy, $C_1$-fluoroalkyl, or —$NR^{N21}R^{N22}$ wherein independently $R^{N21}$ is hydrogen or $C_{1-4}$-alkyl, and $R^{N22}$ is hydrogen, $C_{1-4}$-alkyl or —CO—O-$C_{1-4}$-alkyl;

-$C_{2-6}$-alkylene-, —CO—O-$C_{2-6}$-alkylene-, —CO—NH-$C_{2-6}$-alkylene-, or —$SO_2$—NH-$C_{2-6}$-alkylene-, wherein in the above groups said $C_{2-6}$-alkylene independently is unsubstituted, or mono-substituted with hydroxy, $C_1$-fluoroalkyl, or —$NR^{N23}R^{N24}$ wherein independently $R^{N23}$ is hydrogen or $C_{1-4}$-alkyl, and $R^{N24}$ is hydrogen, $C_{1-4}$-alkyl or —CO—O-$C_{1-4}$-alkyl;

$C_{0-4}$-alkylene-$C_{3-6}$-cycloalkylene-$C_{0-4}$-alkylene-, —CO-$C_{0-4}$-alkylene-$C_{3-6}$-cycloalkylene-$C_{0-4}$-alkylene-, or —$SO_2$-$C_{0-4}$-alkylene-$C_{3-6}$-cycloalkylene-$C_{0-4}$-alkylene-;

-$C_{0-4}$-alkylene-$Cy^2$-$C_{0-4}$-alkylene-, —CO-$C_{0-4}$-alkylene-$Cy^2$-$C_{0-4}$-alkylene-, or —$SO_2$-$C_{0-4}$-alkylene-$Cy^2$-$C_{0-4}$-alkylene-; wherein $Cy^2$ independently represents a $C_{3-6}$-heterocycloalkylene group containing one ring oxygen atom, or one ring nitrogen atom; wherein said ring nitrogen, in case it has a free valency, is independently unsubstituted, or mono-substituted with $C_{1-4}$-alkyl or —CO—O-$C_{1-4}$-alkyl;

-$C_{2-4}$-alkylene-(O-$C_{2-4}$-alkylene)$_p$- or —CO-$C_{1-4}$-alkylene-(O-$C_{2-4}$-alkylene)$_p$-; wherein p independently represents the integer 1 or 2;

-$C_{2-4}$-alkylene-$X^{21}$-$C_{2-4}$-alkylene-; wherein $X^{21}$ represents a nitrogen atom which is unsubstituted, or mono-substituted with $C_{1-4}$-alkyl, $C_{3-6}$-cycloalkyl, or —CO—O-$C_{1-4}$-alkyl;

—CO-$C_{1-4}$-alkylene-$X^{22}$-$C_{2-4}$-alkylene-, —CO-$C_{1-4}$-alkylene-$X^{22}$-$C_{1-4}$-alkylene-$C_{3-6}$-cycloalkylene-, or —$SO_2$-$C_{1-4}$-alkylene-$X^{22}$-$C_{2-4}$-alkylene-; wherein $X^{22}$ represents a nitrogen atom which is independently unsubstituted, or mono-substituted with $C_{1-4}$-alkyl, $C_{3-6}$-cycloalkyl, or —CO—O-$C_{1-4}$-alkyl;

-$C_{2-4}$-alkylene-$X^{23}$-$C_{1-4}$-alkylene-; wherein $X^{23}$ represents —NH—CO—, and wherein said $C_{2-4}$-alkylene independently is unsubstituted, or mono-substituted with hydroxy;

-$C_{1-4}$-alkylene-$X^{24}$-$C_{2-4}$-alkylene-; wherein $X^{24}$ represents —CO—NH—, and wherein said $C_{2-4}$-alkylene independently is unsubstituted, or mono-substituted with hydroxy;

-$L^3$—O—$R^{O31}$ wherein $R^{O31}$ is -$C_{1-4}$-alkyl or —CO-$C_{2-4}$-alkenyl; and -$L^3$- independently represents -$C_{2-6}$-alkylene-, —CO-$C_{1-6}$-alkylene- or —$SO_2$-$C_{1-6}$-alkylene-, —CO—O-$C_{2-6}$-alkylene-, —CO—NH-$C_{2-6}$-alkylene-, or —$SO_2$—NH-$C_{2-6}$-alkylene-;

-$L^4$—$NR^{N1}R^{N2}$ wherein independently $R^{N1}$ is hydrogen or $C_{1-4}$-alkyl; and $R^{N2}$ is hydrogen; $C_{1-4}$-alkyl; $C_{1-3}$-fluoroalkyl; $C_{3-6}$-cycloalkyl; $C_{1-3}$-alkoxy-$C_{2-4}$-alkylene; —CO-$C_{1-4}$-alkyl; —SO$_2$-$C_{1-4}$-alkyl; or —SO$_2$-$C_1$-fluoroalkyl; and -L4- independently represents
-$C_{2-6}$-alkylene-, —CO-$C_{1-6}$-alkylene-, —SO$_2$-$C_{1-6}$-alkylene-, —CO—O-$C_{2-6}$-alkylene-, —CO—NH-$C_{2-6}$-alkylene-, or —SO$_2$—NH-$C_{2-6}$-alkylene-; or
-$C_{0-4}$-alkylene-$Cy^4$-$C_{0-4}$-alkylene-, —CO-$C_{0-4}$-alkylene-$Cy^4$-$C_{0-4}$-alkylene-, or —SO$_2$-$C_{0-4}$-alkylene-$Cy^4$-$C_{0-4}$-alkylene-; wherein $Cy^4$ independently represents a $C_{3-6}$-heterocycloalkylene group containing one ring oxygen atom;

-$L^5$—$NR^{N3}R^{N4}$ wherein $R^{N3}$ is hydrogen, $C_{1-4}$-alkyl, or $C_{1-3}$-alkoxy-$C_{2-4}$-alkylene; and $R^{N4}$ is —CO—O-$C_{1-4}$-alkyl; —CO—$NR^{N51}R^{N52}$ wherein $R^{N51}$ and $R^{N52}$ are independently selected from hydrogen and $C_{1-4}$-alkyl; or —SO$_2$—$NR^{N53}R^{N54}$ wherein independently $R^{N53}$ is hydrogen or $C_{1-4}$-alkyl, and $R^{N54}$ is hydrogen, $C_{1-4}$-alkyl, or —CO-$C_{1-4}$-alkyl;

and -$L^5$- independently represents
-$C_{2-6}$-alkylene-, —CO-$C_{1-6}$-alkylene- or —SO$_2$-$C_{1-6}$-alkylene-, —CO—O-$C_{2-6}$-alkylene-, —CO—NH-$C_{2-6}$-alkylene-, or —SO$_2$—NH-$C_{2-6}$-alkylene-;

-$L^6$—$N(R^{N61})$—O—$R^{O61}$ wherein $R^{N61}$ is hydrogen, —CO-$C_{1-4}$-alkyl, or —CO—O-$C_{1-4}$-alkyl; and $R^{O61}$ independently represents hydrogen, $C_{1-6}$-alkyl, or benzyl;

and -$L^6$- independently represents
-$C_{2-6}$-alkylene-, —CO-$C_{1-6}$-alkylene-, —SO$_2$-$C_{1-6}$-alkylene-, —CO—O-$C_{2-6}$-alkylene-, —CO—NH-$C_{2-6}$-alkylene-, or —SO$_2$—NH-$C_{2-6}$-alkylene-;

-$L^7$—$NR^{N5}R^{N6}$ wherein $R^{N5}$ is hydrogen or $C_{1-4}$-alkyl (especially hydrogen); $R^{N6}$ is hydrogen, $C_{1-4}$-alkyl, —CO-$C_{1-4}$-alkyl, $C_{1-3}$-fluoroalkyl, or $C_{3-6}$-cycloalkyl (especially hydrogen); and -$L^7$- independently represents
—CO—, or —SO$_2$—;

-$L^8$—SO$_2$—$R^{S81}$ wherein $R^{S81}$ independently represents -$C_{1-6}$-alkyl; $C_1$-fluoroalkyl; hydroxy; —$NR^{N81}R^{N82}$ wherein independently $R^{N81}$ is hydrogen or $C_{1-4}$-alkyl, and $R^{N82}$ is hydrogen, $C_{1-4}$-alkyl, or —CO-$C_{1-6}$-alkyl; and L8- independently represents
-$C_{1-6}$-alkylene-, —CO-$C_{1-6}$-alkylene-, —SO$_2$-$C_{1-6}$-alkylene-, —CO—O-$C_{2-6}$-alkylene-, —CO—NH-$C_{1-6}$-alkylene-, or —SO$_2$—NH-$C_{1-6}$-alkylene-;

-$L^9$-$HET^1$, wherein $HET^1$ represents 5- or 6-membered heteroaryl (especially pyrrolyl, pyrazolyl, imidazolyl, triazolyl, tetrazolyl, furanyl, oxazolyl, isoxazolyl, thiazolyl, isothiazolyl, oxadiazolyl, thiadiazolyl, pyridinyl, pyrimidinyl, pyridazinyl, pyrazinyl), wherein said $HET^1$ independently is unsubstituted or mono-, or di-substituted wherein the substituents are independently selected from $C_{1-4}$-alkyl (especially methyl), halogen, cyano, hydroxy, -$C_{0-2}$-alkylene-$Cy^{91}$-$COOR^{O91}$ wherein $R^{O91}$ is hydrogen or $C_{1-4}$-alkyl, and wherein $Cy^{91}$ represents a $C_{3-6}$-cycloalkylene group; or -$C_{0-4}$-alkylene-$COOR^{O92}$ wherein $R^{O92}$ is hydrogen or $C_{1-4}$-alkyl; and -$L^9$- independently represents
-$C_{0-6}$-alkylene-, —CO-$C_{0-6}$-alkylene-, —SO$_2$-$C_{0-6}$-alkylene-, —CO—O-$C_{1-6}$-alkylene-, —CO—NH-$C_{1-6}$-alkylene-, or —SO$_2$—NH-$C_{1-6}$-alkylene-;

-$L^{10}$-$C_{4-6}$-heterocyclyl, wherein the $C_{4-6}$-heterocyclyl independently contains one or two ring heteroatoms independently selected from nitrogen, sulfur and oxygen; wherein in the above groups said $C_{4-6}$-heterocyclyl independently is unsubstituted, or mono-, di-, or tri-substituted wherein the substituents are independently selected from:
one or two oxo substituents each attached to a ring carbon atom in alpha position to a ring nitrogen atom (thus forming together with the nitrogen an amide group, or, in case a ring oxygen is additionally adjacent, a carbamate group, or, in case second ring nitrogen is additionally adjacent, a urea group); and/or
two methyl substituents attached to a ring carbon atom in alpha position to a ring nitrogen atom or a ring oxygen atom (thus forming together with the nitrogen a —$C(CH_3)_2$—N— or with the oxygen a —$C(CH_3)_2$—O— group); and/or
two oxo substituents at a ring sulfur ring atom (thus forming a —SO$_2$— group); and/or
$C_{1-4}$-alkyl, $C_{1-3}$-alkoxy-$C_{2-4}$-alkyl, $C_{2-3}$-fluoroalkyl, or —CO-$C_{1-4}$-alkyl attached to a ring nitrogen atom having a free valency; and -$L^{10}$- independently represents
-$C_{0-6}$-alkylene-, —CO-$C_{0-6}$-alkylene-, —SO$_2$-$C_{0-6}$-alkylene-, —CO—O-$C_{1-6}$-alkylene-, —CO—NH-$C_{1-6}$-alkylene-, or —SO$_2$—NH-$C_{1-6}$-alkylene-;

-$L^{11}$-cyano; wherein -$L^{11}$- represents —CO-$C_{1-6}$-alkylene-, —SO2-$C_{1-6}$-alkylene, or -$C_{0-6}$-alkylene-;

-$L^{12}$—NO$_2$; wherein -$L^{12}$- represents -$C_{2-6}$-alkylene-; or

-$L^{13}$-$C_{1-4}$-alkyl; wherein -$L^{13}$- represents —CO—, —CO—O—.

23) Another embodiment relates to compounds according to any one of embodiments 1) to 21), wherein the group -L—$R^6$ represents
hydrogen;
-$L^1$—CO—$R^{C11}$ wherein $R^{C11}$ independently represents hydroxy, —O-benzyl; —O-$C_{1-6}$-alkyl; $C_1$-fluoroalkyl; or —$NR^{N11}R^{N12}$; wherein independently $R^{N11}$ is hydrogen or $C_{1-4}$-alkyl, and $R^{N12}$ is hydrogen; $C_{1-4}$-alkyl, —SO$_2$-$C_{1-6}$-alkyl, or —O—$R^{O11}$, wherein $R^{O11}$ independently represents hydrogen, $C_{1-6}$-alkyl, or benzyl; and -$L^1$- independently represents
-$C_{1-6}$-alkylene-, —CO-$C_{1-6}$-alkylene-, —SO2-$C_{1-6}$-alkylene-, —CO—O-$C_{1-6}$-alkylene-, —CO—NH-$C_{1-6}$-alkylene-, or —SO$_2$—NH-$C_{1-6}$-alkylene-;
-$C_{1-6}$-alkylene-, —CO-$C_{1-6}$-alkylene-, or —SO2-$C_{1-6}$-alkylene-; wherein in the above groups said $C_{1-6}$-alkylene independently is mono-substituted with hydroxy, $C_{1-3}$-alkoxy, —O—CO-$C_{1-4}$-alkyl, or —$NR^{N13}R^{N14}$; wherein independently $R^{N13}$ is hydrogen or $C_{1-4}$-alkyl, and $R^{N14}$ is hydrogen, $C_{1-4}$-alkyl or —CO—O-$C_{1-4}$-alkyl;
-$C_{2-6}$-alkylene-, —CO-$C_{2-6}$-alkylene-, or —SO$_2$-$C_{2-6}$-alkylene-; wherein in the above groups said $C_{2-6}$-alkylene independently is di-substituted wherein the substituents are independently selected from hydroxy and —$NR^{N15}R^{N16}$; wherein independently $R^{N15}$ is hydrogen or $C_{1-4}$-alkyl, and $R^{N16}$ is hydrogen, $C_{1-4}$-alkyl or —CO-O-$C_{1-4}$-alkyl;
-$C_{0-4}$-alkylene-$C_{3-8}$-cycloalkylene-$C_{0-4}$-alkylene-, —CO-$C_{0-4}$-alkylene-$C_{3-8}$-cycloalkylene-$C_{0-4}$-alkylene-, —SO$_2$-$C_{0-4}$-alkylene-$C_{3-8}$-cycloalkylene-$C_{0-4}$-alkylene-, —CO—NH-$C_{0-4}$alkylene-$C_{3-8}$-cycloalkylene-$C_{0-4}$-alkylene-, or —CO—O-$C_{0-4}$-alkylene-$C_{3-8}$-cycloalkylene-$C_{0-4}$-alkylene-;

-$C_{0-4}$-alkylene-Cy$^1$-$C_{0-4}$-alkylene-, —CO-$C_{0-4}$-alkylene-Cy$^1$-$C_{0-4}$-alkylene-, —CO—O-$C_{0-4}$-alkylene-Cy$^1$-$C_{0-4}$-alkylene-, —CO—NH-$C_{0-4}$-alkylene-Cy$^1$-$C_{0-4}$-alkylene-, —SO$_2$-$C_{0-4}$-alkylene-Cy$^1$-$C_{0-4}$-alkylene-, or —SO$_2$—NH-$C_{0-4}$-alkylene-Cy$^1$-$C_{0-4}$-alkylene-; wherein Cy$^1$ independently represents a $C_{3-6}$-heterocycloalkylene containing one ring oxygen atom, or one ring nitrogen atom, wherein said ring nitrogen, in case it has a free valency, independently is unsubstituted, or mono-substituted with $C_{1-4}$-alkyl or —CO—O-$C_{1-4}$-alkyl;

—CO-$C_{1-4}$-alkylene-X$^{12}$-$C_{1-4}$-alkylene-, —SO$_2$-$C_{1-4}$-alkylene-X$^{12}$-$C_{1-4}$-alkylene-, or —CO-$C_{1-4}$-alkylene-X$^{12}$-$C_{0-4}$-alkylene-$C_{3-6}$-cycloalkylene-$C_{0-4}$-alkylene-; wherein X$^{12}$ independently represents oxygen, or a nitrogen atom which is independently unsubstituted, or mono-substituted with $C_{1-4}$-alkyl, $C_{3-6}$-cycloalkyl, —CO—O-$C_{1-4}$-alkyl, or $C_{1-3}$-alkoxy-$C_{2-4}$-alkyl;

-$C_{2-4}$-alkylene-X$^{13}$-$C_{1-4}$-alkylene-; wherein X$^{13}$ represents —NH—CO—, and wherein said $C_{2-4}$-alkylene independently is unsubstituted, or mono-substituted with hydroxy;

-$C_{2-4}$-alkylene-X$^{13}$-$C_{1-4}$-alkylene-; wherein X$^{13}$ represents —NH—CO—, and wherein said $C_{2-4}$-alkylene independently is unsubstituted, or mono-substituted with hydroxy;

—CO-$C_{2-6}$-alkenylene- or —SO$_2$-$C_{2-6}$-alkenylene-; or

—CO-$C_{2-6}$-fluoroalkylene-;

-L$^2$-hydroxy; wherein -L$^2$- represents

—CO-$C_{1-6}$-alkylene- or —SO$_2$-$C_{1-6}$-alkylene-; wherein in the above groups said $C_{1-6}$-alkylene independently is unsubstituted, or mono-substituted with hydroxy, $C_1$-fluoroalkyl, or —NR$^{N21}$R$^{N22}$ wherein independently R$^{N21}$ is hydrogen or $C_{1-4}$-alkyl, and R$^{N22}$ is hydrogen, $C_{1-4}$-alkyl or —CO—O-$C_{1-4}$-alkyl;

-$C_{2-6}$-alkylene-, —CO—O-$C_{2-6}$-alkylene-, —CO—NH-$C_{2-6}$-alkylene-, or —SO$_2$—NH-$C_{2-6}$-alkylene-, wherein in the above groups said $C_{2-6}$-alkylene independently is unsubstituted, or mono-substituted with hydroxy, $C_1$-fluoroalkyl, or —NR$^{N23}$R$^{N24}$ wherein independently R$^{N23}$ is hydrogen or $C_{1-4}$-alkyl, and R$^{N24}$ is hydrogen, $C_{1-4}$-alkyl or —CO—O-$C_{1-4}$-alkyl;

$C_{0-4}$-alkylene-$C_{3-6}$-cycloalkylene-$C_{0-4}$-alkylene-, —CO-$C_{0-4}$-alkylene-$C_{3-6}$-cycloalkylene-$C_{0-4}$-alkylene-, or —SO$_2$-$C_{0-4}$-alkylene-$C_{3-6}$-cycloalkylene-$C_{0-4}$-alkylene-;

-$C_{0-4}$-alkylene-Cy$^2$-$C_{0-4}$-alkylene-, —CO-$C_{0-4}$-alkylene-Cy$^2$-$C_{0-4}$-alkylene-, or —SO$_2$-$C_{0-4}$-alkylene-Cy$^2$-$C_{0-4}$-alkylene-; wherein Cy$^2$ independently represents a $C_{3-6}$-heterocycloalkylene group containing one ring oxygen atom, or one ring nitrogen atom; wherein said ring nitrogen, in case it has a free valency, is independently unsubstituted, or mono-substituted with $C_{1-4}$-alkyl or —CO—O-$C_{1-4}$-alkyl;

—CO-$C_{1-4}$-alkylene-X$^{22}$-$C_{2-4}$-alkylene-, —CO-$C_{1-4}$-alkylene-X$^{22}$-$C_{1-4}$-alkylene-$C_{3-6}$-cycloalkylene-, or —SO$_2$-$C_{1-4}$-alkylene-X$^{22}$-$C_{2-4}$-alkylene-; wherein X$^{22}$ represents a nitrogen atom which is independently unsubstituted, or mono-substituted with $C_{1-4}$-alkyl, $C_{3-6}$-cycloalkyl, or —CO—O-$C_{1-4}$-alkyl;

-$C_{2-4}$-alkylene-X$^{23}$-$C_{1-4}$-alkylene-; wherein X$^{23}$ represents —NH—CO—, and wherein said $C_{2-4}$-alkylene independently is unsubstituted, or mono-substituted with hydroxy;

-L$^4$—NR$^{N1}$R$^{N2}$ wherein independently R$^{N1}$ is hydrogen or $C_{1-4}$-alkyl; and R$^{N2}$ is hydrogen; $C_{1-4}$-alkyl; $C_{1-3}$-fluoroalkyl; $C_{3-6}$-cycloalkyl; $C_{1-3}$-alkoxy-$C_{2-4}$-alkylene; —CO-$C_{1-4}$-alkyl; —SO$_2$-$C_{1-4}$-alkyl; or —SO$_2$-$C_1$-fluoroalkyl; and -L4- independently represents -$C_{2-6}$-alkylene-, —CO-$C_{1-6}$-alkylene-, —SO$_2$-$C_{1-6}$-alkylene-, —CO—O-$C_{2-6}$-alkylene-, —CO—NH-$C_{2-6}$-alkylene-, or —SO$_2$—NH-$C_{2-6}$-alkylene-; or -$C_{0-4}$-alkylene-Cy$^4$-$C_{0-4}$-alkylene-, —CO-$C_{0-4}$-alkylene-Cy$^4$-$C_{0-4}$-alkylene-, or —SO$_2$-$C_{0-4}$-alkylene-Cy$^4$-$C_{0-4}$-alkylene-; wherein Cy$^4$ independently represents a $C_{3-6}$-heterocycloalkylene group containing one ring oxygen atom;

-L$^5$—NR$^{N3}$R$^{N4}$ wherein R$^{N3}$ is hydrogen, $C_{1-4}$-alkyl, or $C_{1-3}$-alkoxy-$C_{2-4}$-alkylene; and R$^{N4}$ is —CO—O-$C_{1-4}$-alkyl; —CO—NR$^{N51}$R$^{N52}$ wherein R$^{N51}$ and R$^{N52}$ are independently selected from hydrogen and $C_{1-4}$-alkyl; or —SO$_2$—NR$^{N53}$R$^{N54}$ wherein independently R$^{N53}$ is hydrogen or $C_{1-4}$-alkyl, and R$^{N54}$ is hydrogen, $C_{1-4}$-alkyl, or —CO-$C_{1-4}$-alkyl;

and -L$^5$- independently represents

-$C_{2-6}$-alkylene-, —CO-$C_{1-6}$-alkylene- or —SO$_2$-$C_{1-6}$-alkylene-, —CO—O-$C_{2-6}$-alkylene-, —CO—NH-$C_{2-6}$-alkylene-, or —SO$_2$—NH-$C_{2-6}$-alkylene-;

-L$^6$—N(R$^{N61}$)—O—R$^{O61}$ wherein R$^{N61}$ is hydrogen, —CO-$C_{1-4}$-alkyl, or —CO—O-$C_{1-4}$-alkyl; and R$^{O61}$ independently represents hydrogen, $C_{1-6}$-alkyl, or benzyl;

and -L$^6$- independently represents

-$C_{2-6}$-alkylene-, —CO-$C_{1-6}$-alkylene-, —SO$_2$-$C_{1-6}$-alkylene-, —CO—O-$C_{2-6}$-alkylene-, —CO—NH-$C_{2-6}$-alkylene-, or —SO$_2$—NH-$C_{2-6}$-alkylene-;

-L$^7$—NR$^{N5}$R$^{N6}$ wherein R$^{N5}$ is hydrogen or $C_{1-4}$-alkyl (especially hydrogen); R$^{N6}$ is hydrogen, $C_{1-4}$-alkyl, —CO-$C_{1-4}$-alkyl, $C_{1-3}$-fluoroalkyl, or $C_{3-6}$-cycloalkyl (especially hydrogen); and -L$^7$- independently represents —CO—, or —SO$_2$—;

-L$^8$—SO$_2$—R$^{S81}$ wherein R$^{S81}$ independently represents -$C_{1-6}$-alkyl; $C_1$-fluoroalkyl; hydroxy; —NR$^{N81}$R$^{N82}$ wherein independently R$^{N81}$ is hydrogen or $C_{1-4}$-alkyl, and R$^{N82}$ is hydrogen, $C_{1-4}$-alkyl, —CO-$C_{1-6}$-alkyl; and L8- independently represents -$C_{1-6}$-alkylene-, —CO-$C_{1-6}$-alkylene-, —SO$_2$-$C_{1-6}$-alkylene-, —CO—O-$C_{2-6}$-alkylene-, —CO—NH-$C_{1-6}$-alkylene-, or —SO$_2$—NH-$C_{1-6}$-alkylene-;

-L$^9$-HET$^1$, wherein HET$^1$ represents 5- or 6-membered heteroaryl (especially pyrrolyl, pyrazolyl, imidazolyl, triazolyl, tetrazolyl, furanyl, oxazolyl, isoxazolyl, thiazolyl, isothiazolyl, oxadiazolyl, thiadiazolyl, pyridinyl, pyrimidinyl, pyridazinyl, pyrazinyl), wherein said HET$^1$ independently is unsubstituted or mono-, or di-substituted wherein the substituents are independently selected from $C_{1-4}$-alkyl (especially methyl), halogen, cyano, hydroxy, -$C_{0-2}$-alkylene-Cy$^{91}$-COOR$^{O91}$ wherein R$^{O91}$ is hydrogen or $C_{1-4}$-alkyl, and wherein Cy$^{91}$ represents a $C_{3-6}$-cycloalkylene group; or -C$_{0-4}$-alkylene-COOR$^{O92}$ wherein R$^{O92}$ is hydrogen or C$_{1-4}$-alkyl; and
-L$^9$- independently represents
- -C$_{0-6}$-alkylene-, —CO-C$_{0-6}$-alkylene-, —SO$_2$-C$_{0-6}$-alkylene-, —CO—O-C$_{1-6}$-alkylene-, —CO—NH-C$_{1-6}$-alkylene-, or —SO$_2$—NH-C$_{1-6}$-alkylene-;
-L$^{10}$-C$_{4-6}$-heterocyclyl, wherein the C$_{4-6}$-heterocyclyl independently contains one or two ring heteroatoms independently selected from nitrogen, sulfur and oxygen; wherein in the above groups said C$_{4-6}$-heterocyclyl independently is unsubstituted, or mono-, di-, or tri-substituted wherein the substituents are independently selected from:
  - one or two oxo substituents each attached to a ring carbon atom in alpha position to a ring nitrogen atom (thus forming together with the nitrogen an amide group, or, in case a ring oxygen is additionally adjacent, a carbamate group, or, in case second ring nitrogen is additionally adjacent, a urea group); and/or
  - two methyl substituents attached to a ring carbon atom in alpha position to a ring nitrogen atom or a ring oxygen atom (thus forming together with the nitrogen a —C(CH$_3$)$_2$—N— or with the oxygen a —C(CH$_3$)$_2$—O— group); and/or
  - two oxo substituents at a ring sulfur ring atom (thus forming a —SO$_2$— group); and/or
  - C$_{1-4}$-alkyl, C$_{1-3}$-alkoxy-C$_{2-4}$-alkyl, C$_{2-3}$-fluoroalkyl, or —CO-C$_{1-4}$-alkyl attached to a ring nitrogen atom having a free valency; and
-L$^{10}$- independently represents
- -C$_{0-6}$-alkylene-, or —CO-C$_{0-6}$-alkylene-;
-L$^{11}$-cyano; wherein -L$^{11}$- represents —CO-C$_{1-6}$-alkylene-, —SO2-C$_{1-6}$-alkylene, or -C$_{0-6}$-alkylene-; or
-L$^{13}$-C$_{1-4}$-alkyl; wherein -L$^{13}$- represents —CO—, —CO—O—, or —SO$_2$.

24) Another embodiment relates to compounds according to any one of embodiments 1) to 21), wherein the group -L-R$^6$ represents
hydrogen;
-L$^1$—CO—R$^{C11}$ wherein R$^{C11}$ independently represents hydroxy; —O-C$_{1-6}$-alkyl; C$_1$-fluoroalkyl; or —NR$^{N11}$R$^{N12}$; wherein independently R$^{N11}$ is hydrogen, and R$^{N12}$ is —SO$_2$-C$_{1-6}$-alkyl; and
-L$^1$- independently represents
- -C$_{1-6}$-alkylene-, —CO-C$_{1-6}$-alkylene-, —SO2-C$_{1-6}$-alkylene-, —CO—O-C$_{1-6}$-alkylene-, —CO—NH-C$_{1-6}$-alkylene-, or —SO$_2$—NH-C$_{1-6}$-alkylene-;
- -C$_{1-6}$-alkylene-, —CO-C$_{1-6}$-alkylene-, or —SO2-C$_{1-6}$-alkylene-; wherein in the above groups said C$_{1-6}$-alkylene independently is mono-substituted with hydroxy;
- -C$_{0-4}$-alkylene-C$_{3-8}$-cycloalkylene-C$_{0-4}$-alkylene-, —CO-C$_{0-4}$-alkylene-C$_{3-8}$-cycloalkylene-C$_{0-4}$-alkylene-, —SO$_2$-C$_{0-4}$-alkylene-C$_{3-8}$-cycloalkylene-C$_{0-4}$-alkylene-, or —CO—O-C$_{0-4}$-alkylene-C$_{3-8}$-cycloalkylene-C$_{0-4}$-alkylene-;
- -C$_{0-4}$-alkylene-Cy$^1$-C$_{0-4}$-alkylene-, —CO-C$_{0-4}$-alkylene-Cy$^1$-C$_{0-4}$-alkylene-, —CO—O-C$_{0-4}$-alkylene-Cy$^1$-C$_{0-4}$-alkylene-, or —SO$_2$-C$_{0-4}$-alkylene-Cy$^1$-C$_{0-4}$-alkylene-; wherein Cy$^1$ independently represents a C$_{3-6}$-heterocycloalkylene containing one ring oxygen atom;
- —CO-C$_{1-4}$-alkylene-X$^{12}$-C$_{1-4}$-alkylene-; wherein X$^{12}$ independently represents oxygen, or a nitrogen atom which is independently unsubstituted, or mono-substituted with C$_{1-4}$-alkyl or C$_{3-6}$-cycloalkyl;
- —CO-C$_{2-6}$-alkenylene- or —SO$_2$-C$_{2-6}$-alkenylene-; or
- —CO-C$_{2-6}$-fluoroalkylene-;
-L$^2$-hydroxy; wherein -L2- represents
- —CO-C$_{1-6}$-alkylene-; wherein the C$_{1-6}$-alkylene is unsubstituted, or mono-substituted with C$^1$-fluoroalkyl;
- -C$_{2-6}$-alkylene-, wherein the C$_{2-6}$-alkylene is unsubstituted, or mono-substituted with hydroxy;
- -C$_{0-4}$-alkylene-C$_{3-6}$-cycloalkylene-C$_{0-4}$-alkylene-, or —CO-C$_{0-4}$-alkylene-C$_{3-6}$-cycloalkylene-C$_{0-4}$-alkylene-;
- -C$_{0-4}$-alkylene-Cy$^2$-C$_{0-4}$-alkylene-, or —CO-C$_{0-4}$-alkylene-Cy$^2$-C$_{0-4}$-alkylene-; wherein Cy$^2$ independently represents a C$_{3-6}$-heterocycloalkylene group containing one ring oxygen atom;
- —CO-C$_{1-4}$-alkylene-X$^{22}$-C$_{2-4}$-alkylene-; wherein X$^{22}$ represents a nitrogen atom which is independently unsubstituted, or mono-substituted with C$_{1-4}$-alkyl, or C$_{3-6}$-cycloalkyl; or
- -C$_{2-4}$-alkylene-X$^{23}$-C$_{1-4}$-alkylene-; wherein X$^{23}$ represents —NH—CO—, and wherein said C$_{2-4}$-alkylene independently is unsubstituted, or mono-substituted with hydroxy;
-L$^4$-NR$^{N1}$R$^{N2}$ wherein independently R$^{N1}$ is hydrogen or C$_{1-4}$-alkyl; and R$^{N2}$ is hydrogen; C$_{1-4}$-alkyl; C$_{1-3}$-fluoroalkyl; C$_{3-6}$-cycloalkyl; C$_{1-3}$-alkoxy-C$_{2-4}$-alkylene; —CO-C$_{1-4}$-alkyl; —SO$_2$-C$_{1-4}$-alkyl; or —SO$_2$-C$_1$-fluoroalkyl; and
-L$^4$- independently represents
- -C$_{2-6}$-alkylene-, —CO-C$_{1-6}$-alkylene-, —SO$_2$-C$_{1-6}$-alkylene-, -L$^5$—NR$^{N3}$R$^{N4}$ wherein R$^{N3}$ is hydrogen or C$_{1-4}$-alkyl; and R$^{N4}$ is —SO$_2$—NR$^{N53}$R$^{N54}$ wherein independently R$^{N53}$ is hydrogen or C$_{1-4}$-alkyl, and R$^{N54}$ is hydrogen or C$_{1-4}$-alkyl;
and -L5- independently represents
- -C$_{2-6}$-alkylene-, —CO-C$_{1-6}$-alkylene- or —SO$_2$-C$_{1-6}$-alkylene-;
-L$^6$—N(R$^{N61}$)—O—R$^{O61}$ wherein R$^{N61}$ is —CO-C$_{1-4}$-alkyl; and R$^{O61}$ represents hydrogen;
and -L$^6$- independently represents
- -C$_{2-6}$-alkylene-, —CO-C$_{1-6}$-alkylene-, —SO$_2$-C$_{1-6}$-alkylene-;
-L$^7$-NR$^{N5}$R$^{N6}$ wherein R$^{N5}$ is hydrogen or C$_{1-4}$-alkyl (especially hydrogen); R$^{N6}$ is hydrogen, C$_{1-4}$-alkyl, or C$_{3-6}$-cycloalkyl; and
-L$^7$- independently represents
- —CO—, or —SO$_2$—;
-L$^8$—SO$_2$—R$^{S71}$ wherein R$^{S81}$ independently represents -C$_{1-6}$-alkyl; C$_1$-fluoroalkyl; hydroxy; —NR$^{N81}$R$^{N82}$ wherein independently R$^{N81}$ is hydrogen or C$_{1-4}$-alkyl, and R$^{N82}$ is hydrogen, C$_{1-4}$-alkyl, —CO-C$_{1-6}$-alkyl; and
-L$^8$- independently represents
- -C$_{1-6}$-alkylene-, —CO-C$_{1-6}$-alkylene-, or —SO$_2$-C$_{1-6}$-alkylene-;
-L$^9$-HET$^1$, wherein HET$^1$ represents 5- or 6-membered heteroaryl (especially pyrrolyl, pyrazolyl, imidazolyl, triazolyl, tetrazolyl, furanyl, oxazolyl, isoxazolyl; thiazolyl, isothiazolyl, oxadiazolyl, thiadiazolyl, pyridinyl, pyrimidinyl, pyridazinyl, pyrazinyl), wherein said HET$^1$ independently is unsubstituted or mono-, or di-substituted wherein the substituents are independently selected from C$_{1-4}$-alkyl (especially methyl); halogen; cyano; hydroxy; hydroxymethyl; -$C_{0-2}$-alkylene-$Cy^{91}$-$COOR^{O91}$ wherein $R^{O91}$ is hydrogen or $C_{1-4}$-alkyl, and wherein $Cy^{91}$ represents a $C_{3-6}$-cycloalkylene group; or -$C_{0-2}$-alkylene-$COOR^{OO2}$ wherein $R^{O92}$ is hydrogen or $C_{1-4}$-alkyl; and -$L^9$- independently represents
  -$C_{0-6}$-alkylene-, —CO-$C_{0-6}$-alkylene-, —$SO_2$-$C_{0-6}$-alkylene-, or —CO—NH-$C_{1-6}$-alkylene-;

-$L^{10}$-$C_{4-6}$-heterocyclyl, wherein the $C_{4-6}$-heterocyclyl independently contains one or two ring heteroatoms independently selected from nitrogen, sulfur and oxygen; wherein in the above groups said $C_{4-6}$-heterocyclyl independently is unsubstituted, or mono-, or di-substituted wherein the substituents are independently selected from:
  one or two oxo substituents each attached to a ring carbon atom in alpha position to a ring nitrogen atom (thus forming together with the nitrogen an amide group, or, in case a ring oxygen is additionally adjacent, a carbamate group, or, in case second ring nitrogen is additionally adjacent, a urea group); and/or
  two oxo substituents at a ring sulfur ring atom (thus forming a —$SO_2$— group); and/or
  $C_{1-4}$-alkyl attached to a ring nitrogen atom having a free valency; and -$L^{10}$- independently represents
  -$C_{0-6}$-alkylene-, or —CO-$C_{0-6}$-alkylene-;

-$L^{11}$-cyano; wherein -$L^{11}$- represents-$C_{0-6}$-alkylene-; or

-$L^{13}$-$C_{1-4}$-alkyl; wherein -$L^{13}$- represents —CO—.

25) Another embodiment relates to compounds according to any one of embodiments 1) to 21), wherein the group -L—$R^6$ represents
-$L^1$-COOH; wherein
-$L^1$- represents
  -$C_{1-6}$-alkylene-, —CO-$C_{1-6}$-alkylene-, —$SO_2$-$C_{1-6}$-alkylene-, —CO—O-$C_{1-6}$-alkylene-, —CO—NH-$C_{1-6}$-alkylene-, or —$SO_2$—NH-$C_{1-6}$-alkylene-;
  —CO-$C_{1-6}$-alkylene-; wherein said $C_{1-6}$-alkylene is mono-substituted with hydroxy;
  -$C_{0-4}$-alkylene-$C_{3-8}$-cycloalkylene-$C_{0-4}$-alkylene-, —CO-$C_{0-4}$-alkylene-$C_{3-8}$-cycloalkylene-$C_{0-4}$-alkylene-, —$SO_2$-$C_{0-4}$-alkylene-$C_{3-8}$-cycloalkylene-$C_{0-4}$-alkylene-, or —CO—O-$C_{0-4}$-alkylene-$C_{3-8}$-cycloalkylene-$C_{0-4}$-alkylene-;
  —CO-$C_{0-4}$-alkylene-$Cy^1$-$C_{0-4}$-alkylene-; wherein $Cy^1$ independently represents a $C_{3-6}$-heterocycloalkylene containing one ring oxygen atom;
  —CO-$C_{1-4}$-alkylene-$X^{12}$-$C_{1-4}$-alkylene-; wherein $X^{12}$ independently represents a nitrogen atom which is unsubstituted, or mono-substituted with $C_{1-4}$-alkyl;
  —CO-$C_{2-6}$-alkenylene- or —$SO_2$-$C_{2-6}$-alkenylene-; or
  —CO-$C_{2-6}$-fluoroalkylene-;
-$L^2$-hydroxy; wherein -L2- represents
  -$C_{2-6}$-alkylene-, wherein the $C_{2-6}$-alkylene is unsubstituted, or mono-substituted with hydroxy; or
  —CO-$C_{1-4}$-alkylene-$X^{22}$-$C_{2-4}$-alkylene-; wherein $X^{22}$ represents a nitrogen atom which is independently unsubstituted, or mono-substituted with $C_{1-4}$-alkyl or $C_{3-6}$-cycloalkyl;
-$L^7$-$NR^{N5}R^{N6}$ wherein both $R^{N5}$ is hydrogen; $R^{N6}$ is hydrogen, or $C_{3-6}$-cycloalkyl; and
-$L^7$- independently represents
  —CO—, or —$SO_2$—; or -$L^9$-$HET^1$, wherein $HET^1$ represents 5- or 6-membered heteroaryl selected from pyrrolyl, pyrazolyl, imidazolyl, triazolyl, tetrazolyl, furanyl, oxazolyl, isoxazolyl; thiazolyl, isothiazolyl, oxadiazolyl, thiadiazolyl, pyridinyl, pyrimidinyl, pyridazinyl, pyrazinyl [especially pyrrolyl, triazolyl, tetrazolyl, furanyl, oxazolyl, pyridinyl, pyrimidinyl, pyridazinyl, pyrazinyl],
  wherein said $HET^1$ independently is unsubstituted or mono-, or di-substituted wherein the substituents are independently selected from $C_{1-4}$-alkyl (especially methyl); halogen; cyano; hydroxy; hydroxymethyl; -$C_{0-2}$-alkylene-$Cy^{91}$-$COOR^{O91}$ wherein $R^{O91}$ is hydrogen or $C_{1-4}$-alkyl, and wherein $CY^{91}$ represents a $C_{3-6}$-cycloalkylene group; or -$C_{0-2}$-alkylene-CO-$OR^{O92}$ wherein $R^{O92}$ is hydrogen or $C_{1-4}$-alkyl; and
-$L^9$- independently represents
  -$C_{0-6}$-alkylene-, —CO-$C_{0-6}$-alkylene-.

26) Another embodiment relates to compounds according to any one of embodiments 1) to 21), wherein the group -L—$R^6$ represents
-$L^1$-COOH; and
-$L^1$- represents
  —$CH_2$—$CH_2$—, —$CH_2$—$CH_2$—$CH_2$—, —$CH_2$—$C(CH_3)_2$—$CH_2$—, *—$CH_2$—$CH_2$—$C(CH_3)_2$—, *—$CH_2$—$CH_2$—$CH_2$—$C(CH_3)_2$—, *—CO—$CH_2$—$CH_2$—, *—CO—$CH(CH_3)$—$CH_2$—, *—CO—$CH_2$—$C(OH)(CH_3)$—, *—CO—$CH_2$—$CH_2$—$CH_2$—, *—CO—$CH_2$—$C(CH_3)_2$—, *—CO—$C(CH_3)_2$—$CH_2$—, *—$SO_2$—$CH_2$—, *—$SO_2$—$CH_2$—$CH_2$—, *—$SO_2$—$CH_2$—$CH_2$—$CH_2$—, *—$SO_2$-$CH_2$—$C(CH_3)_2$—, *—CO—O—$CH_2$—, *—CO—O—$CH(CH_3)$—, *—CO—O—$CH_2$—$C(CH_3)_2$—, *—CO—NH—$C(CH_3)_2$—$CH_2$—, *—CO—NH—$CH_2$—$C(CH_3)_2$—, *—CO—NH—CH2—$CH_2$—$C(CH_3)_2$—, *—$SO_2$—NH—$CH_2$—; *—$CH_2$—$CH_2$—$CH_2$-cyclopropane-1,1-diyl-, *—CO-cyclopropane-1,2-yl-, *—CO—$CH_2$-cyclopropane-1,1-diyl-, *—CO—$CH_2$-cyclobutane-1,1-diyl-, *—$SO_2$-cyclopropane-1,1-diyl-$CH_2$—, *—CO—O-cyclopropane-1,1-diyl-, *—CO—O—$CH_2$-cyclopropane-1,1-diyl-;
  *—CO—$CH_2$-(tetrahydro-2H-pyran-4,4-diyl);
  *—CO—$CH_2$—N(n-butyl)—$CH_2$—;
  *—$SO_2$—CH═CH—, *—CO—$C(CH_2)$—$CH_2$—; or
  *—CO—$CF_2$—$CH_2$—;
-$L^2$-hydroxy; wherein -$L^2$- represents
  *—$CH_2$—$CH(OH)$—$CH_2$—; or
  *—CO—$CH_2$—NH—$CH_2$—$CH_2$—, *—CO—$CH_2$—NH—$CH(CH_3)$—$CH_2$—, *—CO—$CH_2$—NH—$CH_2$—$CH(CH_3)$—;
-$L^7$—$NH_2$; wherein
-$L^7$- represents
  —$SO_2$—; or
-$L^9$-$HET^1$, wherein -$L^9$-$HET_1$ represents

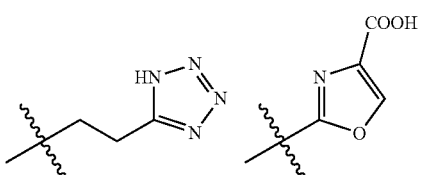

-continued

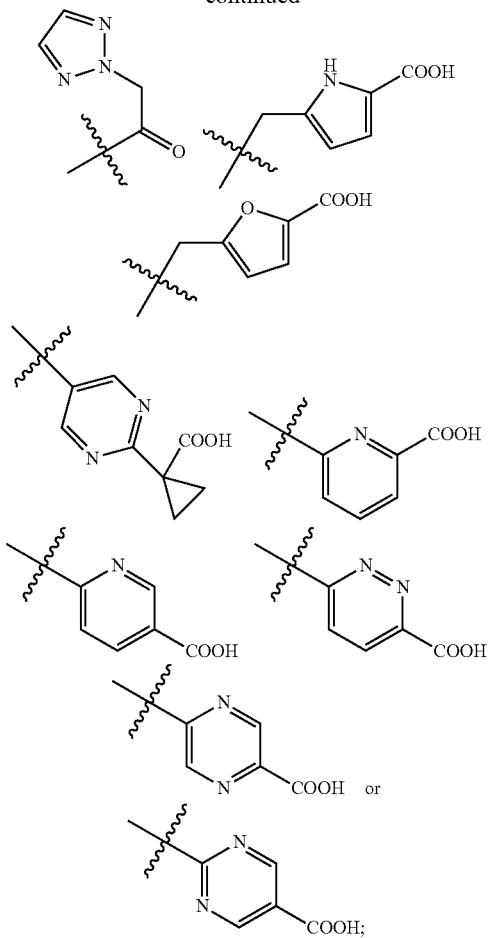

or, in addition to the above-listed groups, the group -L—R⁶ represents

-L⁷—NH-cyclopropyl; wherein

-L⁷- represents

—CO—;

wherein in the above groups the asterisks indicate the bond which is connected to the rest of the molecule.

27) The invention, thus, relates to compounds of the Formula (I) as defined in embodiment 1), or to such compounds further limited by the characteristics of any one of embodiments 2) to 26), under consideration of their respective dependencies; to pharmaceutically acceptable salts thereof; and to the use of such compounds as further described herein below. For avoidance of any doubt, especially the following embodiments relating to the compounds of Formula (I) are thus possible and intended and herewith specifically disclosed in individualized form:

1, 2+1, 5+1, 5+2+1, 6+1, 6+2+1, 6+5+1, 6+5+2+1, 8+1, 8+2+1, 8+5+1, 8+5+2+1, 9+1, 11+1, 12+1, 12+2+1, 12+5+1, 12+5+2+1, 12+6+1, 12+6+2+1, 12+6+5+1, 12+6+5+2+1, 12+8+1, 12+8+2+1, 12+8+5+1, 12+8+5+2+1, 12+9+1, 12+11+1, 14+1, 14+12+1, 14+12+2+1, 14+12+5+1, 14+12+5+2+1, 14+12+6+1, 14+12+6+2+1, 14+12+6+5+1, 14+12+6+5+2+1, 14+12+8+1, 14+12+8+2+1, 14+12+8+5+1, 14+12+8+5+2+1, 14+12+9+1, 14+12+11+1, 18+1, 18+12+1, 18+12+2+1, 18+12+5+1, 18+12+5+2+1, 18+12+6+1, 18+12+6+2+1, 18+12+6+5+1, 18+12+6+5+2+1, 18+12+8+1, 18+12+8+2+1, 18+12+8+5+1, 18+12+8+5+2+1, 18+12+9+1, 18+12+11+1, 18+14+1, 18+14+12+1, 18+14+12+2+1, 18+14+12+5+1, 18+14+12+5+2+1, 18+14+12+6+1, 18+14+12+6+2+1, 18+14+12+6+5+1, 18+14+12+6+5+2+1, 18+14+12+8+1, 18+14+12+8+2+1, 18+14+12+8+5+1, 18+14+12+8+5+2+1, 18+14+12+9+1, 18+14+12+11+1, 19+1, 19+2+1, 19+5+1, 19+5+2+1, 19+6+1, 19+6+2+1, 19+6+5+1, 19+6+5+2+1, 19+8+1, 19+8+2+1, 19+8+5+1, 19+8+5+2+1, 19+9+1, 19+11+1, 21+1, 21+2+1, 21+5+1, 21+5+2+1, 21+6+1, 21+6+2+1, 21+6+5+1, 21+6+5+2+1, 21+8+1, 21+8+2+1, 21+8+5+1, 21+8+5+2+1, 21+9+1, 21+11+1, 21+12+1, 21+12+2+1, 21+12+5+1, 21+12+5+2+1, 21+12+6+1, 21+12+6+2+1, 21+12+6+5+1, 21+12+6+5+2+1, 21+12+8+1, 21+12+8+2+1, 21+12+8+5+1, 21+12+8+5+2+1, 21+12+9+1, 21+12+11+1, 21+14+1, 21+14+12+1, 21+14+12+2+1, 21+14+12+5+1, 21+14+12+5+2+1, 21+14+12+6+1, 21+14+12+6+2+1, 21+14+12+6+5+1, 21+14+12+6+5+2+1, 21+14+12+8+1, 21+14+12+8+2+1, 21+14+12+8+5+1, 21+14+12+8+5+2+1, 21+14+12+9+1, 21+14+12+11+1, 21+18+1, 21+18+12+1, 21+18+12+2+1, 21+18+12+5+1, 21+18+12+5+2+1, 21+18+12+6+1, 21+18+12+6+2+1, 21+18+12+6+5+1, 21+18+12+6+5+2+1, 21+18+12+8+1, 21+18+12+8+2+1, 21+18+12+8+5+1, 21+18+12+8+5+2+1, 21+18+12+9+1, 21+18+12+11+1, 21+18+14+1, 21+18+14+12+1, 21+18+14+12+2+1, 21+18+14+12+5+1, 21+18+14+12+5+2+1, 21+18+14+12+6+1, 21+18+14+12+6+2+1, 21+18+14+12+6+5+1, 21+18+14+12+6+5+2+1, 21+18+14+12+8+1, 21+18+14+12+8+2+1, 21+18+14+12+8+5+1, 21+18+14+12+8+5+2+1, 21+18+14+12+9+1, 21+18+14+12+11+1, 21+19+1, 21+19+2+1, 21+19+5+1, 21+19+5+2+1, 21+19+6+1, 21+19+6+2+1, 21+19+6+5+1, 21+19+6+5+2+1, 21+19+8+1, 21+19+8+2+1, 21+19+8+5+1, 21+19+8+5+2+1, 21+19+9+1, 21+19+11+1, 25+1, 25+2+1, 25+5+1, 25+5+2+1, 25+6+1, 25+6+2+1, 25+6+5+1, 25+6+5+2+1, 25+8+1, 25+8+2+1, 25+8+5+1, 25+8+5+2+1, 25+9+1, 25+11+1, 25+12+1, 25+12+2+1, 25+12+5+1, 25+12+5+2+1, 25+12+6+1, 25+12+6+2+1, 25+12+6+5+1, 25+12+6+5+2+1, 25+12+8+1, 25+12+8+2+1, 25+12+8+5+1, 25+12+8+5+2+1, 25+12+9+1, 25+12+11+1, 25+14+1, 25+14+12+1, 25+14+12+2+1, 25+14+12+5+1, 25+14+12+5+2+1, 25+14+12+6+1, 25+14+12+6+2+1, 25+14+12+6+5+1, 25+14+12+6+5+2+1, 25+14+12+8+1, 25+14+12+8+2+1, 25+14+12+8+5+1, 25+14+12+8+5+2+1, 25+14+12+9+1, 25+14+12+11+1, 25+18+1 25+18+12+1, 25+18+12+2+1, 25+18+12+5+1, 25+18+12+5+2+1, 25+18+12+6+1, 25+18+12+6+2+1, 25+18+12+6+5+1, 25+18+12+6+5+2+1, 25+18+12+8+1, 25+18+12+8+2+1, 25+18+12+8+5+1, 25+18+12+8+5+2+1, 25+18+12+9+1, 25+18+12+11+1, 25+18+14+1, 25+18+14+12+1, 25+18+14+12+2+1, 25+18+14+12+5+1, 25+18+14+12+5+2+1, 25+18+14+12+6+1, 25+18+14+12+6+2+1, 25+18+14+12+6+5+1, 25+18+14+12+6+5+2+1, 25+18+14+12+8+1, 25+18+14+12+8+2+1, 25+18+14+12+8+5+1, 25+18+14+12+8+5+2+1, 25+18+14+12+9+1, 25+18+14+12+11+1, 25+19+1, 25+19+2+1, 25+19+5+1, 25+19+5+2+1, 25+19+6+1, 25+19+6+2+1, 25+19+6+5+1, 25+19+6+5+2+1, 25+19+8+1, 25+19+8+2+1, 25+19+8+5+1, 25+19+8+5+2+1, 25+19+9+1, 25+19+11+1, 25+21+1, 25+21+2+1, 25+21+5+1, 25+21+5+2+1, 25+21+6+1, 25+21+6+2+1, 25+21+6+5+1, 25+21+6+5+2+1, 25+21+8+1, 25+21+8+2+1, 25+21+8+5+1, 25+21+8+5+2+1, 25+21+9+1, 25+21+11+1, 25+21+12+1, 25+21+12+2+

1, 25+21+12+5+1, 25+21+12+5+2+1, 25+21+12+6+1, 25+21+12+6+2+1, 25+21+12+6+5+1, 25+21+12+6+5+2+1, 25+21+12+8+1, 25+21+12+8+2+1, 25+21+12+8+5+1, 25+21+12+8+5+2+1, 25+21+12+9+1, 25+21+12+11+1, 25+21+14+1, 25+21+14+12+1, 25+21+14+12+2+1, 25+21+14+12+5+1, 25+21+14+12+5+2+1, 25+21+14+12+6+1, 25+21+14+12+6+2+1, 25+21+14+12+6+5+1, 25+21+14+12+6+5+2+1, 25+21+14+12+8+1, 25+21+14+12+8+2+1, 25+21+14+12+8+5+1, 25+21+14+12+8+5+2+1, 25+21+14+12+9+1, 25+21+14+12+11+1, 25+21+18+1, 25+21+18+12+1, 25+21+18+12+2+1, 25+21+18+12+5+1, 25+21+18+12+5+2+1, 25+21+18+12+6+1, 25+21+18+12+6+2+1, 25+21+18+12+6+5+1, 25+21+18+12+6+5+2+1, 25+21+18+12+8+1, 25+21+18+12+8+2+1, 25+21+18+12+8+5+1, 25+21+18+12+8+5+2+1, 25+21+18+12+9+1, 25+21+18+12+11+1, 25+21+18+14+1, 25+21+18+14+12+1, 25+21+18+14+12+2+1, 25+21+18+14+12+5+1, 25+21+18+14+12+5+2+1, 25+21+18+14+12+6+1, 25+21+18+14+12+6+2+1, 25+21+18+14+12+6+5+1, 25+21+18+14+12+6+5+2+1, 25+21+18+14+12+8+1, 25+21+18+14+12+8+2+1, 25+21+18+14+12+8+5+1, 25+21+18+14+12+8+5+2+1, 25+21+18+14+12+9+1, 25+21+18+14+12+11+1, 25+21+19+1, 25+21+19+2+1, 25+21+19+5+1, 25+21+19+5+2+1, 25+21+19+6+1, 25+21+19+6+2+1, 25+21+19+6+5+1, 25+21+19+6+5+2+1, 25+21+19+8+1, 25+21+19+8+2+1, 25+21+19+8+5+1, 25+21+19+8+5+2+1, 25+21+19+9+1, 25+21+19+11+1, 26+1, 26+2+1, 26+5+1, 26+5+2+1, 26+6+1, 26+6+2+1, 26+6+5+1, 26+6+5+2+1, 26+8+1, 26+8+2+1, 26+8+5+1, 26+8+5+2+1, 26+9+1, 26+11+1, 26+12+1, 26+12+2+1, 26+12+5+1, 26+12+5+2+1, 26+12+6+1, 26+12+6+2+1, 26+12+6+5+1, 26+12+6+5+2+1, 26+12+8+1, 26+12+8+2+1, 26+12+8+5+1, 26+12+8+5+2+1, 26+12+9+1, 26+12+11+1, 26+14+1, 26+14+12+1, 26+14+12+2+1, 26+14+12+5+1, 26+14+12+5+2+1, 26+14+12+6+1, 26+14+12+6+2+1, 26+14+12+6+5+1, 26+14+12+6+5+2+1, 26+14+12+8+1, 26+14+12+8+2+1, 26+14+12+8+5+1, 26+14+12+8+5+2+1, 26+14+12+9+1, 26+14+12+11+1, 26+18+1, 26+18+12+2+1, 26+18+12+5+1, 26+18+12+5+2+1, 26+18+12+6+1, 26+18+12+6+2+1, 26+18+12+1, 26+18+12+8+1, 26+18+12+6+5+1, 26+18+12+6+5+2+1, 26+18+12+8+1, 26+18+12+8+2+1, 26+18+12+8+5+1, 26+18+12+8+5+2+1, 26+18+12+9+1, 26+18+12+11+1, 26+18+14+1, 26+18+14+12+1, 26+18+14+12+2+1, 26+18+14+12+5+1, 26+18+14+12+5+2+1, 26+18+14+12+6+1, 26+18+14+12+6+2+1, 26+18+14+12+6+5+1, 26+18+14+12+6+5+2+1, 26+18+14+12+8+1, 26+18+14+12+8+2+1, 26+18+14+12+8+5+1, 26+18+14+12+8+5+2+1, 26+18+14+12+9+1, 26+18+14+12+11+1, 26+19+1, 26+19+2+1, 26+19+5+1, 26+19+5+2+1, 26+19+6+1, 26+19+6+2+1, 26+19+6+5+1, 26+19+6+5+2+1, 26+19+8+1, 26+19+8+2+1, 26+19+8+5+1, 26+19+8+5+2+1, 26+19+9+1, 26+19+11+1, 26+21+1, 26+21+2+1, 26+21+5+1, 26+21+5+2+1, 26+21+6+1, 26+21+6+2+1, 26+21+6+5+1, 26+21+6+5+2+1, 26+21+8+1, 26+21+8+2+1, 26+21+8+5+1, 26+21+8+5+2+1, 26+21+9+1, 26+21+11+1, 26+21+12+1, 26+21+12+2+1, 26+21+12+5+1, 26+21+12+5+2+1, 26+21+12+6+1, 26+21+12+6+2+1, 26+21+12+6+5+1, 26+21+12+6+5+2+1, 26+21+12+8+1, 26+21+12+8+2+1, 26+21+12+8+5+1, 26+21+12+8+5+2+1, 26+21+12+9+1, 26+21+12+11+1, 26+21+14+1, 26+21+14+12+1, 26+21+14+12+5+1, 26+21+14+12+5+2+1, 26+21+14+12+6+1, 26+21+14+12+1, 26+21+14+12+2+1, 26+21+14+12+6+2+1, 26+21+14+12+6+5+1, 26+21+14+12+6+5+2+1, 26+21+14+12+8+1, 26+21+14+12+8+2+1, 26+21+14+12+8+5+1, 26+21+14+12+8+5+2+1, 26+21+14+12+9+1, 26+21+14+12+11+1, 26+21+18+1, 26+21+18+12+1, 26+21+18+12+2+1, 26+21+18+12+5+1, 26+21+18+12+5+2+1, 26+21+18+12+6+1, 26+21+18+12+6+2+1, 26+21+18+12+6+5+1, 26+21+18+12+6+5+2+1, 26+21+18+12+8+1, 26+21+18+12+8+2+1, 26+21+18+12+8+5+1, 26+21+18+12+8+5+2+1, 26+21+18+12+9+1, 26+21+18+12+11+1, 26+21+18+14+1, 26+21+18+14+12+1, 26+21+18+14+12+2+1, 26+21+18+14+12+5+1, 26+21+18+14+12+5+2+1, 26+21+18+14+12+6+1, 26+21+18+14+12+6+2+1, 26+21+18+14+12+6+5+1, 26+21+18+14+12+6+5+2+1, 26+21+18+14+12+8+1, 26+21+18+14+12+8+2+1, 26+21+18+14+12+8+5+1, 26+21+18+14+12+8+5+2+1, 26+21+18+14+12+9+1, 26+21+18+14+12+11+1, 26+21+19+1, 26+21+19+2+1, 26+21+19+5+1, 26+21+19+5+2+1, 26+21+19+6+1, 26+21+19+6+2+1, 26+21+19+6+5+1, 26+21+19+6+5+2+1, 26+21+19+8+1, 26+21+19+8+2+1, 26+21+19+8+5+1, 26+21+19+8+5+2+1, 26+21+19+9+1, 26+21+19+11+1.

In the list above the numbers refer to the embodiments according to their numbering provided hereinabove whereas "+" indicates the dependency from another embodiment. The different individualized embodiments are separated by commas. In other words, "26+21+11+1" for example refers to embodiment 26) depending on embodiment 21), depending on embodiment 11), depending on embodiment 1), i.e. embodiment "26+21+11+1" corresponds to the compounds of Formula (I) as defined in embodiment 1), further limited by all the structural features of the embodiments 11), 21), and 26).

28) A second aspect of the invention relates to compounds of the Formula (I) which are compounds of Formula (II),

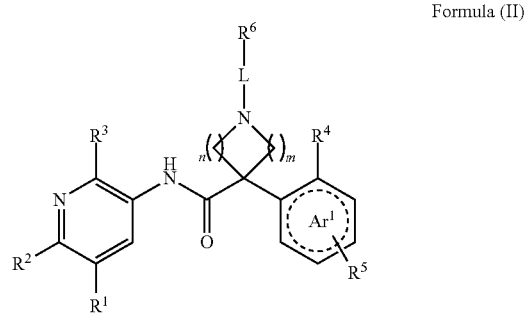

Formula (II)

wherein $R^1$, $R^2$, $R^3$, $Ar^1$, $R^4$, $R^5$, m, n, and the group -L—$R^6$ are as defined in embodiment 1);

wherein the characteristics disclosed in embodiments 2) to 27) are intended to apply mutatis mutandis also to the compounds formula (II) according to embodiment 28); wherein in particular the following embodiments are thus possible and intended and herewith specifically disclosed in individualized form:

28+2, 28+5+2, 28+5, 28+6+2, 28+6+5+2, 28+6+5, 28+6, 28+8+2, 28+8+5+2, 28+8+5, 28+8, 28+12+2, 28+12+5+2, 28+12+5, 28+12+6+2, 28+12+6+5+2, 28+12+6+5, 28+12+6, 28+12+8+2, 28+12+8+5+2, 28+12+8+5, 28+12+8, 28+12, 28+14+12+2, 28+14+12+5+2, 28+14+12+5, 28+14+12+6+2, 28+14+12+6+5+2, 28+14+12+6+5, 28+14+12+6, 28+14+12+8+2, 28+14+

12+8+5+2, 28+14+12+8+5, 28+14+12+8, 28+14+12, 28+14, 28+18+12+2, 28+18+12+5+2, 28+18+12+5, 28+18+12+6+2, 28+18+12+6+5+2, 28+18+12+6+5, 28+18+12+6, 28+18+12+8+2, 28+18+12+8+5+2, 28+18+12+8+5, 28+18+12+8, 28+18+12, 28+18+14+12+2, 28+18+14+12+5, 28+18+14+12+6+2, 28+18+14+12+6+5+2, 28+18+14+12+6+5, 28+18+14+12+5+2, 28+18+14+12+6, 28+18+14+12+8+2, 28+18+14+12+8+5+2, 28+18+14+12+8+5, 28+18+14+12+8, 28+18+14+12, 28+18+14, 28+18, 28+21+2, 28+21+5+2, 28+21+5, 28+21+6+2, 28+21+6+5+2, 28+21+6+5, 28+21+6, 28+21+8+2, 28+21+8+5+2, 28+21+8+5, 28+21+8, 28+21+12+2, 28+21+12+5+2, 28+21+12+5, 28+21+12+6+2, 28+21+12+6+5+2, 28+21+12+6+5, 28+21+12+6, 28+21+12+8+2, 28+21+12+8+5+2, 28+21+12+8+5, 28+21+12+8, 28+21+12, 28+21+14+12+2, 28+21+14+12+5+2, 28+21+14+12+5, 28+21+14+12+6+2, 28+21+14+12+6+5+2, 28+21+14+12+6+5, 28+21+14+12+6, 28+21+14+12+8+2, 28+21+14+12+8+5+2, 28+21+14+12+8+5, 28+21+14+12+8, 28+21+14+12, 28+21+14, 28+21+18+12+2, 28+21+18+12+5+2, 28+21+18+12+5, 28+21+18+12+6+2, 28+21+18+12+6+5+2, 28+21+18+12+6+5, 28+21+18+12+6, 28+21+18+12+8+2, 28+21+18+12+8+5+2, 28+21+18+12+8+5, 28+21+18+12+8, 28+21+18+12, 28+21+18+14+12+2, 28+21+18+14+12+5+2, 28+21+18+14+12+5, 28+21+18+14+12+6+2, 28+21+18+14+12+6+5+2, 28+21+18+14+12+6+5, 28+21+18+14+12+6, 28+21+18+14+12+8+2, 28+21+18+14+12+8+5+2, 28+21+18+14+12+8+5, 28+21+18+14+12+8, 28+21+18+14+12, 28+21+18+14, 28+21+18, 28+21, 28+22+2, 28+22+5+2, 28+22+5, 28+22+6+2, 28+22+6+5+2, 28+22+6+5, 28+22+6, 28+22+8+5, 28+22+8, 28+22+12+2, 28+22+12+5+2, 28+22+12+5, 28+22+8+2, 28+22+8+5+2, 28+22+12+6+5+2, 28+22+12+6+5, 28+22+12+6, 28+22+12+8+2, 28+22+12+8+5+2, 28+22+12+6+2, 28+22+12+8+5, 28+22+12+8, 28+22+12, 28+22+14+12+2, 28+22+14+12+5+2, 28+22+14+12+5, 28+22+14+12+6+2, 28+22+14+12+6+5+2, 28+22+14+12+6+5, 28+22+14+12+6, 28+22+14+12+8+2, 28+22+14+12+8+5+2, 28+22+14+12+8+5, 28+22+14+12+8, 28+22+14+12, 28+22+14, 28+22+18+12+2, 28+22+18+12+5+2, 28+22+18+12+5, 28+22+18+12+6+2, 28+22+18+12+6+5+2, 28+22+18+12+6+5, 28+22+18+12+6, 28+22+18+12+8+2, 28+22+18+12+8+5+2, 28+22+18+12+8+5, 28+22+18+12+8, 28+22+18+12, 28+22+18+14+12+2, 28+22+18+14+12+5+2, 28+22+18+14+12+5, 28+22+18+14+12+6+2, 28+22+18+14+12+6+5+2, 28+22+18+14+12+6+5, 28+22+18+14+12+6, 28+22+18+14+12+8+2, 28+22+18+14+12+8+5+2, 28+22+18+14+12+8+5, 28+22+18+14+12+8, 28+22+18+14+12, 28+22+18+14, 28+22+18, 28+22+21+2, 28+22+21+5+2, 28+22+21+5, 28+22+21+6+2, 28+22+21+6+5+2, 28+22+21+6+5, 28+22+21+8+2, 28+22+21+8+5+2, 28+22+21+8+5, 28+22+21+8, 28+22+21+12+2, 28+22+21+6, 28+22+21+12+5+2, 28+22+21+12+5, 28+22+21+12+6+2, 28+22+21+12+6+5+2, 28+22+21+12+6+5, 28+22+21+12+6, 28+22+21+12+8+2, 28+22+21+12+8+5+2, 28+22+21+12+8+5, 28+22+21+12+8, 28+22+21+12, 28+22+21+14+12+2, 28+22+21+14+12+5+2, 28+22+21+14+12+5, 28+22+21+14+12+6+2, 28+22+21+14+12+6+5+2, 28+22+21+14+12+6+5, 28+22+21+14+12+6, 28+22+21+14+12+8+2, 28+22+21+14+12+8+5+2, 28+22+21+14+12+8+5, 28+22+21+14+12+8, 28+22+21+14+12, 28+22+21+14, 28+22+21+18+12+2, 28+22+21+18+12+5+2, 28+22+21+18+12+5, 28+22+21+18+12+6+2, 28+22+21+18+12+6+5+2, 28+22+21+18+12+6+5, 28+22+21+18+12+6, 28+22+21+18+12+8+2, 28+22+21+18+12+8+5+2, 28+22+21+18+12+8+5, 28+22+21+18+12+8, 28+22+21+18+12, 28+22+21+18+14+12+2, 28+22+21+18+14+12+5+2, 28+22+21+18+14+12+5, 28+22+21+18+14+12+6+2, 28+22+21+18+14+12+6+5+2, 28+22+21+18+14+12+6+5, 28+22+21+18+14+12+6, 28+22+21+18+14+12+8+2, 28+22+21+18+14+12+8+5+2, 28+22+21+18+14+12+8+5, 28+22+21+18+14+12+8, 28+22+21+18+14+12, 28+22+21+18+14, 28+22+21+18, 28+22+21, 28+22, 28+26+2, 28+26+5+2, 28+26+5, 28+26+6+2, 28+26+6+5+2, 28+26+6+5, 28+26+6, 28+26+8+2, 28+26+8+5+2, 28+26+8+5, 28+26+8, 28+26+12+2, 28+26+12+5+2, 28+26+12+5, 28+26+12+6+2, 28+26+12+6+5+2, 28+26+12+6+5, 28+26+12+6, 28+26+12+8+2, 28+26+12+8+5+2, 28+26+12+8+5, 28+26+12+8, 28+26+12, 28+26+14+12+2, 28+26+14+12+5+2, 28+26+14+12+5, 28+26+14+12+6+2, 28+26+14+12+6+5+2, 28+26+14+12+6+5, 28+26+14+12+6, 28+26+14+12+8+2, 28+26+14+12+8+5+2, 28+26+14+12+8+5, 28+26+14+12+8, 28+26+14+12, 28+26+14, 28+26+18+12+2, 28+26+18+12+5+2, 28+26+18+12+5, 28+26+18+12+6+2, 28+26+18+12+6+5+2, 28+26+18+12+6+5, 28+26+18+12+6, 28+26+18+12+8+2, 28+26+18+12+8+5+2, 28+26+18+12+8+5, 28+26+18+12+8, 28+26+18+12, 28+26+18+14+12+2, 28+26+18+14+12+5+2 28+26+18+14+12+5, 28+26+18+14+12+6+2, 28+26+18+14+12+6+5+2, 28+26+18+14+12+6+5, 28+26+18+14+12+6, 28+26+18+14+12+8+2, 28+26+18+14+12+8+5+2, 28+26+18+14+12+8+5, 28+26+18+14+12+8, 28+26+18+14+12, 28+26+18+14, 28+26+18, 28+26+21+2, 28+26+21+5+2, 28+26+21+5, 28+26+21+6+2, 28+26+21+6+5+2, 28+26+21+6+5, 28+26+21+6, 28+26+21+8+2, 28+26+21+8+5+2, 28+26+21+8+5, 28+26+21+8, 28+26+21+12+2, 28+26+21+12+5+2, 28+26+21+12+5, 28+26+21+12+6+2, 28+26+21+12+6+5+2, 28+26+21+12+6+5, 28+26+21+12+6, 28+26+21+12+8+2, 28+26+21+12+8+5+2, 28+26+21+12+8+5, 28+26+21+12+8, 28+26+21+12, 28+26+21+14+12+2, 28+26+21+14+12+5+2, 28+26+21+14+12+5, 28+26+21+14+12+6+2, 28+26+21+14+12+6+5+2, 28+26+21+14+12+6+5, 28+26+21+14+12+6, 28+26+21+14+12+8+2, 28+26+21+14+12+8+5+2, 28+26+21+14+12+8+5, 28+26+21+14+12+8, 28+26+21+14+12, 28+26+21+14, 28+26+21+18+12+2, 28+26+21+18+12+5+2, 28+26+21+18+12+5, 28+26+21+18+12+6+2, 28+26+21+18+12+6+5+2, 28+26+21+18+12+6+5, 28+26+21+18+12+6, 28+26+21+18+12+8+2, 28+26+21+18+12+8+5+2, 28+26+21+18+12+8+5, 28+26+21+18+12+8, 28+26+21+18+12, 28+26+21+18+14+12+2, 28+26+21+18+14+12+5+2, 28+26+21+18+14+12+5, 28+26+21+18+14+12+6+2, 28+26+21+18+14+12+6+5+2, 28+26+21+18+14+12+6+5, 28+26+21+18+14+12+6, 28+26+21+18+14+12+8+2, 28+26+21+18+14+12+8+5+2, 28+26+21+18+14+12+8+5, 28+26+21+18+14+12+8, 28+26+21+18+14+12, 28+26+21+18+14, 28+26+21+18, 28+26+21, 28+26.

In the list above the numbers refer to the embodiments according to their numbering provided hereinabove whereas "+" indicates the limitations as outlined above.

29) A third aspect of the invention relates to compounds of the Formula (I) which are compounds of Formula (III),

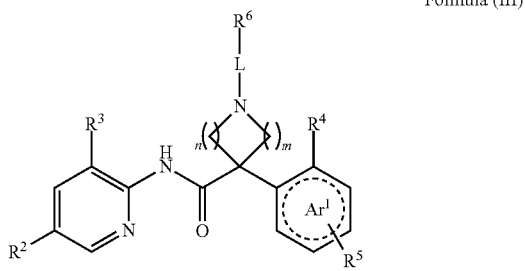

Formula (III)

wherein $R^2$, $R^3$, $Ar^1$, $R^4$, $R^5$, m, n, and the group -L—$R^6$ are as defined in embodiment 1);
wherein the characteristics disclosed in embodiments 2) to 27) are intended to apply mutatis mutandis also to the compounds formula (III) according to embodiment 29); wherein in particular the following embodiments are thus possible and intended and herewith specifically disclosed in individualized form:
29+8, 29+11, 29+12+8, 29+12+11, 29+12, 29+15+8, 29+15+11, 29+15+12+8, 29+15+12+11, 29+15+12, 29+15, 29+18+8, 29+18+11, 29+18+12+8, 29+18+12+11, 29+18+12, 29+18+15+8, 29+18+15+11, 29+18+15+12+8, 29+18+15+12+11, 29+18+15+12, 29+18+15, 29+18, 29+21+8, 29+21+11, 29+21+12+8, 29+21+12+11, 29+21+12, 29+21+15+8, 29+21+15+11, 29+21+15+12+8, 29+21+15+12+11, 29+21+15+12, 29+21+15, 29+21+18+8, 29+21+18+11, 29+21+18+12+8, 29+21+18+12+11, 29+21+18+12, 29+21+18+15+8, 29+21+18+15+11, 29+21+18+15+12+8, 29+21+18+15+12+11, 29+21+18+15+12, 29+21+18+15, 29+21+18, 29+21, 29+26+8, 29+26+11, 29+26+12+8, 29+26+12+11, 29+26+12, 29+26+15+8, 29+26+15+11, 29+26+15+12+8, 29+26+15+12+11, 29+26+15+12, 29+26+15, 29+26+18+8, 29+26+18+11, 29+26+18+12+8, 29+26+18+12+11, 29+26+18+12, 29+26+18+15+8, 29+26+18+15+11, 29+26+18+15+12+8, 29+26+18+15+12+11, 29+26+18+15+12, 29+26+18+15, 29+26+18, 29+26+21+8, 29+26+21+11, 29+26+21+12+8, 29+26+21+12+11, 29+26+21+12, 29+26+21+15+8, 29+26+21+15+11, 29+26+21+15+12+8, 29+26+21+15+12+11, 29+26+21+15+12, 29+26+21+15, 29+26+21+18+8, 29+26+21+18+11, 29+26+21+18+12+8, 29+26+21+18+12+11, 29+26+21+18+12, 29+26+21+18+15+8, 29+26+21+18+15+11, 29+26+21+18+15+12+8, 29+26+21+18+15+12+11, 29+26+21+18+15+12, 29+26+21+18+15, 29+26+21+18, 29+26+21, 29+26, 29.

In the list above the numbers refer to the embodiments according to their numbering provided hereinabove whereas "+" indicates the limitations as outlined above.

30) Another embodiment relates to compounds of formula (III) according to embodiment 29), wherein
$R^2$ is halogen (especially chloro), methyl, ethyl, methoxy or ethoxy;
$R^3$ is $C_{1-3}$-alkoxy (especially methoxy) or $C_{1-3}$-fluoroalkoxy (especially difluoromethoxy);
$Ar^1$ represents phenyl, or 6-membered heteroaryl containing one or two nitrogen atoms (especially pyridinyl); (notably, $Ar^1$ represents phenyl), wherein said group $Ar^1$ is substituted with $R^4$ and $R^5$, wherein
$R^4$ is n-propyl, isopropyl, or $C_{3-6}$-cycloalkyl optionally containing a ring oxygen atom (especially cyclopropyl, cyclobutyl, cyclopentyl, cyclohexyl, tetrahydro-2H-pyran-4-yl); [wherein it is understood that said substituent $R^4$ is attached in ortho-position with regard to the point of the attachment of the rest of the molecule] (wherein $R^4$ is in particular isopropyl) and $R^5$ represents hydrogen or fluoro (wherein $R^5$ is in particular hydrogen);
m and n independently represent the integer 1 or 2 (especially both m and n represent the integer 1); and the group -L—$R^6$ represents
hydrogen;
-$L^1$—CO—$R^{C11}$ wherein $R^{C11}$ independently represents hydroxy; —O-benzyl; —O-$C_{1-6}$-alkyl; $C_1$-fluoroalkyl; or —$NR^{N11}R^{N12}$; wherein independently $R^{N11}$ is hydrogen or $C_{1-4}$-alkyl, and $R^{N12}$ is hydrogen, $C_{1-4}$-alkyl, —$SO_2$-$C_{1-6}$-alkyl, or —O—$R^{O11}$, wherein $R^{O11}$ independently represents hydrogen, $C_{1-6}$-alkyl, or benzyl; and
-$L^1$- independently represents
-$C_{1-6}$-alkylene-, —CO-$C_{1-6}$-alkylene-, —$SO_2$-$C_{1-6}$-alkylene-, —CO—O-$C_{1-6}$-alkylene-, —CO—NH-$C_{1-6}$-alkylene-, or —$SO_2$—NH-$C_{1-6}$-alkylene-;
-$C_{0-4}$-alkylene-$C_{3-8}$-cycloalkylene-$C_{0-4}$-alkylene-, —CO-$C_{0-4}$-alkylene-$C_{3-8}$-cycloalkylene-$C_{0-4}$-alkylene-, —$SO_2$-$C_{0-4}$-alkylene-$C_{3-8}$-cycloalkylene-$C_{0-4}$-alkylene-, —CO—NH-$C_{0-4}$-alkylene-$C_{3-8}$-cycloalkylene-$C_{0-4}$-alkylene-, or —CO—O-$C_{0-4}$-alkylene-$C_{3-8}$-cycloalkylene-$C_{0-4}$-alkylene-;
-$L^2$-hydroxy; wherein -L2- represents
—CO-$C_{1-6}$-alkylene- or —$SO_2$-$C_{1-6}$-alkylene-; wherein in the above groups said $C_{1-6}$-alkylene independently is unsubstituted, or mono-substituted with hydroxy, $C_1$-fluoroalkyl, or —$NR^{N21}R^{N22}$ wherein independently $R^{N21}$ is hydrogen or $C_{1-4}$-alkyl, and $R^{N22}$ is hydrogen, $C_{1-4}$-alkyl or —CO—O-$C_{1-4}$-alkyl;
-$C_{2-6}$-alkylene-, —CO—O-$C_{2-6}$-alkylene-, —CO—NH-$C_{2-6}$-alkylene-, or —$SO_2$—NH-$C_{2-6}$-alkylene-, wherein in the above groups said $C_{2-6}$-alkylene independently is unsubstituted, or mono-substituted with hydroxy, $C_1$-fluoroalkyl, or —$NR^{N23}R^{N24}$ wherein independently $R^{N23}$ is hydrogen or $C_{1-4}$-alkyl, and $R^{N24}$ is hydrogen, $C_{1-4}$-alkyl or —CO—O-$C_{1-4}$-alkyl;
-$C_{0-4}$-alkylene-$C_{3-6}$-cycloalkylene-$C_{0-4}$-alkylene-, —CO-$C_{0-4}$-alkylene-$C_{3-6}$-cycloalkylene-$C_{0-4}$-alkylene-, or —$SO_2$-$C_{0-4}$-alkylene-$C_{3-6}$-cycloalkylene-$C_{0-4}$-alkylene-;
-$L^7$—$NR^{N5}R^{N6}$ wherein $R^{N5}$ is hydrogen or $C_{1-4}$-alkyl (especially hydrogen); $R^{N6}$ is hydrogen, $C_{1-4}$-alkyl, —CO-$C_{1-4}$-alkyl, $C_{1-3}$-fluoroalkyl, or $C_{3-6}$-cycloalkyl (especially hydrogen); and
-$L^7$-independently represents
—CO—, or —$SO_2$—;
-L9-$HET^1$, wherein $HET^1$ represents 5- or 6-membered heteroaryl (especially pyrrolyl, pyrazolyl, imidazolyl, triazolyl, tetrazolyl, furanyl, oxazolyl, isoxazolyl; thiazolyl, isothiazolyl, oxadiazolyl, thiadiazolyl, pyridinyl, pyrimidinyl, pyridazinyl, pyrazinyl), wherein said $HET^1$ independently is unsubstituted or mono-, or di-substituted wherein the substituents are independently selected from $C_{1-4}$-alkyl (especially methyl), halogen, cyano, hydroxy, hydroxymethyl, and -$C_{0-2}$-alkylene-$Cy^{91}$-COO$R^{O91}$ wherein $R^{O91}$ is hydrogen or $C_{1-4}$-alkyl, and wherein $Cy^{91}$ represents a $C_{3-6}$-cycloalkylene group; or-$C_{0-2}$-alkylene-CO-OR$^{O92}$ wherein $R^{O92}$ is hydrogen or $C_{1-4}$-alkyl; and -$L^9$- independently represents
-$C_{0-6}$-alkylene-, —CO-$C_{0-6}$-alkylene-, —$SO_2$-$C_{0-6}$-alkylene-, —CO—O-$C_{1-6}$-alkylene-, —CO—NH-$C_{1-6}$-alkylene-, or —$SO_2$—NH-$C_{1-6}$-alkylene-; or
-$L^{10}$-$C_{4-6}$-heterocyclyl, wherein the $C_{4-6}$-heterocyclyl independently contains one or two ring heteroatoms independently selected from nitrogen, sulfur and oxygen; wherein in the above groups said $C_{4-6}$-heterocyclyl independently is unsubstituted, or mono-, di-, or tri-substituted wherein the substituents are independently selected from:
one or two oxo substituents each attached to a ring carbon atom in alpha position to a ring nitrogen atom (thus forming together with the nitrogen an amide group, or, in case a ring oxygen is additionally adjacent, a carbamate group, or, in case second ring nitrogen is additionally adjacent, a urea group); and/or
two methyl substituents attached to a ring carbon atom in alpha position to a ring nitrogen atom or a ring oxygen atom (thus forming together with the nitrogen a —C(CH$_3$)$_2$—N— or with the oxygen a- C(CH$_3$)$_2$—O— group); and/or
two oxo substituents at a ring sulfur ring atom (thus forming a —$SO_2$— group); and/or
$C_{1-4}$-alkyl, $C_{1-3}$-alkoxy-$C_{2-4}$-alkyl, $C_{2-3}$-fluoroalkyl, or —CO-$C_{1-4}$-alkyl attached to a ring nitrogen atom having a free valency; and
-$L^{10}$- independently represents
-$C_{0-6}$-alkylene-, —CO-$C_{0-6}$-alkylene-, —$SO_2$-$C_{0-6}$-alkylene-, —CO—O-$C_{1-6}$-alkylene-, —CO—NH-$C_{1-6}$-alkylene-, or —$SO_2$—NH-$C_{1-6}$-alkylene-.

31) Another embodiment relates to compounds of formula (III) according to embodiment 29) or 30), wherein R2 is halogen (especially chloro), methyl, or methoxy.

32) Another embodiment relates to compounds of formula (III) according to any one of embodiments 29) to 31), wherein $R^4$ is isopropyl.

33) Another embodiment relates to compounds of formula (III) according to any one of embodiments 29) to 32), wherein the group -L—$R^6$ represents:
hydrogen;
-$L^1$—CO—$R^{C11}$ wherein $R^{C11}$ independently represents hydroxy; —O-benzyl; or —O-$C_{1-6}$-alkyl; and
-$L^1$- independently represents
-$C_{1-6}$-alkylene-, —CO-$C_{1-6}$-alkylene-, —$SO_2$-$C_{1-6}$-alkylene-, —CO—O-$C_{1-6}$-alkylene-, —CO—NH-$C_{1-6}$-alkylene-, or —$SO_2$—NH-$C_{1-6}$-alkylene-;
-$C_{0-4}$-alkylene-$C_{3-8}$-cycloalkylene-$C_{0-4}$-alkylene-, —CO-$C_{0-4}$-alkylene-$C_{3-8}$-cycloalkylene-$C_{0-4}$-alkylene-, —$SO_2$-$C_{0-4}$-alkylene-$C_{3-8}$-cycloalkylene-$C_{0-4}$-alkylene-, —CO—NH-$C_{0-4}$-alkylene-$C_{3-8}$-cycloalkylene-$C_{0-4}$-alkylene-, or —CO—O-$C_{0-4}$-alkylene-$C_{3-8}$-cycloalkylene-$C_{0-4}$-alkylene-;
-$L^7$-NR$^{N5}$R$^{N6}$ wherein R$^{N5}$ is hydrogen or $C_{1-4}$-alkyl (especially hydrogen); R$^{N6}$ is hydrogen, $C_{1-4}$-alkyl, —CO-$C_{1-4}$-alkyl, $C_{1-3}$-fluoroalkyl, or $C_{3-6}$-cycloalkyl (especially hydrogen); and
-$L^7$- independently represents
—CO—, or —$SO_2$—; or
-$L^{10}$-$C_{4-6}$-heterocyclyl, wherein the $C_{4-6}$-heterocyclyl independently contains one or two ring heteroatoms independently selected from nitrogen, sulfur and oxygen; wherein in the above groups said $C_{4-6}$-heterocyclyl independently is unsubstituted, or mono-, di-, or tri-substituted wherein the substituents are independently selected from:
one or two oxo substituents each attached to a ring carbon atom in alpha position to a ring nitrogen atom (thus forming together with the nitrogen an amide group, or, in case a ring oxygen is additionally adjacent, a carbamate group, or, in case second ring nitrogen is additionally adjacent, a urea group); and
-$L^{10}$- independently represents
-$C_{0-6}$-alkylene-, —CO-$C_{0-6}$-alkylene-, —$SO_2$-$C_{0-6}$-alkylene-, —CO—O-$C_{1-6}$-alkylene-, —CO—NH-$C_{1-6}$-alkylene-, or —$SO_2$—NH-$C_{1-6}$-alkylene-.

34) Another embodiment relates to compounds of Formula (I) according to embodiment 1), which are selected from the following compounds:
N-(2-(difluoromethoxy)-6-methylpyridin-3-yl)-3-(2-isopropylphenyl)azetidine-3-carboxamide;
N-(2-(difluoromethoxy)-6-methylpyridin-3-yl)-4-(2-isopropylphenyl)piperidine-4-carboxamide;
N-(2-(difluoromethoxy)-6-methylpyridin-3-yl)-3-(2-isopropylphenyl)pyrrolidine-3-carboxamide;
1-(2-aminoethyl)-N-(2-(difluoromethoxy)-6-methylpyridin-3-yl)-3-(2-isopropylphenyl)azetidine-3-carboxamide;
N-(2-(difluoromethoxy)-6-methylpyridin-3-yl)-1-(2-hydroxyethyl)-3-(2-isopropylphenyl)azetidine-3-carboxamide;
N-(2-(difluoromethoxy)-6-methylpyridin-3-yl)-1-(3-hydroxypropyl)-3-(2-isopropylphenyl)azetidine-3-carboxamide;
1-cyano-N-(2-(difluoromethoxy)-6-methylpyridin-3-yl)-3-(2-isopropylphenyl)azetidine-3-carboxamide;
1-(3-(1H-tetrazol-5-yl)propyl)-N-(2-(difluoromethoxy)-6-methylpyridin-3-yl)-3-(2-isopropylphenyl)azetidine-3-carboxamide;
N-(2-(difluoromethoxy)-6-methylpyridin-3-yl)-1-(3-hydroxy-3-methylbutyl)-3-(2-isopropylphenyl)azetidine-3-carboxamide;
N-(2-(difluoromethoxy)-6-methylpyridin-3-yl)-1-(2-(1-hydroxycyclopropyl)ethyl)-3-(2-isopropylphenyl)azetidine-3-carboxamide;
1-(2-aminopropyl)-N-(2-(difluoromethoxy)-6-methylpyridin-3-yl)-3-(2-isopropylphenyl)azetidine-3-carboxamide;
3-(3-((2-(difluoromethoxy)-6-methylpyridin-3-yl)carbamoyl)-3-(2-isopropylphenyl)azetidin-1-yl)propanoic acid;
1-(2-cyanoethyl)-N-(2-(difluoromethoxy)-6-methylpyridin-3-yl)-3-(2-isopropylphenyl)azetidine-3-carboxamide;
(R)-N-(2-(difluoromethoxy)-6-methylpyridin-3-yl)-1-(2,3-dihydroxypropyl)-3-(2-isopropylphenyl)azetidine-3-carboxamide;
(R)-N-(2-(difluoromethoxy)-6-methylpyridin-3-yl)-1-(2,3-dihydroxypropyl)-4-(2-isopropylphenyl)piperidine-4-carboxamide;
N-(2-(difluoromethoxy)-6-methylpyridin-3-yl)-3-(2-isopropylphenyl)-1-(oxetan-3-yl)azetidine-3-carboxamide;
4-(3-((2-(difluoromethoxy)-6-methylpyridin-3-yl)carbamoyl)-3-(2-isopropylphenyl)azetidin-1-yl)butanoic acid;
4-(3-((2-(difluoromethoxy)-6-methylpyridin-3-yl)carbamoyl)-3-(2-isopropylphenyl)azetidin-1-yl)-2,2-dimethylbutanoic acid;
4-(3-((2-(difluoromethoxy)-6-methylpyridin-3-yl)carbamoyl)-3-(2-isopropylphenyl)azetidin-1-yl)-3,3-dimethylbutanoic acid;
5-((3-((2-(difluoromethoxy)-6-methylpyridin-3-yl)carbamoyl)-3-(2-isopropylphenyl)azetidin-1-yl)methyl)-1H-pyrrole-2-carboxylic acid;

5-((3-((2-(difluoromethoxy)-6-methylpyridin-3-yl)carbamoyl)-3-(2-isopropylphenyl)azetidin-1-yl)methyl)furan-2-carboxylic acid;

N-(2-(difluoromethoxy)-6-methylpyridin-3-yl)-1-(4-hydroxy-4-methylpentyl)-3-(2-isopropylphenyl)azetidine-3-carboxamide;

5-(3-((2-(difluoromethoxy)-6-methylpyridin-3-yl)carbamoyl)-3-(2-isopropylphenyl)azetidin-1-yl)-2,2-dimethylpentanoic acid;

1-(3-(3-((2-(difluoromethoxy)-6-methylpyridin-3-yl)carbamoyl)-3-(2-isopropylphenyl)azetidin-1-yl)propyl)cyclopropane-1-carboxylic acid;

N-(2-(difluoromethoxy)-6-methylpyridin-3-yl)-3-(2-isopropylphenyl)-1-(2-(methylsulfonamido)ethyl)azetidine-3-carboxamide;

(S)-N-(2-(difluoromethoxy)-6-methylpyridin-3-yl)-1-(2-hydroxy-3-(2-hydroxyacetamido)propyl)-3-(2-isopropylphenyl)azetidine-3-carboxamide;

1-(cyanomethyl)-N-(2-(difluoromethoxy)-6-methylpyridin-3-yl)-3-(2-isopropylphenyl)azetidine-3-carboxamide;

1-(2-(1H-tetrazol-5-yl)ethyl)-N-(2-(difluoromethoxy)-6-methylpyridin-3-yl)-3-(2-isopropylphenyl)azetidine-3-carboxamide;

1-(4-cyanobutanoyl)-N-(2-(difluoromethoxy)-6-methylpyridin-3-yl)-3-(2-isopropylphenyl)azetidine-3-carboxamide;

1-acetyl-N-(2-(difluoromethoxy)-6-methylpyridin-3-yl)-3-(2-isopropylphenyl)azetidine-3-carboxamide;

N-(2-(difluoromethoxy)-6-methylpyridin-3-yl)-3-(2-isopropylphenyl)-1-(3-sulfamoylpropanoyl)azetidine-3-carboxamide;

N-(2-(difluoromethoxy)-6-methylpyridin-3-yl)-3-(2-isopropylphenyl)-1-(2-(N-methylsulfamoyl)acetyl)azetidine-3-carboxamide;

N-(2-(difluoromethoxy)-6-methylpyridin-3-yl)-3-(2-isopropylphenyl)-1-((methylsulfonyl)glycyl)azetidine-3-carboxamide;

N-(2-(difluoromethoxy)-6-methylpyridin-3-yl)-3-(2-isopropylphenyl)-1-(N-methyl-N-sulfamoylglycyl)azetidine-3-carboxamide;

N-(2-(difluoromethoxy)-6-methylpyridin-3-yl)-3-(2-isopropylphenyl)-1-(5,5,5-trifluoro-4-oxopentanoyl)azetidine-3-carboxamide;

N-(2-(difluoromethoxy)-6-methylpyridin-3-yl)-4-(2-isopropylphenyl)-1-(5,5,5-trifluoro-4-oxopentanoyl)piperidine-4-carboxamide;

N-(2-(difluoromethoxy)-6-methylpyridin-3-yl)-1-(2-(3-hydroxyoxetan-3-yl)acetyl)-4-(2-isopropylphenyl)piperidine-4-carboxamide;

N-(2-(difluoromethoxy)-6-methylpyridin-3-yl)-1-(3-hydroxyisoxazole-5-carbonyl)-3-(2-isopropylphenyl)azetidine-3-carboxamide [tautomeric form: N-(2-(difluoromethoxy)-6-methylpyridin-3-yl)-1-(3-oxo-2,3-dihydroisoxazole-5-carbonyl)-3-(2-isopropylphenyl)azetidine-3-carboxamide];

1-(2-(1H-tetrazol-1-yl)acetyl)-N-(2-(difluoromethoxy)-6-methylpyridin-3-yl)-4-(2-isopropylphenyl)piperidine-4-carboxamide;

1-(2-(2H-1,2,3-triazol-2-yl)acetyl)-N-(2-(difluoromethoxy)-6-methylpyridin-3-yl)-3-(2-isopropylphenyl)azetidine-3-carboxamide;

1-(2-(2H-1,2,3-triazol-2-yl)acetyl)-N-(2-(difluoromethoxy)-6-methylpyridin-3-yl)-4-(2-isopropylphenyl)piperidine-4-carboxamide;

N-(2-(difluoromethoxy)-6-methylpyridin-3-yl)-1-(2-(3-hydroxy-1H-pyrazol-5-yl)acetyl)-4-(2-isopropylphenyl)piperidine-4-carboxamide [and tautomeric forms thereof, such as N-(2-(difluoromethoxy)-6-methylpyridin-3-yl)-1-(2-(3-oxo-2,3-dihydro-1H-pyrazol-5-yl)acetyl)-4-(2-isopropylphenyl)piperidine-4-carboxamide];

N-(2-(difluoromethoxy)-6-methylpyridin-3-yl)-1-(2-(3-hydroxy-1H-pyrazol-4-yl)acetyl)-3-(2-isopropylphenyl)azetidine-3-carboxamide [and tautomeric forms thereof, such as N-(2-(difluoromethoxy)-6-methylpyridin-3-yl)-1-(2-(3-oxo-2,3-dihydro-1H-pyrazol-4-yl)acetyl)-3-(2-isopropylphenyl)azetidine-3-carboxamide];

N-(2-(difluoromethoxy)-6-methylpyridin-3-yl)-1-(2-(3-hydroxy-1H-pyrazol-4-yl)acetyl)-4-(2-isopropylphenyl)piperidine-4-carboxamide [and tautomeric forms thereof, such as N-(2-(difluoromethoxy)-6-methylpyridin-3-yl)-1-(2-(3-oxo-2,3-dihydro-1H-pyrazol-4-yl)acetyl)-4-(2-isopropylphenyl)piperidine-4-carboxamide];

1-(L-alanyl)-N-(2-(difluoromethoxy)-6-methylpyridin-3-yl)-3-(2-isopropylphenyl)azetidine-3-carboxamide;

N-(2-(difluoromethoxy)-6-methylpyridin-3-yl)-4-(2-isopropylphenyl)-1-((2-methoxyethyl)glycyl)piperidine-4-carboxamide;

N-(2-(difluoromethoxy)-6-methylpyridin-3-yl)-1-((2-hydroxyethyl)glycyl)-4-(2-isopropylphenyl)piperidine-4-carboxamide;

N-(2-(difluoromethoxy)-6-methylpyridin-3-yl)-1-((2-hydroxyethyl)glycyl)-3-(2-isopropylphenyl)azetidine-3-carboxamide;

N-(2-(difluoromethoxy)-6-methylpyridin-3-yl)-3-(2-isopropylphenyl)-1-((2-methoxyethyl)glycyl)azetidine-3-carboxamide;

(R)-N-(2-(difluoromethoxy)-6-methylpyridin-3-yl)-1-((R)-(2-hydroxypropyl)glycyl)-3-(2-isopropylphenyl)azetidine-3-carboxamide;

(S)-N-(2-(difluoromethoxy)-6-methylpyridin-3-yl)-1-((S)-(2-hydroxypropyl)glycyl)-3-(2-isopropylphenyl)azetidine-3-carboxamide;

(R)-N-(2-(difluoromethoxy)-6-methylpyridin-3-yl)-1-((R)-(1-hydroxypropan-2-yl)glycyl)-3-(2-isopropylphenyl)azetidine-3-carboxamide;

(S)-N-(2-(difluoromethoxy)-6-methylpyridin-3-yl)-1-((R)-(1-hydroxypropan-2-yl)glycyl)-3-(2-isopropylphenyl)azetidine-3-carboxamide;

3-(3-((2-(difluoromethoxy)-6-methylpyridin-3-yl)carbamoyl)-3-(2-isopropylphenyl)azetidin-1-yl)-3-oxopropanoic acid;

3-(4-((2-(difluoromethoxy)-6-methylpyridin-3-yl)carbamoyl)-4-(2-isopropylphenyl)piperidin-1-yl)-3-oxopropanoic acid;

4-(3-((2-(difluoromethoxy)-6-methylpyridin-3-yl)carbamoyl)-3-(2-isopropylphenyl)azetidin-1-yl)-4-oxobutanoic acid;

4-(4-((2-(difluoromethoxy)-6-methylpyridin-3-yl)carbamoyl)-4-(2-isopropylphenyl)piperidin-1-yl)-4-oxobutanoic acid;

(S)-4-(3-((2-(difluoromethoxy)-6-methylpyridin-3-yl)carbamoyl)-3-(2-isopropylphenyl)azetidin-1-yl)-2-methyl-4-oxobutanoic acid;

4-(3-((2-(difluoromethoxy)-6-methylpyridin-3-yl)carbamoyl)-3-(2-isopropylphenyl)azetidin-1-yl)-2,2-dimethyl-4-oxobutanoic acid;

1-(2-(3-((2-(difluoromethoxy)-6-methylpyridin-3-yl)carbamoyl)-3-(2-isopropylphenyl)azetidin-1-yl)-2-oxoethyl)cyclopropane-1-carboxylic acid;

1-(2-(3-((2-(difluoromethoxy)-6-methylpyridin-3-yl)carbamoyl)-3-(2-isopropylphenyl)azetidin-1-yl)-2-oxoethyl)cyclobutane-1-carboxylic acid;

(R)-4-(3-((2-(difluoromethoxy)-6-methylpyridin-3-yl)carbamoyl)-3-(2-isopropylphenyl)azetidin-1-yl)-3-methyl-4-oxobutanoic acid;
4-(3-((2-(difluoromethoxy)-6-methylpyridin-3-yl)carbamoyl)-3-(2-isopropylphenyl)azetidin-1-yl)-3,3-dimethyl-4-oxobutanoic acid;
3-(3-((2-(difluoromethoxy)-6-methylpyridin-3-yl)carbamoyl)-3-(2-isopropylphenyl)azetidine-1-carbonyl)but-3-enoic acid;
(1S,2R)-2-(3-((2-(difluoromethoxy)-6-methylpyridin-3-yl)carbamoyl)-3-(2-isopropylphenyl)azetidine-1-carbonyl)cyclopropane-1-carboxylic acid;
(1R,2S)-2-(3-((2-(difluoromethoxy)-6-methylpyridin-3-yl)carbamoyl)-3-(2-isopropylphenyl)azetidine-1-carbonyl)cyclopropane-1-carboxylic acid;
5-(3-((2-(difluoromethoxy)-6-methylpyridin-3-yl)carbamoyl)-3-(2-isopropylphenyl)azetidin-1-yl)-5-oxopentanoic acid;
4-(3-((2-(difluoromethoxy)-6-methylpyridin-3-yl)carbamoyl)-3-(2-isopropylphenyl)azetidin-1-yl)-3,3-difluoro-4-oxobutanoic acid;
(S)-4-(3-((2-(difluoromethoxy)-6-methylpyridin-3-yl)carbamoyl)-3-(2-isopropylphenyl)azetidin-1-yl)-2-hydroxy-2-methyl-4-oxobutanoic acid;
N-(2-(difluoromethoxy)-6-methylpyridin-3-yl)-3-(2-isopropylphenyl)-1-(5,5,5-trifluoro-4-hydroxypentanoyl)azetidine-3-carboxamide;
4-(2-(3-((2-(difluoromethoxy)-6-methylpyridin-3-yl)carbamoyl)-3-(2-isopropylphenyl)azetidin-1-yl)-2-oxoethyl)tetrahydro-2H-pyran-4-carboxylic acid;
N-(2-(difluoromethoxy)-6-methylpyridin-3-yl)-3-(2-isopropylphenyl)-1-(sulfamoylglycyl)azetidine-3-carboxamide;
1-(N-acetyl-N-hydroxyglycyl)-N-(2-(difluoromethoxy)-6-methylpyridin-3-yl)-3-(2-isopropylphenyl)azetidine-3-carboxamide;
2-((3-((2-(difluoromethoxy)-6-methylpyridin-3-yl)carbamoyl)-3-(2-isopropylphenyl)azetidin-1-yl)sulfonyl)acetic acid;
2-((4-((2-(difluoromethoxy)-6-methylpyridin-3-yl)carbamoyl)-4-(2-isopropylphenyl)piperidin-1-yl)sulfonyl)acetic acid;
3-((3-((2-(difluoromethoxy)-6-methylpyridin-3-yl)carbamoyl)-3-(2-isopropylphenyl)azetidin-1-yl)sulfonyl)propanoic acid;
3-((4-((2-(difluoromethoxy)-6-methylpyridin-3-yl)carbamoyl)-4-(2-isopropylphenyl)piperidin-1-yl)sulfonyl)propanoic acid;
3-((3-((2-(difluoromethoxy)-6-methylpyridin-3-yl)carbamoyl)-3-(2-isopropylphenyl)azetidin-1-yl)sulfonyl)-2,2-dimethylpropanoic acid;
2-(1-((3-((2-(difluoromethoxy)-6-methylpyridin-3-yl)carbamoyl)-3-(2-isopropylphenyl)azetidin-1-yl)sulfonyl)cyclopropyl)acetic acid;
4-((3-((2-(difluoromethoxy)-6-methylpyridin-3-yl)carbamoyl)-3-(2-isopropylphenyl)azetidin-1-yl)sulfonyl)butanoic acid;
(E)-3-((3-((2-(difluoromethoxy)-6-methylpyridin-3-yl)carbamoyl)-3-(2-isopropylphenyl)azetidin-1-yl)sulfonyl)acrylic acid;
N-(2-(difluoromethoxy)-6-methylpyridin-3-yl)-1-((3-(hydroxyamino)-3-oxopropyl)sulfonyl)-3-(2-isopropylphenyl)azetidine-3-carboxamide;
2-((3-((2-(difluoromethoxy)-6-methylpyridin-3-yl)carbamoyl)-3-(2-isopropylphenyl)azetidine-1-carbonyl)oxy)acetic acid;
2-((4-((2-(difluoromethoxy)-6-methylpyridin-3-yl)carbamoyl)-4-(2-isopropylphenyl)piperidine-1-carbonyl)oxy)acetic acid;
(R)-2-((3-((2-(difluoromethoxy)-6-methylpyridin-3-yl)carbamoyl)-3-(2-isopropylphenyl)azetidine-1-carbonyl)oxy)propanoic acid;
1-((3-((2-(difluoromethoxy)-6-methylpyridin-3-yl)carbamoyl)-3-(2-isopropylphenyl)azetidine-1-carbonyl)oxy)cyclopropane-1-carboxylic acid;
3-((3-((2-(difluoromethoxy)-6-methylpyridin-3-yl)carbamoyl)-3-(2-isopropylphenyl)azetidine-1-carbonyl)oxy)-2,2-dimethylpropanoic acid;
1-(((3-((2-(difluoromethoxy)-6-methylpyridin-3-yl)carbamoyl)-3-(2-isopropylphenyl)azetidine-1-carbonyl)oxy)methyl)cyclopropane-1-carboxylic acid;
((3-((2-(difluoromethoxy)-6-methylpyridin-3-yl)carbamoyl)-3-(2-isopropylphenyl)azetidin-1-yl)sulfonyl)glycine;
N-(2-(difluoromethoxy)-6-methylpyridin-3-yl)-3-(2-isopropylphenyl)-1-sulfamoylazetidine-3-carboxamide;
N-(2-(difluoromethoxy)pyridin-3-yl)-3-(2-isopropylphenyl)-1-sulfamoylazetidine-3-carboxamide;
N-(2,6-dimethoxypyridin-3-yl)-3-(2-isopropylphenyl)-1-sulfamoylazetidine-3-carboxamide;
N-(6-ethoxy-2-methoxypyridin-3-yl)-3-(2-isopropylphenyl)-1-sulfamoylazetidine-3-carboxamide;
N-(2-(difluoromethoxy)-6-methylpyridin-3-yl)-3-(2-isopropylphenyl)-1-(N-methylsulfamoyl)azetidine-3-carboxamide;
1-(N-cyclopropylsulfamoyl)-N-(2-(difluoromethoxy)-6-methylpyridin-3-yl)-3-(2-isopropylphenyl)azetidine-3-carboxamide;
N-(2-(difluoromethoxy)-6-methylpyridin-3-yl)-3-(2-isopropylphenyl)-1-(2-(sulfamoylamino)ethyl)azetidine-3-carboxamide;
N-(2-(difluoromethoxy)-5-fluoropyridin-3-yl)-3-(2-isopropylphenyl)-1-sulfamoylazetidine-3-carboxamide;
3-(3-((2-(difluoromethoxy)-6-methylpyridin-3-yl)carbamoyl)-3-(2-isopropylphenyl)azetidine-1-carboxamido)-3-methylbutanoic acid;
N1-((1H-imidazol-4-yl)methyl)-N4-(2-(difluoromethoxy)-6-methylpyridin-3-yl)-4-(2-isopropylphenyl)piperidine-1,4-carboxamide;
3-(3-((2-(difluoromethoxy)-6-methylpyridin-3-yl)carbamoyl)-3-(2-isopropylphenyl)azetidine-1-carboxamido)-2,2-dimethylpropanoic acid;
4-(3-((2-(difluoromethoxy)-6-methylpyridin-3-yl)carbamoyl)-3-(2-isopropylphenyl)azetidine-1-carboxamido)-2,2-dimethylbutanoic acid;
N4-(2-(difluoromethoxy)-6-methylpyridin-3-yl)-4-(2-isopropylphenyl)piperidine-1,4-dicarboxamide;
N4-(2-(difluoromethoxy)-6-methylpyridin-3-yl)-N1-(2-hydroxyethyl)-4-(2-isopropylphenyl)piperidine-1,4-dicarboxamide;
6-(3-((2-(difluoromethoxy)-6-methylpyridin-3-yl)carbamoyl)-3-(2-isopropylphenyl)azetidin-1-yl)nicotinic acid;
6-(3-((2-(difluoromethoxy)-6-methylpyridin-3-yl)carbamoyl)-3-(2-isopropylphenyl)azetidin-1-yl)picolinic acid;
2-(3-((2-(difluoromethoxy)-6-methylpyridin-3-yl)carbamoyl)-3-(2-isopropylphenyl)azetidin-1-yl)pyrimidine-5-carboxylic acid;
6-(3-((2-(difluoromethoxy)-6-methylpyridin-3-yl)carbamoyl)-3-(2-isopropylphenyl)azetidin-1-yl)pyridazine-3-carboxylic acid;
5-(3-((2-(difluoromethoxy)-6-methylpyridin-3-yl)carbamoyl)-3-(2-isopropylphenyl)azetidin-1-yl)pyrazine-2-carboxylic acid;

1-(5-(3-((2-(difluoromethoxy)-6-methylpyridin-3-yl)carbamoyl)-3-(2-isopropylphenyl)azetidin-1-yl)pyrimidin-2-yl)cyclopropane-1-carboxylic acid;

N-(2-(difluoromethoxy)-6-methylpyridin-3-yl)-1-(4-fluoropyridin-2-yl)-3-(2-isopropylphenyl)azetidine-3-carboxamide;

N-(2-(difluoromethoxy)-6-methylpyridin-3-yl)-1-(3-fluoropyridin-4-yl)-3-(2-isopropylphenyl)azetidine-3-carboxamide;

N-(2-(difluoromethoxy)-6-methylpyridin-3-yl)-1-(5-fluoropyrimidin-4-yl)-3-(2-isopropylphenyl)azetidine-3-carboxamide;

N-(2-(difluoromethoxy)pyridin-3-yl)-1-(5-fluoropyrimidin-4-yl)-3-(2-isopropylphenyl)azetidine-3-carboxamide;

1-(5-cyanopyridin-2-yl)-N-(2-(difluoromethoxy)-6-methylpyridin-3-yl)-3-(2-isopropylphenyl)azetidine-3-carboxamide;

1-(5-cyanopyridin-2-yl)-N-(2-(difluoromethoxy)pyridin-3-yl)-3-(2-isopropylphenyl)azetidine-3-carboxamide;

1-(5-cyanopyrimidin-2-yl)-N-(2-(difluoromethoxy)-6-methylpyridin-3-yl)-3-(2-isopropylphenyl)azetidine-3-carboxamide;

1-(5-cyanopyrimidin-2-yl)-N-(2-(difluoromethoxy)pyridin-3-yl)-3-(2-isopropylphenyl)azetidine-3-carboxamide;

2-(3-((2-(difluoromethoxy)-6-methylpyridin-3-yl)carbamoyl)-3-(2-isopropylphenyl)azetidin-1-yl)oxazole-4-carboxylic acid;

N-(2-(difluoromethoxy)-6-methylpyridin-3-yl)-1-(5-fluoropyrimidin-2-yl)-3-(2-isopropylphenyl)azetidine-3-carboxamide;

N-(2-(difluoromethoxy)-6-methylpyridin-3-yl)-3-(2-isopropylphenyl)-1-(2-methylpyrimidin-4-yl)azetidine-3-carboxamide;

N-(2-(difluoromethoxy)-6-methylpyridin-3-yl)-3-(2-isopropylphenyl)-1-(4-oxo-4,5-dihydrooxazol-2-yl)azetidine-3-carboxamide [tautomeric form: N-(2-(difluoromethoxy)-6-methylpyridin-3-yl)-3-(2-isopropylphenyl)-1-(4-hydroxy-oxazol-2-yl)azetidine-3-carboxamide];

N-(2-(difluoromethoxy)-6-methylpyridin-3-yl)-1-(5-hydroxy-1,2,4-oxadiazol-3-yl)-3-(2-isopropylphenyl)azetidine-3-carboxamide [tautomeric form: N-(2-(difluoromethoxy)-6-methylpyridin-3-yl)-3-(2-isopropylphenyl)-1-(5-oxo-4,5-dihydro-1,2,4-oxadiazol-3-yl)azetidine-3-carboxamide];

3-(2-cyclopentylphenyl)-N-(2-(difluoromethoxy)-6-methylpyridin-3-yl)azetidine-3-carboxamide;

3-(2-cyclohexylphenyl)-N-(2-(difluoromethoxy)-6-methylpyridin-3-yl)azetidine-3-carboxamide;

4-(3-(2-cyclobutylphenyl)-3-((2-(difluoromethoxy)-6-methylpyridin-3-yl)carbamoyl)azetidin-1-yl)-2,2-dimethyl-4-oxobutanoic acid;

4-(3-(2-cyclopentylphenyl)-3-((2-(difluoromethoxy)-6-methylpyridin-3-yl)carbamoyl)azetidin-1-yl)-2,2-dimethyl-4-oxobutanoic acid;

4-(3-(2-cyclohexylphenyl)-3-((2-(difluoromethoxy)-6-methylpyridin-3-yl)carbamoyl)azetidin-1-yl)-2,2-dimethyl-4-oxobutanoic acid;

4-(3-((2-(difluoromethoxy)-6-methylpyridin-3-yl)carbamoyl)-3-(2-propylphenyl)azetidin-1-yl)-2,2-dimethyl-4-oxobutanoic acid;

N-(2-(difluoromethoxy)-6-methylpyridin-3-yl)-3-(2-fluoro-6-isopropylphenyl)azetidine-3-carboxamide;

4-(3-((2-(difluoromethoxy)-6-methylpyridin-3-yl)carbamoyl)-3-(2-isopropyl-5-methylphenyl)azetidin-1-yl)-2,2-dimethyl-4-oxobutanoic acid;

4-(3-((2-(difluoromethoxy)-6-methylpyridin-3-yl)carbamoyl)-3-(2-fluoro-6-isopropylphenyl)azetidin-1-yl)-2,2-dimethyl-4-oxobutanoic acid;

4-(3-((2-(difluoromethoxy)-6-methylpyridin-3-yl)carbamoyl)-3-(5-fluoro-2-isopropylphenyl)azetidin-1-yl)-2,2-dimethyl-4-oxobutanoic acid; and N-(2-(3-((2-(difluoromethoxy)-6-methylpyridin-3-yl)carbamoyl)-3-(2-isopropylphenyl)azetidin-1-yl)-2-oxoethyl)-N-propylglycine.

35) In addition to the compounds listed in embodiment 33), further compounds of Formula (I) according to embodiment 1), are selected from the following compounds:

Methyl N-(2-(3-((2-(difluoromethoxy)-6-methylpyridin-3-yl)carbamoyl)-3-(2-isopropylphenyl)azetidin-1-yl)-2-oxoethyl)-N-(2-methoxyethyl)glycinate;

N-(2-(3-((2-(difluoromethoxy)-6-methylpyridin-3-yl)carbamoyl)-3-(2-isopropylphenyl)azetidin-1-yl)-2-oxoethyl)-N-(2-methoxyethyl)glycine;

Methyl (2-(3-((2-(difluoromethoxy)-6-methylpyridin-3-yl)carbamoyl)-3-(2-isopropylphenyl)azetidin-1-yl)-2-oxoethyl)glycinate;

(2-(3-((2-(difluoromethoxy)-6-methylpyridin-3-yl)carbamoyl)-3-(2-isopropylphenyl)azetidin-1-yl)-2-oxoethyl)glycine;

N-(2-(3-((2-(difluoromethoxy)-6-methylpyridin-3-yl)carbamoyl)-3-(2-isopropylphenyl)azetidin-1-yl)-2-oxoethyl)-N-ethylglycine;

3-(2-isopropylphenyl)-N-(6-methyl-2-propoxypyridin-3-yl)-1-sulfamoylazetidine-3-carboxamide;

N-(2-(difluoromethoxy)-6-methylpyridin-3-yl)-3-(3-isopropylpyridin-2-yl)azetidine-3-carboxamide;

4-(3-((2-(difluoromethoxy)-6-methylpyridin-3-yl)carbamoyl)-3-(3-isopropylpyridin-2-yl)azetidin-1-yl)-4-oxobutanoic acid;

N-(2-(difluoromethoxy)-6-methylpyridin-3-yl)-3-(3-isopropylpyridin-2-yl)-1-sulfamoylazetidine-3-carboxamide;

N1-cyclopropyl-N3-(2-(difluoromethoxy)-6-methylpyridin-3-yl)-3-(3-isopropylpyridin-2-yl)azetidine-1,3-dicarboxamide;

N-(2-(difluoromethoxy)-6-methylpyridin-3-yl)-1-(5-fluoro-2-methylpyrimidin-4-yl)-3-(3-isopropylpyridin-2-yl)azetidine-3-carboxamide;

N-(2-(difluoromethoxy)-6-methylpyridin-3-yl)-1-(3-fluoro-6-methylpyridin-2-yl)-3-(3-isopropylpyridin-2-yl)azetidine-3-carboxamide;

N-(2-(difluoromethoxy)-6-methylpyridin-3-yl)-3-(3-isopropylpyridin-4-yl)azetidine-3-carboxamide;

N-(2-(difluoromethoxy)-6-methylpyridin-3-yl)-3-(3-isopropylpyridin-4-yl)-1-sulfamoylazetidine-3-carboxamide;

N-(2-(difluoromethoxy)-6-methylpyridin-3-yl)-3-(3-isopropylpyrazin-2-yl)azetidine-3-carboxamide; and N-(2-(difluoromethoxy)-6-methylpyridin-3-yl)-3-(3-isopropylpyrazin-2-yl)-1-sulfamoylazetidine-3-carboxamide.

36) In addition to the compounds listed in embodiments 33) and 34, further compounds of Formula (I) according to embodiment 1), are selected from the following compounds:

N-(5-chloro-3-methoxypyridin-2-yl)-3-(2-isopropylphenyl)azetidine-3-carboxamide;

N-(5-bromo-3-methoxypyridin-2-yl)-3-(2-isopropylphenyl)azetidine-3-carboxamide;

N-(5-chloro-3-(difluoromethoxy)pyridin-2-yl)-3-(2-isopropylphenyl)azetidine-3-carboxamide;

N-(5-bromo-3-(difluoromethoxy)pyridin-2-yl)-3-(2-isopropylphenyl)azetidine-3-carboxamide;

N-(3-(difluoromethoxy)-5-methylpyridin-2-yl)-3-(2-isopropylphenyl)azetidine-3-carboxamide;
N-(3,5-dimethoxypyridin-2-yl)-3-(2-isopropylphenyl)azetidine-3-carboxamide;
N-(5-chloro-3-(difluoromethoxy)pyridin-2-yl)-3-(2-cyclopentylphenyl)azetidine-3-carboxamide;
N-(5-chloro-3-(difluoromethoxy)pyridin-2-yl)-3-(3-isopropylpyridin-2-yl)azetidine-3-carboxamide;
Methyl 4-(3-((5-chloro-3-(difluoromethoxy)pyridin-2-yl)carbamoyl)-3-(2-isopropylphenyl)azetidin-1-yl)-2,2-dimethylbutanoate;
4-(3-((5-chloro-3-(difluoromethoxy)pyridin-2-yl)carbamoyl)-3-(2-isopropylphenyl)azetidin-1-yl)-2,2-dimethylbutanoic acid;
4-(3-((5-bromo-3-(difluoromethoxy)pyridin-2-yl)carbamoyl)-3-(2-isopropylphenyl)azetidin-1-yl)-2,2-dimethylbutanoic acid;
Methyl 4-(3-((5-bromo-3-(difluoromethoxy)pyridin-2-yl)carbamoyl)-3-(2-isopropylphenyl)azetidin-1-yl)-2,2-dimethyl-4-oxobutanoate;
Methyl 4-(3-((5-bromo-3-(difluoromethoxy)pyridin-2-yl)carbamoyl)-3-(2-isopropylphenyl)azetidin-1-yl)-2,2-dimethyl-4-oxobutanoate;
4-(3-((5-chloro-3-(difluoromethoxy)pyridin-2-yl)carbamoyl)-3-(2-isopropylphenyl)azetidin-1-yl)-2,2-dimethyl-4-oxobutanoic acid;
4-(3-((5-chloro-3-methoxypyridin-2-yl)carbamoyl)-3-(2-isopropylphenyl)azetidin-1-yl)-2,2-dimethyl-4-oxobutanoic acid;
4-(3-((5-bromo-3-methoxypyridin-2-yl)carbamoyl)-3-(2-isopropylphenyl)azetidin-1-yl)-2,2-dimethyl-4-oxobutanoic acid;
4-(3-((3-(difluoromethoxy)-5-methylpyridin-2-yl)carbamoyl)-3-(2-isopropylphenyl)azetidin-1-yl)-2,2-dimethyl-4-oxobutanoic acid;
1-(2-(3-((3-(difluoromethoxy)-5-methylpyridin-2-yl)carbamoyl)-3-(2-isopropylphenyl)azetidin-1-yl)-2-oxoethyl)cyclobutane-1-carboxylic acid;
Benzyl 3-((3-((3-(difluoromethoxy)-5-methylpyridin-2-yl)carbamoyl)-3-(2-isopropylphenyl)azetidin-1-yl)sulfonyl)propanoate;
3-((3-((3-(difluoromethoxy)-5-methylpyridin-2-yl)carbamoyl)-3-(2-isopropylphenyl)azetidin-1-yl)sulfonyl)propanoic acid;
N-(5-chloro-3-methoxypyridin-2-yl)-3-(2-isopropylphenyl)-1-sulfamoylazetidine-3-carboxamide;
N-(5-bromo-3-methoxypyridin-2-yl)-3-(2-isopropylphenyl)-1-sulfamoylazetidine-3-carboxamide;
N-(5-chloro-3-(difluoromethoxy)pyridin-2-yl)-3-(2-isopropylphenyl)-1-sulfamoylazetidine-3-carboxamide;
N-(5-bromo-3-(difluoromethoxy)pyridin-2-yl)-3-(2-isopropylphenyl)-1-sulfamoylazetidine-3-carboxamide;
N-(3,5-dimethoxypyridin-2-yl)-3-(2-isopropylphenyl)-1-sulfamoylazetidine-3-carboxamide;
N-(5-chloro-3-(difluoromethoxy)pyridin-2-yl)-3-(2-cyclopentylphenyl)-1-sulfamoylazetidine-3-carboxamide;
N-(5-chloro-3-(difluoromethoxy)pyridin-2-yl)-3-(3-isopropylpyridin-2-yl)-1-sulfamoylazetidine-3-carboxamide;
N3-(5-chloro-3-(difluoromethoxy)pyridin-2-yl)-N1-cyclopropyl-3-(2-isopropylphenyl)azetidine-1,3-dicarboxamide;
N3-(5-bromo-3-(difluoromethoxy)pyridin-2-yl)-N1-cyclopropyl-3-(2-isopropylphenyl)azetidine-1,3-dicarboxamide;
2-methoxy-2-oxoethyl 3-((3-(difluoromethoxy)-5-methylpyridin-2-yl)carbamoyl)-3-(2-isopropylphenyl)azetidine-1-carboxylate;
2-((3-((3-(difluoromethoxy)-5-methylpyridin-2-yl)carbamoyl)-3-(2-isopropylphenyl)azetidine-1-carbonyl)oxy)acetic acid;
1-((3-((3-(difluoromethoxy)-5-methylpyridin-2-yl)carbamoyl)-3-(2-isopropylphenyl)azetidine-1-carbonyl)oxy)cyclopropane-1-carboxylic acid; and
N-(3-(difluoromethoxy)-5-methylpyridin-2-yl)-3-(2-isopropylphenyl)-1-(4-oxo-4,5-dihydrooxazol-2-yl)azetidine-3-carboxamide.

The compounds of formulae (I), (II) and (III) according to embodiments 1) to 36) and their pharmaceutically acceptable salts can be used as medicaments, e.g. in the form of pharmaceutical compositions for enteral (such especially oral e.g. in form of a tablet or a capsule) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention/prophylaxis or treatment of a disease or disorder mentioned herein comprising administering to a subject a pharmaceutically active amount of a compound of formulae (I), (II) or (III) according to embodiments 1) to 36).

For avoidance of any doubt, if compounds are described as useful for the prevention/prophylaxis or treatment of certain diseases, such compounds are likewise suitable for use in the preparation of a medicament for the prevention/prophylaxis or treatment of said diseases. Likewise, such compounds are also suitable in a method for the prevention/prophylaxis or treatment of such diseases, comprising administering to a subject (mammal, especially human) in need thereof, an effective amount of such compound.

The compounds of formulae (I), (II), and (III) according to embodiments 1) to 36) are useful for the prevention and/or treatment of fibrosis (and diseases or disorders associated with fibrosis), or of other disorders mediated by $LPA_1$ receptor signalling.

The terms "fibrosis" refers to conditions that are associated with the abnormal accumulation of cells and/or fibronectin and/or collagen and/or increased fibroblast recruitment in an organ; including fibrosis of individual organs or tissues such as the heart, kidney, liver, joints, lung, pleural tissue, peritoneal tissue, skin, cornea, retina, musculoskeletal and digestive tract.

The term fibrosis may in particular be defined as comprising
all forms of pulmonary fibrosis including lung diseases associated with fibrosis, including idiopathic pulmonary fibrosis; pulmonary fibrosis secondary to systemic inflammatory disease such as rheumatoid arthritis, scleroderma, lupus; cryptogenic fibrosing alveolitis; pulmonary fibrosis secondary to sarcoidosis; iatrogenic pulmonary fibrosis including radiation induced fibrosis; silicosis; asbestos induced pulmonary; and pleural fibrosis;
renal fibrosis; including renal fibrosis associated with CKD, chronic renal failure, tubulointerstitial nephritis, and/orchronic nephropathies such as (primary) glomerulonephritis and glomerulonephritis secondary to systemic inflammatory diseases such as lupus and scleroderma, diabetes, focal segmental glomerular sclerosis, IgA nephropathy, hypertension, renal allograft, and Alport syndrome;

gut fibrosis, including gut fibrosis secondary to scleroderma, and radiation induced gut fibrosis;

all forms of liver fibrosis, including cirrhosis, alcohol induced liver fibrosis, nonalcoholic steatohepatitis, biliary duct injury, primary biliary cirrhosis (also known as primary biliary cholangitis), infection or viral induced liver fibrosis (e.g. chronic HCV infection), and autoimmune hepatitis;

head and neck fibrosis, including radiation induced head and neck fibrosis;

corneal scarring, including sequelae of LASIK (laser-assisted in situ keratomileusis), corneal transplant, and trabeculectomy;

hypertrophic scarring and keloids, including burn induced or surgical hypertrophic scarring and keloids;

and other fibrotic diseases, e.g. endometriosis, spinal cord fibrosis, myelofibrosis, cardiac fibrosis, perivascular fibrosis; as well as formation of scar tissue, Peyronie's disease, abdominal or bowel adhesions, bladder fibrosis, fibrosis of the nasal passages, and fibrosis mediated by fibroblasts.

The term "prevention/prophylaxis of fibrosis" includes the prevention of fibrosis in a subject that has been exposed to one or more environmental conditions that are known to increase the risk of fibrosis of an organ or tissue, especially the risk of lung, liver or kidney fibrosis; or in a subject that has a genetic predisposition of developing fibrosis of an organ or tissue; as well as the prevention or minimization of scarring following injury including surgery.

Other disorders mediated by $LPA_1$ receptor signalling notably comprise dermatological disorders, pain, malignant and benign proliferative diseases, respiratory diseases, nervous system disorders, cardiovascular diseases, and inflammatory disorders, obesity, and insulin resistance.

The term "dermatological disorder," refers to a skin disorder. Such dermatological disorders include proliferative or inflammatory disorders of the skin such as systemic sclerosis, atopic dermatitis, bullous disorders, collagenosis, psoriasis, scleroderma, psoriatic lesions, dermatitis, contact dermatitis, eczema, urticaria, rosacea, wound healing, scarring, hypertrophic scarring, keloids, Kawasaki Disease, rosacea, Sjogren-Larsso syndrome, urticaria; especially systemic sclerosis.

The term "pain" refers to acute pain, chronic pain, and neuropathic pain. A particular example is fibromyalgia, especially fibromyalgia that stems from the formation of fibrous scar tissue in contractile muscles, and cancer pain.

The term "malignant and benign proliferative disease" especially refers to cancer, and the control of proliferation of tumor cells, invasion and/or metastasis of carcinomas.

The term "cancer," refers to all sorts of cancers such as carcinomas; adenocarcinomas; leukemias; sarcomas; lymphomas; myelomas; metastatic cancers; brain tumors; neuroblastomas; pancreatic cancers; gastro-intestinal cancers; lung cancers; breast cancers; prostate cancers; endometrial cancers; skin cancers; bladder cancers; head and neck cancers; neuroendocrine tumors; ovarian cancers; cervical cancers; oral tumors; nasopharyngeal tumors; thoracic cancers; and virally induced tumors. Notably the term refers to pleural mesothelioma, peritoneal mesothelioma, and bone metastases, as well as brain tumors including brain metastases, malignant gliomas, glioblastoma multiforme, medulloblastoma, meningiomas; neuroblastoma; pancreatic cancer including pancreatic adenocarcinoma/pancreatic ductal adenocarcinoma; gastro-intestinal cancers including colon carcinoma, colorectal adenoma, colorectal adenocarcinoma, metastatic colorectal cancer, familial adenomatous polyposis (FAP), gastric cancer, gallbladder cancer, cholangiocarcinoma, hepatocellular carcinoma; Kaposi's sarcoma; leukemias including acute myeloid leukemia, adult T-cell leukemia; lymphomas including Burkitt's lymphoma, Hodgkin's lymphoma, MALT lymphoma, and primary intraocular B-Cell lymphoma; lung cancer including non-small cell lung cancer; breast cancer including triple negative breast carcinoma; rhabdomyosarcoma; prostate cancer including castrate-resistant prostate cancer; esophageal squamous cancer; (oral) squamous cell carcinoma; endometrial cancer; thyroid carcinoma including papillary thyroid carcinoma; metastatic cancers; lung metastasis; skin cancer including melanoma and metastatic melanoma; bladder cancer including urinary bladder cancer, urothelial cell carcinoma; multiple myelomas; osteosarcoma; head and neck cancer; and renal carcinomas including renal cell carcinoma renal clear cell carcinoma, metastatic renal cell carcinoma, metastatic renal clear cell carcinoma; as well as neuroendocrine tumors; ovarian cancer; cervical cancer; oral tumors; nasopharyngeal tumors; thoracic cancer; choriocarcinoma; Ewing's sarcoma; and virally induced tumors.

The term "respiratory disease," refers to diseases affecting the organs that are involved in breathing, such as the nose, throat, larynx, eustachian tubes, trachea, bronchi, lungs, related muscles (e.g. diaphragm and intercostals), and nerves. Respiratory diseases include interstitial pneumonia, asthma referring to any disorder of the lungs characterized by variations in pulmonary gas flow associated with airway constriction of whatever cause (intrinsic, extrinsic, or both; allergic or non-allergic) including adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma; rhinitis including seasonal allergic rhinitis, perennial allergic rhinitis; chronic obstructive pulmonary disease (COPD) including chronic bronchitis or emphysema; airway inflammation, sarcoidosis, cystic fibrosis, hypoxia, and acute lung injury and acute respiratory distress (including bacterial pneumonia induced, trauma induced, viral pneumonia induced, ventilator induced, non-pulmonary sepsis induced, and aspiration induced).

The term "nervous system disorder" refers to conditions that alter the structure or function of the brain, spinal cord or peripheral nervous system, including but not limited to Alzheimer's Disease, cerebral edema, multiple sclerosis, neuropathies, Parkinson's Disease, nervous system disorders resulting from blunt or surgical trauma (including post-surgical cognitive dysfunction and spinal cord or brain stem injury, and head injury), cerebral edema, migraine, as well as the neurological aspects of disorders such as degenerative disk disease and sciatica.

The term "cardiovascular disease," as used herein refers to diseases affecting the heart or blood vessels or both, including but not limited to: arrhythmia (atrial or ventricular or both); atherosclerosis and its sequelae; cerebral ischemia, stroke, angina; cardiac rhythm disturbances; myocardial ischemia; myocardial infarction; cardiac or vascular aneurysm including aortic aneurysm; retinal ischemia; reperfusion injury following ischemia of the brain, heart or other organ or tissue; restenosis; peripheral obstructive arteriopathy of a limb, an organ, or a tissue; endotoxic, surgical, or traumatic shock; hypertension, valvular heart disease, heart failure, abnormal blood pressure; shock; vasoconstriction (including that associated with migraines); vascular abnormality, thrombosis, insufficiency limited to a single organ or tissue.

The term "inflammatory disorder" include psoriasis, rheumatoid arthritis, vasculitis, inflammatory bowel disease, dermatitis, osteoarthritis, inflammatory muscle disease, vaginitis, interstitial cystitis, scleroderma, eczema, allogeneic or xenogeneic transplantation (organ, bone marrow, stem cells and other cells and tissues) graft rejection, graft-versus-host disease, mixed connective tissue disease, lupus erythematosus, type I diabetes, dermatomyositis, phlebitis, Sjogren's syndrome, granulomatosis with polyangiitis (GPA, Wegener's granulomatosis), thyroiditis (e.g., Hashimoto's and autoimmune thyroiditis), myasthenia gravis, autoimmune hemolytic anemia, chronic relapsing hepatitis, allergic conjunctivitis, atopic dermatitis, sinusitis, and inflammation mediated by neutrophils.

Further disorders in which $LPA_1$ receptor plays a role notably comprise prostate and bladder disorders such as benign prostatic hyperplasia, diseases linked to eosinophil and/or basophil and/or dendritic cell and/or neutrophil and/or monocyte and/or T-cell recruitment, cardiomyopathy, myocardial remodeling, vascular remodeling, vascular permeability disorders, renal diseases, renal papillary necrosis, renal failure, tumor growth, metabolic diseases, pruritus, ocular diseases, macular degeneration, endocrine disorders, hyperthyroidism, osteoporosis, diabetes-related disease (nephropathy, retinopathy).

The present invention further relates to the compounds of the formulae (I), (II) and (III) for use in the treatment of the diseases and disorders mentioned herein (especially for the treatment of fibrosis) wherein the compound of formulae (I), (II), and (III) is intended to be used in combination (whether in a single pharmaceutical composition, or in separate treatment) with one or several antifibrotic agents. Examples of such antifibrotic agents include corticosteroids, immunosuppressants, B-cell antagonists, and uteroglobin.

PREPARATION OF COMPOUNDS OF FORMULAE (I), (II), AND (III)

The compounds of formulae (I), (II) and (III) can be prepared by well-known literature methods, by the methods given below, by the methods given in the experimental part below or by analogous methods. Optimum reaction conditions may vary with the particular reactants or solvents used, but such conditions can be determined by a person skilled in the art by routine optimisation procedures. In some cases the order of carrying out the following reaction schemes, and/or reaction steps, may be varied to facilitate the reaction or to avoid unwanted reaction products. In the general sequence of reactions outlined below, the generic groups $R^1$, $R^2$, $R^3$, $R^4$, $R^5$, $R^6$, and L are as defined for Formula (I). Other abbreviations used herein are explicitly defined, or are as defined in the experimental section. In some instances the generic groups $R^1$, $R^2$, $R^3$, $R^4$, $R^5$, $R^6$, and L might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999; P. J. Kocienski, Protecting Groups, Thieme Stuttgart, 1994). For the purposes of this discussion, it will be assumed that such protecting groups as necessary are in place. In some cases the final product may be further modified, for example, by manipulation of substituents to give a new final product. These manipulations may include, but are not limited to, reduction, oxidation, alkylation, acylation, hydrolysis and transition-metal catalysed cross-coupling reactions which are commonly known to those skilled in the art. The compounds obtained may also be converted into salts, especially pharmaceutically acceptable salts, in a manner known per se.

The compounds of formulae (I), (II) and (III) can be manufactured by the methods given below, by the methods given in the experimental part or by analogous methods. Optimum reaction conditions may vary with the particular reactants or solvents used, but such conditions can be determined by a person skilled in the art by routine optimisation procedures.

Compounds of the formulae (I), (II) and (III) of the present invention can be prepared according to the general sequence of reactions outlined below. Only a few of the synthetic possibilities leading to compounds of formulae (I), (II) and (III) are described.

Compounds of Formula (I) are prepared by reacting a compound of Structure 1a or Structure 1b with a compound of Structure 2 in a solvent such as DMF, THF, DCM, EtOAc etc. in the presence of one or more carboxylate activating agents such as $SOCl_2$, $(COCl)_2$, $POCl_3$, EDC, HOBt, HBTU, TBTU, DCC, CDI, T3P etc. and in the presence or absence of a base such as TEA, DIPEA, NaH, $K_2CO_3$, etc. (Montalbetti CA., Falque V. Tetrahedron 2005 (46) 10827-10852; Valeur E., Bradley M. Chem. Soc. Rev. 2009 (389) 606-31). Residue $R^4$ can be present at coupling stage or introduced at a later stage by replacing Br by an alkyl group under Negishi conditions or via a Suzuki/Hydrogenation sequence known to a person skilled in the art. (Matsushita L H., Negishi E. J. Org. Chem. 1982 (47) 4161-4165; Kerins, F. et al. J. Org. Chem. 2002 (67) 4968-4971).

In compound of Formula I, the couplings of Structure 1a and Structure 1b with Structure 2 may be carried out with side chain L—$R^6$=X already present or with a Structure 2 wherein N bears a protecting group =X. Functionality $R^6$ is then introduced, after deprotection, by the formation of an amine, amide, sulfonamide, carbamate, urea or sulfamide linker (L), for example, in a manner known to a person skilled in the art.

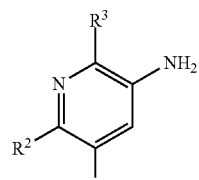

Structure 1a

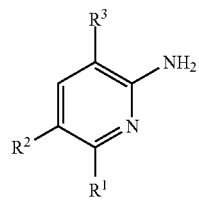

Structure 1b

Structure 2

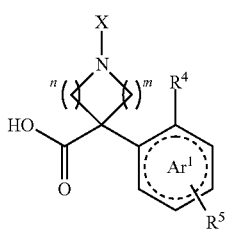

Compounds of Structure 1a and Structure 1b may be commercially available or may be prepared by reducing a compound of Structure 3a or Structure 3b in a solvent such as THF, MeOH, EtOH, iPrOH etc. in the presence of $H_2$/Pd/C or $H_2$/Pt+V/C or Fe etc. (Dolle V. et al. Tetrahedron 1997 (53) 12505-12524; Möbus K. et al. Top. Catal. 2010 (53), 1126-1131; WO2012/055995). If $R^1$=H and $R^2$=Cl or Br, Structure 1a and Structure 1b may also be prepared by chlorinating or brominating a compound of Structure 3c and Structure 3d with N-chlorosuccinimide or N-bromosuccinimide in a manner known to a person skilled in the art.

Structure 3a

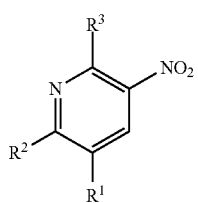

Structure 3b

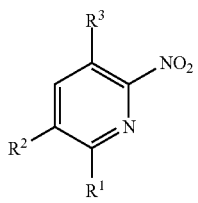

Structure 3c

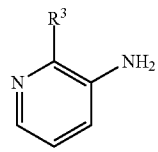

Structure 3d

Structure 4

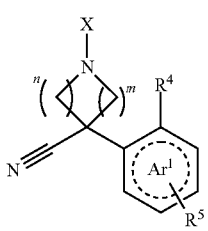

Structure 5

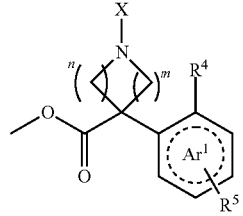

Compounds of Structure 2 may be prepared by reacting a compound of Structure 4 with 25% NaOH or concentrated $H_2SO_4$/AcOH or concentrated HCl at elevated temperature in a solvent such as water, EtOH etc (US20120232026; WO2005/049605; US20080319188). Compounds of Structure 2 may also be prepared by hydrolyzing a compound of Structure 5 with aqueous solution of NaOH, or LiOH etc. in a solvent such as water, MeOH, EtOH, THF etc.

Structure 6a

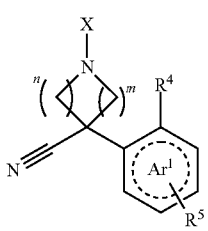

Structure 6b

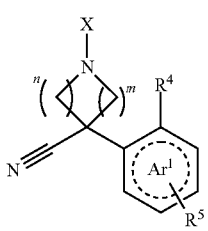

Structure 7a

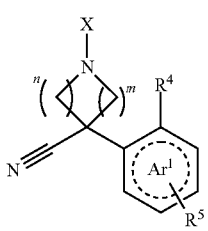

Structure 7b

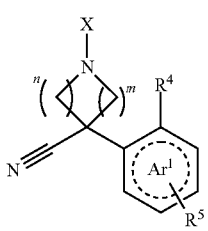

Compounds of Structure 3a, Structure 3b, Structure 3c and Structure 3d may be commercially available or may be prepared by reacting Structure 6a or Structure 6b (where $R^1$ represents H or F and $R^2$ represents H, halogen, $C_{1-2}$-alkyl, OMe or OEt) with sodium chlorodifluoroacetate or 2,2-difluoro-2-(fluorosulfonyl)acetic acid at 60° C. or more in a solvent such as DMF, MeCN, etc. and in the presence of $Na_2SO_4$ or a base such as $Cs_2CO_3$, $K_2CO_3$ etc. (Thomoson C. S. et al. J.Fluorine.Chem. 2014 (168) 34-39; Sperry J. B. et al. Org.ProcessRes.Dev. 2011 (15) 721-725; WO2012/055995). Compounds of Structure 3a, Structure 3b, Structure 3c and Structure 3d may also be prepared by reacting compounds of Structure 7a or Structure 7b with alcoholate such as NaOMe, NaOiPr in a solvent such as THF, DMF etc (WO2010/023181). For Structure 3c and Structure 3d the nitro group is reduced in a following step using $H_2$ and Pd/C for example. Residue $R^3$ can also be introduced at a later stage, after the amide coupling.

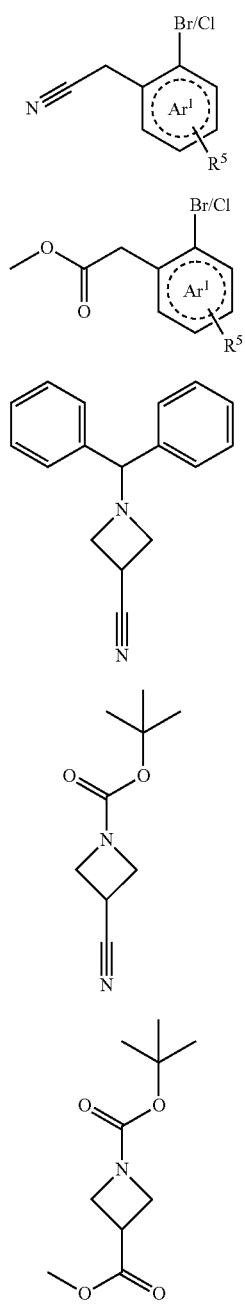

Structure 8

Structure 9

Structure 10

Structure 11

Structure 12

Compounds of Structure 4 and Structure 5 may be commercially available or may be prepared (for n and/or m>1) by reacting 2-(2-haloaryl)acetonitrile (Structure 8) or methyl 2-(2-haloaryl)acetate (Structure 9), respectively, with N-benzyl-N,N-bis(2-chloroethyl)amine or N-boc-N,N-bis (2-chloroethyl)amine at 60° C. or more in a solvent such as THF and in the presence of a base such as NaOH, NaH etc. Compounds of Structure 4 and Structure 5 may also be prepared by reacting 2-(2-bromophenyl)acetonitrile with paraformaldehyde in a solvent such as DMF in the presence of a base such as $K_2CO_3$ followed by a TFA-catalyzed 1,3-dipolar cycloaddition with commercially available N-(methoxymethyl)-N-(trimethylsilylmethyl)benzylamine in DCM (Lit: JP2008110971). For n=m=1, compounds of Structure 4 may be synthesized by reacting a compound of Structure 10, 11 or 12 with a 1,2-dihaloaryl, such as 1-bromo-2-fluorobenzene in a solvent such as THF in the presence of a base such as KHMDS (WO2012/017359). Alternatively, the bromo substituent can be replaced by $R^4$=alkyl in a following step under Negishi conditions or via a Suzuki-hydrogenation sequence known to a person skilled in the art.

Depending on the nature of the functionalities present in residue $R^6$ in formulae (I), (II) and (III), these functionalities may require temporary protection. Appropriate protecting groups are known to a person skilled in the art and include e.g. a benzyl, an acetyl, or a trialkylsilyl group to protect an alcohol, a ketal to protect a diol, an ester to protect an acid etc. These protecting groups may be employed according to standard methodology.

Whenever the compounds of formulae (I), (II) or (III) are obtained in the form of mixtures of stereoisomers such as especially enantiomers, the stereoisomers can be separated using methods known to one skilled in the art: e.g. by formation and separation of diastereomeric salts or by HPLC over a chiral stationary phase such as a Daicel ChiralPak AD-H (5 µm) column, a Daicel ChiralCel OD-H (5 µm) column, a Daicel ChiralCel OD (10 µm) column, a Daicel ChiralPak IA or IB or IC or ID or IE (5 µm) column, Daicel ChiralPak AS-H (5 µm) column or a (R,R)-Whelk-01 (5 µm) column. Typical conditions of chiral HPLC are an isocratic mixture of eluent A (EtOH, in presence or absence of a base like TEA and/or diethylamine or of an acid like TFA) and eluent B (heptane). In Supercritical Fluid Chromatography (SFC) conditions, eluent A is $CO_2$ and eluent B is isopropanol.

Experimental Part

The following examples illustrate the invention but do not at all limit the scope thereof.

All temperatures are stated in ° C. Commercially available starting materials were used as received without further purification. Unless otherwise specified, all reactions were carried out under an atmosphere of nitrogen or argon. Compounds were purified by flash chromatography on silica gel (Biotage), by prep TLC (TLC-plates from Merck, Silica gel 60 $F_{254}$) or by preparative HPLC. Compounds described in the invention are characterized by $^1$H-NMR (400 MHz or 500 MHz Bruker; chemical shifts are given in ppm relative to the solvent used; multiplicities: s=singlet, d=doublet, t=triplet, q=quadruplet, quint=quintuplet, hex=hexet, hept=heptet, m=multiplet, br=broad, coupling constants are given in Hz) and/or by LCMS (retention time $t_R$ is given in min; molecular weight obtained for the mass spectrum is given in g/mol) using the conditions listed below.

LCMS with Acidic Conditions

LCMS-1: Waters Acquity Binary, Solvent Manager, MS: Waters SQ Detector, DAD: Acquity UPLC PDA Detector, ELSD: Acquity UPLC ELSD. Columns: Acquity UPLC CSH C18 1.7 um 2.1×50 mm from Waters, thermostated in the Acquity UPLC Column Manager at 60° C. Eluents: A: $H_2O$+0.05% formic acid; B: AcCN+0.045% FA. Method: Gradient: 2% B 98% B over 2.0 min. Flow: 1.0 mL/min. Detection: UV 214 nm and ELSD.

LCMS-2: Aligent 1100 series with mass spectrometry detection (MS: Finnigan single quadrupole). Column: Zorbax RRHD SB-Aq (1.8 um, 3.0×50 mm). Conditions: MeCN [eluent A]; water+0.04% TFA [eluent B]. Gradient: 95% B→5% B over 5 min (flow: 4.5 mL/min)
Preparative HPLC with Acidic Conditions
Prep-HPLC-1: Column: Waters XBridge C18 (10 um, 75×30 mm). Conditions: MeCN [eluent A]; water+0.5% formic acid [eluent B]. Gradient: 95% B→5% B over 5 min (flow: 75 mL/min). Detection: UV/Vis+MS
Prep-HPLC-2: Column: Waters Zorbax SB-Aq (5 um, 75×30 mm). Conditions: MeCN [eluent A]; water+0.5% formic acid [eluent B]. Gradient: 95% B→5% B over 5 min (flow: 75 mL/min). Detection: UV/Vis+MS
Preparative HPLC with Basic Conditions
Prep-HPLC-3: Column: Waters XBridge C18 (10 um, 75×30 mm). Conditions: MeCN [eluent A]; water+0.5% NH$_4$OH [eluent B]. Gradient: 90% B→5% B over 6.5 min (flow: 75 mL/min). Detection: UV/Vis+MS Racemates can be separated into their enantiomers e.g. by preparative HPLC (column: ChiralPak AS-H 30×250 mm, 5 um, 20% iPrOH in supercritical CO$_2$)

ABBREVIATIONS (AS USED HEREIN)

Ac acetyl
AcOH acetic acid
aq. aqueous
BINAP 2,2'-bis(diphenylphosphino)-1,1'-binaphthyl
Boc tert-butoxycarbonyl
Boc-D-Glu-OtBu Boc-L-glutamic acid 1-tert-butyl ester
Bn benzyl
BSA bovine serum albumin
Bu butyl such as in tert.-Bu (=tertiary butyl)
CDI carbonyl diimidazole
Cs$_2$CO$_3$ cesium carbonate
DBU 1,8-diazabicyclo[5.4.0]undec-7-ene
DCC dicyclohexyl carbodiimide
DCM dichloromethane
DIPEA diisopropyl-ethylamine, Hünig's base, ethyl-diisopropylamine
DMA dimethylacetamide
DMAP 4-dimethylaminopyridine
DMF dimethylformamide
DMSO dimethylsulfoxide
EDC N-(3-dimethylaminopropyl)-N'-ethyl-carbodiimide
eq. equivalent(s)
Et ethyl (such as in OEt: ethoxy)
EtOAc ethyl acetate
EtOH ethanol
Ex. example(s)
h hour(s)
HATU 1-[Bis(dimethylamino)methylene]-1H-1,2,3-triazolo[4,5-b]pyridinium 3-oxid hexafluorophosphate
HBTU O-(benzotriazol-1-yl)-N,N,N',N'-tetramethyluronium hexafluorophosphate
HCl hydrochloric acid
HOBt 1-hydroxybenzotriazole
HPLC high performance liquid chromatography
H$_2$SO$_4$ sulfuric acid
iPr isopropyl
KHMDS potassium bis(trimethylsilyl)amide
K$_2$CO$_3$ potassium carbonate
LCMS liquid chromatography-mass spectrometry
Lit. Literature
LPA lysophosphatidic acid
LPAR$_1$ lysophosphatidic receptor 1
Me methyl (such as in OMe: methoxy)
MeCN acetonitrile
MeOH methanol
NaBH$_4$ sodium borohydride
NaH sodium hydride
NaOtBu sodium tert-butoxide
Na$_2$SO$_4$ sodium sulfate
NMM N-methylmorpholine
POCl$_3$ phosphoryl chloride
Pd$_2$(dba)$_3$ tris(dibenzylideneacetone)dipalladium(0)
Pd(OH)$_2$/C palladium hydroxide in charcoal
Pd(OAc)$_2$ palladium acetate
prep. preparative
r.t. room temperature
sat. saturated
TBME tert-butyl methyl ether
TBTU 2-(1H-benzotriazole-1-yl)-1,2,3,3-tetramethyluronium tetrafluoroborate
TEA triethylamine
TFA trifluoroacetic acid
THF tetrahydrofuran
TLC thin layer chromatography
T3P propylphosphonic anhydride
$t_R$ retention time

PREPARATION OF INTERMEDIATES

Intermediate 1.A:
2-Methoxy-6-methylpyridin-3-amine

Step 1. Methanol (256 uL, 6.39 mmol) is added drop wise into a stirred suspension of NaH (60% dispersion in oil, 256 mg, 6.39 mmol) in anhydrous THF (10 mL) at 0° C. and the resulting solution is stirred for 0.5 h. To this solution is added drop wise a solution of 2-fluoro-6-methyl-3-nitropyridine (1.0 g, 6.09 mmol) in anhydrous THF (5 mL). After complete addition the solution is stirred at 0° C. for 0.5 h, before being allowed to warm to ambient temperature. The reaction is stirred at ambient temperature for 18 h, quenched with water (30 mL) and the aqueous layer extracted with EtOAc (3×50 mL). The combined organic extracts are washed with brine (30 mL), dried over MgSO$_4$, filtered and concentrated in vacuo. 2-Methoxy-6-methyl-3-nitropyridine is obtained as a yellow oil (539 mg, 53% yield) after purification by prep-HPLC (Prep-HPLC-3). $^1$H NMR (400 MHz, DMSO D6) δ: 8.34 (d, J=8.1 Hz, 1 H), 7.09 (d, J=8.1 Hz, 1 H), 4.01 (s, 3 H), 2.51 (s, 3 H).

Step 2. To a degassed solution of 2-methoxy-6-methyl-3-nitropyridine (539 mg, 3.21 mmol) in methanol (10 mL) is added Pd(OH)$_2$/C (255 mg) followed by ammonium formate. The reaction mixture is stirred at 50° C. for 20 h and is then filtered over a Whatmann-Filter and evaporated. The residue is dissolved in EtOAc (30 mL) and the organic solution is washed with sat. NaHCO$_3$ sol. (15 mL) followed by brine (15 mL). The organic phase is dried over MgSO$_4$, filtered and evaporated to give 2-methoxy-6-methylpyridin-3-amine I-1.A as a yellow oil (199 mg, 45% yield). LCMS-2: $t_R$=0.38 min, [M+1]$^+$139.13; $^1$H NMR (400 MHz, DMSO D6) δ: 6.78 (d, J=7.5 Hz, 1 H), 6.54 (d, J=7.5 Hz, 1 H), 4.65 (s, 2 H), 3.82 (s, 3 H), 2.23 (s, 3 H).

Intermediate 1.B:
2-Isopropoxy-6-methylpyridin-3-amine

2-Isopropoxy-6-methylpyridin-3-amine I-1.B is synthesized using the methodology described for I-1.A starting from commercially available 2-fluoro-6-methyl-3-nitropyridine and isopropanol. ¹H NMR (400 MHz, DMSO D6) δ: 6.77 (d, J=7.5 Hz, 1 H), 6.49 (d, J=7.5 Hz, 1 H), 5.22 (m, 1 H), 4.53 (s, 2 H), 2.21 (s, 3 H), 1.27 (d, J=6.2 Hz, 6 H).

Intermediate 1.C:
2-(Difluoromethoxy)-6-methylpyridin-3-amine

Step 1. A suspension of 6-methyl-3-nitropyridin-2-ol (10 g, 61.6 mmol) and Na₂SO₄ (21.89 g, 15.4 mmol) in MeCN (250 mL) is heated up to 60° C. and 2,2-difluoro-2-(fluorosulfonyl)acetic acid (8.8 mL, 80 mmol) is added drop wise over 10 min. The reaction mixture is stirred for another hour and is then quenched with NaOH 3M (250 mL) and the acetonitrile is removed in vacuo. The remaining aqueous component is extracted with EtOAc (3×200 mL). The combined organic extracts are washed with water (50 mL) followed by brine (100 mL), dried over MgSO₄, filtered and concentrated in vacuo. The yellow oil is purified by column chromatography (Biotage, Heptane: EtOAc 1:0 to 1:1) to give 2-(difluoromethoxy)-6-methyl-3-nitropyridine as a yellow oil that crystallized upon standing (10.9 g, 85% yield). ¹H NMR (400 MHz, DMSO D6) δ: 8.51 (d, J=8.2 Hz, 1 H), 7.82 (t, J=71.3 Hz, 1 H), 7.39 (d, J=8.2 Hz, 1 H), 3.37 (s), 2.55 (s, 3 H).

Step 2. To 2-(difluoromethoxy)-6-methyl-3-nitropyridine (4.65 g, 22.8 mmol) in degassed methanol (100 mL) is added 10% palladium on carbon-50% wet (350 mg) and the reaction is hydrogenated at atmospheric pressure for 18 h. The mixture is filtered through Celite pad. The pad is rinsed with THF (3×10 mL) and the organic solution is concentrated in vacuo to afford 2-(difluoromethoxy)-6-methylpyridin-3-amine I-1.C as a pale yellow oil that crystallized upon standing (4.1 g, 92% yield). LCMS-2: $t_R$=0.75 min, no mass; ¹H NMR (400 MHz, CDCl₃) δ: 7.52 (t, J=73.5 Hz, 1 H), 6.96 (d, J=7.8 Hz, 1 H), 6.77 (d, J=7.8 Hz, 1 H), 2.36 (s, 3 H).

Intermediate 2: 1-Benzhydryl-3-(2-bromophenyl)azetidine-3-carboxylic acid

Step 1. To a solution of commercially available 1-bromo-2-fluorobenzene (5 g, 28.6 mmol) in THF (60 mL) is added 1-benzhydrylazetidine-3-carbonitrile (10.6 g, 42.9 mmol) and KHMDS 95% (10.3 mL, 42.9 mmol). The reaction mixture is left stirring at room temperature overnight. The reaction mixture is then concentrated to an oil under vacuum, diluted with EtOAc (100 mL) and washed with water (2×50 mL). The organic phase is dried over MgSO₄ and concentrated under vacuum. The crude material is purified by prep. HPLC (Prep-HPLC-2 conditions) to afford 1-benzhydryl-3-(2-bromophenyl)azetidine-3-carbonitrile as a beige solid (7.64 g, 66% yield). ¹H NMR (400 MHz, DMSO D6) δ: 7.70 (d, J=7.9 Hz, 1 H), 7.47-7.42 (m, 6 H), 7.36-7.31 (m, 5 H), 7.25-7.21 (m, 2 H), 4.56 (s, 1 H), 3.98 (d, J=8.0 Hz, 2 H), 3.49-3.42 (m, 2 H).

Step 2. To a solution of 1-benzhydryl-3-(2-bromophenyl)azetidine-3-carbonitrile (7.2 g, 17.9 mmol) in ethanol (80 mL) is added NaOH 25% (40 mL). The reaction mixture is stirred at 80° C. for 3-4 days (reaction monitored by LCMS) and is then cooled down to 0° C. and acidified by aq. 2M HCl. The mixture is extracted with EtOAc (2×200 mL), dried over MgSO₄, filtered and evaporated. The crude material is purified by column chromatography (eluent: DCM/MeOH 9:1) to give 1-benzhydryl-3-(2-bromophenyl)azetidine-3-carboxylic acid I-2 as yellow foam (6.37 g, 84% yield). LCMS-2: $t_R$=0.83 min, [M+1]⁺423.99; ¹H NMR (400 MHz, DMSO D6) δ: 7.54 (d, J=7.8 Hz, 1 H), 7.43-7.41 (m, 4 H), 7.37 (d, J=4.2 Hz, 2 H), 7.29 (t, J=7.3 Hz, 4 H), 7.21-7.17 (m, 3 H), 4.47 (s, 1 H), 3.88 (d, J=7.8 Hz, 2 H), 3.36 (d, J=7.7 Hz, 2 H).

Intermediate 3:
1-Benzhydryl-3-(2-bromophenyl)azetidine-3-carbonyl chloride

1-Benzhydryl-3-(2-bromophenyl)azetidine-3-carboxylic acid I-3 (538 mg, 1.38 mmol) is dissolved in DCM (10 mL). Three drops of DMF are added followed by thionyl chloride (0.5 mL, 6.9 mmol) and the reaction is stirred at 50° C. for 1 h (monitored by LCMS). The reaction mixture is then evaporated to give crude 1-benzhydryl-3-(2-bromophenyl)azetidine-3-carbonyl chloride I-3 as a wax (620 mg) that is used a such.

Intermediate 4: 1-(tert-butoxycarbonyl)-4-(2-isopropylphenyl)piperidine-4-carboxylic acid Step 1. A mixture of commercially available 2-bromophenylacetonitrile (10 g, 51 mmol) and tetrabutylammonium hydrogen sulfate (1.77 g, 5.1 mmol) in 60 mL of THF and 90 ml of 50% aqueous NaOH solution is heated at reflux for 10 min. Thereafter N-benzyl-N,N-bis(2-chloroethyl)amine hydrochloride (15 g, 56.1 mmol) are added at r.t. and the mixture is refluxed overnight. Cooling to r.t. is followed by dilution with water (120 mL) and extraction with EtOAc (2×200 mL). The combined organic extracts are washed with brine (100 mL), dried with MgSO₄, and concentrated in vacuo. The crude compound is crystallized in acetonitrile to give 1-benzyl-4-(2-bromophenyl)piperidine-4-carbonitrile (12.6 g, 69% yield) as white crystalline solid. ¹H NMR (500 MHz, DMSO D6) δ: 7.75 (dd, J₁=1.3 Hz, J₂=7.9 Hz, 1 H), 7.55 (dd, J₁=1.6 Hz, J₂=8.1 Hz, 1 H), 7.48 (td, J₁=1.3 Hz, J₂=7.4 Hz, 1 H), 7.35-7.32 (m, 5 H), 7.30-7.25 (m, 1 H), 3.58 (s, 2 H), 3.01-2.98 (m, 1 H), 2.98-2.95 (m, 1 H), 2.54-2.52 (m, 2H), 2.43-2.39 (m, 2 H), 2.00 (td, J₁=3.4 Hz, J₂=12.8 Hz, 2 H).

Step 2. A mixture of 1-benzyl-4-(2-bromophenyl)piperidine-4-carbonitrile (29.4 g, 82.9 mmol), acetic acid (75 mL) and concentrated sulfuric acid (75 mL) in water (75 mL) is stirred at reflux for 4 days (reaction monitored by LCMS). The reaction mixture is then diluted with water (50 mL) and 25% aqueous solution HCl (50 mL) and is stirred for 15 min. TBME (100 mL) is added. The mixture for stirred for another 15 min and is stored at 4° C. overnight. The white precipitate is filtered, rinsed with TBME and dried in vacuo to give 1-benzyl-4-(2-bromophenyl)piperidine-4-carboxylic acid (22.1 g, 71% yield) as a white powder. LCMS-2: $t_R$=0.72 min, [M+1]⁺374.17 and 376.18.

Step 3. 1-Benzyl-4-(2-bromophenyl)piperidine-4-carboxylic acid (10 g, 26.7 mmol) and isopropenyl boronic acid pinacolester (15.1 mL, 80.2 mmol) are dissolved in dioxane (120 mL) and water (60 mL). Tripotassium phosphate (29.9 g, 134 mmol) is then added followed by palladium acetate (300 mg, 1.34 mmol) and di(1-adamantyl)-n-butylphosphine (969 mg, 2.67 mmol). The degassed reaction mixture is heated at 100° C. overnight (reaction monitored by LCMS) The reaction is diluted with EtOAc (200 mL) and extracted with 2N HCl (20 mL). The acidic aqueous phase is extracted with EtOAc (3×150 mL). All organic phases are combined (650 mL), washed with brine (20 mL), dried over MgSO₄, filtered and evaporated to give the crude compound that is purified by prep. HPLC (Prep-HPLC-3 conditions) to give 1-benzyl-4-(2-(prop-1-en-2-yl)phenyl)piperidine-4-carboxylic acid I-4 as a beige solid (8.4 g, 93% yield). ¹H NMR (400 MHz, DMSO D6) δ: 12.70 (s, 1 H), 7.44 (d, J=7.9 Hz, 1 H), 7.33-7.18 (m, 7 H), 7.01 (dd, $J_1$=1.2 Hz, $J_2$=7.3 Hz, 1 H), 5.10 (s, 1 H), 4.71 (s, 1 H), 2.43-2.38 (m, 4 H), 2.34-2.31 (m, 2 H), 2.13-2.11 (m, 2 H), 2.01 (s, 3 H).

Step 4. A degassed mixture of 1-benzyl-4-(2-(prop-1-en-2-yl)phenyl)piperidine-4-carboxylic acid (8.4 g, 24.8 mmol) and Pd/C 10%- 50% water (2 g) in MeOH/THF 1:1 (200 mL) is hydrogenated at r.t. for 4 days (reaction monitored by LCMS). The mixture is degassed with argon, filtered on Celite pad, rinsed with THF, dried over $MgSO_4$ and evaporated to give 4-(2-isopropylphenyl)piperidine-4-carboxylic acid (5.6 g, 92% yield) as a white solid. $^1$H NMR (400 MHz, DMSO) δ: 9.06 (s br, 1 H), 7.38 (dd, $J_1$=1.4 Hz, $J_2$=7.8 Hz, 1 H), 7.31-7.27 (m, 2 H), 7.24-7.16 (m, 1 H), 3.44 (s br, 1 H), 3.27-3.12 (m, 5 H), 2.38 (m, 2 H), 2.20-2.12 (m, 2 H), 1.14 (d, J=6.7 Hz, 6 H).

Step 5. A mixture of 4-(2-isopropylphenyl)piperidine-4-carboxylic acid (5.65 g, 23.2 mmol), DIPEA (13.6 mL, 79.7 mmol) and $Boc_2O$ (4.8 g, 21.9 mmol) is stirred at r.t. for 24 h. Water is then added followed by 1N HCl in order to adjust the pH to 1. The reaction mixture is extracted four times with DCM (4 x 200 mL). The combined extracts are dried over $MgSO_4$, dried, filtered an evaporated to give 1-(tert-butoxycarbonyl)-4-(2-isopropylphenyl)piperidine-4-carboxylic acid I-4 (9 g, quantitative) as a yellow oil. $^1$H NMR (400 MHz, DMSO D6) δ: 12.73 (s, 1 H), 7.36-7.31 (m, 2 H), 7.26-7.23 (m, 1 H), 7.18-7.14 (m, 1 H), 3.75-3.65 (m, 2 H), 3.32-3.25 (m, 3 H), 2.28-2.20 (m, 2 H), 1.89-1.77 (m, 2 H), 1.41 (s, 9 H), 1.14 (d, J=6.6 Hz, 6 H).

Alternatively, 1-4 can be prepared from commercial available 4-(2-bromophenyl)-1-(tert-butoxycarbonyl)piperidine-4-carboxylic acid:

Step 1. 1-(tert-Butoxycarbonyl)-4-(2-(prop-1-en-2-yl)phenyl)piperidine-4-carboxylic acid is prepared from commercial available 4-(2-bromophenyl)-1-(tert-butoxycarbonyl)piperidine-4-carboxylic acid following the methodology described for I-4 in step 3 (59% yield). $^1$H NMR (400 MHz, DMSO D6) δ: 7.44 (dd, $J_1$=1.5 Hz, $J_2$=8.0 Hz, 1 H), 7.30-7.22 (m, 2 H), 7.05 (dd, $J_1$=1.8 Hz, $J_2$=7.2 Hz, 1 H), 5.14 (t, J=1.6 Hz, 1 H), 4.75 (d, J=1.0 Hz, 1 H), 3.54-3.48 (m, 2 H), 3.32-3.15 (m, 2 H), 2.27-2.23 (m, 2 H), 2.06-2.00 (m, 5 H).

Step 2. A degassed mixture of 1-(tert-butoxycarbonyl)-4-(2-(prop-1-en-2-yl)phenyl)piperidine-4-carboxylic acid (986 mg, 2.85 mmol) and Pd/C 10%- 50% water (100 mg) in MeOH/THF 1:1 (60 mL) is hydrogenated at r.t. for 1 h (reaction monitored by LCMS). The mixture is degassed with argon, filtered on Celite pad, rinsed with THF, dried over $MgSO_4$ and evaporated to give 1-(tert-butoxycarbonyl)-4-(2-isopropylphenyl)piperidine-4-carboxylic acid I-4 as a white foam (923 mg, 93% yield).

Intermediate 5:
1-benzyl-3-(2-bromophenyl)pyrrolidine-3-carboxylic acid

Step 1. Paraformaldehyde (2.17 ml, 14.8 mmol) and $K_2CO_3$ (1.37 g, 9.9 mmol) are added to a solution of commercially available 2-bromophenylacetonitrile (1.32 mL, 9.9 mmol) in DMF (60 mL). The reaction is stirred at 80° C. for 1 night. After cooling to r.t., water (100 mL) is added and the aqueous layer is extracted with EtOAc (150 mL, 50 mL). The combined organic extracts are washed with brine, dried over $MgSO_4$, filtered and evaporated. The crude compound is purified by prep. HPLC (Prep-HPLC-3 conditions) to give 2-(2-bromophenyl)acrylonitrile (561 mg, 27% yield) as an orange oil. $^1$H NMR (400 MHz, DMSO) δ: 7.77-7.74 (m, 1 H), 7.53-7.48 (m, 2 H), 7.42 (ddd, $J_1$=2.9 Hz, $J_2$=6.3 Hz, $J_3$=8.0 Hz, 1 H), 6.61 (s, 1 H), 6.36 (s, 1 H).

Step 2. 2-(2-Bromophenyl)acrylonitrile (461 mg, 2.22 mmol) and N-(methoxymethyl)-N-(trimethylsilylmethyl) benzylamine (1.18 mL, 4.43 mmol) are dissolved in DCM (10 mL). To this solution TFA (208 uL, 2.66 mmol) is added under ice-cooling. After returning to rt, the reaction is stirred for overnight. The reaction mixture is then poured into water (25 mL) and extracted with DCM (2×50 mL). The combined organic extracts are washed with $NaHCO_3$, followed with brine, is dried over $MgSO_4$, filtered and evaporated. The crude compound is purified by prep HPLC (Prep-HPLC-3 conditions) to give 1-benzyl-3-(2-bromophenyl)pyrrolidine-3-carbonitrile (495 mg, 65% yield) as a yellow oil. LCMS-2: $t_R$=0.74 min, $[M+1]^+$341.22 and 343.20.

Step 3. 1-Benzyl-3-(2-bromophenyl)pyrrolidine-3-carbonitrile (495 mg, 1.45 mmol) is subjected to the hydrolysis conditions described for I-4 to give 1-benzyl-3-(2-bromophenyl)pyrrolidine-3-carboxylic acid I-5 as a beige solid (293 mg, 56% yield). LCMS-2: $t_R$=0.64 min, $[M+1]^+$360.16 and 362.16.

Intermediate 6: 1-(tert-butoxycarbonyl)-4-(2-isopropylphenyl)piperidine-4-carboxylic acid Step 1. To a solution of I-2 (5.0 g, 11.8 mmol) in MeOH (30 mL) is added conc. sulfuric acid (10 mL). The reaction mixture is stirred at 75° C. for 24 h and is then evaporated. The residue is dissolved in EtOAc (100 mL) and washed with sat. $NaHCO_3$. The phases are separated and the organic phase is washed with brine (50 mL), dried over $MgSO_4$, filtered and evaporated. The crude compound is purified by Chromatography (CombiFlash Hept/EtOAc 9:1) to methyl 1-benzhydryl-3-(2-bromophenyl)azetidine-3-carboxylate as yellow oil (4.12 g, 80% yield). $^1$H NMR (400 MHz, $CDCl_3$) δ: 7.54 (dd, $J_1$=1.1 Hz, $J_2$=8.0 Hz, 1 H), 7.49-7.41 (m, 4 H), 7.38-7.32 (m, 1 H), 7.32-7.26 (m, 5 H), 7.24-7.19 (m, 2 H), 7.17 (td, $J_1$=1.9 Hz, $J_2$=7.9 Hz, 1 H), 4.43 (s, 1 H), 4.08 (d, J=8.3 Hz, 2 H), 3.74 (s, 3 H), 3.51 (d, J=8.2 Hz, 2 H).

Step 2. Methyl 1-benzhydryl-3-(2-bromophenyl)azetidine-3-carboxylate (4.12 g, 9.44 mmol) is subjected to the Suzuki conditions described for intermediate 3 to give methyl 1-benzhydryl-3-(2-(prop-1-en-2-yl)phenyl)azetidine-3-carboxylate as a yellow oil (3.64 g, 97% yield). $^1$H NMR (400 MHz, DMSO D6) δ: 7.40-7.38 (m, 4 H), 7.30-7.23 (m, 7 H), 7.21-7.17 (m, 2 H), 7.12-7.10 (m, 1 H), 5.06 (s, 1 H), 4.59 (s, 1 H), 4.42 (s, 1 H), 3.82 (d, J=7.7 Hz, 2 H), 3.66 (s, 3 H), 3.21 (d, J=7.7 Hz, 2 H), 1.92 (s, 3 H).

Step 3. Methyl 1-benzhydryl-3-(2-(prop-1-en-2-yl)phenyl)azetidine-3-carboxylate (3.64 g, 9.16 mmol) is subjected to the saponification conditions described for I-3 to give 1-benzhydryl-3-(2-(prop-1-en-2-yl)phenyl)azetidine-3-carboxylic acid as a beige solid (3.35 g, 95% yield). $^1$H NMR (400 MHz, DMSO D6) δ: 7.39 (d, J=7.3 Hz, 4 H), 7.28 (t, J=7.4 Hz, 4 H), 7.23-7.17 (m, 5 H), 7.11-7.09 (m, 1 H), 5.06 (s, 1 H), 4.71 (s, 1 H), 4.39 (s, 1 H), 3.82 (d, J=7.6 Hz, 2 H), 3.14 (d, J=7.5 Hz, 2 H), 1.95 (s, 3 H).

Step 4. A mixture of 1-benzhydryl-3-(2-(prop-1-en-2-yl)phenyl)azetidine-3-carboxylic acid (3.35 g, 8.74 mmol), 25% HCl solution (18 mL) and $Pd(OH)_2/C$ 20% (1.6 g) in MeOH (100 mL) is degassed and is then hydrogenated at 1 bar for 18 h (reaction monitored by LCMS). The reaction mixture is then degassed with argon and is filtered on Celite pad which is rinsed with MeOH. Volatiles are evaporated and the residue is crystallized in MeCN to give hydrochloride of 3-(2-isopropylphenyl)azetidine-3-carboxylic acid as a white solid (1.17 g, 61% yield). $^1$H NMR (400 MHz, DMSO D6) δ: 13.55 (s br, 1 H), 9.40 (s br, 1 H), 9.15 (s br, 1 H), 7.39 (d, J=6.9 Hz, 1 H), 7.34 (t, J=7.2 Hz, 1 H), 7.24 (t, J=7.0 Hz, 1 H), 7.18 (d, J=7.6 Hz, 1 H), 4.57-4.54 (m, 2 H), 4.39-4.35 (m, 2 H), 1.13 (d, J=6.7 Hz, 6 H).

Step 5. To a suspension of 3-(2-isopropylphenyl)azetidine-3-carboxylic acid hydrochloride (1.17 g, 4.57 mmol) in DCM (25 ml) is added DIPEA (5.9 mL, 34.4 mmol) followed by Boc$_2$O (1.1 g, 5.02 mmol). The mixture stirred at room temperature for 24 h. 1N HCl is added in order to adjust the pH to 1, and the reaction mixture is extracted with DCM (4 times). The combined organic extracts are dried over MgSO$_4$, filtered and evaporated. The residue is purified by chromatography (CombiFlash Hept/EtOAc 1.5:1) to give 1-(tert-butoxycarbonyl)-4-(2-isopropylphenyl)piperidine-4-carboxylic acid I-6 as a white solid (0.85 g, 58% yield). $^1$H NMR (400 MHz, CDCl$_3$) δ: 7.36-7.31 (m, 2 H), 7.26-7.21 (m, 1 H), 7.18 (d, J=7.0 Hz, 1 H), 4.64 (d, J=8.5 Hz, 2 H), 4.37 (d, J=8.5 Hz, 2 H), 2.61 (m, 1 H), 1.46 (s, 9 H), 1.19 (d, J=6.7 Hz, 6 H).

Intermediate 7: 1-benzhydryl-3-(2-bromo-6-methylphenyl)azetidine-3-carboxylic acid Intermediate I-7 is prepared from 3-bromo-2-fluorotoluene according to the method described for I-2. For a cleaner hydrolysis of the nitrile group to the corresponding carboxylic acid a two step sequence is preformed, using first basic conditions (KOH) to form the intermediate amide followed by an acidic hydrolysis of the amide as described for I-4. LCMS-2: t$_R$=0.84 min, [M+1]$^+$435.86.

Intermediate 8: 1-benzhydryl-3-(2-bromo-5-methylphenyl)azetidine-3-carboxylic acid Intermediate I-8 is prepared from 4-bromo-3-fluorotoluene according to the method described for I-2. LCMS-2: t$_R$=0.85 min, [M+1]$^+$435.75.

Intermediate 9: 1-benzhydryl-3-(2-bromo-4-methylphenyl)azetidine-3-carboxylic acid Intermediate I-9 is prepared from 3-bromo-4-fluorotoluene according to the method described for I-2. For a cleaner hydrolysis of the nitrile group to the corresponding carboxylic acid a two step sequence is preformed, using first basic conditions (KOH) to form the intermediate amide followed by an acidic hydrolysis of the amide as described for I-4. LCMS-2: t$_R$=0.86 min, [M+1]$^+$435.93.

Intermediate 10: 1-benzhydryl-3-(2-bromo-6-fluorophenyl)azetidine-3-carboxylic acid Intermediate I-10 is prepared from 1-bromo-2,3-difluorobenzene according to the method described for I-2. LCMS-2: t$_R$=0.83 min, [M+1]$^+$440.24.

Intermediate 11: 1-benzhydryl-3-(2-bromo-5-fluorophenyl)azetidine-3-carboxylic acid Intermediate I-11 is prepared from 1-bromo-2,4-difluorobenzene according to the method described for I-2. LCMS-2: t$_R$=0.83 min, [M+1]$^+$440.21.

Intermediate 12: 1-benzhydryl-3-(2-bromo-5-methoxyphenyl)azetidine-3-carboxylic acid Intermediate I-12 is prepared from 4-bromo-3-fluoroanisole according to the method described for I-2. LCMS-2: t$_R$=0.84 min, [M+1]$^+$451.97.

Intermediate 13: 3-(carboxymethyl)oxetane-3-carboxylic acid

The title compound I-13 is prepared from commercially available ethyl-2-(3-cyanooxetan-2-yl)acetate according to the method described in US20080207573.

Intermediate 14: 3-(2-(benzyloxy)-2-oxoethoxy)propanoic acid

To a solution of benzyl-glycolate (1.0 g, 6.02 mmol) in DMF (60 mL) is added a suspension of NaH (60% dispersion in oil, 433 mg, 10.8 mmol). After 1 h a solution of 2-(3-brom-propoxy)-tetrahydro-2-H-pyran (1.07 g, 4.81 mmol) in DMF (2 mL) is added and the reaction mixture is stirred at 80° C. for 2 h. Water (23 mL) is then added and the mixture is extracted with EtOAc (100 mL). The extract is washed with brine, dried over MgSO$_4$, filtered and evaporated. The yellow residue is purified by prep. HPLC (Prep-HPLC-3 conditions) to give benzyl 2-(3-((tetrahydro-2H-pyran-2-yl)oxy)propoxy)acetate (192 mg) as a yellow oil. Next, a solution of benzyl 2-(3-((tetrahydro-2H-pyran-2-yl)oxy)propoxy)acetate (138 mg, 0.46 mmol) and p-toluenesulfonic acid monohydrate (8.8 mg, 0.05 mmol) in MeOH (10 mL) is stirred at r.t. for 2 h (reaction monitored by LCMS). The reaction is diluted with Et$_2$O (60 mL) and washed with NaHCO$_3$ (10 mL). The organic phase is dried over MgSO$_4$, filtered and evaporated to give crude benzyl 2-(3-hydroxypropoxy)acetate that is dissolved in MeCN (5 ml). Sequentially a buffer solution of NaH$_2$PO$_4$ (0.1 mol/L, 0.5 mL), 2,2,6,6-tetramethylpiperidin-1-oxyl radical (TEMPO, 7.3 mg, 0.05 mmol), aq. solution of sodium chlorite (80 g/L, 1.1 mL) and sodium hypochlorite (50 uL) are added and the reaction mixture is stirred at 50° C. overnight. The mixture is then quenched with saturated sodium sulphite (2 mL) and volatiles are evaporated. The residue is dissolved in 3 mL of DMF/MeCN (1:1) and is purified by prep. HPLC (Prep-HPLC-3 conditions) to give the title compound I-14 as a beige wax (11 mg). LCMS-2: t$_R$=0.76 min, [M+1]$^+$239.18; $^1$H NMR (500 MHz, MeOD) δ: 7.38 (m), 7.42-7.30 (m, 5 H), 5.20 (s, 2 H), 4.19 (s, 2 H), 3.81 (t, J=6.4 Hz, 2 H), 2.58 (t, J=6.4 Hz, 2 H).

Intermediate 15: 3-(methoxycarbonyl)bicyclo[1.1.1]pentane-1-carboxylic acid

The title compound I-15 is prepared from commercially available dimethyl bicyclo[1.1.1]pentane-1,3-dicarboxylate according to the method described in *J.Med.Chem.* 2012, 55(7), 3414-3424 (Stepan, A. F. et al.).

Intermediate 16: 3-(methylsulfonamido)-3-oxopropanoic acid

The title compound I-16 is prepared from commercially available methylpropiolate and methansulfonylazide according to the method described in X. Wang et al. *Tetrahedron* 2011, 67, 6294-6299.

Intermediate 17: 4-ethoxy-3,3-difluoro-4-oxobutanoic acid

To a solution of 2,2-difluorosuccinic acid (100 mg, 0.649 mmol) in isopropylacetate (2 mL) trifluoroacetic anhydride (108 uL, 0.78 mmol) is added. The solution is stirred at 50° C. for 1 h to yield 2,2-difluorosuccinic anhydride that is opened with ethanol (200 uL) to afford crude 3,3-difluoro- 4-methoxy-4-oxobutanoic acid I-17 (160 mg) as a yellow oil. $^1$H NMR (400 MHz, DMSO) δ: 13.20 (s br, 1 H), 4.30 (q, J=7.2 Hz, 1 H), 3.36 (t, $J_{H-F}$=14.9 Hz, 2 H), 1.25 (t, J=7.2 Hz, 3 H).

Intermediate 18: (S)-(+)-Citramalic acid

Intermediate I-18 is prepared from commercially available (R)-(+)-4-methyl-4-(trichloromethyl)-2-oxetanone according to the method described in M. Gill et al., *Aust. J. Chem.* 2000, 53, 245-256.

EXAMPLES

Example 1: 3-(2-isopropylphenyl)-N-(2-methoxy-6-methylpyridin-3-yl)azetidine-3-carboxamide Step 1. To a solution of 2-methoxy-6-methylpyridin-3-amine I-1.A (191 mg, 1.38 mmol) in THF (10 mL) is added a suspension of NaH (60% dispersion in oil, 120 mg, 2.76 mmol). After stirring the mixture for 30 min, a suspension of benzhydryl-3-(2-bromophenyl)azetidine-3-carbonyl chloride I-3 (608 mg, 1.38 mmol) in THF (10 mL) is added drop wise and stirring is continued for 2 h (reaction monitored by LCMS). The reaction mixture is then diluted with DCM (50 mL) and is washed with water (20 mL). The organic phase is dried over MgSO$_4$, filtered and evaporated. The crude compound is crystallized in MeCN to give 1-benzhydryl-3-(2-bromophenyl)-N-(2-methoxy-6-methylpyridin-3-yl)azetidine-3-carboxamide as an off-white solid (278 mg, 37% yield). $^1$H NMR (400 MHz, DMSO D6) δ: 11.10 (s, $^1$H), 8.42 (d, J=7.9 Hz, 1 H), 7.62-7.57 (m, 5 H), 7.40-7.34 (m, 5 H), 7.28-7.18 (m, 4 H), 6.88 (d, J=7.9 Hz, 1 H), 4.73 (s, 1 H), 4.17 (s, 3 H), 4.01 (d, J=7.0 Hz, 2 H), 3.52 (d, J=7.3 Hz, 2 H), 2.42 (s, 3 H).

Step 2. 1-Benzhydryl-N-(2-methoxy-6-methylpyridin-3-yl)-3-(2-(prop-1-en-2-yl)phenyl)azetidine-3-carboxamide is prepared from 1-benzhydryl-3-(2-bromophenyl)-N-(2-methoxy-6-methylpyridin-3-yl)azetidine-3-carboxamide following the methodology described for I-6-step 3 (216 mg, 84% yield). $^1$H NMR (400 MHz, DMSO D6) δ: 11.24 (s, 1 H), 8.44 (d, J=7.9 Hz, 1 H), 7.57 (d, J=7.5 Hz, 4 H), 7.36 (t, J=7.5 Hz, 4 H), 7.26-7.15 (m, 5 H), 7.00 (d, J=7.3 Hz, 1 H), 6.88 (d, J=7.9 Hz, 1 H), 4.98 (s, 1 H), 4.74 (s, 1 H), 4.68 (s, 1 H), 4.16 (s, 3 H), 3.87 (d, J=7.4 Hz, 2 H), 3.33 (d, J=7.4 Hz, 2 H), 2.42 (s, 3 H), 1.94 (s, 3 H).

Step 3. A mixture of 1-benzhydryl-N-(2-methoxy-6-methylpyridin-3-yl)-3-(2-(prop-1-en-2-yl)phenyl)azetidine-3-carboxamide (216 mg, 0.43 mmol), 25% HCl solution (4.5 mL) and Pd(OH)$_2$/C 20% wt. % (300 mg) in MeOH (25 mL) is degassed and is then hydrogenated at 1 bar for 18 h (reaction monitored by LCMS). The reaction mixture is then degassed with argon and is filtered on Celite pad which is rinsed with MeOH (10 mL). Volatiles are evaporated and the residue is dissolved in EtOAc (60 mL). The organic solution is washed with a solution of NaOH 5N aq. (30 mL), is dried over MgSO$_4$, filtered and evaporated. The crude material is purified by prep-TLC (eluent: DCM/MeOH: 9/1) to give 3-(2-isopropylphenyl)-N-(2-methoxy-6-methylpyridin-3-yl)azetidine-3-carboxamide Ex 1 as a white solid (32 mg, 22% yield). LCMS-1: $t_R$=0.68 min, [M+1]$^+$340.43; $^1$H NMR (400 MHz, CD$_3$OD) δ: 8.34 (d, J=7.9 Hz, 1 H), 7.46-7.35 (m, 4 H), 6.78 (d, J=7.9 Hz, 1 H), 4.31 (d, J=8.5 Hz, 2 H), 4.17 (d, J=8.5 Hz, 2 H), 3.72 (s, 3 H), 2.49 (m, 1 H), 2.36 (s, 3 H), 1.13 (d, J=6.7 Hz, 6 H).

Example 2: N-(2-isopropoxy-6-methylpyridin-3-yl)-3-(2-isopropylphenyl)azetidine-3-carboxamide N-(2-isopropoxy-6-methylpyridin-3-yl)-3-(2-isopropylphenyl)azetidine-3-carboxamide is prepared from 2-isopropoxy-6-methylpyridin-3-amine I-1.B (1.8 g) and benzhydryl-3-(2-bromophenyl)azetidine-3-carbonyl chloride I-3 (4.36 g) following the methodology described for Ex 1 (1.29 g, white solid). LCMS-1: $t_R$=0.80 min, [M+1]$^+$368.34; $^1$H NMR (400 MHz, CD$_3$OD) δ: 8.45 (d, J=7.9 Hz, 1 H), 7.49-7.47 (m, 2 H), 7.43-7.40 (m, 2 H), 6.74 (d, J=8.0 Hz, 1 H), 5.51 (s, 1 H), 5.18-5.11 (m, 1 H), 4.38 (d, J=8.2 Hz, 2 H), 4.21 (d, J=8.0 Hz, 2 H), 2.37-2.44 (m, 1 H), 2.33 (s, 3 H), 1.13 (d, J=6.7 Hz, 7 H), 1.02 (d, J=6.2 Hz, 6 H).

Example 3: N-(2-(difluoromethoxy)-6-methylpyridin-3-yl)-3-(2-isopropylphenyl)azetidine-3-carboxamide N-(2-(difluoromethoxy)-6-methylpyridin-3-yl)-3-(2-isopropylphenyl)azetidine-3-carboxamide is prepared from 2-(difluoromethoxy)-6-methylpyridin-3-amine I-1.C (229 mg) and benzhydryl-3-(2-bromophenyl)azetidine-3-carbonyl chloride I-3 (608 mg) following the methodology described for Ex 1 (110 mg, yellow oil). LCMS-1: $t_R$=0.71 min, [M+1]$^+$376.22; $^1$H NMR (500 MHz, DMSO D6) δ: 9.90 (s, 1 H), 8.24 (d, J=8.0 Hz, 1 H), 7.63 (t, J=72.6 Hz, 1 H), 7.33 (dd, $J_1$=1.3 Hz, $J_2$=7.8 Hz, 1 H), 7.28 (td, $J_1$=1.2 Hz, $J_2$=7.3 Hz, 1 H), 7.19 (m, $J_1$=1.4 Hz, $J_2$=7.7 Hz, 1 H), 7.14 (dd, $J_1$=1.1 Hz, $J_2$=7.7 Hz, 1 H), 7.11 (d, J=8.4 Hz, 1 H), 4.07 (m, 2 H), 4.01 (m, 2 H), 2.38 (s, 3 H), 1.09 (d, J=6.7 Hz, 6 H).

Example 4: N-(2-(difluoromethoxy)-6-methylpyridin-3-yl)-4-(2-isopropylphenyl)piperidine-4-carboxamide and Example 4.1: tert-butyl 4-((2-hydroxy-6-methylpyridin-3-yl)carbamoyl)-4-(2-isopropylphenyl)piperidine-1-carboxylate Step 1. To a solution of 1-(tert-butoxycarbonyl)-4-(2-isopropylphenyl)piperidine-4-carboxylic acid I-4 (2 g, 5.76 mmol) and DMF (1 mL) in pyridine (20 mL) is added POCl$_3$ (0.79 mL, 8.63 mmol) drop wise over 35 min (complete conversion into its acyl chloride is monitored by LCMS with MeOH quench). Next, the reaction mixture is evaporated to remove the volatiles. The crude material is suspended in pyridine (20 mL) and added drop wise to a solution of 3-amino-6-methylpyridin-2-ol (14.4 mmol, 1.79 g) in pyridine (10 mL). The reaction mixture is stirred at r.t. for 2 h and is then evaporated. The residue is dissolved in EtOAc (50 mL), is washed with water (20 mL) followed by sat. NaHCO$_3$ solution (50 mL) and brine (50 mL). The organic phase is then dried over MgSO$_4$, filtered and evaporated. The crude product is purified by prep. HPLC (Prep-HPLC-3 conditions) to give tert-butyl 4-((2-hydroxy-6-methylpyridin-3-yl)carbamoyl)-4-(2-isopropylphenyl)piperidine-1-carboxylate (850 mg, 33% yield) as a yellow oil. LCMS-1: $t_R$=1.24 min, [M+1]$^+$454.07; $^1$H NMR (400 MHz, DMSO D6) δ: 11.88 (s, 1 H), 8.12 (d, J=7.4 Hz, 1 H), 7.81 (s, 1 H), 7.52 (d, J=7.5 Hz, 1 H), 7.41 (dd, $J_1$=1.4 Hz, $J_2$=7.8 Hz, 1 H), 7.35 (t, J=7.0 Hz, 1 H), 7.29 (td, $J_1$=1.4 Hz, $J_2$=7.8 Hz, 1 H), 5.99 (d, J=7.5 Hz, 1 H), 3.49 (s br, 4 H), 3.11-3.04 (m, 1 H), 2.28-2.24 (m, 2 H), 2.10 (s, 3 H), 1.99-1.95 (m, 2 H), 1.40 (s, 9 H), 1.02 (d, J=6.6 Hz, 6 H).

Step 2. To a solution of 4-((2-hydroxy-6-methylpyridin-3-yl)carbamoyl)-4-(2-isopropylphenyl)piperidine-1-carboxylate (850 mg, 1.87 mmol) in DMF (20 mL) is added CS₂CO₃ (916 mg, 2.81 mmol) followed by sodium chlorodifluoroacetate (429 mg, 2.81 mmol). The reaction mixture is stirred at 60° C. for 18 h. Next the mixture is diluted with EtOAc (50 mL) and is washed with sat. NaHCO₃ solution (25 mL) followed by brine (25 mL). The organic phase is dried over MgSO₄, filtered and evaporated. The residue is purified by prep. HPLC (Prep-HPLC-3 conditions) to give tert-butyl 4-((2-(difluoromethoxy)-6-methylpyridin-3-yl)carbamoyl)-4-(2-isopropylphenyl)piperidine-1-carboxylate as a beige powder (709 mg) Ex 4-1 that contained about 15% of a regioisomer. LCMS-1: $t_R$=1.48 min, [M+1]⁺504.17. ¹H NMR (400 MHz, DMSO D6) δ: 8.23 (s, 1 H), 7.85 (d, J=8.0 Hz, 1 H), 7.53 (t, J=72.6 Hz, 1 H), 7.50-7.48 (m, 1 H), 7.41 (dd, $J_1$=1.5 Hz, $J_2$=7.8 Hz, 1 H), 7.34 (d, J=6.1 Hz, 1 H), 7.27 (m, 1 H), 7.09 (d, J=8.0 Hz, 1 H), 3.67-3.60 (m, 2 H), 3.53-3.42 (m, 2 H), 3.28-3.20 (m, 1 H), 2.41-2.37 (m, 5 H), 1.98-1.90 (m, 2 H), 1.41 (s, 9 H), 1.09 (d, J=6.6 Hz, 6 H).

Step 3. To a solution of 4-((2-(difluoromethoxy)-6-methylpyridin-3-yl)carbamoyl)-4-(2-isopropylphenyl)piperidine-1-carboxylate (709 mg, 1.41mmol) in DCM (20 mL) is added TFA (1.1 mL, 14.1 mmol) at 10° C. The reaction mixture is stirred at r.t. for 2 h (monitored by LCMS) and is then evaporated. The residue is purified by prep. HPLC (Prep-HPLC-3 conditions) to give N-(2-(difluoromethoxy)-6-methylpyridin-3-yl)-4-(2-isopropyl-phenyl)piperidine-4-carboxamide Ex 4 (416 mg, 73% yield) as a white solid. LCMS-1: $t_R$=0.74 min, [M+1]⁺404.06. ¹H NMR (400 MHz, DMSO D6) δ: 7.97 (d, J=8.0 Hz, 1 H), 7.91 (s, 1 H), 7.53-7.51 (m, 1 H), 7.50 (t, J=72.5 Hz, 1 H), 7.39 (dd, $J_1$=1.5 Hz, $J_2$=7.7 Hz, 1 H), 7.33-7.25 (m, 2 H), 7.09 (d, J=8.0 Hz, 1 H), 3.26-3.17 (m, 1 H), 3.01-2.96 (m, 2 H), 2.75-2.71 (m, 2 H), 2.36 (s, 3 H), 2.34-2.27 (m, 2 H), 1.95-1.89 (m, 2 H), 1.06 (d, J=6.6 Hz, 6 H).

Example 5: N-(6-chloro-2-methoxypyridin-3-yl)-3-(2-isopropylphenyl)azetidine-3-carboxamide Step 1. To a solution of I-6 (40 mg, 0.125 mmol), commercial 6-chloro-2-methoxypyridin-3-amine (25 mg, 0.15 mmol) and pyridine (70 uL, 0.07 mmol) in EtOAc (1 mL) is added T3P 50% sol. in EtOAc (300 uL, 0.5 mmol). The reaction mixture is stirred at 65° C. overnight. Water (5 mL) is then added and the reaction mixture is extracted with EtOAc (3×10 mL). The combined organic extracts are dried over MgSO₄, filtered and evaporated. The residue is purified by prep. HPLC (Prep-HPLC-1 conditions) to afford tert-butyl 3-((6-chloro-2-methoxypyridin-3-yl)carbamoyl)-3-(2-isopropylphenyl)azetidine-1-carboxylate as a yellow oil (54 mg, 62% yield). LCMS-2: $t_R$=1.22 min, [M+1]⁺460.37. ¹H NMR (400 MHz, CDCl₃) δ: 8.58 (d, J=8.2 Hz, 1 H), 7.48-7.41 (m, 2 H), 7.39-7.32 (m, 3 H), 6.92 (d, J=8.2 Hz, 1 H), 4.80-4.54 (m, 2 H), 4.52-4.28 (m, 2 H), 3.75 (s, 3 H), 2.43 (m, 1 H), 1.48 (s, 9 H), 1.14 (d, J=6.6 Hz, 6 H).

Step 2. tert-Butyl 3-((6-chloro-2-methoxypyridin-3-yl)carbamoyl)-3-(2-isopropylphenyl)azetidine-1-carboxylate is subjected to the Boc deprotection conditions described for Ex 4 to give Ex 5 as colorless oil (30 mg, 75% yield). LCMS-1: $t_R$=0.72 min, [M+1]⁺360.30. ¹H NMR (400 MHz, CDCl₃) δ: 8.62 (d, J=8.2 Hz, 1 H), 8.38 (s, 1 H), 7.41-7.36 (m, 2 H), 7.34-7.29 (m, 1 H), 7.17 (d, J=7.7 Hz, 1 H), 6.92 (d, J=8.2 Hz, 1 H), 4.27 (s br, 4 H), 3.85 (s, 3 H), 2.51-2.41 (m, 1 H), 1.14 (d, J=6.7 Hz, 6 H).

Example 6: N-(2,6-dimethoxypyridin-3-yl)-3-(2-isopropylphenyl)azetidine-3-carboxamide hydrochloride and Example 6-1: tert-butyl 3-((2,6-dimethoxypyridin-3-yl)carbamoyl)-3-(2-isopropylphenyl)azetidine-1-carboxylate N-(2,6-dimethoxypyridin-3-yl)-3-(2-isopropylphenyl)azetidine-3-carboxamide hydrochloride Ex 6 and tert-butyl 3-((2,6-dimethoxypyridin-3-yl)carbamoyl)-3-(2-isopropylphenyl)azetidine-1-carboxylate Ex 6-1 are prepared from commercially available 3-amino-2,6-dimethoxypyridine hydrochloride (35 mg) and I-6 (46 mg) following the methodology described for Ex 5.

Ex 6 (65 mg, yellow wax). LCMS-1: $t_R$=0.70 min, [M+1]⁺356.02.

Ex 6-1 (72 mg, white solid). LCMS-1: $t_R$=1.44 min, [M+1]⁺456.24.

Example 7: N-(2-(difluoromethoxy)pyridin-3-yl)-3-(2-isopropylphenyl)azetidine-3-carboxamide hydrochloride N-(2-(difluoromethoxy)pyridin-3-yl)-3-(2-isopropylphenyl)azetidine-3-carboxamide hydrochloride Ex 7 is prepared from commercially available 2-(difluoromethoxy)pyridin-3-amine hydrochloride (32 mg) and I-6 (40 mg) following the methodology described for Ex 5 (31 mg, white solid). LCMS-1: $t_R$=0.68 min, [M+1]⁺362.33; ¹H NMR (500 MHz, DMSO D6) δ: 8.63 (s, 1 H), 8.13 (d, J=7.8 Hz, 1 H), 8.05 (d, J=4.6 Hz, 1 H), 7.58 (t, J=72.2 Hz, 1 H), 7.51 (d, J=7.7 Hz, 1 H), 7.48-7.40 (m, 2 H), 7.39-7.29 (m, 2 H), 4.74-4.61 (m, 2 H), 4.48-4.42 (m, 2 H), 2.46-2.40 (m, 1 H), 1.12 (d, J=6.6 Hz, 6 H).

Example 8: N-(2-(difluoromethoxy)-5-fluoropyridin-3-yl)-3-(2-isopropylphenyl)azetidine-3-carboxamide N-(2-(difluoromethoxy)-5-fluoropyridin-3-yl)-3-(2-isopropylphenyl)azetidine-3-carboxamide Ex 8 is prepared from commercially available 3-amino-5-fluoropyridin-2-ol (89 mg) and I-6 (86 mg) following the methodology described for Ex 4 (13.5 mg, colorless oil). LCMS-1: $t_R$=0.72 min, [M+1]⁺380.13.

Example 9: N-(6-ethoxy-2-methoxypyridin-3-yl)-3-(2-isopropylphenyl)azetidine-3-carboxamide N-(6-ethoxy-2-methoxypyridin-3-yl)-3-(2-isopropylphenyl)azetidine-3-carboxamide Ex 9 is prepared from commercially available 6-ethoxy-2-methoxypyrdin-3-amine (77 mg) and I-6 (70 mg) using the POCl₃ methodology described for Ex 4 (88 mg, yellow oil). LCMS-1: $t_R$=0.76 min, [M+1]⁺470.10.

Example 10: N-(2-(difluoromethoxy)-6-methylpyridin-3-yl)-3-(2-isopropylphenyl)pyrrolidine-3-carboxamide Step 1. 1-Benzyl-3-(2-bromophenyl)pyrrolidine-3-carboxylic acid I-5 (273 mg, 0.76 mmol) is coupled to 2-(difluoromethoxy)-6-methylpyridin-3-amine hydrochloride I-1.C (319, 1.52 mmol) following the methodology described for Ex 1 in step 1 to give 1-benzyl-3-(2-bromophenyl)-N-(2-(difluoromethoxy)-6-methylpyridin-3-yl)

pyrrolidine-3-carboxamide (317 mg, 81% yield) as a pale yellow oil. LCMS-2: $t_R$=0.89 min, [M+1]$^+$516.17 and 518.16.

Step 2. Following the methodology described for I-4-step 3, 1-benzyl-3-(2-bromophenyl)-N-(2-(difluoromethoxy)-6-methylpyridin-3-yl)pyrrolidine-3-carboxamide (307 mg, 0.60 mmol) is reacted with isopropenyl boronic acid pinacolester (0.56 mL, 2.97 mmol) to give 1-benzyl-N-(2-(difluoromethoxy)-6-methylpyridin-3-yl)-3-(2-(prop-1-en-2-yl)phenyl)pyrrolidine-3-carboxamide (228 mg, 80% yield) as a colorless oil. LCMS-2: $t_R$=0.94 min, [M+1]$^+$478.30.

Step 3. To a solution of 1-benzyl-N-(2-(difluoromethoxy)-6-methylpyridin-3-yl)-3-(2-(prop-1-en-2-yl)phenyl)pyrrolidine-3-carboxamide (228 mg, 0.48 mmol) in 10 ml of methanol/THF 1:1 is added Pd/C 10% (100 mg, 0.03 mmol). The reaction mixture is degassed, hydrogenated at 1 bar and stirred for 2 h (reaction progress monitored by LCMS). The mixture is filtered on Celite and is evaporated to dryness to give the title compound Ex 10 (138 mg, 74% washed with water (15 mL) followed by brine (10 mL). The organic phase is dried over MgSO$_4$, filtered and evaporated. The residue is purified by prep. HPLC (Prep-HPLC-3 conditions) to give tert-butyl (2-(3-((2-(difluoromethoxy)-6-methylpyridin-3-yl)carbamoyl)-3-(2-isopropylphenyl)azetidin-1-yl)ethyl)carbamate (180 mg, 0.35 mmol, 66% yield). LCMS-2: $t_R$=0.99 min, [M+1]$^+$519.19.

Step 2. tert-Butyl (2-(3-((2-(difluoromethoxy)-6-methylpyridin-3-yl)carbamoyl)-3-(2-isopropylphenyl)azetidin-1-yl)ethyl)carbamate is dissolved in DCM (10 mL) and TFA (250 uL, 3.27 mmol) is added. The reaction mixture is stirred overnight and is then quenched with sat. NaHCO$_3$ (5 mL). The organic phase is collected and the aqueous phase is extracted with DCM (2×10 mL). The combined organic phases are dried over MgSO$_4$, filtered and evaporated to give 1-(2-aminoethyl)-N-(2-(difluoromethoxy)-6-methylpyridin-3-yl)-3-(2-isopropylphenyl)azetidine-3-carboxamide Ex 11-1 (90 mg, 62% yield) as a wax. LCMS-1: $t_R$=0.64 min, [M+1]$^+$419.4.

TABLE 1

Examples 11-2 to 11-11
Examples 11-2 to 11-11 are synthesized by nucleophilic substitution using the methodology described for example Ex 11-1 starting from Ex 3 or Ex 4 and various haloalkanes. In step 1 other bases than TEA can be used such as NaOAc or Cs$_2$CO$_3$.
In step 1, DCM can be replaced by DMF, MeCN or MeOH.

| Example | Name | Analytics LCMS-1 |
| --- | --- | --- |
| Ex 11-2 | N-(2-(difluoromethoxy)-6-methylpyridin-3-yl)-1-(2-hydroxyethyl)-3-(2-isopropylphenyl)azetidine-3-carboxamide | [M + 1]$^+$ 420.36 $t_R$ 0.71 |
| Ex 11-3 | N-(2-(difluoromethoxy)-6-methylpyridin-3-yl)-1-(2-hydroxyethyl)-4-(2-isopropylphenyl)piperidine-4-carboxamide | [M + 1]$^+$ 448.38 $t_R$ 0.73 |
| Ex 11-4 | N-(2-(difluoromethoxy)-6-methylpyridin-3-yl)-1-(3-hydroxypropyl)-3-(2-isopropylphenyl)azetidine-3-carboxamide | [M + 1]$^+$ 434.17 $t_R$ 0.73 |
| Ex 11-5 | N-(2-(difluoromethoxy)-6-methylpyridin-3-yl)-3-(2-isopropylphenyl)-1-(oxetan-3-ylmethyl)azetidine-3-carboxamide | [M + 1]$^+$ 446.39 $t_R$ 0.74 |
| Ex 11-6 | 1-cyano-N-(2-(difluoromethoxy)-6-methylpyridin-3-yl)-3-(2-isopropylphenyl)azetidine-3-carboxamide | [M + 1]$^+$ 401.43 $t_R$ 1.26 |
| Ex 11-7 | 1-(3-(1H-tetrazol-5-yl)propyl)-N-(2-(difluoromethoxy)-6-methylpyridin-3-yl)-3-(2-isopropylphenyl)azetidine-3-carboxamide | [M + 1]$^+$ 486.44 $t_R$ 0.80 |
| Ex 11-8 | 1-((1H-tetrazol-5-yl)methyl)-N-(2-(difluoromethoxy)-6-methylpyridin-3-yl)-3-(2-isopropylphenyl)azetidine-3-carboxamide | [M + 1]$^+$ 458.10 $t_R$ 0.92 |
| Ex 11-9 | N-(2-(difluoromethoxy)-6-methylpyridin-3-yl)-1-(3-hydroxy-3-methylbutyl)-3-(2-isopropylphenyl)azetidine-3-carboxamide | [M + 1]$^+$ 462.03 $t_R$ 0.84 |
| Ex 11-10 | N-(2-(difluoromethoxy)-6-methylpyridin-3-yl)-1-(2-(1-hydroxycyclopropyl)ethyl)-3-(2-isopropylphenyl)azetidine-3-carboxamide | [M + 1]$^+$ 460.04 $t_R$ 0.83 |
| Ex 11-11 | 1-(2-aminopropyl)-N-(2-(difluoromethoxy)-6-methylpyridin-3-yl)-3-(2-isopropylphenyl)azetidine-3-carboxamide | [M + 1]$^+$ 433.36 $t_R$ 0.75 | yield) as a colorless oil. LCMS-1: $t_R$=0.83 min, [M+1]$^+$ 390.29. $^1$H NMR (400 MHz, CDCl$_3$) δ: 8.49 (d, J=8.1 Hz, 1 H), 7.60 (s, 1 H), 7.45-7.37 (m, 2 H), 7.29 (m, J=76.8 Hz, 1 H), 7.32-7.26 (m, 2 H), 6.92 (d, J=8.0 Hz, 1 H), 3.81-3.68 (m, 1 H), 3.47-3.25 (m, 2 H), 3.15-2.94 (m, 2 H), 2.90-2.75 (m, 1 H), 2.39 (s, 3 H), 2.31-2.18 (m, 1 H), 1.17 (d, J=6.6 Hz, 3 H), 1.13 (d, J=6.6 Hz, 3 H).

Example 11-1: 1-(2-aminoethyl)-N-(2-(difluoromethoxy)-6-methylpyridin-3-yl)-3-(2-isopropylphenyl)azetidine-3-carboxamide Step 1. To a solution of N-(2-(difluoromethoxy)-6-methylpyridin-3-yl)-3-(2-isopropylphenyl)azetidine-3-carboxamide Ex 3 (200 mg, 0.53 mmol) and TEA (222 uL, 1.60 mmol) in DCM (5 mL) is added N-Boc-bromoethylamine (239 mg, 1.07 mmol). The reaction mixture is stirred overnight. Another portion of N-Boc-bromoethylamine (239 mg, 1.07 mmol) is then added and stirring is continued for 24 h. The reaction mixture is diluted with DCM (20 mL) and is Example 11-12: 2-(3-((2-(difluoromethoxy)-6-methylpyridin-3-yl)carbamoyl)-3-(2-isopropylphenyl)azetidin-1-yl)acetic acid Step 1. Cesium carbonate (87 mg, 0.27 mmol) and benzyl bromoacetate (33 uL, 0.2 mmol) are added to a solution of N-(2-(difluoromethoxy)-6-methylpyridin-3-yl)-3-(2-isopropylphenyl)azetidine-3-carboxamide Ex 3 (50 mg, 0.13 mmol,) in DMF (2 mL). The reaction mixture is stirred at r.t. overnight (reaction monitored by LCMS). The mixture is then diluted with water (10 mL) and extracted with EtOAc (2×15 mL). The combined extracts are dried over MgSO$_4$, filtered and evaporated to give benzyl 2-(3-((2-(difluoromethoxy)-6-methylpyridin-3-yl)carbamoyl)-3-(2-isopropylphenyl)azetidin-1-yl)acetate (16 mg, 23% yield) as a colorless oil that is used as such in the next step. LCMS-2: $t_R$=1.01 min, [M+H]$^+$=524.17.

Step 2. To a solution of benzyl 2-(3-((2-(difluoromethoxy)-6-methylpyridin-3-yl)carbamoyl)-3-(2-isopropylphenyl)azetidin-1-yl)acetate (16 mg, 0.03 mmol) 1 mL of ethanol/THF 1:1 is added Pd/C (4 mg, 0.03 mmol). The reaction mixture is degassed, hydrogenated at 1 bar and stirred overnight. The mixture is filtered on Celite and is evaporated to dryness to give the title compound Ex 11-12 (11 mg, 83% yield) as a white solid. LCMS-1: $t_R$=0.86 min, [M+1]$^+$434.30.

Example 11-13: ethyl 3-(3-((2-(difluoromethoxy)-6-methylpyridin-3-yl)carbamoyl)-3-(2-isopropylphenyl)azetidin-1-yl)propanoate and Example 11-14: 3-(3-((2-(difluoromethoxy)-6-methylpyridin-3-yl)carbamoyl)-3-(2-isopropylphenyl)azetidin-1-yl)propanoic acid Step 1. A mixture of Ex 3 hydrochloride (60 mg, 0.15 mmol), methyl acrylate (20 uL, 0.19 mmol) and $CS_2CO_3$ (71 mg, 0.22 mmol) in DMF (15 mL) is stirred at r.t. for 18 h. The reaction mixture is evaporated and the residue is purified by prep-HPLC (Prep-HPLC-3 conditions) to give Ex 11-13 as a white solid (51 mg, 73% yield). LCMS-1: $t_R$=0.82 min, [M+1]$^+$476.33; $^1$H NMR (400 MHz, CDCl$_3$) δ: 9.89 (s, 1 H), 8.60 (d, J=8.1 Hz, 1 H), 7.46 (t, J=73.0 Hz, 1 H), 7.35-7.33 (m, 2 H), 7.26-7.21 (m, 1 H), 7.03 (d, J=7.4 Hz, 1 H), 6.92 (d, J=8.1 Hz, 1 H), 4.22-4.11 (m, 4 H), 3.70-3.55 (m, 2 H), 2.88 (t, J=7.4 Hz, 2 H), 2.58-2.46 (m, 3 H), 2.41 (s, 3 H), 1.28 (t, J=7.1 Hz, 3 H), 1.18 (d, J=6.8 Hz, 6 H).

Step 2. Ethyl 3-(3-((2-(difluoromethoxy)-6-methylpyridin-3-yl)carbamoyl)-3-(2-isopropylphenyl)azetidin-1-yl) propanoate Ex 11-13 (45 mg, 0.09 mmol) is dissolved in MeOH/THF 1:1 (5 mL) and is treated with 2M LiOH (1 mL, 2.0 mmol). The solution is stirred at r.t. for 2 h (reaction progress monitored by LCMS). The reaction mixture is filtered through a syringe filter and is evaporated. The residue is purified by prep-HPLC (Prep-HPLC-3 conditions) to give Ex 11-14 as a white solid (11 mg, 25% yield). LCMS-1: $t_R$=0.77 min, [M+1]$^+$447.99; $^1$H NMR (400 MHz, CDCl$_3$) δ: 8.58 (d, J=8.1 Hz, 1 H), 7.56 (s, 1 H), 7.46-7.42 (m, 2 H), 7.38-7.34 (m, 1 H), 7.30 (t, J=72.8 Hz, 1 H), 7.23 (d, J=7.5 Hz, 1 H), 6.94 (d, J=8.1 Hz, 1 H), 4.48-4.28 (m, 2 H), 3.99-3.75 (m, 2 H), 3.00 (t, J=6.1 Hz, 2 H), 2.50-2.40 (m, 3 H), 2.39 (s, 3 H), 1.15 (d, J=6.5 Hz, 6 H).

Example 11-15: 1-(2-amino-2-oxoethyl)-N-(2-(difluoromethoxy)-6-methylpyridin-3-yl)-3-(2-isopropylphenyl)azetidine-3-carboxamide To a solution of 2-(3-((2-(difluoromethoxy)-6-methylpyridin-3-yl)carbamoyl)-3-(2-isopropylphenyl)azetidin-1-yl)acetic acid Ex 11-12 (11 mg, 0.025 mmol) in DCM (0.5 mL) at 0° C. under nitrogen is added isobutyl chloroformate (8 mg, 0.06 mmol) followed by TEA (8 uL, 0.06 mmol). The reaction mixture is stirred at 0° C. for 30 min then ammonium hydroxide (8 uL, 0.05 mmol) is added. The mixture is allowed to warm up to r.t. and is stirred for 30 min. The volatiles are evaporated in vacuo and the residue is purified by prep. HPLC (Prep-HPLC-3 conditions) to give 1-(2-amino-2-oxoethyl)-N-(2-(difluoromethoxy)-6-methylpyridin-3-yl)-3-(2-isopropylphenyl)azetidine-3-carboxamide Ex 11-15 (10 mg, 80% yield) as a colorless oil. LCMS-1: $t_R$=0.72 min, [M+H]$^+$=433.33.

Example 11-16: 1-(2-cyanoethyl)-N-(2-(difluoromethoxy)-6-methylpyridin-3-yl)-3-(2-isopropylphenyl)azetidine-3-carboxamide 1-(2-Cyanoethyl)-N-(2-(difluoromethoxy)-6-methylpyridin-3-yl)-3-(2-isopropylphenyl)azetidine-3-carboxamide Ex 11-16 is prepared from Ex 3 and acrylonitrile following the methodology described for Ex 11-13 to give the title compound as a beige solid. LCMS-1: $t_R$=0.93 min, [M+H]$^+$= 529.14.

Example 11-17: N-(2-(difluoromethoxy)-6-methylpyridin-3-yl)-1-(3-hydroxy-2,2-dimethylpropyl)-3-(2-isopropylphenyl)azetidine-3-carboxamide To a solution of N-(2-(difluoromethoxy)-6-methylpyridin-3-yl)-3-(2-isopropylphenyl)azetidine-3-carboxamide Ex 3 (68 mg, 0.18 mmol) and 3-hydroxy-2,2-dimethyl-propanal (25 mg, 0.245 mmol) in MeOH (2 mL) under inert atmosphere is added sodium cyanoborohydride (18 mg, 0.29 mmol). The reaction mixture is stirred at 50° C. for 2 h (reaction monitored by LCMS) and is then quenched with water (2 mL). The mixture is diluted with MeCN (2 mL) and is then purified by prep. HPLC (Prep-HPLC-3 conditions) to give the title compound Ex 11-17 (46 mg, 55% yield) as a colorless glass. LCMS-1: $t_R$=0.79 min, [M+1]$^+$462.41; $^1$H NMR (500 MHz, CDCl$_3$) δ: 8.61 (d, J=8.1 Hz, 1 H), 8.07 (s, 1 H), 7.42-7.35 (m, 3 H), 7.33-7.29 (m, 1 H), 7.19 (d, J=7.7 Hz, 1 H), 6.92 (d, J=8.1 Hz, 1 H), 4.25 (s br, 2 H), 3.70 (s br, 2 H), 3.50 (s, 2 H), 2.60 (s, 2 H), 2.53-2.45 (m, 1 H), 2.39 (s, 3 H), 1.14 (d, J=6.7 Hz, 6 H), 0.94 (s, 6 H).

TABLE 2

Examples 11-18 to 11-66

Examples 11-18 to 11-66 are synthesized using the methodology described for example Ex 11-17 starting from Ex 3 or Ex 4 and various aldehydes by using sodium cyanoborohydride or other reducing agents. Functional groups, such as alcohol or acid, may be protected with an appropriate protecting group. For example esters are saponified by 2N LiOH after the reductive amination step.

| Example | Name | Analytics LCMS-1 |
|---|---|---|
| Ex 11-18 | (R)-N-(2-(difluoromethoxy)-6-methylpyridin-3-yl)-1-(2,3-dihydroxypropyl)-3-(2-isopropylphenyl)azetidine-3-carboxamide | [M + 1]$^+$450.22 $t_R$ 0.71 |
| Ex 11-19 | (R)-N-(2-(difluoromethoxy)-6-methylpyridin-3-yl)-1-(2,3-dihydroxypropyl)-4-(2-isopropylphenyl)piperidine-4-carboxamide | [M + 1]$^+$478.39 $t_R$ 0.72 |
| Ex 11-20 | N-(2-(difluoromethoxy)-6-methylpyridin-3-yl)-3-(2-isopropylphenyl)-1-(oxetan-3-yl)azetidine-3-carboxamide | [M + 1]$^+$432.35 $t_R$ 0.84 |
| Ex 11-21 | N-(2-(difluoromethoxy)-6-methylpyridin-3-yl)-3-(2-isopropylphenyl)-1-((2-methyloxazol-4-yl)methyl)azetidine-3-carboxamide | [M + 1]$^+$471.37 $t_R$ 0.81 |
| Ex 11-22 | N-(2-(difluoromethoxy)-6-methylpyridin-3-yl)-3-(2-isopropylphenyl)-1-((1-methyl-1H-pyrazol-5-yl)methyl)azetidine-3-carboxamide | [M + 1]$^+$470.37 $t_R$ 0.86 |
| Ex 11-23 | N-(2-(difluoromethoxy)-6-methylpyridin-3-yl)-3-(2-isopropylphenyl)-1-((1-methyl-1H-pyrazol-4-yl)methyl)azetidine-3-carboxamide | [M + 1]$^+$470.38 $t_R$ 0.74 |

TABLE 2-continued

Examples 11-18 to 11-66

Examples 11-18 to 11-66 are synthesized using the methodology described for example Ex 11-17 starting from Ex 3 or Ex 4 and various aldehydes by using sodium cyanoborohydride or other reducing agents. Functional groups, such as alcohol or acid, may be protected with an appropriate protecting group. For example esters are saponified by 2N LiOH after the reductive amination step.

| Example | Name | Analytics LCMS-1 |
| --- | --- | --- |
| Ex 11-24 | methyl 3-(3-((2-(difluoromethoxy)-6-methylpyridin-3-yl)carbamoyl)-3-(2-isopropylphenyl)azetidin-1-yl)-2,2-dimethylpropanoate | [M + 1]$^+$490.04 $t_R$ 0.96 |
| Ex 11-25 | 3-(3-((2-(difluoromethoxy)-6-methylpyridin-3-yl)carbamoyl)-3-(2-isopropylphenyl)azetidin-1-yl)-2,2-dimethylpropanoic acid | [M + 1]$^+$476.05 $t_R$ 0.93 |
| Ex 11-26 | methyl 1-((3-((2-(difluoromethoxy)-6-methylpyridin-3-yl)carbamoyl)-3-(2-isopropylphenyl)azetidin-1-yl)methyl)cyclopropane-1-carboxylate | [M + 1]$^+$488.29 $t_R$ 0.82 |
| Ex 11-27 | 1-((3-((2-(difluoromethoxy)-6-methylpyridin-3-yl)carbamoyl)-3-(2-isopropylphenyl)azetidin-1-yl)methyl)cyclopropane-1-carboxylic acid | [M + 1]$^+$474.02 $t_R$ 0.85 |
| Ex 11-28 | methyl 4-(3-((2-(difluoromethoxy)-6-methylpyridin-3-yl)carbamoyl)-3-(2-isopropylphenyl)azetidin-1-yl)butanoate | [M + 1]$^+$476.48 $t_R$ 0.82 |
| Ex 11-29 | 4-(3-((2-(difluoromethoxy)-6-methylpyridin-3-yl)carbamoyl)-3-(2-isopropylphenyl)azetidin-1-yl)butanoic acid | [M + 1]$^+$462.35 $t_R$ 0.74 |
| Ex 11-30 | methyl 4-(3-((2-(difluoromethoxy)-6-methylpyridin-3-yl)carbamoyl)-3-(2-isopropylphenyl)azetidin-1-yl)-2,2-dimethylbutanoate | [M + 1]$^+$504.35 $t_R$ 0.86 |
| Ex 11-31 | 4-(3-((2-(difluoromethoxy)-6-methylpyridin-3-yl)carbamoyl)-3-(2-isopropylphenyl)azetidin-1-yl)-2,2-dimethylbutanoic acid | [M + 1]$^+$490.01 $t_R$ 0.78 |
| Ex 11-32 | ethyl 4-(3-((2-(difluoromethoxy)-6-methylpyridin-3-yl)carbamoyl)-3-(2-isopropylphenyl)azetidin-1-yl)-3,3-dimethylbutanoate | [M + 1]$^+$518.02 $t_R$ 0.99 |
| Ex 11-33 | 4-(3-((2-(difluoromethoxy)-6-methylpyridin-3-yl)carbamoyl)-3-(2-isopropylphenyl)azetidin-1-yl)-3,3-dimethylbutanoic acid | [M + 1]$^+$490.33 $t_R$ 0.91 |
| Ex 11-34 | ethyl 5-((3-((2-(difluoromethoxy)-6-methylpyridin-3-yl)carbamoyl)-3-(2-isopropylphenyl)azetidin-1-yl)methyl)isoxazole-3-carboxylate | [M + 1]$^+$529.24 tR 1.24 |
| Ex 11-35 | 5-((3-((2-(difluoromethoxy)-6-methylpyridin-3-yl)carbamoyl)-3-(2-isopropylphenyl)azetidin-1-yl)methyl)isoxazole-3-carboxylic acid | [M + 1]$^+$501.02 $t_R$ 0.95 |
| Ex 11-36 | N-(2-(difluoromethoxy)-6-methylpyridin-3-yl)-3-(2-isopropylphenyl)-1-(isoxazol-5-ylmethyl)azetidine-3-carboxamide | [M + 1]$^+$457.00 $t_R$ 0.88 |
| Ex 11-37 | methyl 4-((3-((2-(difluoromethoxy)-6-methylpyridin-3-yl)carbamoyl)-3-(2-isopropylphenyl)azetidin-1-yl)methyl)-1H-pyrazole-3-carboxylate | [M + 1]$^+$514.38 $t_R$ 0.88 |
| Ex 11-38 | 4-((3-((2-(difluoromethoxy)-6-methylpyridin-3-yl)carbamoyl)-3-(2-isopropylphenyl)azetidin-1-yl)methyl)-1H-pyrazole-3-carboxylic acid | [M + 1]$^+$500.22 $t_R$ 0.88 |
| Ex 11-39 | ethyl 3-((3-((2-(difluoromethoxy)-6-methylpyridin-3-yl)carbamoyl)-3-(2-isopropylphenyl)azetidin-1-yl)methyl)-1H-pyrazole-4-carboxylate | [M + 1]$^+$528.10 $t_R$ 0.84 |
| Ex 11-40 | 3-((3-((2-(difluoromethoxy)-6-methylpyridin-3-yl)carbamoyl)-3-(2-isopropylphenyl)azetidin-1-yl)methyl)-1H-pyrazole-4-carboxylic acid | [M + 1]$^+$500.37 $t_R$ 0.87 |
| Ex 11-41 | methyl 2-(2-((3-((2-(difluoromethoxy)-6-methylpyridin-3-yl)carbamoyl)-3-(2-isopropylphenyl)azetidin-1-yl)methyl)-1H-pyrrol-1-yl)acetate | [M + 1]$^+$527.41 $t_R$ 0.87 |
| Ex 11-42 | 2-(2-((3-((2-(difluoromethoxy)-6-methylpyridin-3-yl)carbamoyl)-3-(2-isopropylphenyl)azetidin-1-yl)methyl)-1H-pyrrol-1-yl)acetic acid | [M + 1]$^+$513.03 $t_R$ 0.97 |
| Ex 11-43 | methyl 5-((3-((2-(difluoromethoxy)-6-methylpyridin-3-yl)carbamoyl)-3-(2-isopropylphenyl)azetidin-1-yl)methyl)-1H-pyrrole-2-carboxylate | [M + 1]$^+$513.14 $t_R$ 0.84 |
| Ex 11-44 | 5-((3-((2-(difluoromethoxy)-6-methylpyridin-3-yl)carbamoyl)-3-(2-isopropylphenyl)azetidin-1-yl)methyl)-1H-pyrrole-2-carboxylic acid | [M + 1]$^+$499.38 $t_R$ 0.77 |
| Ex 11-45 | methyl 6-((3-((2-(difluoromethoxy)-6-methylpyridin-3-yl)carbamoyl)-3-(2-isopropylphenyl)azetidin-1-yl)methyl)picolinate | [M + 1]$^+$525.31 $t_R$ 0.84 |
| Ex 11-46 | 6-((3-((2-(difluoromethoxy)-6-methylpyridin-3-yl)carbamoyl)-3-(2-isopropylphenyl)azetidin-1-yl)methyl)picolinic acid | [M + 1]$^+$511.05 $t_R$ 0.84 |
| Ex 11-47 | N-(2-(difluoromethoxy)-6-methylpyridin-3-yl)-3-(2-isopropylphenyl)-1-(oxazol-2-ylmethyl)azetidine-3-carboxamide | [M + 1]$^+$457.24 $t_R$ 0.96 |
| Ex 11-48 | methyl 2-(4-((3-((2-(difluoromethoxy)-6-methylpyridin-3-yl)carbamoyl)-3-(2-isopropylphenyl)azetidin-1-yl)methyl)-1H-1,2,3-triazol-1-yl)acetate | [M + 1]$^+$529.02 $t_R$ 0.78 |
| Ex 11-49 | 2-(4-((3-((2-(difluoromethoxy)-6-methylpyridin-3-yl)carbamoyl)-3-(2-isopropylphenyl)azetidin-1-yl)methyl)-1H-1,2,3-triazol-1-yl)acetic acid | [M + 1]$^+$515.09 $t_R$ 0.82 |
| Ex 11-50 | methyl 4-((3-((2-(difluoromethoxy)-6-methylpyridin-3-yl)carbamoyl)-3-(2-isopropylphenyl)azetidin-1-yl)methyl)picolinate | [M + 1]$^+$525.04 $t_R$ 0.97 |
| Ex 11-51 | 4-((3-((2-(difluoromethoxy)-6-methylpyridin-3-yl)carbamoyl)-3-(2-isopropylphenyl)azetidin-1-yl)methyl)picolinic acid | [M + 1]$^+$511.03 $t_R$ 0.88 |
| Ex 11-52 | methyl 5-((3-((2-(difluoromethoxy)-6-methylpyridin-3-yl)carbamoyl)-3-(2-isopropylphenyl)azetidin-1-yl)methyl)picolinate | [M + 1]$^+$525.08 $t_R$ 0.92 |
| Ex 11-53 | 5-((3-((2-(difluoromethoxy)-6-methylpyridin-3-yl)carbamoyl)-3-(2-isopropylphenyl)azetidin-1-yl)methyl)picolinic acid | [M + 1]$^+$511.05 $t_R$ 0.85 |
| Ex 11-54 | methyl 5-((3-((2-(difluoromethoxy)-6-methylpyridin-3-yl)carbamoyl)-3-(2-isopropylphenyl)azetidin-1-yl)methyl)pyrazine-2-carboxylate | [M + 1]$^+$526.47 $t_R$ 0.89 |
| Ex 11-55 | 5-((3-((2-(difluoromethoxy)-6-methylpyridin-3-yl)-carbamoyl)3-(2-isopropylphenyl)azetidin-1-yl)methyl)pyrazine-2-carboxylic acid | [M + 1]$^+$512.08 $t_R$ 0.84 |
| Ex 11-56 | methyl 5-((3-((2-(difluoromethoxy)-6-methylpyridin-3-yl)carbamoyl)-3-(2-isopropylphenyl)azetidin-1-yl)methyl)furan-2-carboxylate | [M + 1]$^+$514.42 $t_R$ 0.97 |
| Ex 11-57 | 5-((3-((2-(difluoromethoxy)-6-methylpyridin-3-yl)carbamoyl)-3-(2-isopropylphenyl)azetidin-1-yl)methyl)furan-2-carboxylic acid | [M + 1]$^+$500.27 $t_R$ 0.87 |
| Ex 11-58 | ethyl 2-(2-((3-((2-(difluoromethoxy)-6-methylpyridin-3-yl)carbamoyl)-3-(2-isopropylphenyl)azetidin-1-yl)methyl)oxazol-4-yl)acetate | [M + 1]$^+$543.24 $t_R$ 1.07 |

TABLE 2-continued

Examples 11-18 to 11-66
Examples 11-18 to 11-66 are synthesized using the methodology described for example Ex 11-17 starting from Ex 3 or Ex 4 and various aldehydes by using sodium cyanoborohydride or other reducing agents. Functional groups, such as alcohol or acid, may be protected with an appropriate protecting group. For example esters are saponified by 2N LiOH after the reductive amination step.

| Example | Name | Analytics LCMS-1 |
|---|---|---|
| Ex 11-59 | 2-(2-((3-((2-(difluoromethoxy)-6-methylpyridin-3-yl)carbamoyl)-3-(2-isopropylphenyl)azetidin-1-yl)methyl)oxazol-4-yl)acetic acid | [M + 1]$^+$515.27 $t_R$ 0.90 |
| Ex 11-60 | 1-(4-cyano-4-methylpentyl)-N-(2-(difluoromethoxy)-6-methylpyridin-3-yl)-3-(2-isopropylphenyl)azetidine-3-carboxamide | [M + 1]$^+$471.46 $t_R$ 0.90 |
| Ex 11-61 | N-(2-(difluoromethoxy)-6-methylpyridin-3-yl)-3-(2-isopropylphenyl)-1-(4-methyl-4-nitropentyl)azetidine-3-carboxamide | [M + 1]$^+$505.50 $t_R$ 0.94 |
| Ex 11-62 | N-(2-(difluoromethoxy)-6-methylpyridin-3-yl)-3-(2-isopropylphenyl)-1-(2-(methylamino)ethyl)azetidine-3-carboxamide | [M + 1]$^+$433.05 $t_R$ 0.74 |
| Ex 11-63 | N-(2-(difluoromethoxy)-6-methylpyridin-3-yl)-1-(2-(ethylamino)ethyl)-3-(2-isopropylphenyl)azetidine-3-carboxamide | [M + 1]$^+$447.31 $t_R$ 0.77 |
| Ex 11-64 | N-(2-(difluoromethoxy)-6-methylpyridin-3-yl)-3-(2-isopropylphenyl)-1-(2-methyl-2-(methylamino)propyl)azetidine-3-carboxamide | [M + 1]$^+$461.20 $t_R$ 0.91 |
| Ex 11-65 | 5-(3-((2-(difluoromethoxy)-6-methylpyridin-3-yl)carbamoyl)-3-(2-isopropylphenyl)azetidin-1-yl)-2-methylpentan-2-yl acetate | [M + 1]$^+$510.08 $t_R$ 0.95 |
| Ex 11-66 | N-(2-(difluoromethoxy)-6-methylpyridin-3-yl)-1-(4-hydroxy-4-methylpentyl)-3-(2-isopropylphenyl)azetidine-3-carboxamide | [M + 1]$^+$476.50 $t_R$ 0.85 |

Example 11-67: Methyl 2-(1-((3-((2-(difluoromethoxy)-6-methylpyridin-3-yl)carbamoyl)-3-(2-isopropylphenyl)azetidin-1-yl)methyl)cyclopropyl) acetate and Example 11-68: 2-(1-((3-((2-(difluoromethoxy)-6-methylpyridin-3-yl) carbamoyl)-3-(2-isopropylphenyl)azetidin-1-yl) methyl)cyclopropyl)acetic acid Step 1. A mixture of Ex 3 hydrochloride (50 mg, 0.115 mmol), methyl 2-[1-(bromomethyl)cyclopropyl]acetate (37.5 mg, 0.172 mmol) and CS$_2$CO$_3$ (150 mg, 0.46 mmol) in MeCN (1 mL) is stirred at 50° C. for 18 h. The reaction mixture is evaporated and the residue is purified by prep-HPLC (Prep-HPLC-3 conditions) to give Ex 11-67 as a colorless oil (32 mg, 56% yield). LCMS-1: $t_R$=0.85 min, [M+1]$^+$502.06.

Step 2. methyl 2-(1-((3-((2-(difluoromethoxy)-6-methylpyridin-3-yl)carbamoyl)-3-(2-isopropylphenyl)azetidin-1-yl)methyl)cyclopropyl)acetate Ex 11-67 (30 mg, 0.06 mmol) is dissolved in MeOH (2 mL) and is treated with 2M LiOH (1 mL, 2.0 mmol). The solution is stirred at r.t. overnight (reaction progress monitored by LCMS). The reaction mixture is cooled down to 0° C. and slowly acidified to pH 4 with a solution of 2N HCl. The aqueous solution is then extracted with EtOAc twice. The combined organic extracts are dried over MgSO$_4$, filtered and evaporated to give the hydrochloride salt of Ex 11-68 as a white solid (20 mg, 69% yield). LCMS-1: $t_R$=0.84 min, [M+1]$^+$488.04.

TABLE 3

Examples 11-69 to 11-76
Examples 11-69 to 11-76 are synthesized using the methodology described for example Ex 11-68 starting from Ex 3 that is reacted with funtionalized haloalkanes.

| Example | Name | Analytics LCMS-1 |
|---|---|---|
| Ex 11-69 | 5-(3-((2-(difluoromethoxy)-6-methylpyridin-3-yl)carbamoyl)-3-(2-isopropylphenyl)azetidin-1-yl)-2,2-dimethylpentanoic acid | [M + 1]$^+$504.42 $t_R$ 0.81 |
| Ex 11-70 | methyl 1-(3-(3-((2-(difluoromethoxy)-6-methylpyridin-3-yl)carbamoyl)-3-(2-isopropylphenyl)azetidin-1-yl)propyl)cyclopropane-1-carboxylate | [M + 1]$^+$516.07 $t_R$ 0.87 |
| Ex 11-71 | 1-(3-(3-((2-(difluoromethoxy)-6-methylpyridin-3-yl)carbamoyl)-3-(2-isopropylphenyl)azetidin-1-yl)propyl)cyclopropane-1-carboxylic acid | [M + 1]$^+$502.07 $t_R$ 0.81 |
| Ex 11-72 | 1-(2-(3-((2-(difluoromethoxy)-6-methylpyridin-3-yl)carbamoyl)-3-(2-isopropylphenyl)azetidin-1-yl)ethyl)cyclopropane-1-carboxylic acid | [M + 1]$^+$488.08 $t_R$ 1.14 |
| Ex 11-73 | 1-(2-(3-((2-(difluoromethoxy)-6-methylpyridin-3-yl)carbamoyl)-3-(2-isopropylphenyl)azetidin-1-yl)ethyl)cyclobutane-1-carboxylic acid | [M + 1]$^+$502.09 $t_R$ 1.20 |
| Ex 11-74 | ethyl 2-(2-(3-((2-(difluoromethoxy)-6-methylpyridin-3-yl)carbamoyl)-3-(2-isopropylphenyl)azetidin-1-yl)ethoxy)acetate | [M + 1]$^+$506.48 $t_R$ 0.84 |
| Ex 11-75 | 2-(2-(3-((2-(difluoromethoxy)-6-methylpyridin-3-yl)carbamoyl)-3-(2-isopropylphenyl)azetidin-1-yl)ethoxy)acetic acid | [M + 1]$^+$478.04 $t_R$ 0.80 |
| Ex 11-76 | 3-(2-(3-((2-(difluoromethoxy)-6-methylpyridin-3-yl)carbamoyl)-3-(2-isopropylphenyl)azetidin-1-yl)ethyl)tetrahydrofuran-3-carboxylic acid | [M + 1]$^+$518.12 $t_R$ 1.22 |

Example 11-77: N-(2-(difluoromethoxy)-6-methylpyridin-3-yl)-3-(2-isopropylphenyl)-1-(2-(methylsulfonamido)ethyl)azetidine-3-carboxamide To a solution of 1-(2-aminoethyl)-N-(2-(difluoromethoxy)-6-methylpyridin-3-yl)-3-(2-isopropylphenyl)azetidine-3-carboxamide Ex 11-1 (73 mg, 0.18 mmol) in DCM (10 mL) is added triethylamine (98 uL, 0.78 mmol)

followed by methanesulfonylchloride (27 uL, 0.35 mmol). The reaction mixture is stirred at r.t. overnight. The volatiles are evaporated and the residue is purified by prep. HPLC (Prep-HPLC-1 conditions) to give the title compound Ex 11-77 (18 mg, 21% yield) as a foam. LCMS-1: $t_R$=0.73 min, [M+1]$^+$497.06.

Example 11-78: N-(2-(difluoromethoxy)-6-methylpyridin-3-yl)-1-(2-(dimethylamino)ethyl)-3-(2-isopropylphenyl)azetidine-3-carboxamide 2-(3-((2-(difluoromethoxy)-6-methylpyridin-3-yl)carbamoyl)-3-(2-isopropylphenyl)azetidin-1-yl)ethyl methanesulfonate is synthesized from Ex 11-2 following the methodology described for the preparation of Ex 11-76. The mesylate (40 mg, 0.08 mmol) is then reacted with 1M dimetlyamine in THF (5 mL) and stirred at 60° C. The reaction mixture is evaporated and the residue is purified by purified by prep. HPLC (Prep-HPLC-1 conditions) to give the title compound Ex 11-78 (8 mg, 22% yield) as a foam. LCMS-1: $t_R$=0.80 min, [M+1]$^+$447.03.

Example 11-79: Ethyl (2-(3-((2-(difluoromethoxy)-6-methylpyridin-3-yl)carbamoyl)-3-(2-isopropylphenyl)azetidin-1-yl)ethyl)glycinate and Example 11-80: (2-(3-((2-(difluoromethoxy)-6-methylpyridin-3-yl)carbamoyl)-3-(2-isopropylphenyl)azetidin-1-yl)ethyl)glycine Step 1. methyl (2-(3-((2-(difluoromethoxy)-6-methylpyridin-3-yl)carbamoyl)-3-(2-isopropylphenyl)azetidin-1-yl)ethyl)glycinate Ex 11-79 is synthesized from Ex 11-1 and ethyl chloroacetate according to the protocol described for the preparation of Ex 11-67. LCMS-1: $t_R$=0.87 min, [M+1]$^+$ 505.11.

Step 2. (2-(3-((2-(difluoromethoxy)-6-methylpyridin-3-yl)carbamoyl)-3-(2-isopropylphenyl)azetidin-1-yl)ethyl) glycine Ex 11-80 is synthesized according to the protocol described for the preparation of Ex 11-14. LCMS-1: $t_R$=0.76 min, [M+1]$^+$477.07.

Example 11-81: Ethyl N-(2-(3-((2-(difluoromethoxy)-6-methylpyridin-3-yl)carbamoyl)-3-(2-isopropylphenyl)azetidin-1-yl)ethyl)-N-methylglycinate and Example 11-82: N-(2-(3-((2-(difluoromethoxy)-6-methylpyridin-3-yl)carbamoyl)-3-(2-isopropylphenyl)azetidin-1-yl)ethyl)-N-methylglycine Examples 11-81 and 11-82 are prepared from Ex 11-62 in a similar manner to Ex 11-79 and Ex 11-80. Ex 11-81 LCMS-1: $t_R$=0.94 min, [M+1]$^+$519.06. Ex 11-82 LCMS-1: $t_R$=0.77 min, [M+1]$^+$491.12

Example 11-83: (S)-1-(3-amino-2-hydroxypropyl)-N-(2-(difluoromethoxy)-6-methylpyridin-3-yl)-3-(2-isopropylphenyl)azetidine-3-carboxamide Step 1. To a solution of N-(2-(difluoromethoxy)-6-methylpyridin-3-yl)-3-(2-isopropylphenyl)azetidine-3-carboxamide Ex 3 (450 mg, 1.2 mmol) in isopropanol (5 mL) is added an aqueous solution of 3M NaOH (1.5 mL) followed by R-epichlorhydrin (282 uL, 3.6 mmol). The reaction mixture is stirred at r.t. overnight, is diluted with EtOAc (15 mL) and is washed with water (10 mL). The organic phase is dried over MgSO$_4$, filtered and evaporated. The residue is purified by prep. TLC (eluent: heptane/ethylacetate 4:1) to give (R)-N-(2-(difluoromethoxy)-6-methylpyridin-3-yl)-3-(2-isopropylphenyl)-1-(oxiran-2-ylmethyl)azetidine-3-carboxamide (245 mg, 47% yield) as an oil. LCMS-2: $t_R$=0.89 min, [M+H]$^+$=432.10.

Step 2. To a solution of (R)-N-(2-(difluoromethoxy)-6-methylpyridin-3-yl)-3-(2-isopropylphenyl)-1-(oxiran-2-ylmethyl)azetidine-3-carboxamide (50 mg, 0.12 mmol) in MeOH (1 mL) is added 7M NH$_3$ in MeOH (10 uL, 0.35 mmol). The reaction mixture is stirred at 60° C. for 6 h. The volatiles are then evaporated and the residue is purified by prep. HPLC (Prep-HPLC-3 conditions) to give the title compound Ex 11-83 (53 mg, 100% yield) as a glass. LCMS-1: $t_R$=0.53 min, [M+1]$^+$449.07.

TABLE 4

Examples 11-84 and 11-85
Examples 11-84 and 11-85 are synthesized using the methodology described for example Ex 11-83 using methyl- or dimethylamine as nucleophile.

| Example | Name | Analytics LCMS-1 |
|---|---|---|
| Ex 11-84 | (S)-N-(2-(difluoromethoxy)-6-methylpyridin-3-yl)-1-(2-hydroxy-3-(methylamino)propyl)-3-(2-isopropylphenyl)azetidine-3-carboxamide | [M + 1]$^+$463.08 $t_R$ 0.54 |
| Ex 11-85 | (S)-N-(2-(difluoromethoxy)-6-methylpyridin-3-yl)-1-(3-(dimethylamino)-2-hydroxypropyl)-3-(2-isopropylphenyl)azetidine-3-carboxamide | [M + 1]$^+$477.17 $t_R$ 0.55 |

Example 11-86: (S)-N-(2-(difluoromethoxy)-6-methylpyridin-3-yl)-1-(2-hydroxy-3-(2-hydroxyacetamido)propyl)-3-(2-isopropylphenyl)azetidine-3-carboxamide (S)-1-(3-amino-2-hydroxypropyl)-N-(2-(difluoromethoxy)-6-methylpyridin-3-yl)-3-(2-isopropylphenyl) azetidine-3-carboxamide Ex 11-83 (52 mg, 0.12 mmol) is added to a solution of glycolic acid (0.14 mmol, 11 mg), EDC (33 mg, 0.17 mmol), HOBt (23.5 mg, 0.17 mmol) and DIPEA (40 uL, 0.23 mmol) in DMF (5 ml). The reaction mixture is stirred at r.t. for 1 h, is then evaporated to dryness and purified by prep. HPLC (Prep-HPLC-2 conditions) to give the title compound Ex 11-86 (22 mg, 37% yield) as an oil. LCMS-1: $t_R$=0.68 min, [M+1]$^+$507.35; $^1$H NMR (400 MHz, CDCl$_3$) δ: 8.50 (d, J=8.1 Hz, 1 H), 7.62-7.57 (m, 1 H), 7.49-7.43 (m, 3 H), 7.39-7.35 (m, 1 H), 7.26 (t, J=83.8 Hz, 1 H), 7.21 (d, J=7.7 Hz, 1 H), 6.93 (d, J=8.2 Hz, 1 H), 5.70-5.01 (m, 4H), 4.19-4.05 (m, 3 H), 3.48-3.42 (m, 1 H), 3.42-3.33 (m, 2 H), 3.29-3.20 (m, 1 H), 2.38 (s, 3 H), 2.29-2.18 (m, 1 H), 1.19 (d, J=6.1 Hz, 6 H).

Example 11-87: N-(2-(difluoromethoxy)-6-methylpyridin-3-yl)-1-(2-(2-hydroxyacetamido)ethyl)-3-(2-isopropylphenyl)azetidine-3-carboxamide N-(2-(difluoromethoxy)-6-methylpyridin-3-yl)-1-(2-(2-hydroxyacetamido)ethyl)-3-(2-isopropylphenyl)azetidine-3-carboxamide Ex 11-87 (35 mg, solid) is prepared from -(2-aminoethyl)-N-(2-(difluoromethoxy)-6-methylpyridin-3-yl)-3-(2-isopropylphenyl)azetidine-3-carboxamide Ex 11-1 (73 mg, 0.17 mmol) following the methodology described for Ex 11-86. LCMS-1: $t_R$=0.69 min, [M+1]$^+$ 477.36; $^1$H NMR (400 MHz, CDCl$_3$) δ: 8.56 (d, J=8.1 Hz, 1 H), 8.48 (s, 1 H), 7.24-7.43 (m, 5 H), 7.16 (m, 1 H), 6.94 (d, J=8.1 Hz, 1 H), 4.32-3.14 (m, 2 H), 4.11 (s, 2 H), 3.79-3.57 (m, 2 H), 3.44-3.42 (m, 2 H), 2.79 (t, J=5.6 Hz, 2 H), 2.50-2.43 (m, 1 H), 2.40 (s, 3 H), 1.16 (d, J=6.6 Hz, 6 H).

Example 11-88: 1-(cyanomethyl)-N-(2-(difluoromethoxy)-6-methylpyridin-3-yl)-3-(2-isopropylphenyl)azetidine-3-carboxamide To a solution of Ex 3 hydrochloride (100 mg, 0.24 mmol) and bromoacetonitrile (19 uL, 0.27 mmol) in DMF (2 mL) is added CS$_2$CO$_3$ (158 mg, 0.49 mmol). The reaction mixture is stirred at r.t. for 1 h (reaction monitored by LCMS), is then extracted with DCM (2×20 mL). The organic extracts are washed with water (10 mL), followed by brine (10 mL) and are then dried over MgSO$_4$, filtered and evaporated. The residue is purified by prep. HPLC (Prep-HPLC-1 conditions) to give the title compound Ex 11-88 (50 mg, 50% yield) as a beige solid. LCMS-1: $t_R$=1.25 min, [M+1]$^+$ 415.37; $^1$H NMR (400 MHz, CDCl$_3$) δ: 8.60 (d, J=8.1 Hz, 1 H), 8.17 (s, 1 H), 7.42-7.38 (m, 2 H), 7.32 (t, J=72.8 Hz, 1 H), 7.34-7.30 (m, 1 H), 7.17 (d, J=6.6 Hz, 1 H), 6.94 (d, J=8.1 Hz, 1 H), 4.30-4.21 (m, 2 H), 3.96-3.85 (m, 2 H), 3.65 (s, 2 H), 2.56-2.47 (m, 1 H), 2.40 (s, 3 H), 1.16 (d, J=6.7 Hz, 6 H).

Example 11-89: N-(2-(difluoromethoxy)-6-methylpyridin-3-yl)-1-((3-(hydroxymethyl)oxetan-3-yl)methyl)-3-(2-isopropylphenyl)azetidine-3-carboxamide To a solution of Ex 3 hydrochloride (200 mg, 0.49 mmol) and (3-(bromo-methyl)oxetanyl-3-yl)methanol (88 uL, 0.49 mmol) in MeCN (10 mL) is added CS$_2$CO$_3$ (316 mg, 0.97 mmol). The reaction mixture is stirred at 85° C. for 2 h (reaction monitored by LCMS). Water is added (20 mL) and the mixture is then extracted with EtOAc (2×50 mL). The organic extracts are washed with brine (10 mL), are dried over MgSO$_4$, filtered and evaporated. The residue is purified by prep. HPLC (Prep-HPLC-1 conditions) to give the title compound Ex 11-89 (157 mg, 68% yield) as a beige solid. LCMS-1: $t_R$=0.75 min, [M+1]$^+$476.37.

Example 11-90: methyl 3-((3-((2-(difluoromethoxy)-6-methylpyridin-3-yl)carbamoyl)-3-(2-isopropylphenyl)azetidin-1-yl)methyl)oxetane-3-carboxylate and Example 11-91: 3-((3-((2-(difluoromethoxy)-6-methylpyridin-3-yl)carbamoyl)-3-(2-isopropylphenyl)azetidin-1-yl)methyl)oxetane-3-carboxylic acid Methyl 3-(bromomethyl)oxetane-3-carboxylate (172 mg, 0.82 mmol), prepared from commercially available 3-(bromomethyl)oxetane-3-carboxylic acid and trimethylsilyldiazomethane, is reacted with Ex 3 hydrochloride (150 mg, 0.36 mmol) following the methodology described for Ex 11-89 to give methyl 3-((3-((2-(difluoromethoxy)-6-methylpyridin-3-yl)carbamoyl)-3-(2-isopropylphenyl)azetidin-1-yl)methyl)oxetane-3-carboxylate Ex 11-90. LCMS-1: $t_R$=1.02 min, [M+1]$^+$504.03. The methylester is then saponified with LiOH following the methodology described for Ex 11-14 to afford Ex 11-91 (17 mg, 9% yield) as a beige wax. LCMS-1: $t_R$=0.90 min, [M+1]$^+$490.29.

Example 11-92: N-(2-(difluoromethoxy)-6-methylpyridin-3-yl)-1-(3,3-dimethyl-4-(methylamino)-4-oxobutyl)-3-(2-isopropylphenyl)azetidine-3-carboxamide N-(2-(difluoromethoxy)-6-methylpyridin-3-yl)-1-(3,3-dimethyl-4-(methylamino)-4-oxobutyl)-3-(2-isopropylphenyl)azetidine-3-carboxamide Ex 11-92 is prepared from 4-(3-((2-(difluoromethoxy)-6-methylpyridin-3-yl)carbamoyl)-3-(2-isopropylphenyl)azetidin-1-yl)-2,2-dimethylbutanoic acid Ex 11-31 and 2N methylamine in THF following the methodology described for Ex 11-86. Colorless oil. LCMS-1: $t_R$=0.79 min, [M+1]$^+$503.52.

Example 11-93: 1-(4-amino-3,3-dimethyl-4-oxobutyl)-N-(2-(difluoromethoxy)-6-methylpyridin-3-yl)-3-(2-isopropylphenyl)azetidine-3-carboxamide Ex 11-31 (60 mg, 0.114 mmol) is reacted with allylamine (10 uL, 0.125 mmol) according to the methodology descibed for Ex 11-86. The obtained allylamide is purified by prep HPLC (Prep-HPLC-2 conditions) and is then introduced (48 mg, 0.09 mmol) into a sealed tube containing tetrachlorobis (2,7-dimethyl-2,6-octadienylene)diruthenium (1.7 mg, 0.002 mmol), KlO$_4$ (21 mg, 0.09 mmol) and water (1 mL). The reaction mixture is heated at 100° C. for 2 h under argon atmosphere. Water is added and the mixture is extracted with EtOAc. The organic extract is dried over MgSO$_4$, dried, filtered and evaporated. Crude compound is purified by prep. HPLC (Prep-HPLC-2 conditions) to give the title compound Ex 11-93 as a colorless oil (8 mg, 18%). LCMS-1: $t_R$=0.82 min, [M+1]$^+$489.12.

Example 11-94: 1-(4-amino-4-methylpentyl)-N-(2-(difluoromethoxy)-6-methylpyridin-3-yl)-3-(2-isopropylphenyl)azetidine-3-carboxamide To a solution of Ex 11-61 (82 mg, 0.16 mmol) in AcOH (5 mL) is added ZnBr (2.5 eq, 114 mg) and the mixture is stirred at 100° C. for 2 h in a microwave oven. Another portion of ZnBr (1.1 eq., 50 mg) is added and the reaction mixture is stirred at 100° C. for 2 h. Purification by prep. HPLC (Prep-HPLC-1 conditions) afforded the title compound Ex 11-94 as a beige wax (16 mg, 17% yield). LCMS-1: $t_R$=0.61 min, [M+1]$^+$475.15.

Example 11-95: 1-(2-($^1$H-tetrazol-5-yl)ethyl)-N-(2-(difluoromethoxy)-6-methylpyridin-3-yl)-3-(2-isopropylphenyl)azetidine-3-carboxamide 1-(2-(1H-tetrazol-5-yl)ethyl)-N-(2-(difluoromethoxy)-6-methylpyridin-3-yl)-3-(2-isopropylphenyl)azetidine-3-carboxamide Ex 11-95 was prepared from 3-(2-isopropylphenyl)-N-(2-methoxy-6-methylpyridin-3-yl)azetidine-3-carboxamide Ex 3 and 5-(2-bromoethyl)-1H-1,2,3,4- tetrazole following the methodology described for Ex 11-1 to 11-11. Colorless oil. LCMS-1: $t_R$=0.80 min, [M+1]$^+$ 472.06.

Example 12-1: 1-(4-cyanobutanoyl)-N-(2-(difluoromethoxy)-6-methylpyridin-3-yl)-3-(2-isopropylphenyl)azetidine-3-carboxamide To a solution of 3-(2-isopropylphenyl)-N-(2-methoxy-6-methylpyridin-3-yl)azetidine-3-carboxamide Ex 3 (72 mg, 0.19 mmol) and 4-cyanobutanoic acid (21.6 mg, 0.19 mmol) in DMF (2 mL), EDC (55 mg, 0.29 mmol), HOBt (39 mg, 0.29 mmol) and DIPEA (65 uL, 0.49 mmol) are added. The mixture is stirred at r.t. for 1 h (reaction progress monitored by LCMS) before it is diluted with sat. aq. NaHCO$_3$ and extracted twice with EtOAc. The combined org. extracts are dried over MgSO$_4$, filtered and concentrated. The crude product is purified by prep. HPLC (Prep-HPLC-3 conditions) to give 1-(4-cyanobutanoyl)-N-(2-(difluoromethoxy)-6-methylpyridin-3-yl)-3-(2-isopropylphenyl)azetidine-3-carboxamide Ex 12-1 (52 mg, 58% yield) as a yellow oil; LCMS-1: $t_R$=1.17 min, [M+1]$^+$471.07.

TABLE 5

Examples 12-2 to 12-31
Examples 12-2 to 12-31 are synthesized using the methodology described for Ex 12-1 above starting from Ex 3 or Ex 4. Standard coupling reagents can be used such as EDC/HOBt, TBTU, HATU, T3P. Carboxylic acid reagents are commercially available or prepared according to literature protocols.

| Example | Name | Analytics LCMS-1 |
|---|---|---|
| Ex 12-2 | 1-acetyl-N-(2-(difluoromethoxy)-6-methylpyridin-3-yl)-3-(2-isopropylphenyl)azetidine-3-carboxamide | [M + 1]$^+$ 418.06 $t_R$ 1.14 |
| Ex 12-3 | 2-(3-((2-(difluoromethoxy)-6-methylpyridin-3-yl)carbamoyl)-3-(2-isopropylphenyl)azetidin-1-yl)-2-oxoethane-1-sulfonic acid | [M + 1]$^+$ 498.10 $t_R$ 1.33 |
| Ex 12-4 | N-(2-(difluoromethoxy)-6-methylpyridin-3-yl)-3-(2-isopropylphenyl)-1-(2-sulfamoylacetyl)azetidine-3-carboxamide | [M + 1]$^+$497.10 $t_R$ 1.07 |
| Ex 12-5 | N-(2-(difluoromethoxy)-6-methylpyridin-3-yl)-3-(2-isopropylphenyl)-1-(3-sulfamoylpropanoyl)azetidine-3-carboxamide | [M + 1]$^+$511.17 $t_R$ 1.07 |
| Ex 12-6 | N-(2-(difluoromethoxy)-6-methylpyridin-3-yl)-3-(2-isopropylphenyl)-1-(2-(N-methylsulfamoyl)acetyl)azetidine-3-carboxamide | [M + 1]$^+$511.30 $t_R$ 1.12 |
| Ex 12-7 | N-(2-(difluoromethoxy)-6-methylpyridin-3-yl)-3-(2-isopropylphenyl)-1-((methylsulfonyl)glycyl)azetidine-3-carboxamide | [M + 1]$^+$ 511.15 $t_R$ 1.10 |
| Ex 12-8 | N-(2-(difluoromethoxy)-6-methylpyridin-3-yl)-3-(2-isopropylphenyl)-1-(N-methyl-N-sulfamoylglycyl)azetidine-3-carboxamide | [M + 1]$^+$ 526.18 $t_R$ 1.11 |
| Ex 12-9 | N-(2-(difluoromethoxy)-6-methylpyridin-3-yl)-3-(2-isopropylphenyl)-1-(3-(methylsulfonamido)-3-oxopropanoyl)azetidine-3-carboxamide | [M + 1]$^+$ 539.20 $t_R$ 1.11 |
| Ex 12-10 | 1-(carbamoylglycyl)-N-(2-(difluoromethoxy)-6-methylpyridin-3-yl)-3-(2-isopropylphenyl)azetidine-3-carboxamide | [M + 1]$^+$ 476.44 $t_R$ 0.99 |
| Ex 12-11 | N-(2-(difluoromethoxy)-6-methylpyridin-3-yl)-3-(2-isopropylphenyl)-1-(5,5,5-trifluoro-4-oxopentanoyl)azetidine-3-carboxamide | [M + 1]$^+$ 528.43 $t_R$ 1.21 |
| Ex 12-12 | N-(2-(difluoromethoxy)-6-methylpyridin-3-yl)-4-(2-isopropylphenyl)-1-(5,5,5-trifluoro-4-oxopentanoyl)piperidine-4-carboxamide | [M + 1]$^+$ 556.28 $t_R$ 1.28 |
| Ex 12-13 | N-(2-(difluoromethoxy)-6-methylpyridin-3-yl)-1-(2-(3-hydroxyoxetan-3-yl)acetyl)-3-(2-isopropylphenyl)azetidine-3-carboxamide | [M + 1]$^+$ 490.02 $t_R$ 1.08 |
| Ex 12-14 | N-(2-(difluoromethoxy)-6-methylpyridin-3-yl)-1-(2-(3-hydroxyoxetan-3-yl)acetyl)-4-(2-isopropylphenyl)piperidine-4-carboxamide | [M + 1]$^+$ 518.36 $t_R$ 1.15 |
| Ex 12-15 | N-(2-(difluoromethoxy)-6-methylpyridin-3-yl)-3-(2-isopropylphenyl)-1-(1H-pyrazole-4-carbonyl)azetidine-3-carboxamide | [M + 1]$^+$ 470.09 $t_R$ 1.08 |
| Ex 12-16 | N-(2-(difluoromethoxy)-6-methylpyridin-3-yl)-1-(3-hydroxyisoxazole-5-carbonyl)-3-(2-isopropylphenyl)azetidine-3-carboxamide [tautomeric form: N-(2-(difluoromethoxy)-6-methylpyridin-3-yl)-1-(3-oxo-2,3-dihydroisoxazole-5-carbonyl)-3-(2-isopropylphenyl)azetidine-3-carboxamide] | [M + 1]$^+$ 487.24 $t_R$ 1.16 |
| Ex 12-17 | N-(2-(difluoromethoxy)-6-methylpyridin-3-yl)-1-(3-hydroxy-1H-1,2,4-triazole-5-carbonyl)-3-(2-isopropylphenyl)azetidine-3-carboxamide [and tautomeric forms thereof, such as N-(2-(difluoromethoxy)-6-methylpyridin-3-yl)-1-(3-oxo-4,5-dihydro-1H-1,2,4-triazol-5-carbonyl)-3-(2-isopropylphenyl)azetidine-3-carboxamide] | [M + 1]$^+$ 486.96 $t_R$ 1.05 |
| Ex 12-18 | N-(2-(difluoromethoxy)-6-methylpyridin-3-yl)-3-(2-isopropylphenyl)-1-(1H-tetrazole-5-carbonyl)azetidine-3-carboxamide | [M + 1]$^+$ 472.09 $t_R$ 1.30 |
| Ex 12-19 | 1-(2-(1H-tetrazol-5-yl)acetyl)-N-(2-(difluoromethoxy)-6-methylpyridin-3-yl)-3-(2-isopropylphenyl)azetidine-3-carboxamide | [M + 1]$^+$ 486.06 $t_R$ 1.07 |
| Ex 12-20 | 1-(2-(1H-tetrazol-1-yl)acetyl)-N-(2-(difluoromethoxy)-6-methylpyridin-3-yl)-4-(2-isopropylphenyl)piperidine-4-carboxamide | [M + 1]$^+$ 514.37 $t_R$ 1.16 |
| Ex 12-21 | 1-(2-(2H-1,2,3-triazol-2-yl)acetyl)-N-(2-(difluoromethoxy)-6-methylpyridin-3-yl)-3-(2-isopropylphenyl)azetidine-3-carboxamide | [M + 1]$^+$ 484.99 $t_R$ 1.16 |
| Ex 12-22 | 1-(2-(2H-1,2,3-triazol-2-yl)acetyl)-N-(2-(difluoromethoxy)-6-methylpyridin-3-yl)-4-(2-isopropylphenyl)piperidine-4-carboxamide | [M + 1]$^+$ 513.06 $t_R$ 1.21 |
| Ex 12-23 | 1-(2-(4H-1,2,4-triazol-4-yl)acetyl)-N-(2-(difluoromethoxy)-6-methylpyridin-3-yl)-3-(2-isopropylphenyl)azetidine-3-carboxamide | [M + 1]$^+$ 485.33 $t_R$ 1.01 |
| Ex 12-24 | N-(2-(difluoromethoxy)-6-methylpyridin-3-yl)-1-(2-(3-hydroxy-1H-pyrazol-5-yl)acetyl)-3-(2-isopropylphenyl)azetidine-3-carboxamide [and tautomeric forms thereof, such as N-(2-(difluoromethoxy)-6-methylpyridin-3-yl)-1-(2-(3-oxo-2,3-dihydro-1H-pyrazol-5-yl)acetyl)-3-(2-isopropylphenyl)azetidine-3-carboxamide] | [M + 1]$^+$ 500.11 $t_R$ 1.01 |

TABLE 5-continued

Examples 12-2 to 12-31
Examples 12-2 to 12-31 are synthesized using the methodology described for Ex 12-1 above starting from Ex 3 or Ex 4. Standard coupling reagents can be used such as EDC/HOBt, TBTU, HATU, T3P. Carboxylic acid reagents are commercially available or prepared according to literature protocols.

| Example | Name | Analytics LCMS-1 |
|---|---|---|
| Ex 12-25 | N-(2-(difluoromethoxy)-6-methylpyridin-3-yl)-1-(2-(3-hydroxy-1H-pyrazol-5-yl)acetyl)-4-(2-isopropylphenyl)piperidine-4-carboxamide [and tautomeric forms thereof, such as N-(2-(difluoromethoxy)-6-methylpyridin-3-yl)-1-(2-(3-oxo-2,3-dihydro-1H-pyrazol-5-yl)acetyl)-4-(2-isopropylphenyl)piperidine-4-carboxamide] | $[M + 1]^+$ 528.01 $t_R$ 1.06 |
| Ex 12-26 | N-(2-(difluoromethoxy)-6-methylpyridin-3-yl)-1-(2-(3-hydroxy-1H-pyrazol-4-yl)acetyl)-3-(2-isopropylphenyl)azetidine-3-carboxamide [and tautomeric forms thereof, such as N-(2-(difluoromethoxy)-6-methylpyridin-3-yl)-1-(2-(3-oxo-2,3-dihydro-1H-pyrazol-4-yl)acetyl)-3-(2-isopropylphenyl)azetidine-3-carboxamide] | $[M + 1]^+$ 500.32 $t_R$ 1.03 |
| Ex 12-27 | N-(2-(difluoromethoxy)-6-methylpyridin-3-yl)-1-(2-(3-hydroxy-1H-pyrazol-4-yl)acetyl)-4-(2-isopropylphenyl)piperidine-4-carboxamide [and tautomeric forms thereof, such as N-(2-(difluoromethoxy)-6-methylpyridin-3-yl)-1-(2-(3-oxo-2,3-dihydro-1H-pyrazol-4-yl)acetyl)-4-(2-isopropylphenyl)piperidine-4-carboxamide] | $[M + 1]^+$ 528.21 $t_R$ 1.08 |
| Ex 12-28 | 1-(3-(4H-1,2,4-triazol-4-yl)propanoyl)-N-(2-(difluoromethoxy)-6-methylpyridin-3-yl)-3-(2-isopropylphenyl)azetidine-3-carboxamide | $[M + 1]^+$ 499.36 $t_R$ 1.00 |
| Ex 12-29 | N-(2-(difluoromethoxy)-6-methylpyridin-3-yl)-1-(3-(3-hydroxyisoxazol-5-yl)propanoyl)-3-(2-isopropylphenyl)azetidine-3-carboxamide [tautomeric form: N-(2-(difluoromethoxy)-6-methylpyridin-3-yl)-1-(3-(3-oxo-2,3-dihydroisoxazole-5-yl)propanoyl)-3-(2-isopropylphenyl)azetidine-3-carboxamide] | $[M + 1]^+$ 514.99 $t_R$ 1.12 |
| Ex 12-30 | 1-(4-(1H-tetrazol-5-yl)butanoyl)-N-(2-(difluoromethoxy)-6-methylpyridin-3-yl)-3-(2-isopropylphenyl)azetidine-3-carboxamide | $[M + 1]^+$ 514.17 $t_R$ 1.08 |
| Ex 12-31 | N-(2-(difluoromethoxy)-6-methylpyridin-3-yl)-3-(2-isopropylphenyl)-1-(2-(1-methylpiperidin-4-yl)acetyl)azetidine-3-carboxamide | $[M + 1]^+$ 515.18 $t_R$ 0.77 |

Example 12-32: tert-butyl (1-(4-(2-isopropylphenyl)-4-((2-methoxy-4-methylphenyl)carbamoyl)piperidine-1-carbonyl)cyclopropyl)carbamate and Example 12-33: 1-(L-alanyl)-N-(2-(difluoromethoxy)-6-methylpyridin-3-yl)-3-(2-isopropylphenyl)azetidine-3-carboxamide Step 1. tert-butyl (S)-(1-(3-((2-(difluoromethoxy)-6-methylpyridin-3-yl)carbamoyl)-3-(2-isopropylphenyl)azetidin-1-yl)-1-oxopropan-2-yl)carbamate Ex 12-32 is prepared from Ex 3 (69 mg, 0.183 mmol) and commercially available Boc-alanine (35 mg, 0.183 mmol) following the method described for Ex 12-1. White solid (81 mg, 81% yield). LCMS-1: $t_R$=1.30 min, [M+1]$^+$547.02.

Step 2. 1-(L-alanyl)-N-(2-(difluoromethoxy)-6-methylpyridin-3-yl)-3-(2-isopropylphenyl)azetidine-3-carboxamide Ex 12-33 is prepared from Ex 12-32 (75 mg, 0.137 mmol) following the reaction conditions of step 2 described for Ex 11-1:44 mg, 72% yield after prep. HPLC (Prep-HPLC-3 conditions). LCMS-1: $t_R$=0.74 min, [M+1]$^+$446.99; $^1$H NMR (400 MHz, CDCl$_3$) δ: 8.54 (d, J=8.1 Hz, 1 H), 7.48-7.45 (m, 2 H), 7.42-7.37 (m, 1 H), 7.35-7.31 (m, 1 H), 7.26 (d, J=72.8 Hz, 1 H), 7.24 (s, 1 H), 6.94 (d, J=8.1 Hz, 1 H), 5.17-4.94 (m, 1 H), 4.78-4.40 (m, 3 H), 3.70-3.50 (m, 1 H), 2.46-2.39 (m, 4 H), 1.40 (d, J=6.8 Hz, 1.5 H), 1.27 (d, J=6.8 Hz, 1.5 H), 1.23-1.09 (m, 6 H).

TABLE 6

Examples 12-34 to 12-51
Examples 12-34 to 12-51 are synthesized using the methodology described for Ex 12-33 starting from Ex 3 or Ex 4. Standard coupling reagents can be used such as EDC/HOBt, TBTU, HATU, T3P for example.

| Example | Name | Analytics LCMS-1 |
|---|---|---|
| Ex 12-34 | (S)-4-(3-((2-(difluoromethoxy)-6-methylpyridin-3-yl)carbamoyl)-3-(2-isopropylphenyl)azetidin-1-yl)-2-hydroxy-4-oxobutanoic acid | $[M + 1]^+$ 492.14 $t_R$ 1.05 |
| Ex 12-35 | (R)-4-(3-((2-(difluoromethoxy)-6-methylpyridin-3-yl)carbamoyl)-3-(2-isopropylphenyl)azetidin-1-yl)-2-hydroxy-4-oxobutanoic acid | $[M + 1]^+$ 492.17 $t_R$ 1.05 |
| Ex 12-36 | (S)-N-(2-(difluoromethoxy)-6-methylpyridin-3-yl)-1-(2-(2,2-dimethyl-5-oxo-1,3-dioxolan-4-yl)acetyl)-4-(2-isopropylphenyl)piperidine-4-carboxamide | $[M + 1]^+$ 560.02 $t_R$ 1.31 |
| Ex 12-37 | (S)-4-(4-((2-(difluoromethoxy)-6-methylpyridin-3-yl)carbamoyl)-4-(2-isopropylphenyl)piperidin-1-yl)-2-hydroxy-4-oxobutanoic acid | $[M + 1]^+$ 520.35 $t_R$ 1.11 |
| Ex 12-38 | 1-(2-(3-aminooxetan-3-yl)acetyl)-N-(2-(difluoromethoxy)-6-methylpyridin-3-yl)-3-(2-isopropylphenyl)azetidine-3-carboxamide | $[M + 1]^+$ 489.36 $t_R$ 0.75 |
| Ex 12-39 | tert-butyl (S)-(1-(3-((2-(difluoromethoxy)-6-methylpyridin-3-yl)carbamoyl)-3-(2-isopropylphenyl)azetidin-1-yl)-3-hydroxy-1-oxopropan-2-yl)carbamate | $[M + 1]^+$ 563.20 $t_R$ 1.21 |
| Ex 12-40 | 1-(L-seryl)-N-(2-(difluoromethoxy)-6-methylpyridin-3-yl)-3-(2-isopropylphenyl)azetidine-3-carboxamide | $[M + 1]^+$ 463.36 $t_R$ 0.72 |

TABLE 6-continued

Examples 12-34 to 12-51
Examples 12-34 to 12-51 are synthesized using the methodology described for
Ex 12-33 starting from Ex 3 or Ex 4. Standard coupling reagents can
be used such as EDC/HOBt, TBTU, HATU, T3P for example.

| Example | Name | Analytics LCMS-1 |
| --- | --- | --- |
| Ex 12-41 | N-(2-(difluoromethoxy)-6-methylpyridin-3-yl)-1-((4S)-4-hydroxypyrrolidine-2-carbonyl)-3-(2-isopropylphenyl)azetidine-3-carboxamide | [M + 1]$^+$ 489.37<br>$t_R$ 0.73 |
| Ex 12-42 | (R)-N-(2-(difluoromethoxy)-6-methylpyridin-3-yl)-3-(2-isopropylphenyl)-1-(morpholine-2-carbonyl)azetidine-3-carboxamide | [M + 1]$^+$ 489.38<br>$t_R$ 0.76 |
| Ex 12-43 | N-(2-(difluoromethoxy)-6-methylpyridin-3-yl)-3-(2-isopropylphenyl)-1-(morpholine-3-carbonyl)azetidine-3-carboxamide | [M + 1]$^+$ 489.20<br>$t_R$ 0.76 |
| Ex 12-44 | (S)-N-(2-(difluoromethoxy)-6-methylpyridin-3-yl)-3-(2-isopropylphenyl)-1-(2-(morpholin-3-yl)acetyl)azetidine-3-carboxamide | [M + 1]$^+$ 503.37<br>$t_R$ 0.76 |
| Ex 12-45 | (R)-N-(2-(difluoromethoxy)-6-methylpyridin-3-yl)-3-(2-isopropylphenyl)-1-(2-(morpholin-3-yl)acetyl)azetidine-3-carboxamide | [M + 1]$^+$ 503.16<br>$t_R$ 0.76 |
| Ex 12-46 | N-(2-(difluoromethoxy)-6-methylpyridin-3-yl)-3-(2-isopropylphenyl)-1-(2-(3-oxopiperazin-2-yl)acetyl)azetidine-3-carboxamide | [M + 1]$^+$ 516.17<br>$t_R$ 0.73 |
| Ex 12-47 | tert-butyl (2-(4-((2-(difluoromethoxy)-6-methylpyridin-3-yl)carbamoyl)-4-(2-isopropylphenyl)piperidin-1-yl)-2-oxoethyl)(2-methoxyethyl)carbamate | [M + 1]$^+$ 619.29<br>$t_R$ 1.37 |
| Ex 12-48 | N-(2-(difluoromethoxy)-6-methylpyridin-3-yl)-4-(2-isopropylphenyl)-1-((2-methoxyethyl)glycyl)piperidine-4-carboxamide | [M + 1]$^+$ 519.40<br>$t_R$ 0.80 |
| Ex 12-49 | tert-butyl (2-(4-((2-(difluoromethoxy)-6-methylpyridin-3-yl)carbamoyl)-4-(2-isopropylphenyl)piperidin-1-yl)-2-oxoethyl)(2-hydroxyethyl)carbamate | [M + 1]$^+$ 605.18<br>$t_R$ 1.29 |
| Ex 12-50 | N-(2-(difluoromethoxy)-6-methylpyridin-3-yl)-1-((2-hydroxyethyl)glycyl)-4-(2-isopropylphenyl)piperidine-4-carboxamide | [M + 1]$^+$ 505.34<br>$t_R$ 0.78 |
| Ex 12-51 | N-(2-(difluoromethoxy)-6-methylpyridin-3-yl)-1-(3-(2-(2-hydroxyethoxy)ethoxy)propanoyl)-3-(2-isopropylphenyl)azetidine-3-carboxamide | [M + 1]$^+$ 536.14<br>$t_R$ 1.08 |

Example 12-52: N-(2-(difluoromethoxy)-6-methylpyridin-3-yl)-1-((2-hydroxyethyl)glycyl)-3-(2-isopropylphenyl)azetidine-3-carboxamide Step 1. To an ice-cold solution of Ex 3 (150 mg, 0.4 mmol) and DIPEA (205 uL, 1.2 mmol) in THF (10 mL) is added chloroacetyl chloride (48 uL, 0.6 mmol). The reaction mixture is stirred at r.t. for 18 h and is then diluted with EtOAc. The organic solution is washed with water, dried over MgSO$_4$, filtered and evaporated to give crude chloroacetamide intermediate that is used as such in the next step.

Step 2. Chloroacetamide intermediate is dissolved in MeCN (10 mL). Ethanolamine (49 uL, 0.80 mmol) and K$_2$CO$_3$ (221 mg, 1.6 mmol) are added and the reaction mixture is then stirred at 65° C. for 18 h (reaction progress monitored by LCMS). The mixture is diluted with DCM (20 mL), washed with water (10 mL) dried over MgSO$_4$, filtered and evaporated. The residue is then purified by prep-TLC (DCM/MeOH 9:1) to give Ex 12-52 as pale yellow foam (60 mg, 32% yield). LCMS-1: $t_R$=0.73 min, [M+1]$^+$477.15.

TABLE 7

Examples 12-53 to 12-60
Examples 12-53 to 12-60 are synthesized using the methodology
described above for Ex 12-52 starting from Ex 3.

| Example | Name | Analytics LCMS-1 |
| --- | --- | --- |
| Ex 12-53 | N-(2-(difluoromethoxy)-6-methylpyridin-3-yl)-1-(2-(3-hydroxyazetidin-1-yl)acetyl)-3-(2-isopropylphenyl)azetidine-3-carboxamide | [M + 1]$^+$ 489.29<br>$t_R$ 0.77 |
| Ex 12-54 | N-(2-(difluoromethoxy)-6-methylpyridin-3-yl)-3-(2-isopropylphenyl)-1-((2-methoxyethyl)glycyl)azetidine-3-carboxamide | [M + 1]$^+$ 491.41<br>$t_R$ 0.76 |
| Ex 12-55 | (R)-N-(2-(difluoromethoxy)-6-methylpyridin-3-yl)-1-((R)-(2-hydroxypropyl)glycyl)-3-(2-isopropylphenyl)azetidine-3-carboxamide | [M + 1]$^+$ 491.38<br>$t_R$ 0.75 |
| Ex 12-56 | (S)-N-(2-(difluoromethoxy)-6-methylpyridin-3-yl)-1-((S)-(2-hydroxypropyl)glycyl)-3-(2-isopropylphenyl)azetidine-3-carboxamide | [M + 1]$^+$ 491.07<br>$t_R$ 0.75 |
| Ex 12-57 | N-(2-(difluoromethoxy)-6-methylpyridin-3-yl)-1-(((1-hydroxycyclopropyl)methyl)glycyl)-3-(2-isopropylphenyl)azetidine-3-carboxamide | [M + 1]$^+$ 503.38<br>$t_R$ 0.76 |
| Ex 12-58 | (R)-N-(2-(difluoromethoxy)-6-methylpyridin-3-yl)-1-((R)-(1-hydroxypropan-2-yl)glycyl)-3-(2-isopropylphenyl)azetidine-3-carboxamide | [M + 1]$^+$ 491.40<br>$t_R$ 0.75 |
| Ex 12-59 | (S)-N-(2-(difluoromethoxy)-6-methylpyridin-3-yl)-1-((R)-(1-hydroxypropan-2-yl)glycyl)-3-(2-isopropylphenyl)azetidine-3-carboxamide | [M + 1]$^+$ 491.40<br>$t_R$ 0.75 |
| Ex 12-60 | N-(2-(difluoromethoxy)-6-methylpyridin-3-yl)-1-(3-((2-hydroxyethyl)amino)propanoyl)-3-(2-isopropylphenyl)azetidine-3-carboxamide | [M + 1]$^+$ 491.39<br>$t_R$ 0.74 |

Example 12-61: Methyl 4-(3-(2-isopropylphenyl)-3-((2-methoxy-6-methylpyridin-3-yl)carbamoyl)azetidin-1-yl)-4-oxobutanoate and Example 12-62: 4-(3-(2-isopropylphenyl)-3-((2-methoxy-6-methylpyridin-3-yl)carbamoyl)azetidin-1-yl)-4-oxobutanoic acid Step 1. To a solution of 3-(2-isopropylphenyl)-N-(2-methoxy-6-methylpyridin-3-yl)azetidine-3-carboxamide Ex 1 (30 mg, 0.088 mmol) and 4-methoxy-4-oxobutanoic acid (14.7 mg, 0.11 mmol), HATU (40.3 mg, 0.11 mmol), and DIPEA (45 uL, 0.26 mmol) are added. The mixture is stirred at r.t. for 1 h (reaction progress monitored by LCMS) before it is diluted with sat. aq. NaHCO$_3$ and extracted twice with EtOAc. The combined org. extracts are dried over MgSO$_4$, filtered and concentrated. The crude product is purified by prep. HPLC (Prep-HPLC-3 conditions) to give methyl 4-(3-(2-isopropylphenyl)-3-((2-methoxy-6-methylpyridin-3-yl)carbamoyl)azetidin-1-yl)-4-oxobutanoate Ex 12-61 (20 mg, 50% yield) as a yellow oil. LCMS-1: $t_R$=1.18 min, [M+1]$^+$ 454.39; $^1$H NMR (400 MHz, CDCl$_3$) δ: 8.41 (d, J=7.8 Hz, 1 H), 7.49-7.44 (m, 2 H), 7.40-7.34 (m, 3 H), 6.72 (d, J=8.0 Hz, 1 H), 5.08-4.96 (m, 1 H), 4.72-4.62 (m, 1 H), 4.58-4.45 (m, 2 H), 3.70 (s, 3 H), 3.69 (s, 3 H), 2.79-2.73 (m, 1 H), 2.69-2.61 (m, 1 H), 2.51-2.41 (m, 3 H), 2.38 (s, 3 H), 1.18 (d, J$_1$=6.7 Hz, 3 H), 1.12 (d, J$_1$=6.7 Hz, 3 H).

Step 2. 4-(3-(2-Isopropylphenyl)-3-((2-methoxy-6-methylpyridin-3-yl)carbamoyl)azetidin-1-yl)-4-oxobutanoate (20 mg, 0.044 mmol) is dissolved in MeOH/THF 1:1 (1 mL) and is treated with 2M LiOH (45 uL, 18.4 mmol). The solution is stirred at r.t. for 2 h (reaction progress monitored by LCMS). The reaction mixture is then diluted with water, acidified to pH 1 with 6N HCl and extracted twice with EtOAc. The combined organic extracts are dried over MgSO$_4$, filtered and evaporated to give 4-(3-(2-isopropylphenyl)-3-((2-methoxy-6-methylpyridin-3-yl)carbamoyl)azetidin-1-yl)-4-oxobutanoic acid Ex 12-62 as a pale yellow oil (13 mg, 67% yield). LCMS-1: $t_R$=1.07 min, [M+1]$^+$ 440.36; $^1$H NMR (400 MHz, CDCl$_3$) δ: 8.40 (d, J=7.9 Hz, 1 H), 7.51-7.43 (m, 2 H), 7.41-7.30 (m, 3 H), 6.73 (d, J=7.9 Hz, 1 H), 5.12-4.95 (m, 1 H), 4.69 (d, J=8.5 Hz, 1 H), 4.62-4.44 (m, 2 H), 3.71 (s, 3 H), 2.82-2.64 (m, 2 H), 2.60-2.48 (m, 2 H), 2.45-2.41 (m, 1 H), 2.38 (s, 3 H), 1.19 (d, J=6.6 Hz, 3 H), 1.12 (d, J=6.6 Hz, 3 H).

TABLE 8

Examples 12-63 to 12-114
Examples 12-63 to 12-114 are synthesized using the methodology described for Ex 12-62 starting from Ex 2, Ex 3, Ex 4, Ex 5, Ex 6, Ex7, Ex 8, or Ex 10. Standard coupling reagents can be used such as EDC/HOBt, TBTU, HATU, T3P for example. Carboxylic acid reagents are commercially available or prepared according to literature protocols. If another functional group is present, an additional deprotection step is required such as Boc cleavage of amine under acidic conditions.

| Example | Name | Analytics LCMS-1 |
| --- | --- | --- |
| Ex 12-63 | 3-(3-((2-(difluoromethoxy)-6-methylpyridin-3-yl)carbamoyl)-3-(2-isopropylphenyl)azetidin-1-yl)-3-oxopropanoic acid | [M + 1]$^+$462.01 $t_R$ 1.09 |
| Ex 12-64 | 1-(3-((2-(difluoromethoxy)-6-methylpyridin-3-yl)carbamoyl)-3-(2-isopropylphenyl)azetidine-1-carbonyl)cyclopropane-1-carboxylic acid | [M + 1]$^+$488.13 $t_R$ 1.12 |
| Ex 12-65 | ethyl-3-(4-((2-(difluoromethoxy)-6-methylpyridin-3-yl)carbamoyl)-4-(2-isopropylphenyl)piperidin-1-yl)-3-oxopropanoate | [M + 1]$^+$518.21 $t_R$ 1.27 |
| Ex 12-66 | 3-(4-((2-(difluoromethoxy)-6-methylpyridin-3-yl)carbamoyl)-4-(2-isopropylphenyl)piperidin-1-yl)-3-oxopropanoic acid | [M + 1]$^+$490.21 $t_R$ 1.15 |
| Ex 12-67 | methyl 4-(3-((2-isopropoxy-6-methylpyridin-3-yl)carbamoyl)-3-(2-isopropylphenyl)azetidin-1-yl)-4-oxobutanoate | [M + 1]$^+$482.42 $t_R$ 1.33 |
| Ex 12-68 | 4-(3-((2-isopropoxy-6-methylpyridin-3-yl)carbamoyl)-3-(2-isopropylphenyl)azetidin-1-yl)-4-oxobutanoic acid | [M + 1]$^+$468.38 $t_R$ 1.23 |
| Ex 12-69 | methyl 4-(3-((6-chloro-2-methoxypyridin-3-yl)carbamoyl)-3-(2-isopropylphenyl)azetidin-1-yl)-4-oxobutanoate | [M + 1]$^+$474.13 $t_R$ 1.23 |
| Ex 12-70 | 4-(3-((6-chloro-2-methoxypyridin-3-yl)carbamoyl)-3-(2-isopropylphenyl)azetidin-1-yl)-4-oxobutanoic acid | [M + 1]$^+$460.41 $t_R$ 1.12 |
| Ex 12-71 | 4-(3-((2-(difluoromethoxy)-6-methylpyridin-3-yl)carbamoyl)-3-(2-isopropylphenyl)azetidin-1-yl)-4-oxobutanoic acid | [M + 1]$^+$475.97 $t_R$ 1.09 |
| Ex 12-72 | methyl 4-(4-((2-(difluoromethoxy)-6-methylpyridin-3-yl)carbamoyl)-4-(2-isopropylphenyl)piperidin-1-yl)-4-oxobutanoate | [M + 1]$^+$518.05 $t_R$ 1.25 |
| Ex 12-73 | 4-(4-((2-(difluoromethoxy)-6-methylpyridin-3-yl)carbamoyl)-4-(2-isopropylphenyl)piperidin-1-yl)-4-oxobutanoic acid | [M + 1]$^+$504.20 $t_R$ 1.15 |
| Ex 12-74 | ethyl (E)-4-(3-((2-(difluoromethoxy)-6-methylpyridin-3-yl)carbamoyl)-3-(2-isopropylphenyl)azetidin-1-yl)-4-oxobut-2-enoate | [M + 1]$^+$501.99 $t_R$ 1.29 |
| Ex 12-75 | (E)-4-(3-((2-(difluoromethoxy)-6-methylpyridin-3-yl)carbamoyl)-3-(2-isopropylphenyl)azetidin-1-yl)-4-oxobut-2-enoic acid | [M + 1]$^+$474.13 $t_R$ 1.13 |
| Ex 12-76 | ethyl (Z)-4-(3-((2-(difluoromethoxy)-6-methylpyridin-3-yl)carbamoyl)-3-(2-isopropylphenyl)azetidin-1-yl)-4-oxobut-2-enoate | [M + 1]$^+$502.09 $t_R$ 1.24 |
| Ex 12-77 | (Z)-4-(3-((2-(difluoromethoxy)-6-methylpyridin-3-yl)carbamoyl)-3-(2-isopropylphenyl)azetidin-1-yl)-4-oxobut-2-enoic acid | [M + 1]$^+$474.10 $t_R$ 1.17 |
| Ex 12-78 | 4-(3-((2-(difluoromethoxy)-6-methylpyridin-3-yl)carbamoyl)-3-(2-isopropylphenyl)azetidin-1-yl)-2-methyl-4-oxobutanoic acid | [M + 1]$^+$490.05 $t_R$ 1.13 |
| Ex 12-79 | (S)-4-(3-((2-(difluoromethoxy)-6-methylpyridin-3-yl)carbamoyl)-3-(2-isopropylphenyl)azetidin-1-yl)-2-methyl-4-oxobutanoic acid | [M + 1]$^+$490.00 $t_R$ 1.13 |
| Ex 12-80 | (R)-4-(3-((2-(difluoromethoxy)-6-methylpyridin-3-yl)carbamoyl)-3-(2-isopropylphenyl)azetidin-1-yl)-2-methyl-4-oxobutanoic acid | [M + 1]$^+$490.08 $t_R$ 1.13 |
| Ex 12-81 | methyl 4-(3-((2-(difluoromethoxy)-6-methylpyridin-3-yl)carbamoyl)-3-(2-isopropylphenyl)azetidin-1-yl)-2,2-dimethyl-4-oxobutanoate | [M + 1]$^+$518.01 $t_R$ 1.30 |
| Ex 12-82 | 4-(3-((2-(difluoromethoxy)-6-methylpyridin-3-yl)carbamoyl)-3-(2-isopropylphenyl)azetidin-1-yl)-2,2-dimethyl-4-oxobutanoic acid | [M + 1]$^+$504.19 $t_R$ 1.20 |
| Ex 12-83 | 4-(3-((2-(difluoromethoxy)-6-methylpyridin-3-yl)carbamoyl)-3-(2-isopropylphenyl)pyrrolidin-1-yl)-2,2-dimethyl-4-oxobutanoic acid | [M + 1]$^+$518.02 $t_R$ 1.21 |

TABLE 8-continued

Examples 12-63 to 12-114

Examples 12-63 to 12-114 are synthesized using the methodology described for Ex 12-62 starting from Ex 2, Ex 3, Ex 4, Ex 5, Ex 6, Ex7, Ex 8, or Ex 10. Standard coupling reagents can be used such as EDC/HOBt, TBTU, HATU, T3P for example. Carboxylic acid reagents are commercially available or prepared according to literature protocols. If another functional group is present, an additional deprotection step is required such as Boc cleavage of amine under acidic conditions.

| Example | Name | Analytics LCMS-1 |
|---|---|---|
| Ex 12-84 | 4-(3-((2-(difluoromethoxy)pyridin-3-yl)carbamoyl)-3-(2-isopropylphenyl)azetidin-1-yl)-2,2-dimethyl-4-oxobutanoic acid | [M + 1]$^+$490.14 $t_R$ 1.14 |
| Ex 12-85 | methyl 4-(3-((2,6-dimethoxypyridin-3-yl)carbamoyl)-3-(2-isopropylphenyl)azetidin-1-yl)-2,2-dimethyl-4-oxobutanoate | [M + 1]$^+$498.15 $t_R$ 1.28 |
| Ex 12-86 | 4-(3-((2,6-dimethoxypyridin-3-yl)carbamoyl)-3-(2-isopropylphenyl)azetidin-1-yl)-2,2-dimethyl-4-oxobutanoic acid | [M + 1]$^+$484.03 $t_R$ 1.17 |
| Ex 12-87 | 4-(3-((2-(difluoromethoxy)-5-fluoropyridin-3-yl)carbamoyl)-3-(2-isopropylphenyl)azetidin-1-yl)-2,2-dimethyl-4-oxobutanoic acid | [M + 1]$^+$508.02 $t_R$ 1.19 |
| Ex 12-88 | 1-(2-(3-((2-(difluoromethoxy)-6-methylpyridin-3-yl)carbamoyl)-3-(2-isopropylphenyl)azetidin-1-yl)-2-oxoethyl)cyclopropane-1-carboxylic acid | [M + 1]$^+$502.32 $t_R$ 1.15 |
| Ex 12-89 | 1-(2-(3-((2-(difluoromethoxy)-6-methylpyridin-3-yl)carbamoyl)-3-(2-isopropylphenyl)azetidin-1-yl)-2-oxoethyl)cyclobutane-1-carboxylic acid | [M + 1]$^+$516.00 $t_R$ 1.22 |
| Ex 12-90 | (R)-4-(3-((2-(difluoromethoxy)-6-methylpyridin-3-yl)carbamoyl)-3-(2-isopropylphenyl)azetidin-1-yl)-3-methyl-4-oxobutanoic acid | [M + 1]$^+$490.35 $t_R$ 1.13 |
| Ex 12-91 | 4-(3-((2-(difluoromethoxy)-6-methylpyridin-3-yl)carbamoyl)-3-(2-isopropylphenyl)azetidin-1-yl)-3,3-dimethyl-4-oxobutanoic acid | [M + 1]$^+$504.32 $t_R$ 1.18 |
| Ex 12-92 | methyl 3-(3-((2-(difluoromethoxy)-6-methylpyridin-3-yl)carbamoyl)-3-(2-isopropylphenyl)azetidine-1-carbonyl)but-3-enoate | [M + 1]$^+$502.07 $t_R$ 1.24 |
| Ex 12-93 | 3-(3-((2-(difluoromethoxy)-6-methylpyridin-3-yl)carbamoyl)-3-(2-isopropylphenyl)azetidine-1-carbonyl)but-3-enoic acid | [M + 1]$^+$488.11 $t_R$ 1.15 |
| Ex 12-94 | methyl (1S,2R)-2-(3-((2-(difluoromethoxy)-6-methylpyridin-3-yl)carbamoyl)-3-(2-isopropylphenyl)azetidine-1-carbonyl)cyclopropane-1-carboxylate | [M + 1]$^+$502.34 $t_R$ 1.18 |
| Ex 12-95 | (1S,2R)-2-(3-((2-(difluoromethoxy)-6-methylpyridin-3-yl)carbamoyl)-3-(2-isopropylphenyl)azetidine-1-carbonyl)cyclopropane-1-carboxylic acid | [M + 1]$^+$488.08 $t_R$ 1.10 |
| Ex 12-96 | methyl (1R,2S)-2-(3-((2-(difluoromethoxy)-6-methylpyridin-3-yl)carbamoyl)-3-(2-isopropylphenyl)azetidine-1-carbonyl)cyclopropane-1-carboxylate | [M + 1]$^+$502.17 $t_R$ 1.18 |
| Ex 12-97 | (1R,2S)-2-(3-((2-(difluoromethoxy)-6-methylpyridin-3-yl)carbamoyl)-3-(2-isopropylphenyl)azetidine-1-carbonyl)cyclopropane-1-carboxylic acid | [M + 1]$^+$488.02 $t_R$ 1.10 |
| Ex 12-98 | 3-(2-(3-((2-(difluoromethoxy)-6-methylpyridin-3-yl)carbamoyl)-3-(2-isopropylphenyl)azetidin-1-yl)-2-oxoethyl)oxetane-3-carboxylic acid | [M + 1]$^+$518.08 $t_R$ 1.09 |
| Ex 12-99 | 2-(3-(3-((2-(difluoromethoxy)-6-methylpyridin-3-yl)carbamoyl)-3-(2-isopropylphenyl)azetidine-1-carbonyl)oxetan-3-yl)acetic acid | [M + 1]$^+$518.02 $t_R$ 1.09 |
| Ex 12-100 | ethyl (S)-3-amino-4-(3-((2-(difluoromethoxy)-6-methylpyridin-3-yl)carbamoyl)-3-(2-isopropylphenyl)azetidin-1-yl)-4-oxobutanoate | [M + 1]$^+$ 505.19 $t_R$ 0.75 |
| Ex 12-101 | (S)-3-amino-4-(3-((2-(difluoromethoxy)-6-methylpyridin-3-yl)carbamoyl)-3-(2-isopropylphenyl)azetidin-1-yl)-4-oxobutanoic acid | [M + 1]$^+$ 491.06 $t_R$ 1.19 |
| Ex 12-102 | 5-(3-((2-(difluoromethoxy)-6-methylpyridin-3-yl)carbamoyl)-3-(2-isopropylphenyl)azetidin-1-yl)-5-oxopentanoic acid | [M + 1]$^+$490.05 $t_R$ 1.10 |
| Ex 12-103 | 5-(3-((2-(difluoromethoxy)-6-methylpyridin-3-yl)carbamoyl)-3-(2-isopropylphenyl)azetidin-1-yl)-2,2-dimethyl-5-oxopentanoic acid | [M + 1]$^+$518.07 $t_R$ 1.18 |
| Ex 12-104 | ethyl (R)-3-acetoxy-5-(3-((2-(difluoromethoxy)-6-methylpyridin-3-yl)carbamoyl)-3-(2-isopropylphenyl)azetidin-1-yl)-5-oxopentanoate | [M + 1]$^+$576.38 $t_R$ 1.26 |
| Ex 12-105 | (R)-5-(3-((2-(difluoromethoxy)-6-methylpyridin-3-yl)carbamoyl)-3-(2-isopropylphenyl)azetidin-1-yl)-3-hydroxy-5-oxopentanoic acid | [M + 1]$^+$506.09 $t_R$ 1.05 |
| Ex 12-106 | benzyl 2-(2-(2-(3-((2-(difluoromethoxy)-6-methylpyridin-3-yl)carbamoyl)-3-(2-isopropylphenyl)azetidin-1-yl)-2-oxoethoxy)ethoxy)acetate | [M + 1]$^+$626.09 $t_R$ 1.32 |
| Ex 12-107 | 2-(2-(2-(3-((2-(difluoromethoxy)-6-methylpyridin-3-yl)carbamoyl)-3-(2-isopropylphenyl)azetidin-1-yl)-2-oxoethoxy)ethoxy)acetic acid | [M + 1]$^+$536.00 $t_R$ 1.08 |
| Ex 12-108 | 2-3-((2-(difluoromethoxy)-6-methylpyridin-3-yl)carbamoyl)-3-(2-isopropylphenyl)azetidine-1-carbonyl)bicyclo[1.1.1]pentane-1-carboxylic acid | [M + 1]$^+$514.19 $t_R$ 1.13 |
| Ex 12-109 | benzyl 2-(3-(3-((2-(difluoromethoxy)-6-methylpyridin-3-yl)carbamoyl)-3-(2-isopropylphenyl)azetidin-1-yl)-3-oxopropoxy)acetate | [M + 1]$^+$596.01 $t_R$ 1.33 |
| Ex 12-110 | 2-(3-(3-((2-(difluoromethoxy)-6-methylpyridin-3-yl)carbamoyl)-3-(2-isopropylphenyl)azetidin-1-yl)-3-oxopropoxy)acetic acid | [M + 1]$^+$506.35 $t_R$ 1.11 |
| Ex 12-111 | ethyl 4-(3-((2-(difluoromethoxy)-6-methylpyridin-3-yl)carbamoyl)-3-(2-isopropylphenyl)azetidin-1-yl)-2,2-difluoro-4-oxobutanoate | [M + 1]$^+$539.98 $t_R$ 1.32 |
| Ex 12-112 | 4-(3-((2-(difluoromethoxy)-6-methylpyridin-3-yl)carbamoyl)-3-(2-isopropylphenyl)azetidin-1-yl)-2,2-difluoro-4-oxobutanoic acid | [M + 1]$^+$512.05 $t_R$ 1.30 |
| Ex 12-113 | ethyl 3-(3-((2-(difluoromethoxy)-6-methylpyridin-3-yl)carbamoyl)-3-(2-isopropylphenyl)azetidine-1-carbonyl)azetidine-3-carboxylate | [M + 1]$^+$531.11 $t_R$ 0.81 |
| Ex 12-114 | 3-(3-((2-(difluoromethoxy)-6-methylpyridin-3-yl)carbamoyl)-3-(2-isopropylphenyl)azetidine-1-carbonyl)azetidine-3-carboxylic acid | [M + 1]$^+$503.16 $t_R$ 0.83 |

Example 12-115: 4-(3-((2-(difluoromethoxy)-6-methylpyridin-3-yl)carbamoyl)-3-(2-isopropylphenyl)azetidin-1-yl)-3,3-difluoro-4-oxobutanoic acid 4-(3-((2-(Difluoromethoxy)-6-methylpyridin-3-yl)carbamoyl)-3-(2-isopropylphenyl)azetidin-1-yl)-3,3-difluoro-4-oxobutanoic acid Ex 12-115 is prepared from Ex 3 hydrochloride (50 mg, 0.12 mmol) and 2,2-difluorosuccinic acid (23 mg, 0.15 mmol) following the amide coupling methodology described in Step 1 for Ex 12-1: white solid, 31 mg, 50% yield. LCMS-1: $t_R$=1.21 min, [M+1]$^+$511.97. $^1$H NMR (500 MHz, DMSO-D6) δ: 12.97 (s br, 1 H), 8.36 (s, 1 H), 7.99 (d, J=8.0 Hz, 1 H), 7.57 (d, J=7.4 Hz, 1 H), 7.52 (t, J=72.5 Hz, 1 H), 7.44 (m, 1 H), 7.42-7.39 (m, 1 H), 7.33-7.30 (m, 1 H), 7.12 (d, J=8.0 Hz, 1 H), 5.11 (d, J=9.3 Hz, 1 H), 4.84 (d, J=9.4 Hz, 1 H), 4.72 (d, J=10.2 Hz, 1 H), 4.39 (d, J=10.2 Hz, 1 H), 3.32-3.18 (m, 2 H), 2.38 (s, 3 H), 1.12 (t, J=6.4 Hz, 6 H).

Example 12-116: (R)-4-(3-((2-(difluoromethoxy)-6-methylpyridin-3-yl)carbamoyl)-3-(2-isopropylphenyl)azetidin-1-yl)-2-hydroxy-2-methyl-4-oxobutanoic acid (R)-4-(3-((2-(difluoromethoxy)-6-methylpyridin-3-yl)carbamoyl)-3-(2-isopropylphenyl)azetidin-1-yl)-2-hydroxy-2-methyl-4-oxobutanoic acid Ex 12-116 is prepared from Ex 3 hydrochloride (50 mg, 0.12 mmol) and (R)-(−)-citramalic acid (22 mg, 0.15 mmol) following the amide coupling methodology described in Step 1 for Ex 12-1: white solid, 15 mg, 24% yield. LCMS-1: $t_R$=1.10 min, [M+1]$^+$506.03.

Example 12-117: (S)-4-(3-((2-(difluoromethoxy)-6-methylpyridin-3-yl)carbamoyl)-3-(2-isopropylphenyl)azetidin-1-yl)-2-hydroxy-2-methyl-4-oxobutanoic acid (S)-4-(3-((2-(difluoromethoxy)-6-methylpyridin-3-yl)carbamoyl)-3-(2-isopropylphenyl)azetidin-1-yl)-2-hydroxy-2-methyl-4-oxobutanoic acid Ex 12-117 is prepared from Ex 3 hydrochloride (50 mg, 0.12 mmol) and (S)-(−)-citramalic acid (22 mg, 0.15 mmol) following the amide coupling methodology described in Step 1 for Ex 12-1: colorless oil, 18 mg, 29% yield. LCMS-1: $t_R$=1.11 min, [M+1]$^+$506.38.

Example 12-118: (2R,3R)-4-(3-((2-(difluoromethoxy)-6-methylpyridin-3-yl)carbamoyl)-3-(2-isopropylphenyl)azetidin-1-yl)-2,3-dihydroxy-4-oxobutanoic acid To a solution of Ex 3 (20 mg, 0.05 mmol) in DCM (2 mL) is added diacetyl-L-tartaric anhydride (13 mg, 0.06 mmol) followed by DIPEA (18 uL, 0.10 mmol). The reaction mixture is stirred at r.t. for 15 min and is then concentrated. The residue is dissolved in MeCN (1 mL) and treated with NaOMe. The reaction mixture is stirred for 30 min (reaction monitored by LCMS) and is then quenched with ammonium chloride, is concentrated and purified by prep. HPLC (Prep-HPLC-1 conditions) to give the title compound Ex 12-118 as an oil (15 mg, 56% yield). LCMS-1: $t_R$=1.03 min, [M+1]$^+$ 508.11.

Example 12-119: N-(2-(difluoromethoxy)-6-methylpyridin-3-yl)-3-(2-isopropylphenyl)-1-(4-(methylsulfonamido)-4-oxobutanoyl)azetidine-3-carboxamide N-(2-(difluoromethoxy)-6-methylpyridin-3-yl)-3-(2-isopropylphenyl)-1-(4-(methylsulfonamido)-4-oxobutanoyl)azetidine-3-carboxamide Ex 12-119 is prepared from Ex 12-71 (90 mg, 0.189 mmol) and methansulfonamide (18 mg, 0.189 mmol) following the amide coupling methodology described in Step 1 for Ex 12-1:4 mg, 4% yield. LCMS-1: $t_R$=1.11 min, [M+1]$^+$553.09.

Example 12-120: N-(2-(difluoromethoxy)-6-methylpyridin-3-yl)-3-(2-isopropylphenyl)-1-(5,5,5-trifluoro-4-hydroxypentanoyl)azetidine-3-carboxamide To a solution of Ex 12-11 (10 mg, 0.02 mmol) in MeOH (0.5 mL) is added NaBH$_4$ (10 mg, 0.26 mmol). The reaction mixture is stirred for 2 h, is then quenched with water and extracted with DCM (2×10 mL). The combined extracts are dried over MgSO$_4$, filtered and evaporated. The residue is then purified by prep. HPLC (Prep-HPLC-2 conditions) to give Ex 12-120 (1.5 mg, 15% yield). LCMS-1: $t_R$ =1.22 min, [M+1]$^+$530.21.

Example 12-121: 2-(2-(3-(3-((2-(difluoromethoxy)-6-methylpyridin-3-yl)carbamoyl)-3-(2-isopropylphenyl)azetidin-1-yl)-3-oxopropoxy)ethoxy)acetic acid To a solution of Ex 12-51 (32 mg, 0.06 mmol) in MeCN (5 mL) is sequentially added a buffer solution of NaH$_2$PO$_4$ (0.1mol/L, 0.5 mL), 2,2,6,6-tetramethylpiperidin-1-oxyl radical (TEMPO, 1 mg, 0.006 mmol), aq. solution of sodium chlorite (80 g/L, 0.5 mL) and sodium hypochlorite (50 uL). The reaction mixture is stirred at 50° C. overnight. The mixture is then quenched with saturated sodium sulphite (2 mL) and volatiles are evaporated. The residue is dissolved in 3 mL of DMF/MeCN (1:1) and is purified by prep. HPLC (Prep-HPLC-3 conditions) to give the title compound Ex 12-121 as a beige wax (14.7 mg, 45% yield). LCMS-1: $t_R$=1.08 min, [M+1]$^+$550.09.

Example 12-122: 4-(2-(3-(3-((2-(difluoromethoxy)-6-methylpyridin-3-yl)carbamoyl)-3-(2-isopropylphenyl)azetidin-1-yl)-2-oxoethyl)tetrahydro-2H-pyran-4-carboxylic acid To a solution of Ex 3 hydrochloride (50 mg, 0.121 mmol) in DCM (2 mL), TEA (34 uL, 0.243 mmol) is added, followed by commercially available 2,8-dioxaspiro[4.5]decane-1,3-dione dissolved in DCM (1 mL). The reaction mixture is stirred at r.t. for 1 h and is then evaporated. Crude compound is purified by prep. HPLC (Prep-HPLC 2 conditions) to give the title compound Ex 12-122 as a white solid (41 mg, 62% yield). LCMS-1: $t_R$=1.13 min, [M+1]$^+$546.00.

Example 12-123: 3-(2-(3-(3-((2-(difluoromethoxy)-6-methylpyridin-3-yl)carbamoyl)-3-(2-isopropylphenyl)azetidin-1-yl)-2-oxoethyl)tetrahydrofuran-3-carboxylic acid 3-(2-(3-((2-(difluoromethoxy)-6-methylpyridin-3-yl)carbamoyl)-3-(2-isopropylphenyl)azetidin-1-yl)-2-oxoethyl)tetrahydrofuran-3-carboxylic acid Ex 12-123 (12 mg, white solid) is prepared from Ex 3 and commercially available 2,7-dioxaspiro[4.4]nonane-1,3-dione following the methodology described for Ex 12-122. LCMS-1: $t^R$=1.10 min, [M+1]$^+$531.97.

Example 12-124: 4-(2-(3-(3-((2-(difluoromethoxy)-6-methylpyridin-3-yl)carbamoyl)-3-(2-isopropylphenyl)azetidin-1-yl)-2-oxoethyl)-1-methylpiperidine-4-carboxylic acid 4-(2-(3-((2-(difluoromethoxy)-6-methylpyridin-3-yl)carbamoyl)-3-(2-isopropylphenyl)azetidin-1-yl)-2-oxoethyl)-

1-methylpiperidine-4-carboxylic acid Ex 12-124 (43 mg, white solid) is prepared from Ex 3 and commercially available 8-methyl-2-oxa-8-azaspiro[4.5]decane-1,3-dione hydrochloride following the methodology described for Ex 12-122. LCMS-1: $t_R$=0.77 min, [M+1]$^+$559.10.

Example 12-125: N-(2-(difluoromethoxy)-6-methylpyridin-3-yl)-3-(2-isopropylphenyl)-1-(3-(methoxyamino)-3-oxopropanoyl)azetidine-3-carboxamide To a solution of Ex 12-63 (60 mg, 0.13 mmol) in DCM (4 mL), O-methylhydroxylamine (16 mg, 0.19 mmol), DIPEA (67 uL, 0.39 mmol) and T3P in DCM (50%, 0.16 mmol) are added. The mixture is stirred at r.t. for 18 h, is concentrated in vacuo. The residue is purified by prep. HPLC (Prep-HPLC-1 conditions) to give the title compound Ex 12-125 (48 mg, 75% yield) as a white solid; LCMS-1: $t_R$=1.05 min, [M+1]$^+$491.13.

Example 12-126: N-(2-(difluoromethoxy)-6-methylpyridin-3-yl)-1-(2-(2,4-dioxoimidazolidin-1-yl)acetyl)-3-(2-isopropylphenyl)azetidine-3-carboxamide N-(2-(difluoromethoxy)-6-methylpyridin-3-yl)-1-(2-(2,4-dioxoimidazolidin-1-yl)acetyl)-3-(2-isopropylphenyl)azetidine-3-carboxamide Ex 12-126 (7 mg, white solid) is prepared from Ex 3 and 2-(2,4-dioxoimidazolidin-1-yl)acetic acid following the methodology described for Ex 12-61. LCMS-1: $t_R$=1.06 min, [M+1]$^+$515.99; $^1$H NMR (500 MHz, DMSO) δ: 10.92 (s, 1 H), 8.32 (s, 1 H), 8.00 (d, J=8.0 Hz, 1 H), 7.55 (d, J=7.4 Hz, 1 H), 7.52 (t, J=72.5 Hz, 1 H), 7.44 (dd, J$_1$=1.3 Hz, J$_2$=7.8 Hz, 1 H), 7.40 (t, J=7.5 Hz, 1 _H), 7.32 (m, 1 H), 7.12 (d, J=8.1 Hz, 1 H), 4.89 (d, J=8.5 Hz, 1 H), 4.65 (d, J=8.5 Hz, 1 H), 4.58 (d, J=9.6 Hz, 1 H), 4.36 (d, J=10.1 Hz, 1 H), 4.05 (d, J=17.1 Hz, 1 H), 4.02 (d, J=17.1 Hz, 1 H), 3.90 (s, 2 H), 2.38 (s, 3 H), 1.13 (d, J=6.7 Hz, 3 H), 1.10 (d, J=6.7 Hz, 3 H).

Example 12-127: N-(2-(difluoromethoxy)-6-methylpyridin-3-yl)-1-(2-(2,5-dioxoimidazolidin-1-yl)acetyl)-3-(2-isopropylphenyl)azetidine-3-carboxamide N-(2-(difluoromethoxy)-6-methylpyridin-3-yl)-1-(2-(2,5-dioxoimidazolidin-1-yl)acetyl)-3-(2-isopropylphenyl)azetidine-3-carboxamide Ex 12-127 (22.5 mg, white solid) is prepared from Ex 3 and (2,5-dioxoimidazolidin-1-yl)acetic acid following the methodology described for Ex 5 with T3P as coupling reagent. LCMS-1: $t_R$=1.07 min, [M+1]$^+$515.96; $^1$H NMR (500 MHz, CDCl$_3$) δ: 8.57 (d, J=8.1 Hz, 1 H), 7.51-7.46 (m, 2 H), 7.42-7.39 (m, 1 H), 7.34 (dd, J$_1$=0.9 Hz, J$_2$=7.9 Hz, 1 H), 7.27 (t, J=72.5 Hz, 1 H), 7.24 (s, 1 H), 6.96 (d, J=8.2 Hz, 1 H), 5.46 (s, 1 H), 5.08 (s br, 1 H), 4.70 (s br, 1 H), 4.61 (s br, 2 H), 4.30 (d, J=16.2 Hz, 1 H), 4.13-4.09 (m, 3 H), 2.42-2.37 (m, 4 H), 1.20 (d, J=6.6 Hz, 3 H), 1.13 (d, J=6.5 Hz, 3 H).

Example 12-128: N-(2-(difluoromethoxy)-6-methylpyridin-3-yl)-3-(2-isopropylphenyl)-1-(sulfamoylglycyl)azetidine-3-carboxamide N-(2-(difluoromethoxy)-6-methylpyridin-3-yl)-3-(2-isopropylphenyl)-1-(sulfamoylglycyl)azetidine-3-carboxamide Ex 12-128 (25 mg, white solid) is prepared from Ex 3 and 2-(sulfamoylamino)acetic acid following the methodology described for Ex 5 with T3P as coupling reagent. LCMS-1: $t_R$=1.07 min, [M+1]$^+$512.30; $^1$H NMR (400 MHz, CDCl$_3$) δ: 8.52 (d, J=8.1 Hz, 1 H), 7.56-7.46 (m, 2 H), 7.41 (td, J=2.0 Hz and J=7.7 Hz, 1 H), 7.33-7.28 (m, 2 H), 7.26 (t, J=72.8 Hz, $^1$H), 6.95 (d, J=8.1 Hz, 1 H), 5.11-4.99 (s br, 1 H), 4.84-4.67 (s br, 1 H), 4.67-4.46 (s br, 2 H), 3.97 (d, J=16.4 Hz, 1 H), 3.75 (d, J=16.4 Hz, 1 H), 2.40 (s, 3 H), 2.38-2.33 (m, 1 H), 1.20 (d, J=6.5 Hz, 3 H), 1.14 (d, J=6.5 Hz, 3 H).

Example 12-129: N-(2-(difluoromethoxy)-6-methylpyridin-3-yl)-1-(1,1-dioxidothietane-3-carbonyl)-3-(2-isopropylphenyl)azetidine-3-carboxamide N-(2-(difluoromethoxy)-6-methylpyridin-3-yl)-1-(1,1-dioxidothietane-3-carbonyl)-3-(2-isopropylphenyl)azetidine-3-carboxamide Ex 12-129 (21 mg, white solid) is prepared from Ex 3 and thietane-3-carboxylic acid 1,1-dioxide following the methodology described for Ex 5 with EDC/HOBt as coupling reagents. LCMS-1: $t^R$=1.15 min, [M+1]$^+$508.32.

Example 12-130: N-(2-(difluoromethoxy)-6-methylpyridin-3-yl)-1-(3-(N-hydroxyacetamido)propanoyl)-3-(2-isopropylphenyl)azetidine-3-carboxamide Step 1. To a solution of Ex 3 hydrochloride (300 mg, 0.73 mmol) and DIPEA (822 uL, 4.79 mmol) in THF (30 mL) at 0° C. is added acryloyl chloride (89 uL, 1.09 mmol) dropwise. The reaction mixture is stirred at 0° C. for 30 min (reaction monitored by LCMS), is then diluted with Et$_2$O, washed with NaHCO$_3$ (10 mL), dried over MgSO$_4$, filtered and evaporated to give the crude acrylamide intermediate that is purified by prep. HPLC (Prep-HPLC-1 conditions) to afford a colorless glassy compound (259 mg, 83% yield). $^1$H NMR (500 MHz, CDCl$_3$) δ: 8.55 (d, J=8.1 Hz, 1 H), 7.50-7.44 (m, 2 H), 7.40-7.38 (m, 1 H), 7.37-7.34 (m, 1 H), 7.28 (t, J=72.6 Hz), 7.25 (s, 1 H), 6.94 (d, J=8.2 Hz, 1 H), 6.38 (dd, J$_1$=1.8 Hz, J$_2$=17.0 Hz, 1 H), 6.28 (dd, J$_1$=10.3 Hz, J$_2$=17.0 Hz, 1 H), 5.74 (dd, J$_1$=1.8 Hz, J$_2$=10.3 Hz, 1 H), 5.13-5.04 (s br, 1 H), 4.97-4.85 (br s, 1 H), 4.79-4.75 (s br, 1 H), 4.59-4.48 (s br, 1 H), 2.46-2.40 (m, 1 H), 2.38 (s, 3 H), 1.19 (d, J=6.6 Hz, 3 H), 1.14 (d, J=6.5 Hz, 3 H).

Step 2. To a solution of acrylamide intermediate (250 mg, 0.58 mmol) and tert-butyl N-(benzyloxy)carbamate (569 mg, 1.16 mmol) in DMF is added CS$_2$CO$_3$ (569 mg, 1.75 mmol). The reaction mixture is stirred at 65° C. for 4 h (reaction monitored by LCMS), is then diluted with EtOAc (50 mL), is washed with water (20 mL) followed by brine (20 mL) and is dried over MgSO$_4$. The organic solution is filtered, evaporated and purified by prep. HPLC (Prep-HPLC-1 conditions) to give tert-butyl (benzyloxy)(3-(3-((2-(difluoromethoxy)-6-methylpyridin-3-yl)carbamoyl)-3-(2-isopropylphenyl)azetidin-1-yl)-3-oxopropyl)carbamate as a colorless wax (289 mg, 76% yield). $^1$H NMR (500 MHz, CDCl$_3$) δ: 8.54 (d, J=8.1 Hz, 1 H), 7.49-7.43 (m, 2 H), 7.42-7.36 (m, 3 H), 7.34-7.30 (m, 3 H), 7.28 (s, 1 H), 7.26 (t, J=72.6 Hz, 1 H), 7.22 (s, 1 H), 6.94 (d, J=8.2 Hz, 1 H), 4.95-4.79 (m, 3 H), 4.71-4.60 (m, 1 H), 4.54-4.30 (m, 2 H), 3.80 (t, J=7.3 Hz, 2 H), 2.47-2.42 (m, 2 H), 2.40-2.34 (m, 4 H), 1.50 (s, 9 H), 1.15 (d, J=6.6 Hz, 3 H), 1.12 (d, J=6.6 Hz, 3 H).

Step 3. tert-butyl (benzyloxy)(3-(3-((2-(difluoromethoxy)-6-methylpyridin-3-yl)carbamoyl)-3-(2-isopropylphenyl)azetidin-1-yl)-3-oxopropyl)carbamate (285 mg, 0.44 mmol) is subjected to the Boc deprotection conditions described for Ex 4 to give after prep. HPLC (Prep-HPLC-3 conditions) Ex 12-130 as a white solid (231 mg, 96% yield).

LCMS-1: $t_R$=1.30 min, [M+1]$^+$553.40. $^1$H NMR (500 MHz, CDCl$_3$) δ: 8.55 (d, J=8.1 Hz, 1 H), 7.50-7.45 (m, 2 H), 7.39 (td, J$_1$=1.9 Hz, J$_2$=7.8 Hz, 1 H), 7.36-7.28 (m, 6 H), 7.27 (t, J=72.9 Hz, $^1$H), 7.24 (s, 1 H), 6.94 (d, J=8.2 Hz, 1 H), 5.98 (s br, 1 H), 5.03-4.88 (m, 1 H), 4.74-4.61 (m, 3 H), 4.58-4.40 (m, 2 H), 3.31-3.23 (m, 2 H), 2.50-2.41 (m, 2 H), 2.40-2.37 (m, 4 H), 1.17 (d, J=6.6 Hz, 3 H), 1.14 (d, J=6.6 Hz, 3 H).

Example 12-131: 1-(3-(N-(benzyloxy)acetamido) propanoyl)-N-(2-(difluoromethoxy)-6-methylpyridin-3-yl)-3-(2-isopropylphenyl)azetidine-3-carboxamide and Example 12-132: N-(2-(difluoromethoxy)-6-methylpyridin-3-yl)-1-(3-(N-hydroxyacetamido)propanoyl)-3-(2-isopropylphenyl) azetidine-3-carboxamide Step 1. To a solution of N-(2-(difluoromethoxy)-6-methylpyridin-3-yl)-1-(3-(N-hydroxyacetamido)propanoyl)-3-(2-isopropylphenyl)azetidine-3-carboxamide Ex 12-130 (225 mg, 0.41 mmol) in DCM (7 mL), DIPEA (105 uL, 0.61 mmol) and Ac$_2$O (58 uL, 0.61 mmol) are added successively. The solution is stirred at r.t. for 1.5 h (reaction monitored by LCMS), is then concentrated and purified by prep. HPLC (Prep-HPLC-1 conditions) to afford 1-(3-(N-(benzyloxy)acetamido)propanoyl)-N-(2-(difluoromethoxy)-6-methylpyridin-3-yl)-3-(2-isopropylphenyl)azetidine-3-carboxamide Ex 12-131 as a white solid (228 mg, 94% yield). LCMS-1: $t_R$=1.29 min, [M+1]$^+$595.26.

Step 2. 1-(3-(N-(benzyloxy)acetamido)propanoyl)-N-(2-(difluoromethoxy)-6-methylpyridin-3-yl)-3-(2-isopropylphenyl)azetidine-3-carboxamide (220 mg, 0.37 mmol) is subjected to the hydrogenation conditions described for I-1.A to give the title compound Ex 12-132 as a white solid (114 mg, 60% yield). LCMS-1: $t_R$=1.08 min, [M+1]$^+$505.39; $^1$H NMR (500 MHz, CDCl$_3$) δ: 8.54 (d, J=8.1 Hz, 1 H), 7.52-7.47 (m, 2 H), 7.43-7.39 (m, 1 H), 7.32 (d, J=7.7 Hz, 1 H), 7.28 (m, 1 H), 7.27 (t, J=72.5 Hz, 1 H), 6.95 (d, J=8.1 Hz, 1 H), 5-05-4.85 (s br, 1 H), 4.83-4.65 (s br, 1 H), 4.63-4.44 (s br, 2 H), 4.04-3.96 (m, 1 H), 3.94-3.88 (m, 1 H), 2.71-2.64 (m, 1 H), 2.61-2.54 (m, 1 H), 2.42-2.34 (m, 4 H), 2.15 (s, 3 H), 1.19 (d, J=6.5 Hz, 3 H), 1.15 (d, J=6.1 Hz, 3 H).

Example 12-133: N-(2-(difluoromethoxy)-6-methylpyridin-3-yl)-1-(3-(hydroxyamino)propanoyl)-3-(2-isopropylphenyl)azetidine-3-carboxamide To a stirred solution of tert-butyl N-(benzyloxy)carbamate (45 mg, 0.20 mmol) in anhydrous DMF (5 ml), NaH (60 wt %, 9 mg, 0.22 mol) is added and the resulting mixture is stirred at r.t. for 30 min. 1-(2-Bromoacetyl)-N-(2-(difluoromethoxy)-6-methylpyridin-3-yl)-3-(2-isopropylphenyl)-azetidine-3-carboxamide (100 mg, 0.20 mmol), prepared from Ex 3 and 2-bromoacetyl bromide according to Step 1 of Ex 12-52, is added and the reaction mixture is stirred at r.t. for 18 h. The reaction is then quenched with water (10 mL) and is extracted with hexane (50 mL and 2×10 mL). The combined extracts are dried over MgSO$_4$, filtered and evaporated. The residue is purified by prep. HPLC (Prep-HPLC-1 conditions) to give the title compound Ex 12-133 as beige solid (65 mg, 51% yield). LCMS-1: $t_R$=1.45 min, [M+1]$^+$639.05.

Example 12-134: 1-((benzyloxy)glycyl)-N-(2-(difluoromethoxy)-6-methylpyridin-3-yl)-3-(2-isopropylphenyl)azetidine-3-carboxamide Ex 12-133 (60 mg, 0.09 mmol) is subjected to the Boc deprotection conditions described for Ex 4 to give after prep. HPLC (Prep-HPLC-3 conditions) Ex 12-134 as a beige solid (30 mg, 59% yield). LCMS-1: $t_R$=1.31 min, [M+1]$^+$539.49.

Example 12-135: 1-(N-acetyl-N-(benzyloxy)glycyl)-N-(2-(difluoromethoxy)-6-methylpyridin-3-yl)-3-(2-isopropylphenyl)azetidine-3-carboxamide and
Example 12-136: 1-(N-acetyl-N-hydroxyglycyl)-N-(2-(difluoromethoxy)-6-methylpyridin-3-yl)-3-(2-isopropylphenyl)azetidine-3-carboxamide Examples Ex 12-135 and Ex 12-136 are prepared from Ex 12-134 according to the methodology described for Ex 12-131 and Ex 12-132.

Ex 12-135: beige solid. LCMS-1: $t_R$=1.29 min, [M+1]$^+$ 581.58.

Ex 12-136: white solid. LCMS-1: $t_R$=1.07 min, [M+1]$^+$ 491.42; $^1$H NMR (400 MHz, CDCl$_3$) δ: 8.54 (d, J=8.1 Hz, 1 H), 8.44-8.05 (s br, 1 H), 7.50-7.45 (m, 2 H), 7.40 (m, 1 H), 7.31 (d, J=7.7 Hz, 1 H), 7.28 (t, J=65.3 Hz, 1 H), 7.26 (s, 1 H), 6.95 (d, J=8.2 Hz, 1 H), 4.98 (s br, 1 H), 4.73 (s br, 1 H), 4.58-4.48 (m, 3 H), 4.36 (d, J=16.7 Hz, 1 H), 2.39 (s, 3 H), 2.36 (m, 1 H), 2.23 (s, 3 H), 1.19 (d, J=6.6 Hz, 3 H), 1.14 (d, J=6.6 Hz, 3 H).

Example 12-137: 1-(2-(1-acetylpiperidin-4-yl) acetyl)-N-(2-(difluoromethoxy)-6-methylpyridin-3-yl)-3-(2-isopropylphenyl)azetidine-3-carboxamide 1-(2-(1-acetylpiperidin-4-yl)acetyl)-N-(2-(difluoromethoxy)-6-methylpyridin-3-yl)-3-(2-isopropylphenyl) azetidine-3-carboxamide Ex 12-137 (11 mg, colorless oil) is prepared from Ex 3 and commercially available 1-acetyl-4-piperdine acetic acid following the methodology described for Ex 5 with EDC/HOBt as coupling reagents. LCMS-1: $t_R$=1.15 min, [M+1]$^+$543.06.

Example 12-138: N-(2-(difluoromethoxy)-6-methylpyridin-3-yl)-3-(2-isopropylphenyl)-1-(2-(piperidin-4-yl)acetyl)azetidine-3-carboxamide N-(2-(difluoromethoxy)-6-methylpyridin-3-yl)-3-(2-isopropylphenyl)-1-(2-(piperidin-4-yl)acetyl)azetidine-3-carboxamide Ex 12-138 (36 mg, colorless oil) is prepared from Ex 3 and commercially available 2-(1-(t-butoxycarbonyl) piperidin-4-yl)acetic acid following the coupling methodology described for Ex 5 and a Boc deprotection with HCl in dioxane. LCMS-1: $t_R$=0.82 min, [M+1]$^+$501.49.

Example 12-139: N-(2-(difluoromethoxy)-6-methylpyridin-3-yl)-3-(2-isopropylphenyl)-1-(2-(1-(2-methoxyethyl)piperidin-4-yl)acetyl)azetidine-3-carboxamide N-(2-(difluoromethoxy)-6-methylpyridin-3-yl)-1-(2-(1-(2-hydroxyethyl)piperidin-4-yl)acetyl)-3-(2-isopropylphenyl)azetidine-3-carboxamide Ex 12-139 (16 mg, colorless oil) is prepared from Ex 3 and commercially available 2-bromoethyl methyl ether following the coupling methodology described for Ex 11-67. LCMS-1: $t_R$=0.84 min, [M+1]$^+$559.12.

Example 12-140: N-(2-(difluoromethoxy)-6-methylpyridin-3-yl)-1-(2-(1-(2-hydroxyethyl)piperidin-4-yl)acetyl)-3-(2-isopropylphenyl)azetidine-3-carboxamide N-(2-(difluoromethoxy)-6-methylpyridin-3-yl)-1-(2-(1-(2-hydroxyethyl)piperidin-4-yl)acetyl)-3-(2-isopropylphenyl)azetidine-3-carboxamide Ex 12-140 (16 mg, colorless oil) is prepared from Ex 3 and commercially available 2-bromoethanol following the coupling methodology described for Ex 11-67 LCMS-1: $t_R$=0.81 min, [M+1]$^+$ 454.29

Example 12-141: N-(2-(difluoromethoxy)-6-methylpyridin-3-yl)-1-(2-(1-(2-fluoroethyl)piperidin-4-yl)acetyl)-3-(2-isopropylphenyl)azetidine-3-carboxamide To a suspension of N-(2-(difluoromethoxy)-6-methylpyridin-3-yl)-3-(2-isopropylphenyl)-1-(2-(piperidin-4-yl)acetyl)azetidine-3-carboxamide Ex 12-138 (34 mg, 0.06 mmol), 1-fluoro-2-iodomethane (22 mg, 0.13 mmol) and Bu$_4$NF (4 mg, 0.01 mmol) in acetone (1 mL) is added K$_2$CO$_3$ (43.7 mg, 0.32 mmol), The reaction mixture is stirred at rt under nitrogen atmosphere for 16 h. Two other portions of 1-fluoro-2-iodomethane (22 mg, 0.13 mmol) are added after 2 h and 4 h to get full conversion. The mixture is evaporated and the residue is partitioned between EtOAc and water. The organic phase is collected, dried over MgSO$_4$, filtered, and concentrated. The crude product is purified by prep-HPLC (Prep-HPLC-2 conditions) to afford N-(2-(difluoromethoxy)-6-methylpyridin-3-yl)-1-(2-(1-(2-fluoroethyl)piperidin-4-yl)acetyl)-3-(2-isopropylphenyl)azetidine-3-carboxamide Ex 12-141 as a colorless oil (29 g, 84% yield). LCMS-1: $t_R$=0.83 min, [M+1]$^+$547.03.

Example 12-142: N-(2-(3-((2-(difluoromethoxy)-6-methylpyridin-3-yl)carbamoyl)-3-(2-isopropylphenyl)azetidin-1-yl)-2-oxoethyl)-N-methylglycine Example 12-142 is prepared according to the methodology described for Ex 12-52 using bromoacetyl bromide, an amino carboxylic ester (sacrosine methyl ester) and Ex 3. Yellow oil. LCMS-1: $t_R$=0.93 min, [M+1]$^+$505.30.

Example 13-1: 2-((3-((2-(difluoromethoxy)-6-methylpyridin-3-yl)carbamoyl)-3-(2-isopropylphenyl)azetidin-1-yl)sulfonyl)acetic acid Step 1. To a solution Ex 3 (90 mg, 0.239 mmol) and TEA (100 uL, 0.73 mmol, 3 eq.) in DCM (5 mL) is added chlorosulfonyl acetic acid ethyl ester (44.6 mg, 0.239 mmol) dropwise. The reaction mixture is stirred at r.t. overnight and is then concentrated. The residue is purified by prep. HPLC (Prep-HPLC-2 conditions) to give ethyl 2-((3-((2-(difluoromethoxy)-6-methylpyridin-3-yl)carbamoyl)-3-(2-isopropylphenyl)azetidin-1-yl)sulfonyl)acetate (43 mg, 34% yield). LCMS-2: $t_R$=1.16 min, [M+1]$^+$526.20.

Step 2. A solution of ethyl 2-((3-((2-(difluoromethoxy)-6-methylpyridin-3-yl)carbamoyl)-3-(2-isopropylphenyl)azetidin-1-yl)sulfonyl)acetate (43 mg, 0.082 mmol) in EtOH/THF (1:1, 1 mL) is treated with 2N LiOH aq. (85 mL, 170 mmol). The reaction mixture is stirred at r.t. for 2 h and are then concentrated. The residue is dissolved in water. The resulting solution is acidified to pH 1 with 1N HCl aq. solution and is then extracted with EtOAc (2×10 mL). The combined extracts are dried over MgSO$_4$, filtered and evaporated to give Ex 13-1 (41 mg, 100% yield). LCMS-1: $t_R$=1.19 min, [M+1]$^+$498.16; $^1$H NMR (400 MHz, CDCl$_3$) δ: 8.55 (d, J=8.1 Hz, 1 H), 7.53-7.43 (m, 2 H), 7.42-7.37 (m, 1 H), 7.36 (s, 1 H), 7.30-7.23 (m, 2 H), 6.95 (d, J=8.1 Hz, 1 H), 5.32 (s, 2 H), 4.81-4.58 (m, 2 H), 4.25 (s, 2 H), 2.40 (s, 3 H), 2.38-2.31 (m, 1 H), 1.16 (d, J=6.6 Hz, 6 H).

TABLE 9

Examples 13-2 to 13-27
Examples 13-2 to 13-27 are synthesized using the methodology described for Ex 13-1 starting from Ex 3, Ex 4 or Ex 7. In case of benzylester, hydrogenation is performed as second step to obtain the corresponding carboxylic acid.

| Example | Name | Analytics LCMS-1 |
|---|---|---|
| Ex 13-2 | methyl 2-((4-((2-(difluoromethoxy)-6-methylpyridin-3-yl)carbamoyl)-4-(2-isopropylphenyl)piperidin-1-yl)sulfonyl)acetate | [M + 1]$^+$539.93 $t_R$ 1.27 |
| Ex 13-3 | 2-((4-((2-(difluoromethoxy)-6-methylpyridin-3-yl)carbamoyl)-4-(2-isopropylphenyl)piperidin-1-yl)sulfonyl)acetic acid | [M + 1]$^+$526.10 $t_R$ 1.22 |
| Ex 13-4 | Benzyl 3-((3-((2-(difluoromethoxy)-6-methylpyridin-3-yl)carbamoyl)-3-(2-isopropylphenyl)azetidin-1-yl)sulfonyl)propanoate | [M + 1]$^+$602.12 $t_R$ 1.39 |
| Ex 13-5 | 3-((3-((2-(difluoromethoxy)-6-methylpyridin-3-yl)carbamoyl)-3-(2-isopropylphenyl)azetidin-1-yl)sulfonyl)propanoic acid | [M + 1]$^+$512.20 $t_R$ 1.16 |
| Ex 13-6 | methyl 3-((4-((2-(difluoromethoxy)-6-methylpyridin-3-yl)carbamoyl)-4-(2-isopropylphenyl)piperidin-1-yl)sulfonyl)propanoate | [M + 1]$^+$554.03 $t_R$ 1.30 |
| Ex 13-7 | benzyl 3-((4-((2-(difluoromethoxy)-6-methylpyridin-3-yl)carbamoyl)-4-(2-isopropylphenyl)piperidin-1-yl)sulfonyl)propanoate | [M + 1]$^+$630.04 $t_R$ 1.43 |
| Ex 13-8 | 3-((4-(difluoromethoxy)-6-methylpyridin-3-yl)carbamoyl)-4-(2-isopropylphenyl)piperidin-1-yl)sulfonyl)propanoic acid | [M + 1]$^+$540.13 $t_R$ 1.20 |
| Ex 13-9 | benzyl 3-((3-((2-(difluoromethoxy)pyridin-3-yl)carbamoyl)-3-(2-isopropylphenyl)azetidin-1-yl)sulfonyl)propanoate | [M + 1]$^+$588.02 $t_R$ 1.35 |
| Ex 13-10 | 3-((3-((2-(difluoromethoxy)pyridin-3-yl)carbamoyl)-3-(2-isopropylphenyl)azetidin-1-yl)sulfonyl)propanoic acid | [M + 1]$^+$498.23 $t_R$ 1.10 |
| Ex 13-11 | methyl 3-((3-((2-(difluoromethoxy)-6-methylpyridin-3-yl)carbamoyl)-3-(2-isopropylphenyl)azetidin-1-yl)sulfonyl)-2,2-dimethylpropanoate | [M + 1]$^+$554.00 $t_R$ 1.33 |
| Ex13-12 | 3-((3-((2-(difluoromethoxy)-6-methylpyridin-3-yl)carbamoyl)-3-(2-isopropylphenyl)azetidin-1-yl)sulfonyl)-2,2-dimethylpropanoic acid | [M + 1]$^+$539.98 $t_R$ 1.23 |
| Ex 13-13 | ethyl 2-(1-((3-((2-(difluoromethoxy)-6-methylpyridin-3-yl)carbamoyl)-3-(2-isopropylphenyl)azetidin-1-yl)sulfonyl)cyclopropyl)acetate | [M + 1]$^+$566.58 $t_R$ 1.38 |
| Ex 13-14 | 2-(1-((3-((2-(difluoromethoxy)-6-methylpyridin-3-yl)carbamoyl)-3-(2-isopropylphenyl)azetidin-1-yl)sulfonyl)cyclopropyl)acetic acid | [M + 1]$^+$538.09 $t_R$ 1.21 |
| Ex 13-15 | methyl 3-(((3-((2-(difluoromethoxy)-6-methylpyridin-3-yl)carbamoyl)-3-(2-isopropylphenyl)azetidin-1-yl)sulfonyl)methyl)oxetane-3-carboxylate | [M + 1]$^+$568.07 $t_R$ 1.25 |
| Ex 13-16 | 3-(((3-((2-(difluoromethoxy)-6-methylpyridin-3-yl)carbamoyl)-3-(2-isopropylphenyl)azetidin-1-yl)sulfonyl)methyl)oxetane-3-carboxylic acid | [M + 1]$^+$554.00 $t_R$ 1.16 |

TABLE 9-continued

Examples 13-2 to 13-27
Examples 13-2 to 13-27 are synthesized using the methodology described for Ex 13-1 starting from Ex 3, Ex 4 or Ex 7. In case of benzylester, hydrogenation is performed as second step to obtain the corresponding carboxylic acid.

| Example | Name | Analytics LCMS-1 |
| --- | --- | --- |
| Ex 13-17 | 4-((3-((2-(difluoromethoxy)-6-methylpyridin-3-yl)carbamoyl)-3-(2-isopropylphenyl)azetidin-1-yl)sulfonyl)butanoic acid | [M + 1]$^+$526.18 $t_R$ 1.16 |
| Ex 13-18 | methyl 5-((3-((2-(difluoromethoxy)-6-methylpyridin-3-yl)carbamoyl)-3-(2-isopropylphenyl)azetidin-1-yl)sulfonyl)pentanoate | [M + 1]$^+$554.02 $t_R$ 1.30 |
| Ex 13-19 | 5-((3-((2-(difluoromethoxy)-6-methylpyridin-3-yl)carbamoyl)-3-(2-isopropylphenyl)azetidin-1-yl)sulfonyl)pentanoic acid | [M + 1]$^+$540.01 $t_R$ 1.19 |
| Ex13-20 | methyl (E)-3-((3-((2-(difluoromethoxy)-6-methylpyridin-3-yl)carbamoyl)-3-(2-isopropylphenyl)azetidin-1-yl)sulfonyl)acrylate | [M + 1]$^+$524.44 $t_R$ 1.32 |
| Ex 12-21 | (E)-3-((3-((2-(difluoromethoxy)-6-methylpyridin-3-yl)carbamoyl)-3-(2-isopropylphenyl)azetidin-1-yl)sulfonyl)acrylic acid | [M + 1]$^+$509.96 $t_R$ 1.25 |
| Ex 13-22 | methyl 4-((3-((2-(difluoromethoxy)-6-methylpyridin-3-yl)carbamoyl)-3-(2-isopropylphenyl)azetidin-1-yl)sulfonyl)-1H-pyrazole-5-carboxylate | [M + 1]$^+$564.16 $t_R$ 1.17 |
| Ex 13-23 | 4-((3-((2-(difluoromethoxy)-6-methylpyridin-3-yl)carbamoyl)-3-(2-isopropylphenyl)azetidin-1-yl)sulfonyl)-1H-pyrazole-5-carboxylic acid | [M + 1]$^+$550.22 $t_R$ 1.13 |
| Ex 13-24 | ethyl 5-((3-((2-(difluoromethoxy)-6-methylpyridin-3-yl)carbamoyl)-3-(2-isopropylphenyl)azetidin-1-yl)sulfonyl)-1H-pyrazole-4-carboxylate | [M + 1]$^+$578.13 $t_R$ 1.22 |
| Ex 13-25 | 5-((3-((2-(difluoromethoxy)-6-methylpyridin-3-yl)carbamoyl)-3-(2-isopropylphenyl)azetidin-1-yl)sulfonyl)-1H-pyrazole-4-carboxylic acid | [M + 1]$^+$550.10 $t_R$ 1.07 |
| Ex 13-26 | methyl 5-((3-((2-(difluoromethoxy)-6-methylpyridin-3-yl)carbamoyl)-3-(2-isopropylphenyl)azetidin-1-yl)sulfonyl)isoxazole-3-carboxylate | [M + 1]$^+$565.04 $t_R$ 1.34 |
| Ex 13-27 | 3-((3-((2-(difluoromethoxy)-6-methylpyridin-3-yl)carbamoyl)-3-(2-isopropylphenyl)azetidin-1-yl)sulfonyl)-3-methoxypropanoic acid | [M + 1]$^+$542.00 $t_R$ 1.20 |

Example 13-28: 1-((3-((benzyloxy) amino)-3-oxopropyl)sulfonyl)-N-(2-(difluoromethoxy)-6-methylpyridin-3-yl)-3-(2-isopropylphenyl)azetidine-3-carboxamide and Example 13-29: N-(2-(difluoromethoxy)-6-methylpyridin-3-yl)-1-((3-(hydroxyamino)-3-oxopropyl)sulfonyl)-3-(2-isopropylphenyl)azetidine-3-carboxamide Step 1. To a solution of 3-chlorosulfonylpropionyl chloride (prepared from 1,2-oxathiolane-5-one 2-dioxide: lit. U.S. Pat. No. 6,734,184, Novartis AG) (28 mg, 0.15 mmol) and TEA (39 uL, 0.67 mmol) in DMF is added O-benzylhydroxylamine (18.6 mg, 0.15 mmol). The reaction mixture is stirred at r.t. for 5 min and Ex 3 hydrochloride (55 mg, 0.13 mmol) is then added and stirring is continued for 18 h. Water is added and the reaction mixture is purified by prep. HPLC (Prep-HPLC-3 conditions) to give Ex 13-28 as a white solid (12.5 mg, 15% yield). LCMS-1: $t_R$=1.28 min, [M+1]$^+$618.10.

Step 2. Ex 13-28 (12 mg, 0.02 mmol) is hydrogenated according to the method described for Ex 11-12 to give Ex 13-29 as a pale yellow oil (8 mg, 76% yield). LCMS-1: $t_R$=1.08 min, [M+1]$^+$527.01; $^1$H NMR (400 MHz, MeOD) δ: 8.29 (d, J=8.1 Hz, 1 H), 7.57 (s, 0.25 H), 7.49-7.46 (m, 3 H), 7.43-7.37 (m, 2 H), 7.21 (s, 0.25 H), 7.06 (d, J=8.1 Hz, 1 H), 4.64 (d, J=8.0 Hz, 2 H), 4.47 (d, J=8.0 Hz, 2 H), 3.45 (t, J=7.4 Hz, 2 H), 2.61 (t, J=7.4 Hz, 2 H), 2.52-2.44 (m, 1 H), 2.41 (s, 3 H), 1.17 (d, J=6.7 Hz, 6 H).

Example 13-30: 3-((3-((2-(difluoromethoxy)-6-methylpyridin-3-yl)carbamoyl)-3-(2-isopropylphenyl)azetidin-1-yl)sulfonyl)propane-1-sulfonic acid Ex 3 hydrochloride (50 mg) is reacted with commercially available 3-(chlorosulfonyl)propane-1-sulfonyl fluoride (32 mg) following the same conditions as step 1 of Ex 13-1. The fluorosulfonyl product (32 mg, 0.057 mmol) is then hydrolyzed with NaOH 32% aq. (1 mL) at 50° C. for 18 h to give the title compound Ex 13-30 that is isolated according to step 2 of Ex 13-1 (19 mg, 28% yield over 2 steps, oil). LCMS-1: $t_R$=1.35 min, [M+1]$^+$562.10; $^1$H NMR (400 MHz, CD$_3$OD) δ: 8.31 (d, J=8.0 Hz, 1 H), 7.51-7.42 (m, 3 H), 7.39 (dd, J$_1$=2.3 Hz, J$_2$=14.1 Hz, 1 H), 7.38 (t, J=72.8 Hz, 1 H), 7.06 (d, J=8.1 Hz, 1 H), 4.66 (d, J=7.9 Hz, 2 H), 4.46 (d, J=7.9 Hz, 2 H), 3.40-3.34 (m, 2 H), 3.06-2.98 (m, 2 H), 2.54-2.48 (m, 1 H), 2.41 (s, 3 H), 2.31 (m, 2 H), 1.16 (d, J=6.7 Hz, 6 H).

Example 14-1: 2-((3-((2-(difluoromethoxy)-6-methylpyridin-3-yl)carbamoyl)-3-(2-isopropylphenyl)azetidine-1-carbonyl)oxy)acetic acid Step 1. To a solution of methylglycolate (500 mg, 1.18 mmol) and TEA (2.34 mL, 16.7 mmol) in MeCN (20 mL), is added N,N-disuccinimidylcarbonate (1.56 g, 6.11 mmol). The reaction mixture is stirred overnight, is then diluted with EtOAc, washed with brine, dried over MgSO$_4$, filtered and concentrated to give methyl 2-(((((2,5-dioxopyrrolidin-1-yl)oxy)carbonyl)oxy)acetate (940 mg, 73% yield). The former compound is added to a solution of Ex 3 (50 mg, 0.133 mmol) and DIPEA (57 uL, 0.33 mmol) in DMF (5 mL). The reaction mixture is stirred for 18 h, concentrated and purified by prep HPLC (Prep-HPLC-2 conditions) to give 2-methoxy-2-oxoethyl 3-((2-(difluoromethoxy)-6-methylpyridin-3-yl)carbamoyl)-3-(2-isopropylphenyl)azetidine-1-carboxylate: 48 mg, 73% yield.

Step 2. 2-Methoxy-2-oxoethyl 3-((2-(difluoromethoxy)-6-methylpyridin-3-yl)carbamoyl)-3-(2-isopropylphenyl)azetidine-1-carboxylate (48 mg, 0.098 mmol) is dissolved in THF (3 mL) and is treated with 2M LiOH (130 uL). The solution is stirred at r.t. for 2 h (reaction progress monitored by LCMS). The reaction mixture is then diluted with water, acidified to pH 1 with 6N HCl and extracted twice with EtOAc. The combined organic extracts are dried over MgSO$_4$, filtered and evaporated. The residue is purified by prep. HPLC (Prep-HPLC-2 conditions) to give Ex 14-1 as a white solid (24 mg, 51% yield). LCMS-1: $t_R$=1.18 min, [M+1]$^+$478.45.

TABLE 10

Examples 14-2 to 14-14
Examples 14-2 to 14-14 are synthesized using the methodology described for Ex 14-1 starting from Ex 3 or Ex 4.

| Example | Name | Analytics LCMS-1 |
|---|---|---|
| Ex 14-2 | 2-((4-((2-(difluoromethoxy)-6-methylpyridin-3-yl)carbamoyl)-4-(2-isopropylphenyl)piperidine-1-carbonyl)oxy)acetic acid | $[M + 1]^+$ 520.12<br>$t_R$ 1.32 |
| Ex 14-3 | 2-((4-((2-(difluoromethoxy)-6-methylpyridin-3-yl)carbamoyl)-4-(2-isopropylphenyl)piperidine-1-carbonyl)oxy)acetic acid | $[M + 1]^+$ 506.07<br>$t_R$ 1.23 |
| Ex 14-4 | (S)-2-((3-((2-(difluoromethoxy)-6-methylpyridin-3-yl)carbamoyl)-3-(2-isopropylphenyl)azetidine-1-carbonyl)oxy)propanoic acid | $[M + 1]^+$ 492.08<br>$t_R$ 1.22 |
| Ex 14-5 | (R)-2-((3-((2-(difluoromethoxy)-6-methylpyridin-3-yl)carbamoyl)-3-(2-isopropylphenyl)azetidine-1-carbonyl)oxy)propanoic acid | $[M + 1]^+$ 492.00<br>$t_R$ 1.22 |
| Ex 14-6 | 1-methoxy-2-methyl-1-oxopropan-2-yl 3-((2-(difluoromethoxy)-6-methylpyridin-3-yl)carbamoyl)-3-(2-isopropylphenyl)azetidine-1-carboxylate | $[M + 1]^+$ 520.08<br>$t_R$ 1.42 |
| Ex 14-7 | 1-(methoxycarbonyl)cyclopropyl 3-((2-(difluoromethoxy)-6-methylpyridin-3-yl)carbamoyl)-3-(2-isopropylphenyl)azetidine-1-carboxylate | $[M + 1]^+$ 534.26<br>$t_R$ 1.32 |
| Ex 14-8 | 1-((3-((2-(difluoromethoxy)-6-methylpyridin-3-yl)carbamoyl)-3-(2-isopropylphenyl)azetidine-1-carbonyl)oxy)cyclopropane-1-carboxylic acid | $[M + 1]^+$ 504.06<br>$t_R$ 1.22 |
| Ex 14-9 | 3-methoxy-2,2-dimethyl-3-oxopropyl 3-((2-(difluoromethoxy)-6-methylpyridin-3-yl)carbamoyl)-3-(2-isopropylphenyl)azetidine-1-carboxylate | $[M + 1]^+$ 534.26<br>$t_R$ 1.37 |
| Ex 14-10 | 3-((3-((2-(difluoromethoxy)-6-methylpyridin-3-yl)carbamoyl)-3-(2-isopropylphenyl)azetidine-1-carbonyl)oxy)-2,2-dimethylpropanoic acid | $[M + 1]^+$ 520.17<br>$t_R$ 1.25 |
| Ex 14-11 | (1-(methoxycarbonyl)cyclopropyl)methyl 3-((2-(difluoromethoxy)-6-methylpyridin-3-yl)carbamoyl)-3-(2-isopropylphenyl)azetidine-1-carboxylate | $[M + 1]^+$ 532.13<br>$t_R$ 1.33 |
| Ex 14-12 | 1-(((3-((2-(difluoromethoxy)-6-methylpyridin-3-yl)carbamoyl)-3-(2-isopropylphenyl)azetidine-1-carbonyl)oxy)methyl)cyclopropane-1-carboxylic acid | $[M + 1]^+$ 518.02<br>$t_R$ 1.22 |
| Ex 14-13 | (3-(methoxycarbonyl)oxetan-3-yl)methyl 3-((2-(difluoromethoxy)-6-methylpyridin-3-yl)carbamoyl)-3-(2-isopropylphenyl)azetidine-1-carboxylate | $[M + 1]^+$ 548.09<br>$t_R$ 1.27 |
| Ex 14-14 | 3-(((3-((2-(difluoromethoxy)-6-methylpyridin-3-yl)carbamoyl)-3-(2-isopropylphenyl)azetidine-1-carbonyl)oxy)methyl)oxetane-3-carboxylic acid | $[M + 1]^+$ 534.10<br>$t_R$ 1.17 |

Example 15-1: Ethyl ((3-((2-(difluoromethoxy)-6-methylpyridin-3-yl)carbamoyl)-3-(2-isopropylphenyl)azetidin-1-yl)sulfonyl)glycinate and Example 15-2: ((3-((2-(difluoromethoxy)-6-methylpyridin-3-yl)carbamoyl)-3-(2-isopropylphenyl)azetidin-1-yl)sulfonyl)glycine Step 1. A solution of chlorosulfonyl isocyanate (42 uL, 0.48 mmol) in DCM (1 mL) is cooled down to 0° C. and 2-bromoethanol (35 uL, 0.48 mmol) in DCM (1 mL) is added. The reaction mixture stirred for 1 h at 0° C., then ethyl 2-aminoacetate (52 mg, 0.48 mmol) in DCM (1 mL) is added followed by TEA (200 uL, 1.43 mmol, 3 eq.). The reaction is stirred at 35° C. for 14 h and is then concentrated under reduced pressure. The residue is dissolved in DMF (1 mL) and is added to a solution of Ex 3 (51 mg, 0.14 mmol) and TEA (285 uL, 2.05 mmol) in DMF (1.5 mL). The reaction mixture is stirred at 95° C. overnight. The reaction mixture is then concentrated and the residue is purified by prep. HPLC (Prep-HPLC-3 conditions) yielding Ex 15-1 as an off-white solid (32 mg, 43% yield). LCMS-1: $t_R$=1.24 min, $[M+1]^+$541.23; $^1$H NMR (500 MHz, CDCl$_3$) δ: 8.55 (d, J=8.1 Hz, 1 H), 7.47-7.40 (m, 2 H), 7.39-7.35 (m, 1 H), 7.33 (s, 1 H), 7.28 (t, $J_{HF}$=72.5 Hz, 1 H), 7.27 (dd, $J_1$=0.9 Hz, $J_2$=7.8 Hz, 1 H), 6.94 (d, J=8.1 Hz, 1 H), 4.96 (s, 1 H), 4.67-4.52 (m, 2 H), 4.51-4.36 (m, 2 H), 4.25 (q, J=7.2 Hz, 2 H), 3.93 (s, 2 H), 2.44-2.36 (m, 4 H), 1.31 (s, 3 H), 1.14 (d, J=6.7 Hz, 6 H).

Step 2. A solution of Ex 15-1 (28 mg, 0.052 mmol) in MeOH/THF (1:1, 1 mL) is treated with 2N LiOH aq. (104 uL, 0.10 mmol). The reaction mixture is stirred at r.t. for 18 h and organic solvents are then evaporated. The residue is dissolved in water. The resulting solution is acidified to pH 1 with 1N HCl aq solution and is then extracted with EtOAc (3'10 mL). The combined extracts are dried over MgSO$_4$, filtered and evaporated to give Ex 15-2 as a yellow oil (26 mg, 98% yield). LCMS-1: $t_R$=1.13 min, $[M+1]^+$513.10; $^1$H NMR (400 MHz, CDCl$_3$) δ: 8.56 (d, J=8.1 Hz, 1 H), 7.48-7.42 (m, 3 H), 7.39-7.35 (m, 1 H), 7.27 (t, $J_{HF}$=72.5 Hz, 1 H), 7.25 (d, J=7.7 Hz, 1 H), 6.98 (d, J=8.2 Hz, 1 H), 4.63-4.52 (m, 2 H), 4.51-4.40 (m, 2 H), 4.01 (s, 2 H), 2.45-2.34 (m, 4 H), 1.15 (d, J=6.6 Hz, 6 H).

Example 15-3: N-(2-(difluoromethoxy)-6-methylpyridin-3-yl)-1-(N-(2-hydroxyethyl)sulfamoyl)-3-(2-isopropylphenyl)azetidine-3-carboxamide Step 1. A solution of chlorosulfonyl isocyanate (12 uL, 0.14 mmol) in DCM (1 mL) is cooled down to 0° C. and 2-bromoethanol (10 uL, 0.13 mmol) in DCM (1 mL) is added. The reaction mixture stirred for 1 h at 0° C., then Ex 3 (57 mg, 0.14 mmol) in DCM (2 mL) is added followed by TEA (78 uL, 0.55 mmol, 4 eq.). The reaction is stirred at r.t. for 1.5 h and is then concentrated under reduced pressure to give crude N-(2-(difluoromethoxy)-6-methylpyridin-3-yl)-3-(2-isopropylphenyl)-1-((2-oxooxazolidin-3-yl)sulfonyl)azetidine-3-carboxamide. LCMS-2: $t_R$=1.12 min, $[M+1]^+$ 525.14.

Step 2. N-(2-(difluoromethoxy)-6-methylpyridin-3-yl)-3-(2-isopropylphenyl)-1-((2-oxooxazolidin-3-yl)sulfonyl)azetidine-3-carboxamide (70 mg, 0.13 mmol) is dissolved in EtOH (1 mL) and NaOH 6N (0.4 mL, 2.4 mmol) is added. The reaction mixture is stirred for 2 h and is then diluted with water (5 ml) and extracted with DCM (3×20 mL). The organic extracts are dried over MgSO$_4$, filtered and evaporated. The residue is purified by prep. HPLC (Prep-HPLC-1 conditions) yielding Ex 15-3 as a beige solid (32 mg, 44% yield over 2 steps). LCMS-1: $t_R$=1.12 min, $[M+1]^+$499.10. $^1$H NMR (400 MHz, CDCl$_3$) δ: 8.55 (d, J=8.1 Hz, 1 H), 7.50-7.43 (m, 2 H), 7.40-7.34 (s, 2 H), 7.26 (t, J=71.8 Hz, 1

H), 7.25 (d, J=7.7 Hz, 1 H), 6.94 (d, J=8.1 Hz, 1 H), 4.55 (s, 2 H), 4.46 (s, 2 H), 3.84 (t, J=4.8 Hz, 2 H), 3.37 (t, J=4.8 Hz, 2 H), 2.39 (m, 4 H), 1.15 (d, J=6.6 Hz, 6 H).

Example 15-4: N-(2-(difluoromethoxy)-6-methylpyridin-3-yl)-1-(N-(2-fluoroethyl)sulfamoyl)-3-(2-isopropylphenyl)azetidine-3-carboxamide N-(2-(difluoromethoxy)-6-methylpyridin-3-yl)-1-(N-(2-fluoroethyl)sulfamoyl)-3-(2-isopropyl-phenyl)azetidine-3-carboxamide Ex 15-4 (3.5 mg, yellow solid) is prepared from Ex 3 and commercially available 2-fluoroethylamine following the methodology described for Ex 15-3. LCMS-1: $t_R$=1.10 min, [M+1]$^+$501.00.

Example 15-5: N-(2-(difluoromethoxy)-6-methylpyridin-3-yl)-3-(2-isopropylphenyl)-1-sulfamoylazetidine-3-carboxamide To a solution of Ex 3 (50 mg, 0.12 mmol) and TEA (51 uL, 0.36 mmol) in dioxane (2 mL) is added sulfamide (12 mg, 0.12 mmol). The reaction mixture is stirred at 100° C. for 18 h and is then evaporated. The crude compound is purified by prep. HPLC (Prep HPLC 2) to give the title compound Ex 15-5 as a white solid (35 mg, 63% yield). LCMS-1: $t_R$=1.14 min, [M+1]$^+$455.39; $^1$H NMR (400 MHz, CDCl$_3$) δ: 8.55 (d, J=8.1 Hz, 1 H), 7.50-7.44 (m, 2 H), 7.41-7.39 (m, 1 H), 7.37-7.34 (m, 1 H), 7.31-7.27 (m, 2 H), 6.95 (d, J=8.1 Hz, 1 H), 4.78 (s, 2 H), 4.72-4.59 (m, 2 H), 4.53-4.37 (m, 2 H), 2.44-2.33 (m, 4 H), 1.15 (d, J=6.7 Hz, 6 H).

TABLE 11

Examples 15-6 to 15-18
Examples 15-6 to 15-18 are synthesized using the methodology described for Ex 15-5 starting from Ex 1, Ex 2, Ex 3, Ex 6, Ex 7, Ex 8 or Ex 9 that are reacted with sulfamide or mono-alkyl sulfamides.

| Example | Name | Analytics LCMS-1 |
|---|---|---|
| Ex 15-6 | N-(2-(difluoromethoxy)pyridin-3-yl)-3-(2-isopropylphenyl)-1-sulfamoylazetidine-3-carboxamide | [M + 1]$^+$ 441.13 $t_R$ 1.06 |
| Ex 15-7 | N-(2,6-dimethoxypyridin-3-yl)-3-(2-isopropylphenyl)-1-sulfamoylazetidine-3-carboxamide | [M + 1]$^+$ 434.99 $t_R$ 1.10 |
| Ex15-8 | N-(6-ethoxy-2-methoxypyridin-3-yl)-3-(2-isopropylphenyl)-1-sulfamoylazetidine-3-carboxamide | [M + 1]$^+$ 449.15 $t_R$ 1.17 |
| Ex 15-9 | N-(2-(difluoromethoxy)-6-methylpyridin-3-yl)-3-(2-isopropylphenyl)-1-(N-methylsulfamoyl)azetidine-3-carboxamide | [M + 1]$^+$ 469.21 $t_R$ 1.21 |
| Ex 15-10 | N-(2-(difluoromethoxy)-6-methylpyridin-3-yl)-1-(N-ethylsulfamoyl)-3-(2-isopropylphenyl)azetidine-3-carboxamide | [M + 1]$^+$ 483.11 $t_R$ 1.25 |
| Ex 15-11 | N-(2-(difluoromethoxy)-6-methylpyridin-3-yl)-3-(2-isopropylphenyl)-1-(N-propylsulfamoyl)azetidine-3-carboxamide | [M + 1]$^+$ 496.99 $t_R$ 1.30 |
| Ex 15-12 | N-(2-(difluoromethoxy)-6-methylpyridin-3-yl)-3-(2-isopropylphenyl)-1-(N-isopropylsulfamoyl)azetidine-3-carboxamide | [M + 1]$^+$ 497.00 $t_R$ 1.29 |
| Ex 15-13 | 1-(N-cyclopropylsulfamoyl)-N-(2-(difluoromethoxy)-6-methylpyridin-3-yl)-3-(2-isopropylphenyl)azetidine-3-carboxamide | [M + 1]$^+$ 495.00 $t_R$ 1.26 |
| Ex 15-14 | N-(2-(difluoromethoxy)-6-methylpyridin-3-yl)-3-(2-isopropylphenyl)-1-(2-(sulfamoylamino)ethyl)azetidine-3-carboxamide | [M + 1]$^+$ 498.29 $t_R$ 0.72 |
| Ex 15-15 | N-(2-(difluoromethoxy)-5-fluoropyridin-3-yl)-3-(2-isopropylphenyl)-1-sulfamoylazetidine-3-carboxamide | [M + 1]$^+$ 459.13 $t_R$ 1.13 |
| Ex 15-16 | 3-(2-isopropylphenyl)-N-(2-methoxy-6-methylpyridin-3-yl)-1-sulfamoylazetidine-3-carboxamide | [M + 1]$^+$ 419.05 $t_R$ 1.13 |
| Ex 15-17 | N-(2-ethoxy-6-methylpyridin-3-yl)-3-(2-isopropylphenyl)-1-sulfamoylazetidine-3-carboxamide | [M + 1]$^+$ 433.34 $t_R$ 1.21 |
| Ex 15-18 | N-(2-isopropoxy-6-methylpyridin-3-yl)-3-(2-isopropylphenyl)-1-sulfamoylazetidine-3-carboxamide | [M + 1]$^+$ 447.14 $t_R$ 1.28 |

Example 16-1: 1-(N-acetylsulfamoyl)-N-(2-(difluoromethoxy)-6-methylpyridin-3-yl)-3-(2-isopropylphenyl)azetidine-3-carboxamide A mixture of Ex 15-5 (35 mg, 0.08 mmol) NMM (85 uL, 0.08 mmol) and DMAP (1 mg, 0.008 mmol) in DCM (2 mL) is chilled in ice and acetic anhydride (5 drops) is added. The reaction is stirred for 3 h and quenched with MeOH. The mixture is evaporated to dryness and purified by prep. HPLC (Prep-HPLC-2 conditions) to give the title compound Ex 16-1 as a white solid (18 mg, 47% yield). LCMS-1: $t_R$=1.17 min, [M+1]$^+$497.01; $^1$H NMR (500 MHz, CDCl$_3$) δ: 8.60 (s br, 1 H), 8.53 (d, J=8.1 Hz, 1 H), 7.52-7.46 (m, 2 H), 7.43-7.38 (m, 1 H), 7.31-7.27 (m, 2 H), 7.26 (t, J=72.5 Hz, 1 H), 6.95 (d, J=8.1 Hz, 1 H), 5.02-4.84 (m, 2 H), 4.76-4.54 (m, 2 H), 2.40 (s, 3 H), 2.35-2.28 (m, 1 H), 2.25 (s, 3 H), 1.16 (d, J=6.5 Hz, 6 H).

TABLE 12

Examples 16-2 to 16-5
Examples 16-2 to 16-5 are synthesized using the methodology described for Ex 16-1 starting from Ex 12-4, Ex 12-5, Ex 12-8 or Ex 15-6.

| Example | Name | Analytics LCMS-1 |
|---|---|---|
| Ex 16-2 | 1-(N-acetylsulfamoyl)-N-(2-(difluoromethoxy)pyridin-3-yl)-3-(2-isopropylphenyl)azetidine-3-carboxamide | [M + 1]$^+$ 483.00 $t_R$ 1.11 |
| Ex 16-3 | 1-(2-(N-acetylsulfamoyl)acetyl)-N-(2-(difluoromethoxy)-6-methylpyridin-3-yl)-3-(2-isopropylphenyl)azetidine-3-carboxamide | [M + 1]$^+$ 539.41 $t_R$ 1.12 |
| Ex 16-4 | 1-(3-(N-acetylsulfamoyl)propanoyl)-N-(2-(difluoromethoxy)-6-methylpyridin-3-yl)-3-(2-isopropylphenyl)azetidine-3-carboxamide | [M + 1]$^+$ 553.48 $t_R$ 1.12 |
| Ex 16-5 | 1-(N-(N-acetylsulfamoyl)-N-methylglycyl)-N-(2-(difluoromethoxy)-6-methylpyridin-3-yl)-3-(2-isopropylphenyl)azetidine-3-carboxamide | [M + 1]$^+$ 568.03 $t_R$ 1.14 |

Example 17-1: Methyl 3-(3-((2-(difluoromethoxy)-6-methylpyridin-3-yl)carbamoyl)-3-(2-isopropylphenyl)azetidine-1-carboxamido)-3-methylbutanoate and Example 17-2: 3-(3-((2-(difluoromethoxy)-6-methylpyridin-3-yl)carbamoyl)-3-(2-isopropylphenyl)azetidine-1-carboxamido)-3-methylbutanoic acid Method A Step 1. To a solution Ex 3 hydrochloride (35 mg, 0.085 mmol) and TEA (24 uL, 0.17 mmol, 2 eq.) in DCM (5 mL) is added methyl 3-isocyanato-3-methylbutanoate (15 mg, 0.085 mmol) dropwise. The reaction mixture is stirred at r.t. for 1 h (reaction progress monitored by LCMS) and is then concentrated. The residue is purified by prep. HPLC (Prep-HPLC-3 conditions) to give Ex 17-1 as a white solid (37.5 mg, 83% yield); LCMS-1: $t_R$=1.30 min, [M+1]$^+$533.44; $^1$H NMR (400 MHz, CDCl$_3$) δ: 8.57 (d, J=8.1 Hz, 1 H), 7.48-7.40 (m, 2 H), 7.39-7.33 (m, 2 H), 7.30 (t, $J_{H-F}$=72.6 Hz, 1 H), 7.28 (d, J=5.3 Hz, 1 H), 6.93 (d, J=8.1 Hz, 1 H), 4.93 (s, 1 H), 4.72-4.56 (m, 2 H), 4.48-4.29 (m, 2 H), 3.67 (s, 3 H), 2.69 (s, 2 H), 2.42-2.50 (m, 1 H), 2.38 (s, 3 H), 1.45 (s, 6 H), 1.15 (d, J=6.7 Hz, 6 H).

Step 2. A solution of Ex 16-1 (33 mg, 0.063 mmol) in MeOH/THF (1:3, 4 mL) is treated with 2N LiOH aq. (1 mL, 1.0 mmol). The reaction mixture is stirred at r.t. for 5 h and are then concentrated. The residue is purified by prep HPLC (Prep-HPLC-2 conditions) yielding Ex 17-2 as a white solid (23 mg, 71% yield). LCMS-1: $t_R$=1.16 min, [M+1]$^+$519.40; $^1$H NMR (500 MHz, CDCl$_3$) δ: 8.52 (d, J=8.1 Hz, 1 H), 7.44-7.39 (m, 2 H), 7.34-7.31 (m, 3 H), 7.24 (t, $J_{H-F}$=72.6 Hz, 1 H), 6.89 (d, J=8.2 Hz, 1 H), 5.98-5.78 (m, 1 H), 4.74-4.50 (m, 2 H), 4.50-4.27 (m, 2 H), 2.54 (s, 2 H), 2.39 (qt, J=6.1 Hz, 1 H), 2.34 (s, 3 H), 1.36 (s, 6 H), 1.12 (d, J=6.1 Hz, 6 H).

Example 17-3: N1-((1H-imidazol-4-yl)methyl)-N4-(2-(difluoromethoxy)-6-methylpyridin-3-yl)-4-(2-isopropylphenyl)piperidine-1,4-carboxamide Method B To a solution of C-(1H-imidazol-4 (5)-yl)-methylamine.2HCl (46 mg, 0.34 mmol, 2.5 eq) in MeCN (2 mL), are added bis(2,2,2-trifluoroethyl)carbonate (52 uL, 0.34 mmol 2.5 eq) and DIPEA (142 uL, 0.82 mmol, 6 eq). The resulting mixture is heated at 75° C. for 2 h and then is allowed to cool to r.t. A solution of Ex 4 (55 mg, 0.14 mmol) and DBU (6 uL, 0.04 mmol, 0.3 eq) in MeCN (1 mL) is added and the mixture is heated at 75° C. overnight. DCM (20 mL) is then added and the organic solution is washed with water (10 mL), dried over MgSO$_4$, filtered and evaporated under reduced pressure. Crude product is purified by prep HPLC (Prep-HPLC-3 conditions) to give Ex 17-3 as an off white solid (17.6 mg, 25% yield). LCMS-1: $t_R$=0.79 min, [M+1]$^+$527.35; $^1$H NMR (400 MHz, CDCl$_3$) δ: 8.46 (d, J=8.1 Hz, 1 H), 7.61 (s, 1 H), 7.46-7.39 (m, 3 H), 7.33-7.30 (m, 1 H), 7.27 (t, $J_{H-F}$=72.5 Hz, 1 H), 7.11 (s, 1 H), 6.92 (d, J=8.2 Hz, 1 H), 6.89 (s, 1 H), 5.60-6.32 (s br, 1 H), 5.51 (t, J=5.0 Hz, 1 H), 4.34 (d, J=5.1 Hz, 2 H), 3.73-3.60 (m, 4 H), 3.16-3.10 (m, 1 H), 2.52-2.47 (m, 2 H), 2.38 (s, 3 H), 2.20-2.14 (m, 2 H), 1.10 (d, J=6.6 Hz, 6 H).

TABLE 13

Examples 17-4 to 17-24
Examples 17-4 to 17-24 are synthesized using either Method A or B described for Ex 17-2 and Ex 17-3 respectively starting from Ex 3 or Ex 4. For Method B, bis(2,2,2-trifluoroethyl) carbonate can be replaced by CDI.

| Example | Name | method | Analytics LCMS-1 |
|---|---|---|---|
| Ex 17-4 | (3-((2-(difluoromethoxy)-6-methylpyridin-3-yl)carbamoyl)-3-(2-isopropylphenyl)azetidine-1-carbonyl)glycine | A | $[M + 1]^+$ 477.00 $t_R$ 1.05 |
| Ex 17-5 | 3-(3-((2-(difluoromethoxy)-6-methylpyridin-3-yl)carbamoyl)-3-(2-isopropylphenyl)azetidine-1-carboxamido)propanoic acid | A | $[M + 1]^+$ 491.17 $t_R$ 1.05 |
| Ex 17-6 | methyl (3-((2-(difluoromethoxy)-6-methylpyridin-3-yl)carbamoyl)-3-(2-isopropylphenyl)azetidine-1-carbonyl)-L-valinate | B | $[M + 1]^+$ 533.02 $t_R$ 1.29 |
| Ex 17-7 | (3-((2-(difluoromethoxy)-6-methylpyridin-3-yl)carbamoyl)-3-(2-isopropylphenyl)azetidine-1-carbonyl)-L-valine | B | $[M + 1]^+$ 519.12 $t_R$ 1.19 |
| Ex 17-8 | methyl (3-((2-(difluoromethoxy)-6-methylpyridin-3-yl)carbamoyl)-3-(2-isopropylphenyl)azetidine-1-carbonyl)-L-alaninate | B | $[M + 1]^+$ 505.02 $t_R$ 1.18 |
| Ex 17-9 | (3-((2-(difluoromethoxy)-6-methylpyridin-3-yl)carbamoyl)-3-(2-isopropylphenyl)azetidine-1-carbonyl)-L-alanine | B | $[M + 1]^+$ 491.06 $t_R$ 1.10 |
| Ex 17-10 | ethyl 1-(3-((2-(difluoromethoxy)-6-methylpyridin-3-yl)carbamoyl)-3-(2-isopropylphenyl)azetidine-1-carboxamido)cyclopropane-1-carboxylate | B | $[M + 1]^+$ 531.10 $t_R$ 1.21 |
| Ex 17-11 | 1-(3-((2-(difluoromethoxy)-6-methylpyridin-3-yl)carbamoyl)-3-(2-isopropylphenyl)azetidine-1-carboxamido)cyclopropane-1-carboxylic acid | B | $[M + 1]^+$ 503.47 $t_R$ 1.10 |
| Ex 17-12 | ethyl 2-(3-((2-(difluoromethoxy)-6-methylpyridin-3-yl)carbamoyl)-3-(2-isopropylphenyl)azetidine-1-carboxamido)-2-methylpropanoate | B | $[M + 1]^+$ 533.15 $t_R$ 1.27 |
| Ex 17-13 | 2-(3-((2-(difluoromethoxy)-6-methylpyridin-3-yl)carbamoyl)-3-(2-isopropylphenyl)azetidine-1-carboxamido)-2-methylpropanoic acid | B | $[M + 1]^+$ 505.48 $t_R$ 1.15 |
| Ex 17-14 | methyl 1-((3-((2-(difluoromethoxy)-6-methylpyridin-3-yl)carbamoyl)-3-(2-isopropylphenyl)azetidine-1-carboxamido)methyl)cyclopropane-1-carboxylate | B | $[M + 1]^+$ 531.09 $t_R$ 1.23 |
| Ex 17-15 | 1-((3-((2-(difluoromethoxy)-6-methylpyridin-3-yl)carbamoyl)-3-(2-isopropylphenyl)azetidine-1-carboxamido)methyl)cyclopropane-1-carboxylic acid | B | $[M + 1]^+$ 517.09 $t_R$ 1.13 |
| Ex 17-16 | methyl 3-(3-((2-(difluoromethoxy)-6-methylpyridin-3-yl)carbamoyl)-3-(2-isopropylphenyl)azetidine-1-carboxamido)-2,2-dimethylpropanoate | B | $[M + 1]^+$ 533.13 $t_R$ 1.25 |
| Ex 17-17 | 3-(3-((2-(difluoromethoxy)-6-methylpyridin-3-yl)carbamoyl)-3-(2-isopropylphenyl)azetidine-1-carboxamido)-2,2-dimethylpropanoic acid | B | $[M + 1]^+$ 519.03 $t_R$ 1.14 |
| Ex 17-18 | methyl 4-(3-((2-(difluoromethoxy)-6-methylpyridin-3-yl)carbamoyl)-3-(2-isopropylphenyl)azetidine-1-carboxamido)-2,2-dimethylbutanoate | B | $[M + 1]^+$ 547.24 $t_R$ 1.27 |
| Ex 17-19 | 4-(3-((2-(difluoromethoxy)-6-methylpyridin-3-yl)carbamoyl)-3-(2-isopropylphenyl)azetidine-1-carboxamido)-2,2-dimethylbutanoic acid | B | $[M + 1]^+$ 533.06 $t_R$ 1.17 |
| Ex 17-20 | N4-(2-(difluoromethoxy)-6-methylpyridin-3-yl)-4-(2-isopropylphenyl)piperidine-1,4-dicarboxamide | A | $[M + 1]^+$ 447.00 $t_R$ 1.10 |
| Ex 17-21 | 2-(4-((2-(difluoromethoxy)-6-methylpyridin-3-yl)carbamoyl)-4-(2-isopropylphenyl)piperidine-1-carboxamido)ethyl methacrylate | A | $[M + 1]^+$ 559.27 $t_R$ 1.29 |
| Ex 17-22 | N4-(2-(difluoromethoxy)-6-methylpyridin-3-yl)-N1-(2-hydroxyethyl)-4-(2-isopropylphenyl)piperidine-1,4-dicarboxamide | A | $[M + 1]^+$ 491.21 $t_R$ 1.09 |
| Ex 17-23 | methyl (3-((2-(difluoromethoxy)-6-methylpyridin-3-yl)carbamoyl)-3-(2-isopropylphenyl)azetidine-1-carbonyl)-D-alaninate | B | $[M + 1]^+$ 505.01 $t_R$ 1.18 |
| Ex 17-24 | (3-((2-(difluoromethoxy)-6-methylpyridin-3-yl)carbamoyl)-3-(2-isopropylphenyl)azetidine-1-carbonyl)-D-alanine | B | $[M + 1]^+$ 491.03 $t_R$ 1.10 |

Example 17-25: N-(2-(difluoromethoxy)-6-methylpyridin-3-yl)-3-(2-isopropylphenyl)-1-(piperazine-1-carbonyl)azetidine-3-carboxamide A solution of Ex 3 hydrochloride (30 mg, 0.07 mmol) and TEA (30 uL, 0.22 mmol) in DMF (1 mL) under argon is cooled down to 0°° C. before addition of a solution of tert-butyl 4-(carbonochloridoyl)piperazine-1-carboxylate (24.8 mg, 0.09 mmol) in 1mL DMF. The reaction mixture is stirred at r.t. for 1 h (reaction monitored by LCMS) and is then quenched with water (0.5 mL). Purification by prep. HPLC (Prep-HPLC-3 conditions) afforded tert-butyl-4-(3-((2-(difluoromethoxy)-6-methylpyridin-3-yl)carbamoyl)-3-(2-isopropylphenyl)azetidine-1-carbonyl)piperazine-1-carboxylate as a white solid (42 mg, 98 5 yield). LCMS-1: $t_R$=1.37 min, $[M+1]^+$588.02. tert-Butyl-4-(3-((2-(difluoromethoxy)-6-methylpyridin-3-yl)carbamoyl)-3-(2-isopropylphenyl)azetidine-1-carbonyl)piperazine-1-carboxylate (40 mg) is then treated with TFA as described for Ex 4 to afford the title compound Ex 17-25 as yellow solid (27 mg, 80%). LCMS-1: $t_R$=0.76 min, $[M+1]^+$488.40.

Example 17-26: N-(2-(difluoromethoxy)-6-methylpyridin-3-yl)-3-(2-isopropylphenyl)-1-(4-methylpiperazine-1-carbonyl)azetidine-3-carboxamide N-(2-(difluoromethoxy)-6-methylpyridin-3-yl)-3-(2-isopropylphenyl)-1-(4-methylpiperazine-1-carbonyl)azetidine-3-carboxamide Ex 17-26 is prepared from 4-methyl-1-piperazincarbonylchloride according to the methiology described for Ex 17-25. White solid. LCMS-1: $t_R$=0.77 min, $[M+1]^+$502.18.

Example 17-27: N-(2-(difluoromethoxy)-6-methylpyridin-3-yl)-3-(2-isopropylphenyl)-1-(morpholine-4-carbonyl)azetidine-3-carboxamide N-(2-(difluoromethoxy)-6-methylpyridin-3-yl)-3-(2-isopropylphenyl)-1-(morpholine-4-carbonyl)azetidine-3-carboxamide Ex 16-27 is prepared from 4-morpholincarbonyl-chloride according to the methodology described for Ex 16-25. White solid. LCMS-1: $t_R$=1.19 min, [M+1]$^+$489.10

Example 18-1: Methyl 6-(3-((2-(difluoromethoxy)-6-methylpyridin-3-yl)carbamoyl)-3-(2-isopropylphenyl)azetidin-1-yl)nicotinate and Example 18-2: 6-(3-((2-(difluoromethoxy)-6-methylpyridin-3-yl)carbamoyl)-3-(2-isopropylphenyl)azetidin-1-yl)nicotinic acid Method C Step 1. Ex 3 hydrochloride (30 mg, 0.073 mmol), methyl 6-chloropyridine-3-carboxylate (28.7 mg, 0.164 mmol, 2.2 eq.) and Cs$_2$CO$_3$ (53 mg, 0.164 mmol, 2.2 eq.) are suspended in DMA and the mixture is stirred at 90° C. for 18 h (reaction monitored by LCMS). The mixture is cooled down to r.t., diluted with EtOAc (50 mL) and washed sequentially with water and brine. The organic phase is dried over MgSO$_4$, filtered and evaporated. The crude product is purified by prep HPLC (Prep-HPLC-3 conditions) to give Ex 17-1 as a white solid (18 mg, 50% yield). LCMS-1: $t_R$=1.36 min, [M+1]$^+$511.31; $^1$H NMR (400 MHz, CDCl$_3$) δ: 8.83-8.82 (m, 1 H), 8.58 (d, J=8.1 Hz, 1 H), 8.06 (dd, J$_1$=2.2 Hz, J$_2$=8.8 Hz, 1 H), 7.50-7.45 (m, 2 H), 7.43-7.36 (m, 3 H), 7.28 (t, J$_{H-F}$=72.5 Hz, 1 H), 6.94 (d, J=8.2 Hz, 1 H), 6.37 (d, J=8.8 Hz, 1 H), 4.97-4.85 (m, 2 H), 4.67-4.51 (m, 2 H), 3.89 (s, 3 H), 2.59-2.49 (m, 1 H), 2.39 (s, 3 H), 1.19 (d, J=6.7 Hz, 6 H).

Step 2. A solution of Ex 18-1 (18 mg, 0.035 mmol) in MeOH/THF (1:1, 1 mL) is treated with 2N LiOH (0.088 mL). The reaction mixture is stirred at r.t. for 18 h and organic solvents are then evaporated. The residue is dissolved in water. The resulting solution is acidified to pH 1 with 1N HCl aq solution and is then extracted with EtOAc (3×10 mL). The combined extracts are dried over MgSO$_4$, filtered and evaporated to give Ex 18-2 as a colorless oil (14 mg, 80% yield). LCMS-1: $t_R$=1.21 min, [M+1]$^+$497.35; $^1$H NMR (400 MHz, CDCl$_3$) δ: 8.86 (d, J=1.6 Hz, 1 H), 8.56 (d, J=8.1 Hz, 1 H), 8.14 (dd, J$_1$=1.6 Hz, J$_2$=8.9 Hz, 1 H), 7.52-7.38 (m, 4 H), 7.36 (s, 1 H), 7.21 (t, J$_{H-F}$=72.6 Hz, 1 H), 6.94 (d, J=8.1 Hz, 1 H), 6.45 (d, J=8.9 Hz, 1 H), 5.14-4.93 (s br, 2 H), 4.85-4.57 (m, 2 H), 2.53-2.43 (m, 1 H), 2.39 (s, 3 H), 1.20 (d, J=6.5 Hz, 6H).

Example 18-3: 6-(3-((2-(difluoromethoxy)-6-methylpyridin-3-yl)carbamoyl)-3-(2-isopropylphenyl)azetidin-1-yl)picolinic acid Method D To a solution of Ex 3 hydrochloride (52 mg, 0.126 mmol) in toluene (2 mL), are added ethyl-6-bromopicolinate (43.6 mg, 0.189 mmol, 1.5 eq), NaOtBu (36 mg, 0.379 mmol, 3 eq.), Pd$_2$(dba)$_3$ (11.6 mg, 0.013 mmol, 0.1 eq.) and BINAP (16.2 mg, 0.025 mmol, 0.2 eq.). The resulting mixture is degassed and is heated at 110°° C. overnight. The reaction is quenched with 2N HCl aq. (10 mL) and the mixture is diluted with EtOAc. The phases are separated. The organic phase is dried over MgSO$_4$, filtered and evaporated. The crude product is purified by prep TLC (eluent: DCM/MeOH: 9/1) to give Ex 18-3 as a yellow solid (10 mg, 17% yield). LCMS-1: $t_R$=1.22 min, [M+1]$^+$497.34; $^1$H NMR (400 MHz, CDCl$_3$) δ: 8.57 (d, J=8.0 Hz, 1 H), 7.76-7.66 (m, 1 H), 7.58 (d, J=7.0 Hz, 1 H), 7.47 (s, 2 H), 7.46-7.33 (m, 3 H), 7.27 (t, J=70.5 Hz, 1 H), 6.94 (d, J=8.1 Hz, 1 H), 6.67 (d, J=7.9 Hz, 1 H), 5-03-4.78 (m, 2 H), 4.69-4.40 (m, 2 H), 2.59-2.47 (m, 1 H), 2.39 (s, 3 H), 1.20 (d, J=6.4 Hz, 6 H).

TABLE 14

Examples 18-4 to 18-33
Examples 18-4 to 18-33 are synthesized according to Method C or Method D described for Ex 18-2 and Ex 18-3 respectively, starting from Ex 3 or Ex 7.

| Example | Name | Method | Analytics LCMS-1 |
|---|---|---|---|
| Ex 18-4 | methyl 2-(3-((2-(difluoromethoxy)-6-methylpyridin-3-yl)carbamoyl)-3-(2-isopropylphenyl)azetidin-1-yl)pyrimidine-5-carboxylate | C | [M + 1]$^+$ 512.18 $t_R$ 1.36 |
| Ex 18-5 | 2-(3-((2-(difluoromethoxy)-6-methylpyridin-3-yl)carbamoyl)-3-(2-isopropylphenyl)azetidin-1-yl)pyrimidine-5-carboxylic acid | C | [M + 1]$^+$ 498.09 $t_R$ 1.24 |
| Ex 18-6 | methyl 6-(3-((2-(difluoromethoxy)-6-methylpyridin-3-yl)carbamoyl)-3-(2-isopropylphenyl)azetidin-1-yl)pyridazine-3-carboxylate | C | [M + 1]$^+$ 512.38 $t_R$ 1.22 |
| Ex 18-7 | 6-(3-((2-(difluoromethoxy)-6-methylpyridin-3-yl)carbamoyl)-3-(2-isopropylphenyl)azetidin-1-yl)pyridazine-3-carboxylic acid | C | [[M + 1]$^+$ 498.35 $t_R$ 1.14 |
| Ex 18-8 | methyl 5-(3-((2-(difluoromethoxy)-6-methylpyridin-3-yl)carbamoyl)-3-(2-isopropylphenyl)azetidin-1-yl)pyrazine-2-carboxylate | C | [M + 1]$^+$ 512.21 $t_R$ 1.29 |
| Ex 18-9 | 5-(3-((2-(difluoromethoxy)-6-methylpyridin-3-yl)carbamoyl)-3-(2-isopropylphenyl)azetidin-1-yl)pyrazine-2-carboxylic acid | C | [M + 1]$^+$ 498.48 $t_R$ 1.20 |
| Ex 18-10 | ethyl 4-(3-((2-(difluoromethoxy)-6-methylpyridin-3-yl)carbamoyl)-3-(2-isopropylphenyl)azetidin-1-yl)pyrimidine-2-carboxylate | C | [M + 1]$^+$ 526.28 $t_R$ 1.23 |
| Ex 18-11 | 4-(3-((2-(difluoromethoxy)-6-methylpyridin-3-yl)carbamoyl)-3-(2-isopropylphenyl)azetidin-1-yl)pyrimidine-2-carboxylic acid | C | [M + 1]$^+$ 498.08 $t_R$ 0.95 |
| Ex 18-12 | methyl 6-(3-((2-(difluoromethoxy)-6-methylpyridin-3-yl)carbamoyl)-3-(2-isopropylphenyl)azetidin-1-yl)pyrimidine-4-carboxylate | C | [M + 1]$^+$ 512.37 $t_R$ 1.21 |
| Ex 18-13 | 6-(3-((2-(difluoromethoxy)-6-methylpyridin-3-yl)carbamoyl)-3-(2-isopropylphenyl)azetidin-1-yl)pyrimidine-4-carboxylic acid | C | [M + 1]$^+$ 498.35 $t_R$ 1.00 |
| Ex 18-14 | ethyl 2-(3-((2-(difluoromethoxy)-6-methylpyridin-3-yl)carbamoyl)-3-(2-isopropylphenyl)azetidin-1-yl)pyrimidine-4-carboxylate | C | [M + 1]$^+$ 526.38 $t_R$ 1.38 |
| Ex 18-15 | 2-(3-((2-(difluoromethoxy)-6-methylpyridin-3-yl)carbamoyl)-3-(2-isopropylphenyl)azetidin-1-yl)pyrimidine-4-carboxylic acid | C | [M + 1]$^+$ 498.34 $t_R$ 1.25 |
| Ex 18-16 | methyl 1-(5-(3-((2-(difluoromethoxy)-6-methylpyridin-3-yl)carbamoyl)-3-(2-isopropylphenyl)azetidin-1-yl)pyrimidin-2-yl)cyclopropane-1-carboxylate | D | [M + 1]$^+$ 552.23 $t_R$ 1.31 |
| Ex 18-17 | 1-(5-(3-((2-(difluoromethoxy)-6-methylpyridin-3-yl)carbamoyl)-3-(2-isopropylphenyl)azetidin-1-yl)pyrimidin-2-yl)cyclopropane-1-carboxylic acid | D | [M + 1]$^+$ 538.31 $t_R$ 1.32 |

TABLE 14-continued

Examples 18-4 to 18-33
Examples 18-4 to 18-33 are synthesized according to Method C or Method D
described for Ex 18-2 and Ex 18-3 respectively, starting from Ex 3 or Ex 7.

| Example | Name | Method | Analytics LCMS-1 |
|---|---|---|---|
| Ex 18-18 | N-(2-(difluoromethoxy)-6-methylpyridin-3-yl)-1-(4-fluoropyridin-2-yl)-3-(2-isopropylphenyl)azetidine-3-carboxamide | C | $[M + 1]^+$ 471.40 $t_R$ 1.34 |
| Ex 18-19 | N-(2-(difluoromethoxy)-6-methylpyridin-3-yl)-1-(3-fluoropyridin-4-yl)-3-(2-isopropylphenyl)azetidine-3-carboxamide | C | $[M + 1]^+$ 471.01 $t_R$ 0.84 |
| Ex 18-20 | N-(2-(difluoromethoxy)-6-methylpyridin-3-yl)-1-(5-fluoropyrimidin-4-yl)-3-(2-isopropylphenyl)azetidine-3-carboxamide | C | $[M + 1]^+$ 472.40 $t_R$ 1.25 |
| Ex 18-21 | N-(2-(difluoromethoxy)pyridin-3-yl)-1-(5-fluoropyrimidin-4-yl)-3-(2-isopropylphenyl)azetidine-3-carboxamide | C | $[M + 1]^+$ 457.98 $t_R$ 1.19 |
| Ex 18-22 | 1-(5-cyanopyridin-2-yl)-N-(2-(difluoromethoxy)-6-methylpyridin-3-yl)-3-(2-isopropylphenyl)azetidine-3-carboxamide | C | $[M + 1]^+$ 478.38 $t_R$ 1.35 |
| Ex 18-23 | 1-(5-cyanopyridin-2-yl)-N-(2-(difluoromethoxy)pyridin-3-yl)-3-(2-isopropylphenyl)azetidine-3-carboxamide | C | $[M + 1]^+$ 464.30 $t_R$ 1.29 |
| Ex 18-24 | 1-(5-cyanopyrimidin-2-yl)-N-(2-(difluoromethoxy)-6-methylpyridin-3-yl)-3-(2-isopropylphenyl)azetidine-3-carboxamide | C | $[M + 1]^+$ 479.16 $t_R$ 1.33 |
| Ex 17-25 | 1-(5-cyanopyrimidin-2-yl)-N-(2-(difluoromethoxy)pyridin-3-yl)-3-(2-isopropylphenyl)azetidine-3-carboxamide | C | $[M + 1]^+$ 465.00 $t_R$ 1.27 |
| Ex 18-26 | 1-(4-chloro-6-methylpyrimidin-2-yl)-N-(2-(difluoromethoxy)-6-methylpyridin-3-yl)-3-(2-isopropylphenyl)azetidine-3-carboxamide | C | $[M + 1]^+$ 502.00 $t_R$ 1.39 |
| Ex 18-27 | ethyl 2-(3-((2-(difluoromethoxy)-6-methylpyridin-3-yl)carbamoyl)-3-(2-isopropylphenyl)azetidin-1-yl)oxazole-4-carboxylate | C | $[M + 1]^+$ 515.46 $t_R$ 1.36 |
| Ex 18-28 | 2-(3-((2-(difluoromethoxy)-6-methylpyridin-3-yl)carbamoyl)-3-(2-isopropylphenyl)azetidin-1-yl)oxazole-4-carboxylic acid | C | $[M + 1]^+$ 487.08 $t_R$ 1.21 |
| Ex 18-29 | ethyl 2-(3-((2-(difluoromethoxy)pyridin-3-yl)carbamoyl)-3-(2-isopropylphenyl)azetidin-1-yl)oxazole-4-carboxylate | C | $[M + 1]^+$ 500.98 $t_R$ 1.29 |
| Ex 18-30 | 2-(3-((2-(difluoromethoxy)pyridin-3-yl)carbamoyl)-3-(2-isopropylphenyl)azetidin-1-yl)oxazole-4-carboxylic acid | C | $[M + 1]^+$ 473.21 $t_R$ 1.13 |
| Ex 18-31 | ethyl 2-(3-((2-(difluoromethoxy)-6-methylpyridin-3-yl)carbamoyl)-3-(2-isopropylphenyl)azetidin-1-yl)oxazole-5-carboxylate | C | $[M + 1]^+$ 515.13 $t_R$ 1.36 |
| Ex 18-32 | 2-(3-((2-(difluoromethoxy)-6-methylpyridin-3-yl)carbamoyl)-3-(2-isopropylphenyl)azetidin-1-yl)oxazole-5-carboxylic acid | C | $[M + 1]^+$ 487.01 $t_R$ 1.20 |
| Ex 18-33 | N-(2-(difluoromethoxy)-6-methylpyridin-3-yl)-1-(5-fluoropyrimidin-2-yl)-3-(2-isopropylphenyl)azetidine-3-carboxamide | C | $[M + 1]^+$ 471.99 $t_R$ 1.40 |

Example 18-34: N-(2-(difluoromethoxy)-6-methylpyridin-3-yl)-3-(2-isopropylphenyl)-1-(2-methylpyrimidin-4-yl)azetidine-3-carboxamide Ex 18-26 (65 mg, 0.129 mmol) is subjected to the hydrogenation conditions described for I-1.A to give N-(2-(difluoromethoxy)-6-methylpyridin-3-yl)-3-(2-isopropylphenyl)-1-(2-methylpyrimidin-4-yl)azetidine-3-carboxamide Ex 18-34 as a white solid (53 mg, 83% yield). LCMS-1: $t_R$=0.84 min, [M+1]$^+$468.38; $^1$H NMR (500 MHz, CDCl$_3$) δ: 8.56 (d, J=8.1 Hz, 1 H), 8.16 (d, J=5.9 Hz, 1 H), 7.47 (d, J=1.3 Hz, 2 H), 7.43-7.39 (m, 2 H), 7.32 (s, 1 H), 7.26 (t, $J_{HF}$=73.5 Hz 1 H), 6.93 (d, J=8.2 Hz, 1 H), 6.15 (d, J=5.9 Hz, 1 H), 5.00-4.76 (m, 2 H), 4.64-4.45 (m, 2 H), 2.55 (s, 3 H), 2.54-2.48 (m, 1 H), 2.39 (s, 3 H), 1.19 (d, J=6.7 Hz, 6 H).

Example 18-35: methyl 2-(3-((2-(difluoromethoxy)-6-methylpyridin-3-yl)carbamoyl)-3-(2-isopropylphenyl)azetidin-1-yl)-1-methyl-1H-imidazole-5-carboxylate and Example 18-36: 2-(3-((2-(difluoromethoxy)-6-methylpyridin-3-yl)carbamoyl)-3-(2-isopropylphenyl)azetidin-1-yl)-1-methyl-1H-imidazole-5-carboxylic acid Step 1. To a mixture of the Ex 3 hydrochloride (100 mg, 0.243 mol), 2-bromo-3-methyl-3H-imidazole-4-carboxylic acid methyl ester (56 mg, 0.243 mmol), DIPEA (83 uL, 0.486 mmol), 18-crown-6 (1.29 g, 4.86 mmol) and CsF (38 mg, 0.243 mmol) is heated to 120° C. overnight. The mixture is then evaporated and the residue is purified by prep. HPLC (Prep-HPLC-3 conditions) to give methyl 2-(3-((2-(difluoromethoxy)-6-methylpyridin-3-yl)carbamoyl)-3-(2-isopropylphenyl)azetidin-1-yl)-1-methyl-1H-imidazole-5-carboxylate Ex 18-35 (20 mg, 16%) as a yellow oil. LCMS-1: $t_R$=1.16 min, [M+1]$^+$514.19.

Step 2. Ex 18-35 (20 mg, 0.039 mmol) is saponified according to the methodology described for Ex 12-62 to give Ex 18-36 (13 mg, 68%) as white solid. LCMS-1: $t_R$=0.98 min, [M+1]$^+$500.00.

Example 19: N-(2-(difluoromethoxy)-6-methylpyridin-3-yl)-3-(2-isopropylphenyl)-1-(4-oxo-4,5-dihydrooxazol-2-yl)azetidine-3-carboxamide [tautomeric form: N-(2-(difluoromethoxy)-6-methylpyridin-3-yl)-3-(2-isopropylphenyl)-1-(4-hydroxy-oxazol-2-yl)azetidine-3-carboxamide]

To a solution of Ex 3 (80 mg, 0.21 mmol) in DCM (3 mL), chloroacetyl isocyanate (19 uL, 0.21 mmol) is added. The reaction mixture is stirred for 1 h at r.t. (The reaction progress is monitored by LCMS). The mixture is poured into water and is extracted with DCM (2×15 mL). The combined extracts are dried over MgSO$_4$, filtered and concentrated. The residue is dissolved in THF (4 mL) and DBU (72 uL, 0.48 mmol, 2 eq.) is added. The reaction mixture is stirred at r.t. for 1 h, is then poured into aq. 1N HCl and is extracted with EtOAc (2×20 mL). The combined extracts are dried over MgSO$_4$, filtered and concentrated. The crude product is then purified by prep. HPLC (Prep-HPLC-1 conditions) to give Ex 19 as a colorless oil (72 mg, 65% yield). LCMS-1: $t_R$=1.11 min, [M+1]$^+$459.21; $^1$H NMR (400 MHz, CDCl$_3$) δ:

8.55 (d, J=8.1 Hz, 1 H), 7.57-7.48 (m, 2 H), 7.44-7.39 (m, 1 H), 7.32 (d, J=7.8 Hz, 1 H), 7.27 (m, 2 H), 6.96 (d, J=8.1 Hz, 1 H), 5.10-4.89 (m, 2 H), 4.86-4.72 (m, 1 H), 4.67-4.53 (m, 3 H), 2.39 (s, 3 H), 2.34 (m, 1 H), 1.17 (dd, $J_1$=6.7 Hz, $J_2$=11.7 Hz, 6 H).

Example 20: N-(2-(difluoromethoxy)-6-methylpyridin-3-yl)-3-(2-isopropylphenyl)-1-(1H-tetrazol-5-yl)azetidine-3-carboxamide To a solution of Ex 11-6 (32 mg, 0.08 mmol) in DMF (2.5 mL) is added ammonium chloride (6.4 mg, 0.12 mmol) and sodium azide (7.8 mg, 0.12 mmol) at r.t. The mixture is then heated to 100° C. for 2 h. The reaction mixture is injected in prep. HPLC (Prep-HPLC-1 conditions) to afford the title compound Ex 20 as a white solid (24 mg, 68% yield). LCMS-1: $t_R$=1.12 min, [M+1]$^+$444.42; $^1$H NMR (400 MHz, CDCl$_3$) δ: 8.42 (d, J=8.1 Hz, 1 H), 7.40-7.27 (m, 4 H), 7.21-7.11 (m, 3 H), 6.77 (d, J=8.2 Hz, 1 H), 4.91-4.65 (m, 2 H), 4.58-4.35 (m, 2 H), 2.35-2.27 (m, 1 H), 2.26 (s, 3 H), 1.00 (d, J=6.4 Hz, 6 H).

Example 21: N-(2-(difluoromethoxy)-6-methylpyridin-3-yl)-1-(5-hydroxy-1,2,4-oxadiazol-3-yl)-3-(2-isopropylphenyl)azetidine-3-carboxamide [tautomeric form: N-(2-(difluoromethoxy)-6-methylpyridin-3-yl)-3-(2-isopropylphenyl)-1-(5-oxo-4,5-dihydro-1,2,4-oxadiazol-3-yl)azetidine-3-carboxamide]

To an ethanolic solution (1mL) of Ex 11-6 (41 mg, 0.102 mmol) is added hydroxylamine hydrochloride (11 mg, 0.158 mmol) and TEA (36 uL, 0.258 mmol). The reaction mixture is heated to 80° C. for 2 h. It is then cooled, concentrated in vacuo, dissolved in EtOAc, washed with water, dried over MgSO$_4$ and concentrated in vacuo again. The crude material is redissolved in MeCN (2 mL), and CDI (21 mg, 0.129 mmol) is added. The reaction mixture is heated to 60° C. for 2 h and is then cooled and concentrated. Purification by prep. HPLC (Prep-HPLC-3 conditions) afforded the title compound Ex 21 as a white solid (37 mg, 79% yield). LCMS-1: $t_R$=1.16 min, [M+1]$^+$460.04; $^1$H NMR (400 MHz, DMSO) δ: 12.19 (s, 1 H), 8.56 (s, 1 H), 7.92 (d, J=7.9 Hz, 1 H), 7.53 (d, $J_{H-F}$=72.5 Hz, 1 H), 7.48 (d, J=7.7 Hz, 1 H), 7.39-7.44 (m, 1 H), 7.34-7.38 (m, 1 H), 7.27-7.32 (m, 1 H), 7.12 (d, J=8.1 Hz, 1 H), 4.64 (d, J=8.0 Hz, 2 H), 4.40 (d, J=8.0 Hz, 2 H), 2.62-2.54 (m, 1 H), 2.38 (s, 3 H), 1.11 (d, J=6.7 Hz, 6 H).

Example 22: N-(2-(difluoromethoxy)-6-methylpyridin-3-yl)-1-((5-hydroxy-1,2,4-oxadiazol-3-yl)methyl)-3-(2-isopropylphenyl)azetidine-3-carboxamide [tautomeric form: N-(2-(difluoromethoxy)-6-methylpyridin-3-yl)-3-(2-isopropylphenyl)-1-((5-oxo-4,5-dihydro-1,2,4-oxadiazol-3-yl)methyl)azetidine-3-carboxamide]

The title compound Ex 22 is prepared from Ex 10-48 according to the method described for Ex 21. Yellow solid. LCMS-1: $t_R$=1.11 min, [M+1]$^+$474.34. $^1$H NMR (500 MHz, CDCl$_3$) δ: 8.53 (d, J=8.1 Hz, 1 H), 8.06 (s, 1 H), 7.40 (m, 2 H), 7.34 (t, J=72.6 Hz, 1 H), 7.30-7.34 (m, 1 H), 7.15 (d, J=7.6 Hz, 1 H), 6.94 (d, J=8.2 Hz, 1 H), 4.34-4.23 (m, 2 H), 3.87-3.70 (m, 2 H), 3.65 (s, 2 H), 2.52-2.44 (m, 1 H), 2.40 (s, 3 H), 1.15 (d, J=6.5 Hz, 6 H).

Example 23: 3-(2-cyclopropylphenyl)-N-(2-(difluoromethoxy)-6-methylpyridin-3-yl)azetidine-3-carboxamide 3-(2-cyclopropylphenyl)-N-(2-(difluoromethoxy)-6-methylpyridin-3-yl)azetidine-3-carboxamide Ex 23 is prepared from 1-benzhydryl-3-(2-bromophenyl)-N-(2-(difluoromethoxy)-6-methylpyridin-3-yl)azetidine-3-carboxamide and cyclopropylboronic acid pinacol ester according to the method described for Ex 1. Colorless oil. LCMS-1: $t_R$=0.71 min, [M+1]$^+$374.23. $^1$H NMR (500 MHz, CDCl$_3$) δ: 8.62 (d, J=8.1 Hz, 1 H), 8.57 (s, 1 H), 7.37 (t, J=72.9 Hz, 1 H), 7.31-7.29 (m, 2 H), 7.18 (dd, $J_1$=3.5 Hz, $J_2$=5.6 Hz, 1 H), 6.99 (dd, $J_1$=3.5 Hz, $J_2$=5.6 Hz, 1 H), 6.94 (d, J=8.1 Hz, 1 H), 4.37 (d, J=8.0 Hz, 2 H), 4.29 (d, J=8.0 Hz, 2 H), 2.40 (s, 3 H), 1.46 (m, 1 H), 0.89-0.86 (m, 2 H), 0.73-0.68 (m, 2 H)

Example 24: 3-(2-cyclobutylphenyl)-N-(2-(difluoromethoxy)-6-methylpyridin-3-yl)azetidine-3-carboxamide Step 1. To a solution of 1-benzhydryl-3-(2-bromophenyl)-N-(2-(difluoromethoxy)-6-methylpyridin-3-yl)azetidine-3-carboxamide (200 mg, 0.09 mmol) in THF (2 mL) degassed with argon is added (dppp) NiCl$_2$ (5.6 mg, 0.01 mmol). Cyclobutylzinc bromide 0.5M in THF (2.7 mL, 1.38 mmol) is then added dropwise at room temperature. The mixture is warmed up to 80° C. and stirred overnight. The mixture is then quenched with water and NaHCO$_3$ is added. The aqueous solution is extracted with EtOAc (2×60 mL). The organic extracts are dried over MgSO$_4$, filtered and evaporated. The residue is purified by prep. HPLC (Prep-HPLC-1 conditions) afforded 1-benzhydryl-3-(2-cyclobutylphenyl)-N-(2-(difluoromethoxy)-6-methylpyridin-3-yl)azetidine-3-carboxamide as a colorless oil (115 mg, 60% yield). LCMS-2: $t_R$=1.09 min, [M+1]$^+$554.36.

Step 2. 3-(2-cyclobutylphenyl)-N-(2-(difluoromethoxy)-6-methylpyridin-3-yl)azetidine-3-carboxamide Ex 24 is prepared from 1-benzhydryl-3-(2-cyclobutylphenyl)-N-(2-(difluoromethoxy)-6-methylpyridin-3-yl)azetidine-3-carboxamide according to the hydrogenation conditions described for Ex 1. Beige solid (10 mg, 73% yield). LCMS-1: $t_R$=0.74 min, [M+1]$^+$388.31.

Example 25: 3-(2-cyclopentylphenyl)-N-(2-(difluoromethoxy)-6-methylpyridin-3-yl)azetidine-3-carboxamide 1-Benzhydryl-3-(2-(cyclopent-1-en-1-yl)phenyl)-N-(2-(difluoromethoxy)-6-methylpyridin-3-yl)azetidine-3-carboxamide Ex 25 is prepared from 1-benzhydryl-3-(2-bromophenyl)-N-(2-(difluoromethoxy)-6-methylpyridin-3-yl)azetidine-3-carboxamide and cyclopenten-1-yl boronic acid according to the method described for Ex 1, Colorless oil. LCMS-1: $t_R$=0.78 min, [M+1]$^+$402.37.

Example 26: 3-(2-(cyclopent-1-en-1-yl)phenyl)-N-(2-(difluoromethoxy)-6-methylpyridin-3-yl)azetidine-3-carboxamide 1-benzhydryl-3-(2-(cyclopent-1-en-1-yl)phenyl)-N-(2-(difluoromethoxy)-6-methylpyridin-3-yl)azetidine-3-carboxamide (50 mg, 0.09 mmol), prepared according to the synthetical route described for Ex 1, is dissolved in 1,2-dichloroethane (2 mL). 1-Chloroethyl chloroformate (14 uL, 0.133 mmol) is added and the reaction mixture is stirred in a microwave (175 Watt) at 80° C. for 8 h (formation of 1-chloroethyl 3-(2-(cyclopent-1-en-1-yl)phenyl)-3-((2-(difluoromethoxy)-6-methylpyridin-3-yl)carbamoyl)azetidine-1-carboxylate intermediate monitored by LCMS). Then MeOH (1 mL) is added. The reaction mixture is stirred at 45° C. for 30 min and is then concentrated. The residue is purified by prep. HPLC (Prep-HPLC-1 conditions) to afford Ex 26 as a pale yellow oil (36 mg, 100% yield). LCMS-1: $t_R$=0.76 min, [M+1]$^+$400.35.

Example 27: 3-(2-cyclohexylphenyl)-N-(2-(difluoromethoxy)-6-methylpyridin-3-yl)azetidine-3-carboxamide 3-(2-Cyclohexylphenyl)-N-(2-(difluoromethoxy)-6-methylpyridin-3-yl)azetidine-3-carboxamide Ex 27 is prepared prepared from 1-benzhydryl-3-(2-bromophenyl)-N-(2-(difluoromethoxy)-6-methylpyridin-3-yl)azetidine-3-carboxamide and cyclohexeny-1-yl boronic acid according to the method described for Ex 1. Colorless oil. LCMS-1: $t_R$=0.82 min, [M+1]$^+$416.27. $^1$H NMR (400 MHz, CDCl$_3$) δ: 8.59 (d, J=8.1 Hz, 1 H), 8.14 (s, 1 H), 7.34 (t, J=72.8 Hz, 1 H), 7.41-7.35 (m, 2 H), 7.33-7.29 (m, 1 H), 7.17 (m, 1 H), 6.93 (d, J=8.1 Hz, 1 H), 4.32 (br s, 4 H), 2.40 (s, 3 H), 2.07-1.98 (m, 1 H), 1.78-1.71 (m, 2 H), 1.65-1.61 (m, 2 H), 1.47-1.38 (m, 2 H), 1.25-1.29 (m, 4 H).

Example 28: N-(2-(difluoromethoxy)-6-methylpyridin-3-yl)-3-(2-(tetrahydro-2H-pyran-4-yl)phenyl) azetidine-3-carboxamide N-(2-(difluoromethoxy)-6-methylpyridin-3-yl)-3-(2-(tetrahydro-2H-pyran-4-yl)phenyl)azetidine-3-carboxamide Ex 28 can be prepared from 1-benzhydryl-3-(2-bromophenyl)-N-(2-(difluoromethoxy)-6-methylpyridin-3-yl)azetidine-3-carboxamide and 3,6-dihydro-2H-pyran-4-boronic acid pinacol ester according to the method described for Ex 1. LCMS-1: $t_R$=0.62 min, [M+1]$^+$418.22.

Example 29: N-(2-(difluoromethoxy)-6-methylpyridin-3-yl)-3-(2-propylphenyl)azetidine-3-carboxamide N-(2-(difluoromethoxy)-6-methylpyridin-3-yl)-3-(2-propylphenyl)azetidine-3-carboxamide Ex 29 is prepared from the hydrogenation of Ex 23 according to the method described for Ex 1. LCMS-1: $t_R$=0.72 min, [M+1]$^+$376.10.

Example 30: N-(2-(difluoromethoxy)-6-methylpyridin-3-yl)-1-sulfamoyl-3-(2-(tetrahydro-2H-pyran-4-yl)phenyl)azetidine-3-carboxamide N-(2-(difluoromethoxy)-6-methylpyridin-3-yl)-1-sulfamoyl-3-(2-(tetrahydro-2H-pyran-4-yl)phenyl)azetidine-3-carboxamide Ex 30 is prepared from Ex 28 according to the method described for Ex 15-5. LCMS-1: $t_R$=1.00 min, [M+1]$^+$497.13.

TABLE 15

Examples 31-1 to 31-7
Examples 31-1 to 31-7 are synthesized using the methodology described for Ex 12-61 and Ex 12-62 starting from Ex 23, Ex 24, Ex 25, Ex 27, Ex 28, or Ex-29.

| Example | Name | Analytics LCMS-1 |
|---|---|---|
| Ex 31-1 | 4-(3-(2-cyclopropylphenyl)-3-((2-(difluoromethoxy)-6-methylpyridin-3-yl)carbamoyl)azetidin-1-yl)-2,2-dimethyl-4-oxobutanoic acid | [M + 1]$^+$ 502.04 $t_R$ 1.16 |
| Ex 31-2 | 4-(3-(2-cyclobutylphenyl)-3-((2-(difluoromethoxy)-6-methylpyridin-3-yl)carbamoyl)azetidin-1-yl)-2,2-dimethyl-4-oxobutanoic acid | [M + 1]$^+$ 516.00 $t_R$ 1.23 |
| Ex 31-3 | 4-(3-(2-cyclopentylphenyl)-3-((2-(difluoromethoxy)-6-methylpyridin-3-yl)carbamoyl)azetidin-1-yl)-2,2-dimethyl-4-oxobutanoic acid | [M + 1]$^+$ 530.03 $t_R$ 1.28 |
| Ex 31-4 | 4-(3-(2-(cyclopent-1-en-1-yl)phenyl)-3-((2-(difluoromethoxy)-6-methylpyridin-3-yl)carbamoyl)azetidin-1-yl)-2,2-dimethyl-4-oxobutanoic acid | [M + 1]$^+$ 528.00 $t_R$ 1.25 |
| Ex 31-5 | 4-(3-(2-cyclohexylphenyl)-3-((2-(difluoromethoxy)-6-methylpyridin-3-yl)carbamoyl)azetidin-1-yl)-2,2-dimethyl-4-oxobutanoic acid | [M + 1]$^+$ 544.39 $t_R$ 1.32 |
| Ex 31-6 | 4-(3-((2-(difluoromethoxy)-6-methylpyridin-3-yl)carbamoyl)-3-(2-(tetrahydro-2H-pyran-4-yl)phenyl)azetidin-1-yl)-2,2-dimethyl-4-oxobutanoic acid | [M + 1]$^+$ 546.12 $t_R$ 1.06 |
| Ex 31-7 | 4-(3-((2-(difluoromethoxy)-6-methylpyridin-3-yl)carbamoyl)-3-(2-propylphenyl)azetidin-1-yl)-2,2-dimethyl-4-oxobutanoic acid | [M + 1]$^+$ 504.13 $t_R$ 1.21 |

Example 32: 2-(3-((2-(difluoromethoxy)-6-methylpyridin-3-yl)carbamoyl)-3-(2-(tetrahydro-2H-pyran-4-yl)phenyl)azetidin-1-yl)oxazole-4-carboxylic acid 2-(3-((2-(Difluoromethoxy)-6-methylpyridin-3-yl)carbamoyl)-3-(2-(tetrahydro-2H-pyran-4-yl)phenyl)azetidin-1-yl)oxazole-4-carboxylic acid Ex 32 is prepared from Ex 28 following the methodology described for Ex 18-28 (beige solid). LCMS-1: $t_R$=1.06 min, [M+1]$^+$528.98.

Example 33: N-(2-(difluoromethoxy)-6-methylpyridin-3-yl)-3-(2-isopropyl-6-methylphenyl)azetidine-3-carboxamide N-(2-(difluoromethoxy)-6-methylpyridin-3-yl)-3-(2-isopropyl-6-methylphenyl)azetidine-3-carboxamide Ex 33 is prepared from 2-(difluoromethoxy)-6-methylpyridin-3- amine I-1.C and intermediate I-7 following the methodology described for Ex 1 (colorless oil). LCMS-1: $t_R$=0.73 min, [M+1]$^+$390.35.

Example 34: N-(2-(difluoromethoxy)-6-methylpyridin-3-yl)-3-(2-isopropyl-5-methylphenyl)azetidine-3-carboxamide N-(2-(difluoromethoxy)-6-methylpyridin-3-yl)-3-(2-isopropyl-5-methylphenyl)azetidine-3-carboxamide Ex 34 is prepared from 2-(difluoromethoxy)-6-methylpyridin-3-amine I-1.C and intermediate I-8 following the methodology described for Ex 1 (colorless oil). LCMS-1: $t_R$=0.77 min, [M+1]$^+$390.02; $^1$H NMR (500 MHz, CDCl$_3$) δ: 8.60 (d, J=8.1 Hz, 1 H), 8.12 (s, 1 H), 7.33 (t, J=72.8 Hz, 1 H), 7.28 (d, J=8.0 Hz, 1 H), 7.22 (d, J=8.1 Hz, 1 H), 6.96 (s, 1 H), 6.93 (d, J=8.1 Hz, 1 H), 4.34 (m, 4 H), 2.45-2.33 (m, 7 H), 1.13 (d, J=6.6 Hz, 6 H).

Example 35: N-(2-(difluoromethoxy)-6-methylpyridin-3-yl)-3-(2-isopropyl-4-methylphenyl)azetidine-3-carboxamide N-(2-(difluoromethoxy)-6-methylpyridin-3-yl)-3-(2-isopropyl-4-methylphenyl)azetidine-3-carboxamide Ex 35 is prepared from 2-(difluoromethoxy)-6-methylpyridin-3-amine I-1.C and intermediate I-9 following the methodology described for Ex 1 (colorless oil). LCMS-1: $t_R$=0.77 min, [M+1]$^+$389.97.

Example 36: N-(2-(difluoromethoxy)-6-methylpyridin-3-yl)-3-(2-fluoro-6-isopropylphenyl)azetidine-3-carboxamide N-(2-(difluoromethoxy)-6-methylpyridin-3-yl)-3-(2-fluoro-6-isopropylphenyl)azetidine-3-carboxamide Ex 36 is prepared from 2-(difluoromethoxy)-6-methylpyridin-3-amine I-1.C and intermediate I-10 following the methodology described for Ex 1 (white solid). LCMS-1: $t_R$=0.71 min, [M+1]$^+$394.14.

Example 37: N-(2-(difluoromethoxy)-6-methylpyridin-3-yl)-3-(5-fluoro-2-isopropylphenyl)azetidine-3-carboxamide N-(2-(difluoromethoxy)-6-methylpyridin-3-yl)-3-(5-fluoro-2-isopropylphenyl)azetidine-3-carboxamide Ex 37 is prepared from 2-(difluoromethoxy)-6-methylpyridin-3-amine I-1.C and intermediate I-11 following the methodology described for Ex 1. LCMS-1: $t_R$=0.73 min, [M+1]$^+$ 394.32.

Example 38: N-(2-(difluoromethoxy)-6-methylpyridin-3-yl)-3-(2-isopropyl-5-methoxyphenyl)azetidine-3-carboxamide N-(2-(difluoromethoxy)-6-methylpyridin-3-yl)-3-(2-isopropyl-5-methoxyphenyl)azetidine-3-carboxamide Ex 38 is prepared from 2-(difluoromethoxy)-6-methylpyridin-3-amine I-1.C and intermediate I-12 following the methodology described for Ex 1. LCMS-1: $t_R$=0.74 min, [M+1]$^+$ 406.35.

TABLE 16

Examples 39-1 to 39-6
Examples 39-1 to 39-6 are synthesized using the methodology described for Ex 12-61 and Ex 12-62 starting from Ex 33, Ex 34, Ex 35, Ex 36, Ex 37, or Ex 38.

| Example | Name | Analytics LCMS-1 |
|---|---|---|
| Ex 39-1 | 4-(3-((2-(difluoromethoxy)-6-methylpyridin-3-yl)carbamoyl)-3-(2-isopropyl-6-methylphenyl)azetidin-1-yl)-2,2-dimethyl-4-oxobutanoic acid | [M + 1]$^+$ 518.05 $t_R$ 1.26 |
| Ex 39-2 | 4-(3-((2-(difluoromethoxy)-6-methylpyridin-3-yl)carbamoyl)-3-(2-isopropyl-5-methylphenyl)azetidin-1-yl)-2,2-dimethyl-4-oxobutanoic acid | [M + 1]$^+$ 518.06 $t_R$ 1.26 |
| Ex 39-3 | 4-(3-((2-(difluoromethoxy)-6-methylpyridin-3-yl)carbamoyl)-3-(2-isopropyl-4-methylphenyl)azetidin-1-yl)-2,2-dimethyl-4-oxobutanoic acid | [M + 1]$^+$ 518.23 $t_R$ 1.23 |
| Ex 39-4 | 4-(3-((2-(difluoromethoxy)-6-methylpyridin-3-yl)carbamoyl)-3-(2-fluoro-6-isopropylphenyl)azetidin-1-yl)-2,2-dimethyl-4-oxobutanoic acid | [M + 1]$^+$ 522.18 $t_R$ 1.20 |
| Ex 39-5 | 4-(3-((2-(difluoromethoxy)-6-methylpyridin-3-yl)carbamoyl)-3-(5-fluoro-2-isopropylphenyl)azetidin-1-yl)-2,2-dimethyl-4-oxobutanoic acid | [M + 1]$^+$ 522.00 $t_R$ 1.20 |
| Ex 39-6 | 4-(3-((2-(difluoromethoxy)-6-methylpyridin-3-yl)carbamoyl)-3-(2-isopropyl-5-methoxyphenyl)azetidin-1-yl)-2,2-dimethyl-4-oxobutanoic acid | [M + 1]$^+$ 534.01 $t_R$ 1.21 |

Example 40: 2-(2-(3-((2-(difluoromethoxy)-6-methylpyridin-3-yl)carbamoyl)-3-(2-isopropylphenyl)azetidin-1-yl)ethoxy)-2-methylpropanoic acid 2-(2-(3-((2-(difluoromethoxy)-6-methylpyridin-3-yl)carbamoyl)-3-(2-isopropylphenyl)azetidin-1-yl)ethoxy)-2-methylpropanoic acid Ex 40 is prepared from Ex 3 and methyl 2-methyl-2-(2-oxoethoxy)propanoate (preparation in WO2017177004), according to a reductive amination as described for Ex 11-17. The methyl ester group is then hydrolyzed under basic conditions using LiOH 2N. LCMS-1: $t_R$=0.84 min, [M+1]$^+$516.12.

Example 41: 4-((3-((2-(difluoromethoxy)-6-methylpyridin-3-yl)carbamoyl)-3-(2-isopropylphenyl)azetidin-1-yl)methyl)cyclohexane-1-carboxylic acid 4-((3-((2-(difluoromethoxy)-6-methylpyridin-3-yl)carbamoyl)-3-(2-isopropylphenyl)azetidin-1-yl)methyl)cyclohexane-1-carboxylic acid Ex 41 is prepared from Ex 3 and commercially available 4-formyl-cylohexanecarboxylic acid ethyl ester, according to a reductive amination as described for Ex 11-17. The ethyl ester group is then hydrolyzed under basic conditions using LiOH 2N. LCMS-1: $t_R$=0.82 min, [M+1]$^+$516.30.

Examples 42 to 48 are synthesized using the methodology described for Ex 12-142.

| Example | Name | Analytics LCMS-1 |
|---|---|---|
| Ex 42 | N-(2-(3-((2-(difluoromethoxy)-6-methylpyridin-3-yl)carbamoyl)-3-(2-isopropylphenyl)azetidin-1-yl)-2-oxoethyl)-N-propylglycine | [M + 1]$^+$ 533.33 $t_R$ 0.99 |
| Ex 43 | N-cyclopropyl-N-(2-(3-((2-(difluoromethoxy)-6-methylpyridin-3-yl)carbamoyl)-3-(2-isopropylphenyl)azetidin-1-yl)-2-oxoethyl)glycine | [M + 1]$^+$ 531.31 $t_R$ 1.15 |
| Ex 44 | 3-((2-(3-((2-(difluoromethoxy)-6-methylpyridin-3-yl)carbamoyl)-3-(2-isopropylphenyl)azetidin-1-yl)-2-oxoethyl)amino)propanoic acid | [M + 1]$^+$ 505.31 $t_R$ 0.80 |
| Ex 45 | 3-((2-(3-((2-(difluoromethoxy)-6-methylpyridin-3-yl)carbamoyl)-3-(2-isopropylphenyl)azetidin-1-yl)-2-oxoethyl)amino)-2,2-dimethylpropanoic acid | [M + 1]$^+$ 533.07 $t_R$ 0.88 |
| Ex 46 | 1-(((2-(3-((2-(difluoromethoxy)-6-methylpyridin-3-yl)carbamoyl)-3-(2-isopropylphenyl)azetidin-1-yl)-2-oxoethyl)amino)methyl)cyclopropane-1-carboxylic acid | [M + 1]$^+$ 530.96 $t_R$ 0.83 |
| Ex 47 | 3-((2-(3-((2-(difluoromethoxy)-6-methylpyridin-3-yl)carbamoyl)-3-(2-isopropylphenyl)azetidin-1-yl)-2-oxoethyl)amino)-3-methylbutanoic acid | [M + 1]$^+$ 533.33 $t_R$ 0.89 |
| Ex 48 | 1-(2-(3-((2-(difluoromethoxy)-6-methylpyridin-3-yl)carbamoyl)-3-(2-isopropylphenyl)azetidin-1-yl)-2-oxoethyl)piperidine-4-carboxylic acid | [M + 1]$^+$ 545.32 $t_R$ 0.80 |

Example 49: (R)-2-amino-5-(3-((2-(difluoromethoxy)-6-methylpyridin-3-yl)carbamoyl)-3-(2-isopropylphenyl)azetidin-1-yl)-5-oxopentanoic acid (R)-2-amino-5-(3-((2-(difluoromethoxy)-6-methylpyridin-3-yl)carbamoyl)-3-(2-isopropylphenyl)azetidin-1-yl)-5-oxopentanoic acid Ex 49 (51 mg, beige solid) is prepared from Ex 3 and commercially available Boc-D-Glu-OtBu following the methodology described for Ex 12-63 to 12-114. LCMS-1: $t_R$=0.89 min, [M+1]$^+$487.08.

Examples 50 to 52

Examples 50-52 are synthesized using the methodology described for Ex 12-62 starting from Ex 3.

| Example | Name | Analytics LCMS-1 |
|---|---|---|
| Ex 50 | (1s,4s)-4-(3-((2-(difluoromethoxy)-6-methylpyridin-3-yl)carbamoyl)-3-(2-isopropylphenyl)azetidine-1-carbonyl)cyclohexane-1-carboxylic acid | [M + 1]$^+$ 530.11 $t_R$ 1.22 |
| Ex 51 | (1S,3R)-3-(3-((2-(difluoromethoxy)-6-methylpyridin-3-yl)carbamoyl)-3-(2-isopropylphenyl)azetidine-1-carbonyl)cyclohexane-1-carboxylic acid | [M + 1]$^+$ 529.97 $t_R$ 1.19 |
| Ex 52 | 4-(2-(3-((2-(difluoromethoxy)-6-methylpyridin-3-yl)carbamoyl)-3-(2-isopropylphenyl)azetidin-1-yl)-2-oxoethyl)cyclohexane-1-carboxylic acid | [M + 1]$^+$ 543.97 $t_R$ 1.20 |

Example 53: N-(2-(difluoromethoxy)-6-methylpyridin-3-yl)-1-(3,3-dimethyl-4-(methylsulfonamido)-4-oxobutyl)-3-(2-isopropylphenyl)azetidine-3-carboxamide N-(2-(difluoromethoxy)-6-methylpyridin-3-yl)-1-(3,3-dimethyl-4-(methylsulfonamido)-4-oxobutyl)-3-(2-isopropylphenyl)azetidine-3-carboxamide Ex 53 is prepared by reacting Ex 11-31 (20 mg, 0.038 mmol) with DCC (10 mg, 0.049 mmol) and methanesulfonamide (14 mg, 0.15 mmol) in DCM (5 mL), in the presence of DMAP (6.5 mg, 0.053 mmol). White solid (10 mg, 45% yield). LCMS-1: $t_R$=0.84 min, $[M+1]^+$567.08.

TABLE 17

Examples 54 to 58

Examples 54 to 58 are prepared according to the methodology described for Ex 12-142 using bromoacetyl bromide, an amino carboxylic ester and Ex 3. Alternatively this type of derivatives can be prepared from [(t-butoxycarbonyl)amino]acetic acid and Ex 3, followed by Boc deprotection and nucleophilic substitution on methyl bromoacetate. The complete side chain could also be assembled before coupling with Ex 3. For example, N-ethyl-N-(2-methoxy-2-oxoethyl)glycine is prepared from commercially available N-(tert-butoxycarbonyl)-N-ethylglycine which is reacted with benzyl bromide, followed by nucleophilic substitution on methyl bromoacetate and hydrogenation: $^1$H NMR (400 MHz, CDCl$_3$) δ: 9.43-9.02 (s br, 1 H), 3.79 (s, 3 H), 3.67 (s, 2 H), 3.51 (s, 2 H), 2.95 (q, J = 7.2 Hz, 2 H), 1.19 (t, J = 7.2 Hz, 3 H).

| Example | Name | Analytics LCMS-1 |
|---|---|---|
| Ex 54 | methyl N-(2-(3-((2-(difluoromethoxy)-6-methylpyridin-3-yl)carbamoyl)-3-(2-isopropylphenyl)azetidin-1-yl)-2-oxoethyl)-N-(2-methoxyethyl)glycinate | $[M + 1]^+$ 563.43 $t_R$ 1.14 |
| Ex 55 | (N-(2-(3-((2-(difluoromethoxy)-6-methylpyridin-3-yl)carbamoyl)-3-(2-isopropylphenyl)azetidin-1-yl)-2-oxoethyl)-N-(2-methoxyethyl)glycine | $[M + 1]^+$549.37 $t_R$ 0.97 |
| Ex 56 | methyl (2-(3-((2-(difluoromethoxy)-6-methylpyridin-3-yl)carbamoyl)-3-(2-isopropylphenyl)azetidin-1-yl)-2-oxoethyl)glycinate | $[M + 1]^+$ 505,34 $t_R$ 0.82 |
| Ex 57 | (2-(3-((2-(difluoromethoxy)-6-methylpyridin-3-yl)carbamoyl)-3-(2-isopropylphenyl)azetidin-1-yl)-2-oxoethyl)glycine | $[M + 1]^+$ 491.33 $t_R$ 0.89 |
| Ex 58 | N-(2-(3-((2-(difluoromethoxy)-6-methylpyridin-3-yl)carbamoyl)-3-(2-isopropylphenyl)azetidin-1-yl)-2-oxoethyl)-N-ethylglycine | $[M + 1]^+$ 519.38 $t_R$ 0.94 |

Example 59: 3-(2-isopropylphenyl)-N-(6-methyl-2-propoxypyridin-3-yl)-1-sulfamoylazetidine-3-carboxamide 1) 3-(2-isopropylphenyl)-N-(6-methyl-2-propoxypyridin-3-yl)azetidine-3-carboxamide is prepared from commercially available 6-methyl-2-propoxypyridin-3-amine I-1.D (73 mg) and I-6 (70 mg) using the POCl$_3$ methodology described for Ex 4 (36 mg, yellow oil). LCMS-1: $t_R$=1.29 min, $[M+1]^+$447.33. 6-Methyl-2-propoxypyridin-3-amine I-1.D is synthesized using the methodology described for I-1.A starting from commercially available 2-fluoro-6-methyl-3-nitropyridine and n-propanol. $^1$H NMR (400 MHz, CDCl$_3$) δ: 6.87 (d, J=7.5 Hz, 1 H), 6.56 (d, J=7.5 Hz, 1 H), 4.34 (s, 2 H), 2.38 (s, 3 H), 1.84 (d, J=7.2 Hz, 2 H), 1.06 (s, 3 H).

2) 3-(2-isopropylphenyl)-N-(6-methyl-2-propoxypyridin-3-yl)-1-sulfamoylazetidine-3-carboxamide Ex 59 is prepared from 3-(2-isopropylphenyl)-N-(6-methyl-2-propoxypyridin-3-yl)azetidine-3-carboxamide according to the method described for Ex 15-5. LCMS-1: $t_R$=1.29 min, $[M+1]^+$447.33.

Intermediate I-19: 5-chloro-3-(difluoromethoxy)pyridin-2-amine 3-(Difluoromethoxy)pyridin-2-amine (500 mg, 2.97 mmol) is dissolved in DMF (8 mL). N-Chlorosuccinimide (485 mg, 3.56 mmol) is added and the mixture is stirred at 80° C. for 2 h (reaction monitored by LCMS). Water is added, and the compound is extracted with EtOAc. The organic phase is dried over MgSO$_4$, filtered and evaporated. The residue is purified by Prep-HPLC-2. The HPLC fractions are extracted with DCM (3×50 mL) and the collected organic layers are dried over MgSO$_4$, filtered and evaporated to give the title compound I-19 as a brown solid (424 mg, 73% yield). $^1$H NMR (400 MHz, DMSO d6) δ: 7.85 (s, 1 H), 7.45 (s, 1 H), 7.17 (t, J=73.4 Hz, 1 H), 6.34 (s br, 2 H).

Intermediate I-20: 1-(tert-butoxycarbonyl)-3-(2-cyclopentylphenyl)azetidine-3-carboxylic acid 1-Boc-3-(2-cyclopentylphenyl)azetidine-3-carboxylic acid I-20 is prepared in analogy to I-6 starting from 1-benzhydryl-3-(2-bromophenyl)azetidine-3-carbonitrile and cyclopenten-1-ylboronic acid. $^1$H NMR (400 MHz, DMSO d6) δ: 13.15-12.90 (s br, 1 H), 7.33 (d, J=7.6 Hz, 1 H), 7.30-7.24 (m, 1 H), 7.22 (d, J=7.6 Hz, 1 H), 7.20-7.14 (m, 1 H), 4.42 (d, J=7.9 Hz, 2 H), 4.21 (d, J=7.9 Hz, 2 H), 2.63-2.53 (m, 1 H), 1.98-1.89 (m, 2 H), 1.83-1.74 (m, 2 H), 1.65-1.59 (m, 2 H), 1.52-1.45 (m, 2 H), 1.39 (s, 9 H).

Intermediate I-21: 3-(3-bromopyridin-2-yl)-1-(tert-butoxycarbonyl)azetidine-3-carboxylic acid 3-(3-bromopyridin-2-yl)-1-Boc-azetidine-3-carboxylic acid I-21 is prepared in analogy to the procedure described for I-6 starting from ethyl 1-Boc-3-cyanoazetidine and 3-bromo-2-fluoropyridine. $^1$H NMR (400 MHz, DMSO d6) δ: 8.45 (dd, $J_1$=1.4 Hz, $J_2$=4.7 Hz, 1 H), 7.91 (dd, $J_1$=1.4 Hz, $J_2$=7.9 Hz, 1 H), 7.14 (dd, $J_1$=4.7 Hz, $J_2$=7.9 Hz, 1 H), 4.31-4.16 (m, 4 H), 1.37 (s, 9 H).

Intermediate I-22: 1-(tert-butoxycarbonyl)-3-(6-fluoro-3-isopropylpyridin-2-yl)azetidine-3-carboxylic acid 1-Boc-3-(6-fluoro-3-isopropylpyridin-2-yl)azetidine-3-carboxylic acid I-22 is prepared in analogy to I-6 starting from ethyl 1-Boc-azetidine-3-carboxylate and 3-bromo-2,6-difluoropyridine. $^1$H NMR (400 MHz, DMSO d6) δ: 8.02 (t, J=8.3 Hz, 1 H), 7.15 (dd, $J_1$=2.5 Hz, $J_2$=8.8 Hz, 1H), 4.42-4.27 (m, 4 H), 2.48-2.42 (m, 1 H), 1.39 (s, 9 H), 1.14 (d, J=6.6 Hz, 6 H).

Intermediate I-23: 3-(3-bromopyridin-2-yl)-1-(tert-butoxycarbonyl)azetidine-3-carboxylic acid 3-(3-Bromopyridin-2-yl)-1-Boc-azetidine-3-carboxylic acid I-23 is prepared in analogy to the procedure described for I-6 starting from ethyl 1-Boc-3-cyanoazetidine and 3-chloro-4-cyanopyridine. $^1$H NMR (400 MHz, DMSO d6) δ: 8.42 (s, 1 H), 8.38 (d, J=4.9 Hz, 1 H), 7.33 (d, J=4.9 Hz, 1 H), 4.44-4.19 (m, 4 H), 1.37 (s, 9 H).

Intermediate I-24: 1-benzyl-4-(2-bromopyridin-3-yl)piperidine-4-carboxylic acid 1-benzyl-4-(2-bromopyridin-3-yl)piperidine-4-carboxylic acid I-24 was prepared according to the procedure described for intermediate I-4. LCMS-2: $t_R$=0.55 min, [M+1]$^+$374.99 and 377.06.

Intermediate I-25: 1-(tert-butoxycarbonyl)-4-(4-chloropyridin-3-yl)piperidine-4-carboxylic acid 1-Boc-4-(4-chloropyridin-3-yl)piperidine-4-carboxylic acid I-25 is prepared according to the procedure described in WO2009051715 starting from tert-butyl bis(2-chloroethyl)carbamate and 2-(4-chloropyridin-3-yl)acetonitrile (Synthesis 1992, 6, 528-30).

Intermediate I-26: 1-(tert-butoxycarbonyl)-3-(3-chloropyrazin-2-yl)azetidine-3-carboxylic acid 1-Boc-3-(3-chloropyrazin-2-yl)azetidine-3-carboxylic acid I-26 is prepared in analogy to procedure described for I-6 starting from ethyl 1-Boc-3-cyanoazetidine and 2,3-dichloropyrazine. $^1$H NMR (400 MHz, DMSO d6) δ: 8.70 (d, J=2.5 Hz, 1 H), 8.52 (d, J=2.5 Hz, 1 H), 4.49 (d, J=8.6 Hz, 2 H), 4.41-4.25 (m, 2 H), 1.37 (s, 9 H).

Intermediate I-27: 4-(5-bromopyrimidin-4-yl)-1-(tert-butoxycarbonyl)piperidine-4-carboxylic acid 4-(5-Bromopyrimidin-4-yl)-1-Boc-piperidine-4-carboxylic acid I-27 is prepared in analogy to the procedure described in WO2009051715 starting from tert-butyl bis(2-chloroethyl)carbamate and 2-(5-chloropyrimidin-4-yl)acetonitrile.

Intermediate I-28: 4-(4-bromopyrimidin-5-yl)-1-(tert-butoxycarbonyl)piperidine-4-carboxylic acid 4-(4-Bromopyrimidin-5-yl)-1-Boc-piperidine-4-carboxylic acid I-28 is prepared in analogy to the procedure described in WO2009051715 starting from tert-butyl bis(2-chloroethyl)carbamate and 2-(4-bromopyrimidin-5-yl)acetonitrile. 2-(4-Bromopyrimidin-5-yl)acetonitrile is synthesized by nucleophilic substitution of sodium cyanide on 4-bromo-5-(bromomethyl)pyrimidine.

Example 60: N-(2-(difluoromethoxy)-6-methylpyridin-3-yl)-3-(3-isopropylpyridin-2-yl)azetidine-3-carboxamide N-(2-(Difluoromethoxy)-6-methylpyridin-3-yl)-3-(3-isopropylpyridin-2-yl)azetidine-3-carboxamide Ex 60 is prepared from I-1.C and I-21 under POCl$_3$/Pyr/DMF conditions followed by Suzuki coupling of isopropenyl boronic acid pinacolester, hydrogenation and finally Boc deprotection with TFA. LCMS-1: $t_R$=0.67 min, [M+1]$^+$377.27.

Example 61: 4-(3-((2-(difluoromethoxy)-6-methylpyridin-3-yl)carbamoyl)-3-(3-isopropylpyridin-2-yl)azetidin-1-yl)-4-oxobutanoic acid 4-(3-((2-(Difluoromethoxy)-6-methylpyridin-3-yl)carbamoyl)-3-(3-isopropylpyridin-2-yl)azetidin-1-yl)-4-oxobutanoic acid Ex 61 is prepared from Ex 60 according to the method described for Ex 12-62. LCMS-1: $t_R$=1.02 min, [M+1]$^+$477.34.

Example 62: N-(2-(difluoromethoxy)-6-methylpyridin-3-yl)-3-(3-isopropylpyridin-2-yl)-1-sulfamoylazetidine-3-carboxamide N-(2-(Difluoromethoxy)-6-methylpyridin-3-yl)-3-(3-isopropylpyridin-2-yl)-1-sulfamoylazetidine-3-carboxamide Ex 62 is prepared from Ex 60 according to the method described for Ex 15-5. LCMS-1: $t_R$=1.08 min, [M+1]$^+$ 456.28.

Example 63: N1-cyclopropyl-N3-(2-(difluoromethoxy)-6-methylpyridin-3-yl)-3-(3-isopropylpyridin-2-yl)azetidine-1,3-dicarboxamide N1-Cyclopropyl-N3-(2-(difluoromethoxy)-6-methylpyridin-3-yl)-3-(3-isopropylpyridin-2-yl)azetidine-1,3-dicarboxamide Ex 63 is prepared from Ex 60 according to the method described for Ex 17-2. LCMS-1: $t_R$=1.09 min, [M+1]$^+$460.36.

TABLE 18

Examples 64 and 65
Examples 64 and 65 are prepared from Ex 60 and 4-chloro-5-fluoro-2-methylpyrimidine or 2-chloro-3-fluoro-6-picoline according to the methodology C described for Ex 18-2.

| Example | Name | Analytics LCMS-1 |
| --- | --- | --- |
| Ex 64 | N-(2-(difluoromethoxy)-6-methylpyridin-3-yl)-1-(5-fluoro-2-methylpyrimidin-4-yl)-3-(3-isopropylpyridin-2-yl)azetidine-3-carboxamide | [M + 1]$^+$ 487.33 $t_R$ 1.00 |
| Ex 65 | N-(2-(difluoromethoxy)-6-methylpyridin-3-yl)-1-(3-fluoro-6-methylpyridin-2-yl)-3-(3-isopropylpyridin-2-yl)azetidine-3-carboxamide | [M + 1]$^+$ 486.32 $t_R$ 1.42 |

Example 66: N-(2-(difluoromethoxy)-6-methylpyridin-3-yl)-3-(3-isopropylpyridin-4-yl)azetidine-3-carboxamide N-(2-(Difluoromethoxy)-6-methylpyridin-3-yl)-3-(3-isopropylpyridin-4-yl)azetidine-3-carboxamide Ex 66 is prepared from I-1.C and I-24 under POCl$_3$/Pyr/DMF conditions followed by Suzuki coupling of isopropenyl boronic acid pinacolester, hydrogenation and finally Boc deprotection with TFA. LCMS-1: $t_R$=0.50 min, [M+1]$^+$377.28.

Example 67: N-(2-(difluoromethoxy)-6-methylpyridin-3-yl)-3-(3-isopropylpyridin-4-yl)-1-sulfamoylazetidine-3-carboxamide N-(2-(Difluoromethoxy)-6-methylpyridin-3-yl)-3-(3-isopropylpyridin-4-yl)-1-sulfamoylazetidine-3-carboxamide Ex 67 is prepared from Ex 66 according to the method described for Ex 15-5. LCMS-1: $t_R$=0.73 min, [M+1]$^+$ 456.27.

Example 68: N-(2-(difluoromethoxy)-6-methylpyridin-3-yl)-3-(3-isopropylpyrazin-2-yl)azetidine-3-carboxamide N-(2-(Difluoromethoxy)-6-methylpyridin-3-yl)-3-(3-isopropylpyrazin-2-yl)azetidine-3-carboxamide Ex 68 is prepared from I-1.C and I-26 under POCl$_3$/Pyr/DMF conditions followed by Suzuki coupling of isopropenyl boronic acid pinacolester, hydrogenation and finally Boc deprotection with TFA. LCMS-1: $t_R$=0.60 min, [M+1]$^+$378.29.

Example 69: N-(2-(difluoromethoxy)-6-methylpyridin-3-yl)-3-(3-isopropylpyrazin-2-yl)-1-sulfamoylazetidine-3-carboxamide N-(2-(Difluoromethoxy)-6-methylpyridin-3-yl)-3-(3-isopropylpyrazin-2-yl)-1-sulfamoylazetidine-3-carboxamide Ex 69 is prepared from Ex 68 according to the method described for Ex 15-5. LCMS-1: $t_R$=1.00 min, [M+1]$^+$ 457.27.

TABLE 19

Examples 70 to 77:
Examples 70 to 77 are prepared from commercially available or synthesized 3-alkoxy-pyridin-2-amines and intermediates I-6, I-20 or I-21 using the POCl$_3$ methodology described for Ex 4. In case I-21 is used, the Suzuki/Hydrogenation sequence is performed to introduce the iPr unit after the amide coupling.

| Example | Name | Analytics LCMS-1 |
| --- | --- | --- |
| Ex 70 | N-(5-chloro-3-methoxypyridin-2-yl)-3-(2-isopropylphenyl)azetidine-3-carboxamide | [M + 1]$^+$ 361.23 $t_R$ 0.63 |
| Ex 71 | N-(5-bromo-3-methoxypyridin-2-yl)-3-(2-isopropylphenyl)azetidine-3-carboxamide | [M + 1]$^+$ 404.25 and 406.23 $t_R$ 0.65 |
| Ex 72 | N-(5-chloro-3-(difluoromethoxy)pyridin-2-yl)-3-(2-isopropylphenyl)azetidine-3-carboxamide | [M + 1]$^+$ 396.25 $t_R$ 0.68 |
| Ex 73 | N-(5-bromo-3-(difluoromethoxy)pyridin-2-yl)-3-(2-isopropylphenyl)azetidine-3-carboxamide | [M + 1]$^+$ 440.21 and 442.21 $t_R$ 0.69 |
| Ex 74 | N-(3-(difluoromethoxy)-5-methylpyridin-2-yl)-3-(2-isopropylphenyl)azetidine-3-carboxamide | [M + 1]$^+$ 376.29 $t_R$ 0.64 |
| Ex 75 | N-(3,5-dimethoxypyridin-2-yl)-3-(2-isopropylphenyl)azetidine-3-carboxamide | [M + 1]$^+$ 356.27 $t_R$ 0.64 |
| Ex 76 | N-(5-chloro-3-(difluoromethoxy)pyridin-2-yl)-3-(2-cyclopentylphenyl)azetidine-3-carboxamide | [M + 1]$^+$ 422.27 $t_R$ 0.76 |
| Ex 77 | N-(5-chloro-3-(difluoromethoxy)pyridin-2-yl)-3-(3-isopropylpyridin-2-yl)azetidine-3-carboxamide | [M + 1]$^+$ 397.23 $t_R$ 0.62 |

TABLE 20

Examples 78-1 to 78-3:
Examples 78-1 to 78-3 are synthesized by reductive amination as described for example Ex 11-17 starting from Ex 72 or Ex 73. Functional groups, such as acid or alcohol, may be protected with an appropriate protecting group. For example, esters are saponified by 2N LiOH after the reductive amination step.

| Example | Name | Analytics LCMS-1 |
| --- | --- | --- |
| Ex 78-1 | methyl 4-(3-((5-chloro-3-(difluoromethoxy)pyridin-2-yl)carbamoyl)-3-(2-isopropylphenyl)azetidin-1-yl)-2,2-dimethylbutanoate | [M + 1]$^+$ 524.32 $t_R$ 0.82 |
| Ex 78-2 | 4-(3-((5-chloro-3-(difluoromethoxy)pyridin-2-yl)carbamoyl)-3-(2-isopropylphenyl)azetidin-1-yl)-2,2-dimethylbutanoic acid | [M + 1]$^+$ 510.30 $t_R$ 0.76 |
| Ex 78-3 | 4-(3-((5-bromo-3-(difluoromethoxy)pyridin-2-yl)carbamoyl)-3-(2-isopropylphenyl)azetidin-1-yl)-2,2-dimethylbutanoic acid | [M + 1]$^+$ 554.28 and 556.28 $t_R$ 0.78 |

TABLE 21

Examples 79-1 to 79-7
Examples 79-1 to 79-7 are synthesized by amide coupling from Ex 70, Ex 71, Ex 72, Ex 73 or Ex 74 and an acylchloride or a carboxylic acid in the presence of EDC/HOBt, or T3P and an organic base (DIPEA, pyridine for ex.). Functional groups, such as acid or alcohol, may be protected with an appropriate protecting group. For exemple esters are saponified by 2N LiOH after the reductive amination step.

| Example | Name | Analytics LCMS-1 |
|---|---|---|
| Ex 79-1 | methyl 4-(3-((5-bromo-3-(difluoromethoxy)pyridin-2-yl)carbamoyl)-3-(2-isopropylphenyl)azetidin-1-yl)-2,2-dimethyl-4-oxobutanoate | $[M + 1]^+$ 582.28 and 584.28 $t_R$ 1.24 |
| Ex 79-2 | 4-(3-((5-bromo-3-(difluoromethoxy)pyridin-2-yl)carbamoyl)-3-(2-isopropylphenyl)azetidin-1-yl)-2,2-dimethyl-4-oxobutanoic acid | $[M + 1]^+$ 568.24 and 570.24 $t_R$ 1.14 |
| Ex 79-3 | 4-(3-((5-chloro-3-(difluoromethoxy)pyridin-2-yl)carbamoyl)-3-(2-isopropylphenyl)azetidin-1-yl)-2,2-dimethyl-4-oxobutanoic acid | $[M + 1]^+$ 524.28 $t_R$ 1.12 |
| Ex 79-4 | 4-(3-((5-chloro-3-methoxypyridin-2-yl)carbamoyl)-3-(2-isopropylphenyl)azetidin-1-yl)-2,2-dimethyl-4-oxobutanoic acid | $[M + 1]^+$ 488.30 $t_R$ 1.06 |
| Ex 79-5 | 4-(3-((5-bromo-3-methoxypyridin-2-yl)carbamoyl)-3-(2-isopropylphenyl)azetidin-1-yl)-2,2-dimethyl-4-oxobutanoic acid | $[M + 1]^+$ 532.26 and 534.26 $t_R$ 1.08 |
| Ex 79-6 | 4-(3-((3-(difluoromethoxy)-5-methylpyridin-2-yl)carbamoyl)-3-(2-isopropylphenyl)azetidin-1-yl)-2,2-dimethyl-4-oxobutanoic acid | $[M + 1]^+$ 504.30 $t_R$ 1.06 |
| Ex 79-7 | 1-(2-(3-((3-(difluoromethoxy)-5-methylpyridin-2-yl)carbamoyl)-3-(2-isopropylphenyl)azetidin-1-yl)-2-oxoethyl)cyclobutane-1-carboxylic acid | $[M + 1]^+$ 516.40 $t_R$ 1.08 |

TABLE 22

Examples 80-1 and 80-2
Examples 80-1 and 80-2 are synthesized using the methodology described for Ex 13-1 to 13-27 starting from Ex 74.

| Example | Name | Analytics LCMS-1 |
|---|---|---|
| Ex 80-1 | benzyl 3-((3-((3-(difluoromethoxy)-5-methylpyridin-2-yl)carbamoyl)-3-(2-isopropylphenyl)azetidin-1-yl)sulfonyl)propanoate | $[M + 1]^+$ 602.36 $t_R$ 1.30 |
| Ex 80-2 | 3-((3-((3-(difluoromethoxy)-5-methylpyridin-2-yl)carbamoyl)-3-(2-isopropylphenyl)azetidin-1-yl)sulfonyl)propanoic acid | $[M + 1]^+$ 512.27 $t_R$ 1.05 |

TABLE 23

Examples 81-1 to 81-5:
Examples 81-1 to 81-5 are synthesized according to the methodology described for Ex 15-5 starting from Ex 70, Ex 71, Ex 72, Ex 73, Ex 75, Ex 76 or Ex 77.

| Example | Name | Analytics LCMS-1 |
|---|---|---|
| Ex 81-1 | N-(5-chloro-3-methoxypyridin-2-yl)-3-(2-isopropylphenyl)-1-sulfamoylazetidine-3-carboxamide | $[M + 1]^+$ 439.27 $t_R$ 0.99 |
| Ex 81-2 | N-(5-bromo-3-methoxypyridin-2-yl)-3-(2-isopropylphenyl)-1-sulfamoylazetidine-3-carboxamide | $[M + 1]^+$ 483.10 and 485.10 $t_R$ 1.00 |
| Ex 81-3 | N-(5-chloro-3-(difluoromethoxy)pyridin-2-yl)-3-(2-isopropylphenyl)-1-sulfamoylazetidine-3-carboxamide | $[M + 1]^+$ 475.22 $t_R$ 1.06 |
| Ex 81-4 | N-(5-bromo-3-(difluoromethoxy)pyridin-2-yl)-3-(2-isopropylphenyl)-1-sulfamoylazetidine-3-carboxamide | $[M + 1]^+$ 521.20 $t_R$ 1.2 |
| Ex 81-5 | N-(3,5-dimethoxypyridin-2-yl)-3-(2-isopropylphenyl)-1-sulfamoylazetidine-3-carboxamide | $[M + 1]^+$ 435.31 $t_R$ 0.90 |
| Ex 81-6 | N-(5-chloro-3-(difluoromethoxy)pyridin-2-yl)-3-(2-cyclopentylphenyl)-1-sulfamoylazetidine-3-carboxamide | $[M + 1]^+$ 501.23 $t_R$ 1.15 |
| Ex 81-7 | N-(5-chloro-3-(difluoromethoxy)pyridin-2-yl)-3-(3-isopropylpyridin-2-yl)-1-sulfamoylazetidine-3-carboxamide | $[M + 1]^+$ 476.14 $t_R$ 0.98 |

TABLE 24

Examples 82-1 and 82-2
Examples 82-1 and 82-2 are synthesized from isocyanatocyclopropane and
Ex 72 or Ex 73 using Method A described for Ex 17-2.

| Example | Name | method | Analytics LCMS-1 |
|---|---|---|---|
| Ex 82-1 | N3-(5-chloro-3-(difluoromethoxy)pyridin-2-yl)-N1-cyclopropyl-3-(2-isopropylphenyl)azetidine-1,3-dicarboxamide | A | $[M+1]^+$ 479.29 $t_R$ 1.09 |
| Ex 82-2 | N3-(5-bromo-3-(difluoromethoxy)pyridin-2-yl)-N1-cyclopropyl-3-(2-isopropylphenyl)azetidine-1,3-dicarboxamide | A | $[M+1]^+$ 523.24 and 525.24 $t_R$ 1.10 |

TABLE 25

Examples 83-1 to 83-3
Examples 83-1 to 83-3 are synthesized from Ex 74 using the methodology described for Ex 14-1.

| Example | Name | Analytics LCMS-1 |
|---|---|---|
| Ex 83-1 | 2-methoxy-2-oxoethyl 3-((3-(difluoromethoxy)-5-methylpyridin-2-yl)carbamoyl)-3-(2-isopropylphenyl)azetidine-1-carboxylate | $[M+1]^+$ 492.30 $t_R$ 1.13 |
| Ex 83-2 | 2-((3-((3-(difluoromethoxy)-5-methylpyridin-2-yl)carbamoyl)-3-(2-isopropylphenyl)azetidine-1-carbonyl)oxy)acetic acid | $[M+1]^+$ 478.30 $t_R$ 1.04 |
| Ex 83-3 | 1-((3-((3-(difluoromethoxy)-5-methylpyridin-2-yl)carbamoyl)-3-(2-isopropylphenyl)azetidine-1-carbonyl)oxy)cyclopropane-1-carboxylic acid | $[M+1]^+$ 518.32 $t_R$ 1.09 |

Example 84: N-(3-(difluoromethoxy)-5-methylpyridin-2-yl)-3-(2-isopropylphenyl)-1-(4-oxo-4,5-dihydrooxazol-2-yl)azetidine-3-carboxamide N-(3-(Difluoromethoxy)-5-methylpyridin-2-yl)-3-(2-isopropylphenyl)-1-(4-oxo-4,5-dihydrooxazol-2-yl)azetidine-3-carboxamide Ex 84 is synthesized from Ex 74 using the methodology described for Ex 19. LCMS-1: $t_R$=0.97 min, $[M+1]^+$459.31.

Reference Example 85: N-(2-methoxypyridin-3-yl)-3-phenylazetidine-3-carboxamide

1) A solution of intermediate I-2 (678 mg, 1.61 mmol) in THF (30 mL) and MeOH (60 mL) is degassed with argon. Palladium hydroxide (210 mg) is then added and the reaction is hydrogenated at atmospheric pressure for 2 h. The mixture is filtered through Celite pad. The pad is rinsed with THF/MeOH (1:1) and the organic solution is concentrated in vacuo to afford 3-phenylazetidine-3-carboxylic acid (271 mg, 95%). The latter (271 mg, 1.53 mmol) is dissolved in THF/water (60/10 mL), and DIPEA (1.05 mL) is added followed by Boc$_2$O (334 mg, 1.53 mmol). After 2 h, the volatiles are evaporated and the remaining aqueous solution is extracted with DCM (20 mL, then 3×10 mL). The organic extracts are combined and evaporated. The residue is purified by prep-HPLC (Prep-HPLC-1 conditions) to give 1-(tert-butoxycarbonyl)-3-phenylazetidine-3-carboxylic acid as a white solid (340 mg, 80% yield). $^1$H NMR (400 MHz, CDCl$_3$) δ: 7.43-7.37 (m, 2 H), 7.36-7.30 (m, 3 H), 4.63 (d, J=8.7 Hz, 2 H), 4.34 (d, J=8.7 Hz, 2 H).
2) 1-Boc-3-phenylazetidine-3-carboxylic acid is coupled to commercially available 2-methoxy-pyridin-3-amine under POCl$_3$/Pyr/DMF conditions followed by Boc deprotection with TFA to give the title compound Ex 85 as a white solid. LCMS-1: $t_R$=0.49 min, $[M+1]^+$284.18.

Reference Example 86: 1-(N-(2-methoxyethyl)sulfamoyl)-N-(2-methoxypyridin-3-yl)-3-phenylazetidine-3-carboxamide 1-(N-(2-Methoxyethyl)sulfamoyl)-N-(2-methoxypyridin-3-yl)-3-phenylazetidine-3-carboxamide Ex 86 is prepared from Ex 85 in analogy to Ex 15-1. LCMS-1:0.97 min, $[M+1]^+$421.30. $^1$H NMR (400 MHz, CDCl$_3$) δ: 8.59 (d, J=7.8 Hz, 1 H), 7.85 (d, J=4.8 Hz, 1 H), 7.61 (s, 1 H), 7.55-7.47 (m, 2 H), 7.47-7.40 (m, 1 H), 7.35 (d, J=7.7 Hz, 2 H), 6.90 (dd, J$_1$=5.1 Hz, J$_2$=7.7 Hz, 1 H), 4.67 (t, J=5.8 Hz, 1 H), 4.63 (d, J=7.6 Hz, 2 H), 4.37 (d, J=7.6 Hz, 2 H), 3.85 (s, 3 H), 3.53 (t, J=4.9 Hz, 2 H), 3.40-3.31 (m, 5 H).

Biological Assays

Beta-Arrestin Recruitment Assay to Determine IC$_{50}$ Values for Human LPAR$_1$ The Tango™ EDG2-bla U2OS cells are obtained from Invitrogen. These cells contain the human LPA$_1$ receptor cDNA linked to a TEV protease site and a Gal4-VP16 transcription factor integrated into the Tango™ GPCR-bla U2OS parental cell line. This parental cell line stably expresses a beta-arrestin/TEV protease fusion protein and the beta-lactamase (bla) reporter gene under the control of a UAS response element. Upon LPA (agonist) binding, LPA$_1$ receptor gets activated, leading to arrestin-protease recruitment and proteolytic release of the transcription factor: The transcription factor then regulates transcription of a beta-lactamase reporter construct, which is measured upon addition of the live-cell substrate.

10'000 Tango™ EDG2-bla U2OS cells are seeded in a 384-well black with clear bottom plate in 30 µl Freestyle 293 Expression Medium (Invitrogen) and incubated for 20 h at 37° C., 5% $CO_2$. For antagonist assays, 5 µl of test compound (dilution series in DMSO/Freestyle 293 Expression medium/0.1% fatty acid free BSA (Sigma) or buffer control are added per well and incubated for 30 min at 37° C., 5% $CO_2$. 5 µl of LPA 18:1 (500 nM final) (solution in Freestyle 293 Expression medium/0.1% fatty acid free BSA (Sigma)) are added per well and the plate incubated for 16 h at 37° C., 5% $CO_2$. Cells are then loaded with LiveBLAzer-FRET™ B/G Substrate (Invitrogen) for 2 h in the dark and the fluorescence emission at 460 nm and 530 nm is measured using the SynergyMx reader (BioTek). Following the background subtraction from both channels, the 460/530 nm emission ratio for each well is calculated, then plotted and fitted to a 4-parameter logistic function to obtain IC50 values. IC50 is the concentration of antagonist inhibiting 50% of the maximal response.

Antagonistic activities ($IC_{50}$ values) of exemplified compounds have been measured and antagonistic activities are displayed in Table 26.

TABLE 26

| Example | $IC_{50}$ $LPAR_1$ [nM] | Example | $IC_{50}$ $LPAR_1$ [nM] | Example | $IC_{50}$ $LPAR_1$ [nM] |
|---|---|---|---|---|---|
| 1 | 421 | 12-36 | 21 | 14-6 | 143 |
| 2 | 320 | 12-37 | 22 | 14-7 | 79 |
| 3 | 10 | 12-38 | 25 | 14-8 | 14 |
| 4 | 8 | 12-39 | 481 | 14-9 | 42 |
| 4-1 | 19 | 12-40 | 60 | 14-10 | 4 |
| 5 | 594 | 12-41 | 69 | 14-11 | 127 |
| 6 | 84 | 12-42 | 71 | 14-12 | 5 |
| 6-1 | 605 | 12-43 | 106 | 14-13 | 29 |
| 7 | 413 | 12-44 | 79 | 14-14 | 30 |
| 8 | 338 | 12-45 | 61 | 15-1 | 5 |
| 9 | 163 | 12-46 | 556 | 15-2 | 7 |
| 10 | 7 | 12-47 | 59 | 15-3 | 11 |
| 11-1 | 6 | 12-48 | 9 | 15-4 | 15 |
| 11-2 | 5 | 12-49 | 30 | 15-5 | 1.3 |
| 11-3 | 32 | 12-50 | 9 | 15-6 | 10 |
| 11-4 | 5 | 12-51 | 360 | 15-7 | 4 |
| 11-5 | 29 | 12-52 | 9 | 15-8 | 4 |
| 11-6 | 11 | 12-53 | 17 | 15-9 | 10 |
| 11-7 | 13 | 12-54 | 10 | 15-10 | 10 |
| 11-8 | 55 | 12-55 | 3 | 15-11 | 6 |
| 11-9 | 14 | 12-56 | 7 | 15-12 | 25 |
| 11-10 | 12 | 12-57 | 17 | 15-13 | 11 |
| 11-11 | 5 | 12-58 | 10 | 15-14 | 2 |
| 11-12 | 22 | 12-59 | 10 | 15-15 | 10 |
| 11-13 | 16 | 12-60 | 58 | 15-16 | 50 |
| 11-14 | 14 | 12-61 | 276 | 15-17 | 31 |
| 11-15 | 22 | 12-62 | 65 | 15-18 | 7 |
| 11-16 | 4 | 12-63 | 10 | 16-1 | 69 |
| 11-17 | 48 | 12-64 | 19 | 16-2 | 158 |
| 11-18 | 8 | 12-65 | 3 | 16-3 | 83 |
| 11-19 | 14 | 12-66 | 12 | 16-4 | 120 |
| 11-20 | 6 | 12-67 | 75 | 16-5 | 47 |
| 11-21 | 60 | 12-68 | 33 | 17-1 | 18 |
| 11-22 | 108 | 12-69 | 230 | 17-2 | 12 |
| 11-23 | 775 | 12-70 | 60 | 17-3 | 8 |
| 11-24 | 280 | 12-71 | 10 | 17-4 | 34 |
| 11-25 | 20 | 12-72 | 4 | 17-5 | 41 |
| 11-26 | 400 | 12-73 | 7 | 17-6 | 9 |
| 11-27 | 38 | 12-74 | 97 | 17-7 | 26 |
| 11-28 | 12 | 12-75 | 50 | 17-8 | 4 |
| 11-29 | 11 | 12-76 | 7 | 17-9 | 48 |
| 11-30 | 98 | 12-77 | 31 | 17-10 | 13 |
| 11-31 | 7 | 12-78 | 27 | 17-11 | 46 |
| 11-32 | 805 | 12-79 | 15 | 17-12 | 11 |
| 11-33 | 8 | 12-80 | 18 | 17-13 | 25 |
| 11-34 | 79 | 12-81 | 34 | 17-14 | 7 |
| 11-35 | 43 | 12-82 | 6 | 17-15 | 16 |
| 11-36 | 9 | 12-83 | 24 | 17-16 | 9 |
| 11-37 | 6 | 12-84 | 51 | 17-17 | 12 |
| 11-38 | 270 | 12-85 | 140 | 17-18 | 6 |
| 11-39 | 10 | 12-86 | 27 | 17-19 | 7 |
| 11-40 | 270 | 12-87 | 41 | 17-20 | 11 |
| 11-41 | 67 | 12-88 | 5 | 17-21 | 5 |
| 11-42 | 43 | 12-89 | 2 | 17-22 | 9 |
| 11-43 | 310 | 12-90 | 14 | 17-23 | 5 |
| 11-44 | 5 | 12-91 | 5 | 17-24 | 86 |
| 11-45 | 64 | 12-92 | 110 | 17-25 | 270 |
| 11-46 | 17 | 12-93 | 7 | 17-26 | 240 |
| 11-47 | 41 | 12-94 | 51 | 17-27 | 210 |
| 11-48 | 304 | 12-95 | 14 | 18-1 | 16 |
| 11-49 | 547 | 12-96 | 34 | 18-2 | 6 |

TABLE 26-continued

| | | IC$_{50}$ | | | |
|---|---|---|---|---|---|
| Example | IC$_{50}$ LPAR$_1$ [nM] | Example | IC$_{50}$ LPAR$_1$ [nM] | Example | IC$_{50}$ LPAR$_1$ [nM] |
| 11-50 | 47 | 12-97 | 13 | 18-3 | 7 |
| 11-51 | 41 | 12-98 | 26 | 18-4 | 31 |
| 11-52 | 79 | 12-99 | 16 | 18-5 | 11 |
| 11-53 | 115 | 12-100 | 23 | 18-6 | 10 |
| 11-54 | 95 | 12-101 | 83 | 18-7 | 12 |
| 11-55 | 142 | 12-102 | 12 | 18-8 | 10 |
| 11-56 | 64 | 12-103 | 19 | 18-9 | 11 |
| 11-57 | 12 | 12-104 | 41 | 18-10 | 120 |
| 11-58 | 68 | 12-105 | 54 | 18-11 | 34 |
| 11-59 | 38 | 12-106 | 59 | 18-12 | 11 |
| 11-60 | 47 | 12-107 | 150 | 18-13 | 17 |
| 11-61 | 39 | 12-108 | 28 | 18-14 | 560 |
| 11-62 | 48 | 12-109 | 20 | 18-15 | 47 |
| 11-63 | 92 | 12-110 | 66 | 18-16 | 2 |
| 11-64 | 63 | 12-111 | 18 | 18-17 | 8 |
| 11-65 | 315 | 12-112 | 39 | 18-18 | 1 |
| 11-66 | 14 | 12-113 | 53 | 18-19 | 2 |
| 11-67 | 326 | 12-114 | 2675 | 18-20 | 2 |
| 11-68 | 23 | 12-115 | 7 | 18-21 | 10 |
| 11-69 | 15 | 12-116 | 63 | 18-22 | 1 |
| 11-70 | 69 | 12-117 | 7 | 18-23 | 4 |
| 11-71 | 7 | 12-118 | 30 | 18-24 | 2 |
| 11-72 | 52 | 12-119 | 35 | 18-25 | 5 |
| 11-73 | 46 | 12-120 | 11 | 18-26 | 48 |
| 11-74 | 28 | 12-121 | 310 | 18-27 | 10 |
| 11-75 | 29 | 12-122 | 15 | 18-28 | 6 |
| 11-76 | 18 | 12-123 | 41 | 18-29 | 71 |
| 11-77 | 4.6 | 12-124 | 56 | 18-30 | 41 |
| 11-78 | 191 | 12-125 | 35 | 18-31 | 20 |
| 11-79 | 19 | 12-126 | 46 | 18-32 | 34 |
| 11-80 | 297 | 12-127 | 43 | 18-33 | 3 |
| 11-81 | 88 | 12-128 | 10 | 18-34 | 3 |
| 11-82 | 193 | 12-129 | 58 | 18-35 | 30 |
| 11-83 | 20 | 12-130 | 48 | 18-36 | 16 |
| 11-84 | 45 | 12-131 | 640 | 19 | 4 |
| 11-85 | 191 | 12-132 | 35 | 20 | 37 |
| 11-86 | 10 | 12-133 | 140 | 21 | 12 |
| 11-87 | 26 | 12-134 | 6 | 22 | 21 |
| 11-88 | 6 | 12-135 | 8 | 23 | 664 |
| 11-89 | 73 | 12-136 | 9 | 24 | 31 |
| 11-90 | 45 | 12-137 | 225 | 25 | 8.6 |
| 11-91 | 46 | 12-138 | 43 | 26 | 235 |
| 11-92 | 44 | 12-139 | 165 | 27 | 13 |
| 11-93 | 65 | 12-140 | 122 | 28 | 23 |
| 11-94 | 64 | 12-141 | 204 | 29 | 420 |
| 11-95 | 15 | 12-142 | 18 | 30 | 33 |
| 12-1 | 15 | 13-1 | 7 | 31-1 | 19 |
| 12-2 | 10 | 13-2 | 7 | 31-2 | 6 |
| 12-3 | 16 | 13-3 | 14 | 31-3 | 5 |
| 12-4 | 20 | 13-4 | 10 | 31-4 | 89 |
| 12-5 | 14 | 13-5 | 4 | 31-5 | 14 |
| 12-6 | 13 | 13-6 | 26 | 31-6 | 185 |
| 12-7 | 13 | 13-7 | 17 | 31-7 | 8 |
| 12-8 | 10 | 13-8 | 7 | 32 | 447 |
| 12-9 | 27 | 13-9 | 37 | 33 | 33 |
| 12-10 | 155 | 13-10 | 20 | 34 | 142 |
| 12-11 | 7 | 13-11 | 366 | 35 | 75 |
| 12-12 | 7 | 13-12 | 4 | 36 | 8 |
| 12-13 | 17 | 13-13 | 1755 | 37 | 112 |
| 12-14 | 7 | 13-14 | 10 | 38 | 287 |
| 12-15 | 36 | 13-15 | 280 | 39-1 | 51 |
| 12-16 | 9 | 13-16 | 16 | 39-2 | 15 |
| 12-17 | 25 | 13-17 | 7.0 | 39-3 | 40 |
| 12-18 | 25 | 13-18 | 72 | 39-4 | 5 |
| 12-19 | 17 | 13-19 | 55 | 39-5 | 10 |
| 12-20 | 2 | 13-20 | 18 | 39-6 | 56 |
| 12-21 | 5.6 | 13-21 | 14 | 40 | 29 |
| 12-22 | 7 | 13-22 | 270 | 41 | 96 |
| 12-23 | 21 | 13-23 | 100 | 42 | 7 |
| 12-24 | 19 | 13-24 | 750 | 43 | 14 |
| 12-25 | 15 | 13-25 | 400 | 44 | 155 |
| 12-26 | 7 | 13-26 | 25 | 45 | 63 |
| 12-27 | 4 | 13-27 | 28 | 46 | 100 |
| 12-28 | 222 | 13-28 | 110 | 47 | 95 |
| 12-29 | 32 | 13-29 | 10 | 48 | 103 |
| 12-30 | 25 | 13-30 | 49 | 49 | 44 |

TABLE 26-continued

| Example | IC$_{50}$ LPAR$_1$ [nM] | Example | IC$_{50}$ LPAR$_1$ [nM] | Example | IC$_{50}$ LPAR$_1$ [nM] |
|---|---|---|---|---|---|
| 12-31 | 337 | 14-1 | 12 | 50 | 68 |
| 12-32 | 1715 | 14-2 | 4.3 | 51 | 80 |
| 12-33 | 10 | 14-3 | 6 | 52 | 51 |
| 12-34 | 33 | 14-4 | 16 | 53 | 17 |
| 12-35 | 41 | 14-5 | 9 | 80-1 | 55 |
| 54 | 69 | 71 | 564 | 80-2 | 110 |
| 55 | 44 | 72 | 15 | 81-1 | 15 |
| 56 | 8 | 73 | 10 | 81-2 | 13 |
| 57 | 54 | 74 | 486 | 81-3 | 2 |
| 58 | 48 | 75 | 4380 | 81-4 | 2 |
| 59 | 270 | 76 | 19 | 81-5 | 63 |
| 60 | 333 | 77 | 1030 | 81-6 | 22 |
| 61 | 70 | 78-1 | 457 | 81-7 | 5 |
| 62 | 3 | 78-2 | 17 | 82-1 | 3 |
| 63 | 8 | 78-3 | 13 | 82-2 | 3 |
| 64 | 15 | 79-1 | 65 | 83-1 | 74 |
| 65 | 37 | 79-2 | 11 | 83-2 | 88 |
| 66 | 1660 | 79-3 | 17 | 83-3 | 76 |
| 67 | 82 | 79-4 | 123 | 84 | 310 |
| 68 | 7620 | 79-5 | 104 | | |
| 69 | 27 | 79-6 | 200 | | |
| 70 | 866 | 79-7 | 61 | | |
| Ref. example 85 | >10 000 | Ref. example 86 | >10 000 | | |

Assessment of In Vivo Potency

The in vivo potency of the compounds of formulae (I), (II) and (III) can be determined using a mouse LPA-induced skin vascular leakage model. Female Balb/c mice are treated with either vehicle or test compound (p.o.) for at least 1 h prior to administration of the albumin marker Evans blue (50 mg/kg, i.v., 0.9% NaCl) and subsequent challenge with LPA (5 µg, i.d.). After 30 minutes, mice are sacrificed by CO$_2$ inhalation. Discs of skin from the injection sites are removed, digested in formamide (500 µl, 37° C., 24 hrs) and the content of Evans blue quantified by colorimetric assay. Results are expressed as extravasated Evans blue per skin disc (µg/disc).

As an example, the compound of Ex 12-21 is able to effectively reduce LPA-induced vascular leakage after oral administration of 100 mg/kg to mice as compared to a group of animals treated with vehicle only. Reduction of vascular leakage compared to vehicle group was ≥60%.

The invention claimed is:
1. A compound of Formula (I),

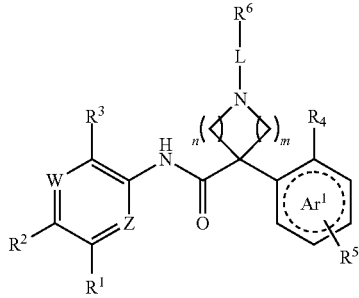

Formula (I)

wherein
W represents N, and Z represents CH; or
Z represents N, and W represents CH;
$R^1$ is hydrogen or fluoro;
$R^2$ is hydrogen, halogen, methyl, ethyl, methoxy or ethoxy;
$R^3$ is $C_{1-3}$-fluoroalkoxy;
$Ar^1$ represents phenyl, wherein said group $Ar^1$ is substituted with $R^4$ and $R^5$, wherein
  $R^4$ is n-propyl, isopropyl, $C_{3-6}$-cycloalkyl optionally containing a ring oxygen atom, or cyclopent-1-en-1-yl; and
  $R^5$ represents one substituent independently selected from hydrogen, fluoro, methyl or methoxy;
m and n represent the integer 1; and
the group -L—$R^6$ represents
  -L$^1$-COOH; wherein
    -L$^1$- represents
      -$C_{1-6}$-alkylene-, —CO—$C_{1-6}$-alkylene-, —SO$_2$-$C_{1-6}$-alkylene-, —CO—O-$C_{1-6}$-alkylene-, —CO—NH-$C_{1-6}$-alkylene-, or —SO$_2$—NH-$C_{1-6}$-alkylene-;
      —CO-$C_{1-6}$-alkylene-; wherein said $C_{1-6}$-alkylene is mono-substituted with hydroxy;
      -$C_{0-4}$-alkylene-$C_{3-8}$-cycloalkylene-$C_{0-4}$-alkylene-, —CO-$C_{0-4}$-alkylene-$C_{3-8}$-cycloalkylene-$C_{0-4}$-alkylene-, —SO$_2$-$C_{0-4}$-alkylene-$C_{3-8}$-cycloalkylene-$C_{0-4}$-alkylene-, or —CO-O-$C_{0-4}$-alkylene-$C_{3-8}$-cycloalkylene-$C_{0-4}$-alkylene-;
      —CO-$C_{0-4}$-alkylene-Cy$^1$-$C_{0-4}$-alkylene-; wherein Cy$^1$ independently represents a $C_{3-6}$-heterocycloalkylene containing one ring oxygen atom;
      —CO-$C_{1-4}$-alkylene-X$^{12}$-$C_{1-4}$-alkylene-; wherein X$^{12}$ independently represents a nitrogen atom which is unsubstituted, or mono-substituted with $C_{1-4}$-alkyl;
      —CO-$C_{2-6}$-alkenylene- or —SO$_2$-$C_{2-6}$-alkenylene-; or
      —CO-$C_{2-6}$-fluoroalkylene-;
  -L$^2$-hydroxy; wherein -L$^2$- represents
    -$C_{2-6}$-alkylene-, wherein the $C_{2-6}$-alkylene is unsubstituted, or mono-substituted with hydroxy; or
    —CO-$C_{1-4}$-alkylene-X$^{22}$-$C_{2-4}$-alkylene-; wherein X$^{22}$ represents a nitrogen atom which is independently unsubstituted, or mono-substituted with $C_{1-4}$-alkyl or $C_{3-6}$-cycloalkyl; or -$L^9$-HET$^1$, wherein HET$^1$ represents 5- or 6-membered heteroaryl selected from pyrrolyl, pyrazolyl, imidazolyl, triazolyl, tetrazolyl, furanyl, oxazolyl, isoxazolyl, thiazolyl, isothiazolyl, oxadiazolyl, thiadiazolyl, pyridinyl, pyrimidinyl, pyridazinyl, and pyrazinyl; wherein said HET$^1$ independently is unsubstituted or mono-, or di-substituted wherein the substituents are independently selected from $C_{1-4}$-alkyl; halogen; cyano; hydroxy; hydroxymethyl; -$C_{0-2}$-alkylene-Cy$^{91}$-COOR$^{O91}$ wherein R$^{O91}$ is hydrogen or $C_{1-4}$-alkyl, and wherein Cy$^{91}$ represents a $C_{3-6}$-cycloalkylene group; or -$C_{0-2}$-alkylene-CO-OR$^{O92}$ wherein R$^{O92}$ is hydrogen or $C_{1-4}$-alkyl; and -$L^9$- independently represents -$C_{0-6}$-alkylene-, or —CO-$C_{0-6}$-alkylene-;

or a pharmaceutically acceptable salt thereof.

2. A compound according to claim 1, wherein W represents N, Z represents CH; and R$^2$ is hydrogen, methyl, methoxy or ethoxy;

or a pharmaceutically acceptable salt thereof.

3. A compound according to claim 1, wherein R$^3$ represents difluoromethoxy;

or a pharmaceutically acceptable salt thereof.

4. A compound according to claim 1, wherein the fragment:

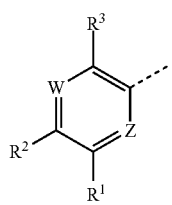

represents:

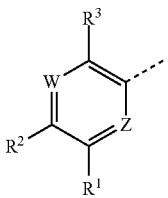

wherein R$^1$ is hydrogen or fluoro; R$^2$ is hydrogen, chloro, methyl, ethyl, methoxy or ethoxy; and R3 is -C1 3-alkoxy or C1-3-fluoroalkoxy; or

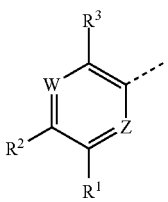

wherein R$^1$ is hydrogen; R$^2$ is halogen, methyl, or methoxy; and R$^3$ is $C_{1-3}$-fluoroalkoxy;

or a pharmaceutically acceptable salt thereof.

5. A compound according to claim 1, wherein the fragment:

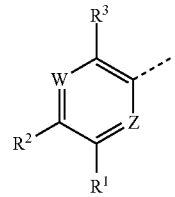

represents a ring independently selected from the following groups A) or B):

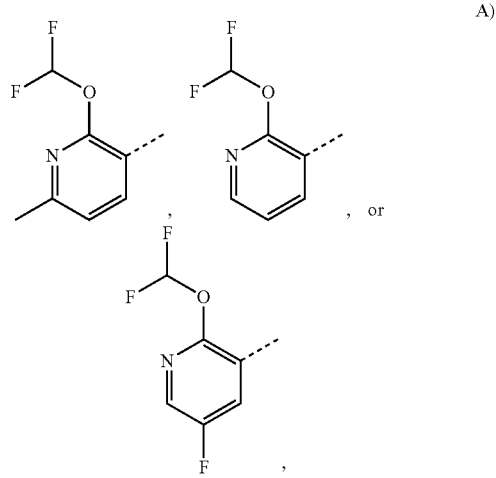

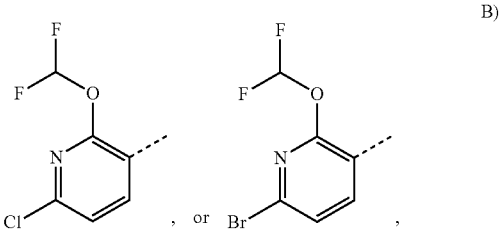

or a pharmaceutically acceptable salt thereof.

6. A compound according to claim 1, wherein Ar$^1$ represents phenyl;

wherein said phenyl group is substituted with R$^4$ and R$^5$, wherein

R$^4$ represents n-propyl, isopropyl, or monocyclic $C_{3-6}$-cycloalkyl; and

R$^5$ represents hydrogen, fluoro, or methyl;

or a pharmaceutically acceptable salt thereof.

7. A compound according to claim 1, wherein the fragment:

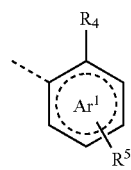

represents a ring independently selected from the following groups:

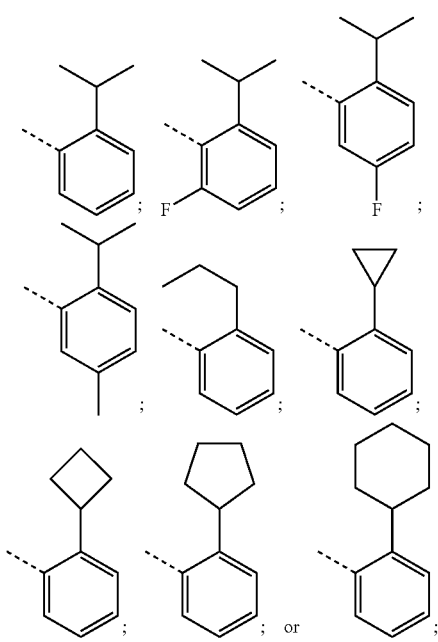

or a pharmaceutically acceptable salt thereof.

8. A compound according to claim 1, wherein the group -L—R$^6$ represents

-L$^1$-COOH; and

-L$^1$- represents

—CH$_2$—CH$_2$—, —CH$_2$—CH$_2$—CH$_2$—, —CH$_2$—C(CH$_3$)$_2$—CH$_2$—, *—CH$_2$—CH$_2$—C(CH$_3$)$_2$—, *—CH$_2$—CH$_2$—CH$_2$—C(CH$_3$)$_2$—, *—CO—CH$_2$—CH$_2$—, *—CO—CH(CH$_3$)—CH$_2$—, *—CO—CH$_2$—C(OH)(CH$_3$)—, *—CO—CH$_2$—CH$_2$—CH$_2$—, *—CO—CH$_2$—C(CH$_3$)$_2$—, *—CO—C(CH$_3$)$_2$—CH$_2$—, *—SO$_2$—CH$_2$—, *—SO$_2$—CH$_2$—CH$_2$—, *—SO$_2$—CH$_2$—CH$_2$—CH$_2$—, *—SO$_2$—CH$_2$—C(CH$_3$)$_2$—, *—CO—O—CH$_2$—, *—CO—O—CH(CH$_3$)—, *—CO—O—CH$_2$—C(CH$_3$)$_2$—, *—CO—NH—C(CH$_3$)$_2$—CH$_2$—, *—CO—NH—CH$_2$—C(CH$_3$)$_2$—, *—CO—NH—CH$_2$—CH$_2$—C(CH$_3$)$_2$—, *—SO$_2$—NH—CH$_2$—; *—CH$_2$—CH$_2$—CH$_2$-cyclopropane-1,1-diyl-, *—CO-cyclopropane-1,2-yl-, *—CO—CH$_2$-cyclopropane-1,1-diyl-, *—CO—CH$_2$-cyclobutane-1,1-diyl-, *—SO$_2$-cyclopropane-1,1-diyl—CH$_2$—, *—CO—O-cyclopropane-1,1-diyl-, *—CO—O—CH$_2$-cyclopropane-1,1-diyl-;

*—CO—CH$_2$—(tetrahydro-2H-pyran-4,4-diyl)-;

*—CO—CH$_2$—N(n-butyl)—CH$_2$—;

*—SO$_2$—CH═CH—, *—CO—C(CH$_2$)—CH$_2$—; or

*—CO—CF$_2$—CH$_2$—;

-L$^2$-hydroxy; wherein -L$^2$- represents

*—CH$_2$—CH(OH)—CH$_2$—; or

*—CO—CH$_2$—NH—CH$_2$—CH$_2$—, *—CO—CH$_2$—NH—CH(CH$_3$)—CH$_2$—, *—CO—CH$_2$—NH—CH$_2$—CH(CH$_3$)—; or

-L$^9$-HET$^1$, wherein -L$^9$-HET$^1$ represents

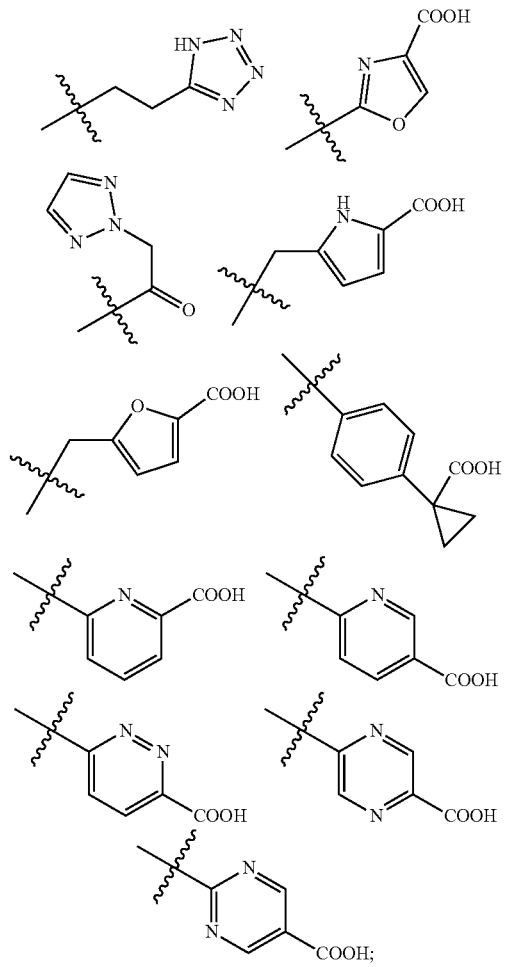

wherein in the above groups the asterisks indicate the bond which is connected to the rest of the molecule; or a pharmaceutically acceptable salt thereof.

9. A compound, wherein said compound is:

N-(2-(difluoromethoxy)-6-methylpyridin-3-yl)-3-(2-isopropylphenyl)azetidine-3-carboxamide;

1-(2-aminoethyl)-N-(2-(difluoromethoxy)-6-methylpyridin-3-yl)-3-(2-isopropylphenyl)azetidine-3-carboxamide;

N-(2-(difluoromethoxy)-6-methylpyridin-3-yl)-1-(2-hydroxyethyl)-3-(2-isopropylphenyl)azetidine-3-carboxamide;

N-(2-(difluoromethoxy)-6-methylpyridin-3-yl)-1-(3-hydroxypropyl)-3-(2-isopropylphenyl)azetidine-3-carboxamide;

1-cyano-N-(2-(difluoromethoxy)-6-methylpyridin-3-yl)-3-(2-isopropylphenyl)azetidine-3-carboxamide;

1-(3-(1H-tetrazol-5-yl)propyl)-N-(2-(difluoromethoxy)-6-methylpyridin-3-yl)-3-(2-isopropylphenyl)azetidine-3-carboxamide;

N-(2-(difluoromethoxy)-6-methylpyridin-3-yl)-1-(3-hydroxy-3-methylbutyl)-3-(2-isopropylphenyl)azetidine-3-carboxamide;

N-(2-(difluoromethoxy)-6-methylpyridin-3-yl)-1-(2-(1-hydroxycyclopropyl)ethyl)-3-(2-isopropylphenyl)azetidine-3-carboxamide;

1-(2-aminopropyl)-N-(2-(difluoromethoxy)-6-methylpyridin-3-yl)-3-(2-isopropylphenyl)azetidine-3-carboxamide;

3-(3-((2-(difluoromethoxy)-6-methylpyridin-3-yl)carbamoyl)-3-(2-isopropylphenyl)azetidin-1-yl)propanoic acid;

1-(2-cyanoethyl)-N-(2-(difluoromethoxy)-6-methylpyridin-3-yl)-3-(2-isopropylphenyl)azetidine-3-carboxamide;

(R)-N-(2-(difluoromethoxy)-6-methylpyridin-3-yl)-1-(2,3-dihydroxypropyl)-3-(2-isopropylphenyl)azetidine-3-carboxamide;

N-(2-(difluoromethoxy)-6-methylpyridin-3-yl)-3-(2-isopropylphenyl)-1-(oxetan-3-yl)azetidine-3-carboxamide;

4-(3-((2-(difluoromethoxy)-6-methylpyridin-3-yl)carbamoyl)-3-(2-isopropylphenyl)azetidin-1-yl)butanoic acid;

4-(3-((2-(difluoromethoxy)-6-methylpyridin-3-yl)carbamoyl)-3-(2-isopropylphenyl)azetidin-1-yl)-2,2-dimethylbutanoic acid;

4-(3-((2-(difluoromethoxy)-6-methylpyridin-3-yl)carbamoyl)-3-(2-isopropylphenyl)azetidin-1-yl)-3,3-dimethylbutanoic acid;

5-((3-((2-(difluoromethoxy)-6-methylpyridin-3-yl)carbamoyl)-3-(2-isopropylphenyl)azetidin-1-yl)methyl)-1H-pyrrole-2-carboxylic acid;

5-((3-((2-(difluoromethoxy)-6-methylpyridin-3-yl)carbamoyl)-3-(2-isopropylphenyl)azetidin-1-yl)methyl)furan-2-carboxylic acid;

N-(2-(difluoromethoxy)-6-methylpyridin-3-yl)-1-(4-hydroxy-4-methylpentyl)-3-(2-isopropylphenyl)azetidine-3-carboxamide;

5-(3-((2-(difluoromethoxy)-6-methylpyridin-3-yl)carbamoyl)-3-(2-isopropylphenyl)azetidin-1-yl)-2,2-dimethylpentanoic acid;

1-(3-(3-((2-(difluoromethoxy)-6-methylpyridin-3-yl)carbamoyl)-3-(2-isopropylphenyl)azetidin-1-yl)propyl)cyclopropane-1-carboxylic acid;

N-(2-(difluoromethoxy)-6-methylpyridin-3-yl)-3-(2-isopropylphenyl)-1-(2-(methylsulfonamido)ethyl)azetidine-3-carboxamide;

(S)-N-(2-(difluoromethoxy)-6-methylpyridin-3-yl)-1-(2-hydroxy-3-(2-hydroxyacetamido)propyl)-3-(2-isopropylphenyl)azetidine-3-carboxamide;

1-(cyanomethyl)-N-(2-(difluoromethoxy)-6-methylpyridin-3-yl)-3-(2-isopropylphenyl)azetidine-3-carboxamide;

1-(2-(1H-tetrazol-5-yl)ethyl)-N-(2-(difluoromethoxy)-6-methylpyridin-3-yl)-3-(2-isopropylphenyl)azetidine-3-carboxamide;

1-(4-cyanobutanoyl)-N-(2-(difluoromethoxy)-6-methylpyridin-3-yl)-3-(2-isopropylphenyl)azetidine-3-carboxamide;

1-acetyl-N-(2-(difluoromethoxy)-6-methylpyridin-3-yl)-3-(2-isopropylphenyl)azetidine-3-carboxamide;

N-(2-(difluoromethoxy)-6-methylpyridin-3-yl)-3-(2-isopropylphenyl)-1-(3-sulfamoylpropanoyl)azetidine-3-carboxamide;

N-(2-(difluoromethoxy)-6-methylpyridin-3-yl)-3-(2-isopropylphenyl)-1-(2-(N-methylsulfamoyl)acetyl)azetidine-3-carboxamide;

N-(2-(difluoromethoxy)-6-methylpyridin-3-yl)-3-(2-isopropylphenyl)-1-((methylsulfonyl)glycyl)azetidine-3-carboxamide;

N-(2-(difluoromethoxy)-6-methylpyridin-3-yl)-3-(2-isopropylphenyl)-1-(N-methyl-N-sulfamoylglycyl)azetidine-3-carboxamide;

N-(2-(difluoromethoxy)-6-methylpyridin-3-yl)-3-(2-isopropylphenyl)-1-(5,5,5-trifluoro-4-oxopentanoyl)azetidine-3-carboxamide;

N-(2-(difluoromethoxy)-6-methylpyridin-3-yl)-1-(3-hydroxyisoxazole-5-carbonyl)-3-(2-isopropylphenyl)azetidine-3-carboxamide;

N-(2-(difluoromethoxy)-6-methylpyridin-3-yl)-1-(3-oxo-2,3-dihydroisoxazole-5-carbonyl)-3-(2-isopropylphenyl)azetidine-3-carboxamide;

1-(2-(2H-1,2,3-triazol-2-yl)acetyl)-N-(2-(difluoromethoxy)-6-methylpyridin-3-yl)-3-(2-isopropylphenyl)azetidine-3-carboxamide;

N-(2-(difluoromethoxy)-6-methylpyridin-3-yl)-1-(2-(3-hydroxy-1H-pyrazol-4-yl)acetyl)-3-(2-isopropylphenyl)azetidine-3-carboxamide;

N-(2-(difluoromethoxy)-6-methylpyridin-3-yl)-1-(2-(3-oxo-2,3-dihydro-1H-pyrazol-4-yl)acetyl)-3-(2-isopropylphenyl)azetidine-3-carboxamide;

1-(L-alanyl)-N-(2-(difluoromethoxy)-6-methylpyridin-3-yl)-3-(2-isopropylphenyl)azetidine-3-carboxamide;

N-(2-(difluoromethoxy)-6-methylpyridin-3-yl)-1-((2-hydroxyethyl)glycyl)-3-(2-isopropylphenyl)azetidine-3-carboxamide;

N-(2-(difluoromethoxy)-6-methylpyridin-3-yl)-3-(2-isopropylphenyl)-1-((2-methoxyethyl)glycyl)azetidine-3-carboxamide;

(R)-N-(2-(difluoromethoxy)-6-methylpyridin-3-yl)-1-((R)-(2-hydroxypropyl)glycyl)-3-(2-isopropylphenyl)azetidine-3-carboxamide;

(S)-N-(2-(difluoromethoxy)-6-methylpyridin-3-yl)-1-((S)-(2-hydroxypropyl)glycyl)-3-(2-isopropylphenyl)azetidine-3-carboxamide;

(R)-N-(2-(difluoromethoxy)-6-methylpyridin-3-yl)-1-((R)-(1-hydroxypropan-2-yl)glycyl)-3-(2-isopropylphenyl)azetidine-3-carboxamide;

(S)-N-(2-(difluoromethoxy)-6-methylpyridin-3-yl)-1-((R)-(1-hydroxypropan-2-yl)glycyl)-3-(2-isopropylphenyl)azetidine-3-carboxamide;

3-(3-((2-(difluoromethoxy)-6-methylpyridin-3-yl)carbamoyl)-3-(2-isopropylphenyl)azetidin-1-yl)-3-oxopropanoic acid;

3-(4-((2-(difluoromethoxy)-6-methylpyridin-3-yl)carbamoyl)-4-(2-isopropylphenyl)piperidin-1-yl)-3-oxopropanoic acid;

4-(3-((2-(difluoromethoxy)-6-methylpyridin-3-yl)carbamoyl)-3-(2-isopropylphenyl)azetidin-1-yl)-4-oxobutanoic acid;

4-(4-((2-(difluoromethoxy)-6-methylpyridin-3-yl)carbamoyl)-4-(2-isopropylphenyl)piperidin-1-yl)-4-oxobutanoic acid;

(S)-4-(3-((2-(difluoromethoxy)-6-methylpyridin-3-yl)carbamoyl)-3-(2-isopropylphenyl)azetidin-1-yl)-2-methyl-4-oxobutanoic acid;

4-(3-((2-(difluoromethoxy)-6-methylpyridin-3-yl)carbamoyl)-3-(2-isopropylphenyl)azetidin-1-yl)-2,2-dimethyl-4-oxobutanoic acid;

1-(2-(3-((2-(difluoromethoxy)-6-methylpyridin-3-yl)carbamoyl)-3-(2-isopropylphenyl)azetidin-1-yl)-2-oxoethyl)cyclopropane-1-carboxylic acid;

1-(2-(3-((2-(difluoromethoxy)-6-methylpyridin-3-yl)carbamoyl)-3-(2-isopropylphenyl)azetidin-1-yl)-2-oxoethyl)cyclobutane-1-carboxylic acid;

(R)-4-(3-((2-(difluoromethoxy)-6-methylpyridin-3-yl)carbamoyl)-3-(2-isopropylphenyl)azetidin-1-yl)-3-methyl-4-oxobutanoic acid;

4-(3-((2-(difluoromethoxy)-6-methylpyridin-3-yl)carbamoyl)-3-(2-isopropylphenyl)azetidin-1-yl)-3,3-dimethyl-4-oxobutanoic acid;

3-(3-((2-(difluoromethoxy)-6-methylpyridin-3-yl)carbamoyl)-3-(2-isopropylphenyl)azetidine-1-carbonyl)but-3-enoic acid;

(1S,2R)-2-(3-((2-(difluoromethoxy)-6-methylpyridin-3-yl)carbamoyl)-3-(2-isopropylphenyl)azetidine-1-carbonyl)cyclopropane-1-carboxylic acid;

(1R,2S)-2-(3-((2-(difluoromethoxy)-6-methylpyridin-3-yl)carbamoyl)-3-(2-isopropylphenyl)azetidine-1-carbonyl)cyclopropane-1-carboxylic acid;

5-(3-((2-(difluoromethoxy)-6-methylpyridin-3-yl)carbamoyl)-3-(2-isopropylphenyl)azetidin-1-yl)-5-oxopentanoic acid;

4-(3-((2-(difluoromethoxy)-6-methylpyridin-3-yl)carbamoyl)-3-(2-isopropylphenyl)azetidin-1-yl)-3,3-difluoro-4-oxobutanoic acid;

(S)-4-(3-((2-(difluoromethoxy)-6-methylpyridin-3-yl)carbamoyl)-3-(2-isopropylphenyl)azetidin-1-yl)-2-hydroxy-2-methyl-4-oxobutanoic acid;

N-(2-(difluoromethoxy)-6-methylpyridin-3-yl)-3-(2-isopropylphenyl)-1-(5,5,5-trifluoro-4-hydroxypentanoyl)azetidine-3-carboxamide;

4-(2-(3-((2-(difluoromethoxy)-6-methylpyridin-3-yl)carbamoyl)-3-(2-isopropylphenyl)azetidin-1-yl)-2-oxoethyl)tetrahydro-2H-pyran-4-carboxylic acid;

N-(2-(difluoromethoxy)-6-methylpyridin-3-yl)-3-(2-isopropylphenyl)-1-(sulfamoylglycyl)azetidine-3-carboxamide;

1-(N-acetyl-N-hydroxyglycyl)-N-(2-(difluoromethoxy)-6-methylpyridin-3-yl)-3-(2-isopropylphenyl)azetidine-3-carboxamide;

2-((3-((2-(difluoromethoxy)-6-methylpyridin-3-yl)carbamoyl)-3-(2-isopropylphenyl)azetidin-1-yl)sulfonyl)acetic acid;

3-((3-((2-(difluoromethoxy)-6-methylpyridin-3-yl)carbamoyl)-3-(2-isopropylphenyl)azetidin-1-yl)sulfonyl)propanoic acid;

3-((3-((2-(difluoromethoxy)-6-methylpyridin-3-yl)carbamoyl)-3-(2-isopropylphenyl)azetidin-1-yl)sulfonyl)-2,2-dimethylpropanoic acid;

2-(1-((3-((2-(difluoromethoxy)-6-methylpyridin-3-yl)carbamoyl)-3-(2-isopropylphenyl)azetidin-1-yl)sulfonyl)cyclopropyl)acetic acid;

4-((3-((2-(difluoromethoxy)-6-methylpyridin-3-yl)carbamoyl)-3-(2-isopropylphenyl)azetidin-1-yl)sulfonyl)butanoic acid;

(E)-3-((3-((2-(difluoromethoxy)-6-methylpyridin-3-yl)carbamoyl)-3-(2-isopropylphenyl)azetidin-1-yl)sulfonyl)acrylic acid;

N-(2-(difluoromethoxy)-6-methylpyridin-3-yl)-1-((3-(hydroxyamino)-3-oxopropyl)sulfonyl)-3-(2-isopropylphenyl)azetidine-3-carboxamide;

2-((3-((2-(difluoromethoxy)-6-methylpyridin-3-yl)carbamoyl)-3-(2-isopropylphenyl)azetidine-1-carbonyl)oxy)acetic acid;

(R)-2-((3-((2-(difluoromethoxy)-6-methylpyridin-3-yl)carbamoyl)-3-(2-isopropylphenyl)azetidine-1-carbonyl)oxy)propanoic acid;

1-((3-((2-(difluoromethoxy)-6-methylpyridin-3-yl)carbamoyl)-3-(2-isopropylphenyl)azetidine-1-carbonyl)oxy)cyclopropane-1-carboxylic acid;

3-((3-((2-(difluoromethoxy)-6-methylpyridin-3-yl)carbamoyl)-3-(2-isopropylphenyl)azetidine-1-carbonyl)oxy)-2,2-dimethylpropanoic acid;

1-(((3-((2-(difluoromethoxy)-6-methylpyridin-3-yl)carbamoyl)-3-(2-isopropylphenyl)azetidine-1-carbonyl)oxy)methyl)cyclopropane-1-carboxylic acid;

((3-((2-(difluoromethoxy)-6-methylpyridin-3-yl)carbamoyl)-3-(2-isopropylphenyl)azetidin-1-yl)sulfonyl)glycine;

N-(2-(difluoromethoxy)-6-methylpyridin-3-yl)-3-(2-isopropylphenyl)-1-(2-(sulfamoylamino)ethyl)azetidine-3-carboxamide;

3-(3-((2-(difluoromethoxy)-6-methylpyridin-3-yl)carbamoyl)-3-(2-isopropylphenyl)azetidine-1-carboxamido)-3-methylbutanoic acid;

3-(3-((2-(difluoromethoxy)-6-methylpyridin-3-yl)carbamoyl)-3-(2-isopropylphenyl)azetidine-1-carboxamido)-2,2-dimethylpropanoic acid;

4-(3-((2-(difluoromethoxy)-6-methylpyridin-3-yl)carbamoyl)-3-(2-isopropylphenyl)azetidine-1-carboxamido)-2,2-dimethylbutanoic acid;

6-(3-((2-(difluoromethoxy)-6-methylpyridin-3-yl)carbamoyl)-3-(2-isopropylphenyl)azetidin-1-yl)nicotinic acid;

6-(3-((2-(difluoromethoxy)-6-methylpyridin-3-yl)carbamoyl)-3-(2-isopropylphenyl)azetidin-1-yl)picolinic acid;

2-(3-((2-(difluoromethoxy)-6-methylpyridin-3-yl)carbamoyl)-3-(2-isopropylphenyl)azetidin-1-yl)pyrimidine-5-carboxylic acid;

6-(3-((2-(difluoromethoxy)-6-methylpyridin-3-yl)carbamoyl)-3-(2-isopropylphenyl)azetidin-1-yl)pyridazine-3-carboxylic acid;

5-(3-((2-(difluoromethoxy)-6-methylpyridin-3-yl)carbamoyl)-3-(2-isopropylphenyl)azetidin-1-yl)pyrazine-2-carboxylic acid;

1-(5-(3-((2-(difluoromethoxy)-6-methylpyridin-3-yl)carbamoyl)-3-(2-isopropylphenyl)azetidin-1-yl)pyrimidin-2-yl)cyclopropane-1-carboxylic acid;

N-(2-(difluoromethoxy)-6-methylpyridin-3-yl)-1-(4-fluoropyridin-2-yl)-3-(2-isopropylphenyl)azetidine-3-carboxamide;

N-(2-(difluoromethoxy)-6-methylpyridin-3-yl)-1-(3-fluoropyridin-4-yl)-3-(2-isopropylphenyl)azetidine-3-carboxamide;

N-(2-(difluoromethoxy)-6-methylpyridin-3-yl)-1-(5-fluoropyrimidin-4-yl)-3-(2-isopropylphenyl)azetidine-3-carboxamide;

N-(2-(difluoromethoxy)pyridin-3-yl)-1-(5-fluoropyrimidin-4-yl)-3-(2-isopropylphenyl)azetidine-3-carboxamide;

1-(5-cyanopyridin-2-yl)-N-(2-(difluoromethoxy)-6-methylpyridin-3-yl)-3-(2-isopropylphenyl)azetidine-3-carboxamide;

1-(5-cyanopyridin-2-yl)-N-(2-(difluoromethoxy)pyridin-3-yl)-3-(2-isopropylphenyl)azetidine-3-carboxamide;

1-(5-cyanopyrimidin-2-yl)-N-(2-(difluoromethoxy)-6-methylpyridin-3-yl)-3-(2-isopropylphenyl)azetidine-3-carboxamide;

1-(5-cyanopyrimidin-2-yl)-N-(2-(difluoromethoxy)pyridin-3-yl)-3-(2-isopropylphenyl)azetidine-3-carboxamide;

2-(3-((2-(difluoromethoxy)-6-methylpyridin-3-yl)carbamoyl)-3-(2-isopropylphenyl)azetidin-1-yl)oxazole-4-carboxylic acid;

N-(2-(difluoromethoxy)-6-methylpyridin-3-yl)-1-(5-fluoropyrimidin-2-yl)-3-(2-isopropylphenyl)azetidine-3-carboxamide;
N-(2-(difluoromethoxy)-6-methylpyridin-3-yl)-3-(2-isopropylphenyl)-1-(2-methylpyrimidin-4-yl)azetidine-3-carboxamide;
N-(2-(difluoromethoxy)-6-methylpyridin-3-yl)-3-(2-isopropylphenyl)-1-(4-oxo-4,5-dihydrooxazol-2-yl)azetidine-3-carboxamide;
N-(2-(difluoromethoxy)-6-methylpyridin-3-yl)-3-(2-isopropylphenyl)-1-(4-hydroxy-oxazol-2-yl)azetidine-3-carboxamide];
N-(2-(difluoromethoxy)-6-methylpyridin-3-yl)-1-(5-hydroxy-1,2,4-oxadiazol-3-yl)-3-(2-isopropylphenyl)azetidine-3-carboxamide;
N-(2-(difluoromethoxy)-6-methylpyridin-3-yl)-3-(2-isopropylphenyl)-1-(5-oxo-4,5-dihydro-1,2,4-oxadiazol-3-yl)azetidine-3-carboxamide];
3-(2-cyclopentylphenyl)-N-(2-(difluoromethoxy)-6-methylpyridin-3-yl)azetidine-3-carboxamide;
3-(2-cyclohexylphenyl)-N-(2-(difluoromethoxy)-6-methylpyridin-3-yl)azetidine-3-carboxamide;
4-(3-(2-cyclobutylphenyl)-3-((2-(difluoromethoxy)-6-methylpyridin-3-yl)carbamoyl)azetidin-1-yl)-2,2-dimethyl-4-oxobutanoic acid;
4-(3-(2-cyclopentylphenyl)-3-((2-(difluoromethoxy)-6-methylpyridin-3-yl)carbamoyl)azetidin-1-yl)-2,2-dimethyl-4-oxobutanoic acid;
4-(3-(2-cyclohexylphenyl)-3-((2-(difluoromethoxy)-6-methylpyridin-3-yl)carbamoyl)azetidin-1-yl)-2,2-dimethyl-4-oxobutanoic acid;
4-(3-((2-(difluoromethoxy)-6-methylpyridin-3-yl)carbamoyl)-3-(2-propylphenyl)azetidin-1-yl)-2,2-dimethyl-4-oxobutanoic acid;
N-(2-(difluoromethoxy)-6-methylpyridin-3-yl)-3-(2-fluoro-6-isopropylphenyl)azetidine-3-carboxamide;
4-(3-((2-(difluoromethoxy)-6-methylpyridin-3-yl)carbamoyl)-3-(2-isopropyl-5-methylphenyl)azetidin-1-yl)-2,2-dimethyl-4-oxobutanoic acid;
4-(3-((2-(difluoromethoxy)-6-methylpyridin-3-yl)carbamoyl)-3-(2-fluoro-6-isopropylphenyl)azetidin-1-yl)-2,2-dimethyl-4-oxobutanoic acid;
4-(3-((2-(difluoromethoxy)-6-methylpyridin-3-yl)carbamoyl)-3-(5-fluoro-2-isopropylphenyl)azetidin-1-yl)-2,2-dimethyl-4-oxobutanoic acid;
N-(2-(3-((2-(difluoromethoxy)-6-methylpyridin-3-yl)carbamoyl)-3-(2-isopropylphenyl)azetidin-1-yl)-2-oxoethyl)-N-propylglycine;
Methyl N-(2-(3-((2-(difluoromethoxy)-6-methylpyridin-3-yl)carbamoyl)-3-(2-isopropylphenyl)azetidin-1-yl)-2-oxoethyl)-N-(2-methoxyethyl)glycinate;
N-(2-(3-((2-(difluoromethoxy)-6-methylpyridin-3-yl)carbamoyl)-3-(2-isopropylphenyl)azetidin-1-yl)-2-oxoethyl)-N-(2-methoxyethyl)glycine;
Methyl (2-(3-((2-(difluoromethoxy)-6-methylpyridin-3-yl)carbamoyl)-3-(2-isopropylphenyl)azetidin-1-yl)-2-oxoethyl)glycinate;
(2-(3-((2-(difluoromethoxy)-6-methylpyridin-3-yl)carbamoyl)-3-(2-isopropylphenyl)azetidin-1-yl)-2-oxoethyl)glycine;
N-(2-(3-((2-(difluoromethoxy)-6-methylpyridin-3-yl)carbamoyl)-3-(2-isopropylphenyl)azetidin-1-yl)-2-oxoethyl)-N-ethylglycine;
N-(5-chloro-3-methoxypyridin-2-yl)-3-(2-isopropylphenyl)azetidine-3-carboxamide;
N-(5-bromo-3-methoxypyridin-2-yl)-3-(2-isopropylphenyl)azetidine-3-carboxamide;
N-(5-chloro-3-(difluoromethoxy)pyridin-2-yl)-3-(2-isopropylphenyl)azetidine-3-carboxamide;
N-(5-bromo-3-(difluoromethoxy)pyridin-2-yl)-3-(2-isopropylphenyl)azetidine-3-carboxamide;
N-(3-(difluoromethoxy)-5-methylpyridin-2-yl)-3-(2-isopropylphenyl)azetidine-3-carboxamide;
N-(3,5-dimethoxypyridin-2-yl)-3-(2-isopropylphenyl)azetidine-3-carboxamide;
N-(5-chloro-3-(difluoromethoxy)pyridin-2-yl)-3-(2-cyclopentylphenyl)azetidine-3-carboxamide;
Methyl 4-(3-((5-chloro-3-(difluoromethoxy)pyridin-2-yl)carbamoyl)-3-(2-isopropylphenyl)azetidin-1-yl)-2,2-dimethylbutanoate;
4-(3-((5-chloro-3-(difluoromethoxy)pyridin-2-yl)carbamoyl)-3-(2-isopropylphenyl)azetidin-1-yl)-2,2-dimethylbutanoic acid;
4-(3-((5-bromo-3-(difluoromethoxy)pyridin-2-yl)carbamoyl)-3-(2-isopropylphenyl)azetidin-1-yl)-2,2-dimethylbutanoic acid;
4-(3-((5-bromo-3-(difluoromethoxy)pyridin-2-yl)carbamoyl)-3-(2-isopropylphenyl)azetidin-1-yl)-2,2-dimethyl-4-oxobutanoic acid;
Methyl 4-(3-((5-bromo-3-(difluoromethoxy)pyridin-2-yl)carbamoyl)-3-(2-isopropylphenyl)azetidin-1-yl)-2,2-dimethyl-4-oxobutanoate;
4-(3-((5-chloro-3-(difluoromethoxy)pyridin-2-yl)carbamoyl)-3-(2-isopropylphenyl)azetidin-1-yl)-2,2-dimethyl-4-oxobutanoic acid;
4-(3-((5-chloro-3-methoxypyridin-2-yl)carbamoyl)-3-(2-isopropylphenyl)azetidin-1-yl)-2,2-dimethyl-4-oxobutanoic acid;
4-(3-((5-bromo-3-methoxypyridin-2-yl)carbamoyl)-3-(2-isopropylphenyl)azetidin-1-yl)-2,2-dimethyl-4-oxobutanoic acid;
4-(3-((3-(difluoromethoxy)-5-methylpyridin-2-yl)carbamoyl)-3-(2-isopropylphenyl)azetidin-1-yl)-2,2-dimethyl-4-oxobutanoic acid;
1-(2-(3-((3-(difluoromethoxy)-5-methylpyridin-2-yl)carbamoyl)-3-(2-isopropylphenyl)azetidin-1-yl)-2-oxoethyl)cyclobutane-1-carboxylic acid;
Benzyl 3-((3-((3-(difluoromethoxy)-5-methylpyridin-2-yl)carbamoyl)-3-(2-isopropylphenyl)azetidin-1-yl)sulfonyl)propanoate;
3-((3-((3-(difluoromethoxy)-5-methylpyridin-2-yl)carbamoyl)-3-(2-isopropylphenyl)azetidin-1-yl)sulfonyl)propanoic acid;
$N^3$-(5-chloro-3-(difluoromethoxy)pyridin-2-yl)-$N^1$-cyclopropyl-3-(2-isopropylphenyl)azetidine-1,3-dicarboxamide;
$N^3$-(5-bromo-3-(difluoromethoxy)pyridin-2-yl)-$N^1$-cyclopropyl-3-(2-isopropylphenyl)azetidine-1,3-dicarboxamide;
2-methoxy-2-oxoethyl 3-((3-(difluoromethoxy)-5-methylpyridin-2-yl)carbamoyl)-3-(2-isopropylphenyl)azetidine-1-carboxylate;
2-((3-((3-(difluoromethoxy)-5-methylpyridin-2-yl)carbamoyl)-3-(2-isopropylphenyl)azetidine-1-carbonyl)oxy)acetic acid;
1-((3-((3-(difluoromethoxy)-5-methylpyridin-2-yl)carbamoyl)-3-(2-isopropylphenyl)azetidine-1-carbonyl)oxy)cyclopropane-1-carboxylic acid; or
N-(3-(difluoromethoxy)-5-methylpyridin-2-yl)-3-(2-isopropylphenyl)-1-(4-oxo-4,5-dihydrooxazol-2-yl)azetidine-3-carboxamide;
or a pharmaceutically acceptable salt thereof.

10. A pharmaceutical composition comprising a compound according to claim 1, or a pharmaceutically acceptable salt thereof, and at least one pharmaceutically acceptable carrier.

11. A method for the prophylaxis or treatment of fibrosis, or dermatological disorders which are proliferative or inflammatory disorders of the skin; comprising administering to a subject in need thereof an effective amount of a compound as defined in claim 1, or of a pharmaceutically acceptable salt thereof.

12. A compound, wherein said compound is:

4-(3-((2-(difluoromethoxy)-6-methylpyridin-3-yl)carbamoyl)-3-(2-isopropylphenyl)azetidin-1-yl)-2,2-dimethylbutanoic acid;

or a pharmaceutically acceptable salt thereof.

13. A compound, wherein said compound is:

4-(3-((2-(difluoromethoxy)-6-methylpyridin-3-yl)carbamoyl)-3-(2-isopropylphenyl)azetidin-1-yl)-2,2-dimethyl-4-oxobutanoic acid;

or a pharmaceutically acceptable salt thereof.

14. A pharmaceutical composition comprising a compound according to claim 9, or a pharmaceutically acceptable salt thereof, and at least one pharmaceutically acceptable carrier.

15. A pharmaceutical composition comprising the compound according to claim 12, or a pharmaceutically acceptable salt thereof, and at least one pharmaceutically acceptable carrier.

16. A pharmaceutical composition comprising the compound according to claim 13, or a pharmaceutically acceptable salt thereof, and at least one pharmaceutically acceptable carrier.

17. A method for the prophylaxis or treatment of fibrosis, or dermatological disorders which are proliferative or inflammatory disorders of the skin; comprising administering to a subject in need thereof an effective amount of the compound as defined in claim 12, or of a pharmaceutically acceptable salt thereof.

18. A method for the prophylaxis or treatment of fibrosis, or dermatological disorders which are proliferative or inflammatory disorders of the skin; comprising administering to a subject in need thereof an effective amount of the compound as defined in claim 13, or of a pharmaceutically acceptable salt thereof.

19. A method for the treatment of pulmonary fibrosis or systemic sclerosis;

comprising administering to a subject in need thereof an effective amount of a compound as defined in claim 1, or of a pharmaceutically acceptable salt thereof.

20. A method for the treatment of pulmonary fibrosis or systemic sclerosis;

comprising administering to a subject in need thereof an effective amount of the compound as defined in claim 12, or of a pharmaceutically acceptable salt thereof.

21. A method for the treatment of pulmonary fibrosis or systemic sclerosis; comprising administering to a subject in need thereof an effective amount of the compound as defined in claim 13, or of a pharmaceutically acceptable salt thereof.

\* \* \* \* \*